US008323987B2

(12) United States Patent
Threadgill et al.

(10) Patent No.: US 8,323,987 B2
(45) Date of Patent: Dec. 4, 2012

(54) MODULATION OF EPIDERMAL GROWTH FACTOR HETERODIMER ACTIVITY

(75) Inventors: David Threadgill, Chapel Hill, NC (US); Daekee Lee, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1114 days.

(21) Appl. No.: 10/584,960

(22) PCT Filed: Feb. 17, 2005

(86) PCT No.: PCT/US2005/004968
§ 371 (c)(1),
(2), (4) Date: Nov. 4, 2008

(87) PCT Pub. No.: WO2005/079434
PCT Pub. Date: Sep. 1, 2005

(65) Prior Publication Data
US 2010/0015124 A1    Jan. 21, 2010

Related U.S. Application Data

(60) Provisional application No. 60/545,185, filed on Feb. 17, 2004.

(51) Int. Cl.
| | |
|---|---|
| C12Q 1/00 | (2006.01) |
| G01N 33/53 | (2006.01) |
| G01N 33/536 | (2006.01) |
| G01N 33/537 | (2006.01) |
| G01N 33/539 | (2006.01) |
| G01N 33/541 | (2006.01) |
| C12N 5/00 | (2006.01) |
| C12N 5/02 | (2006.01) |
| C12N 5/06 | (2006.01) |
| C12N 5/16 | (2006.01) |

(52) U.S. Cl. ..................................... 436/538
(58) Field of Classification Search .................. None
See application file for complete search history.

(56) References Cited

U.S. PATENT DOCUMENTS

| 7,662,374 B2 * | 2/2010 | Greene et al. ............. 424/130.1 |
| 2004/0191249 A1 * | 9/2004 | Hallahan et al. ........... 424/141.1 |

OTHER PUBLICATIONS

International Search Report and the Written Opinion of the International Searching Authority, or the Declaration dated Jan. 27, 2006.
Roberts et al. *Modeling the cancer patient with genetically engineered mice: Prediction of toxicity from molecule-targeted therapies* Cancer Cell, vol. 5, (2004), pp. 115-120.
Notification Concerning Transmittal of International Preliminary Report on Patentability corresponding to the International Patent Application No. PCT/US2005/004968 dated Aug. 31, 2006.
Apostolakis et al. (2000) Epidermal growth factor activates reproductive behavior independent of ovarian steroids in female rodents. Mol Endocrinol. 14:1086-1098.
Coker et al. (1994) A kinse-negative epidermal growth factor receptor that retains the capacity to stimulate DNA synthesis. Proc Natl Acad Aci USA. 91:6967-6971.
Qian et al. (1994) Heterodimerization of epidermal growth factor receptor and wild-type or kinase deficient Neu: a mechanism of interreceptor kinase activation and transphosphorylation. Proc Natl Acad Sci USA. 91:1500-1504.
Roberts et al. (2001) Importance of epidermal growth factor receptor signaling in establishment of adenomas and maintenance of carcinomas during intestinal tumorigenesis. Proc Natl Acad Sci USA. 99:1521-1526.
Thaung et al. (2002) Novel ENU-induced eye mutations in the mouse: models for human eye disease. Hum Mol Genet. 11:755-67.
Threadgill et al. (1995) Targeted disruption of mouse EGF receptor: effect of genetic background on mutant phenotype. Science. 269:230-234.
Wong et al. (1992) Structural alterations of the epidermal growth factor receptor gene in human gliomas. Proc Natl Acad Sci USA. 89:2965-9.

* cited by examiner

*Primary Examiner* — Alana Harris Dent
(74) *Attorney, Agent, or Firm* — Jenkins, Wilson, Taylor & Hunt, P.A.

(57) ABSTRACT

Provided is a method for screening a plurality of compounds for an ability to bind to a heterodimer of EGFR and another ERBB family member. Also provided are compounds that bind to heterodimers of EGFR and another ERBB family member, and methods of using the identified compounds to suppress the growth of a tumor associated with EGFR heterodimer activity in a subject.

12 Claims, 6 Drawing Sheets

SEQUENCE LISTING

```
<160> NUMBER OF SEQ ID NOS: 21

<210> SEQ ID NO 1
<211> LENGTH: 5616
<212> TYPE: DNA
<213> ORGANISM: Homo sapiens
<220> FEATURE:
<221> NAME/KEY: CDS
<222> LOCATION: (247)..(3879)

<400> SEQUENCE: 1 cccggcgca gcgcggccgc agcagcctcc gcccccgca cggtgtgagc gcccgacgcg      60
gccgaggcgg ccggagtccc gagctagccc cggcggccgc cgccgcccag accggacgac     120
aggccacctc gtcggcgtcc gcccgagtcc ccgcctcgcc gccaacgcca caaccaccgc     180
gcacggcccc ctgactccgt ccagtattga tcgggagagc cggagcgagc tcttcgggga     240 gcagcg atg cga ccc tcc ggg acg gcc ggg gca gcg ctc ctg gcg ctg         288
       Met Arg Pro Ser Gly Thr Ala Gly Ala Ala Leu Leu Ala Leu
       1               5                   10 ctg gct gcg ctc tgc ccg gcg agt cgg gct ctg gag gaa aag aaa gtt        336
Leu Ala Ala Leu Cys Pro Ala Ser Arg Ala Leu Glu Glu Lys Lys Val
15                  20                  25                  30 tgc caa ggc acg agt aac aag ctc acg cag ttg ggc act ttt gaa gat        384
Cys Gln Gly Thr Ser Asn Lys Leu Thr Gln Leu Gly Thr Phe Glu Asp
                35                  40                  45 cat ttt ctc agc ctc cag agg atg ttc aat aac tgt gag gtg gtc ctt        432
His Phe Leu Ser Leu Gln Arg Met Phe Asn Asn Cys Glu Val Val Leu
            50                  55                  60 ggg aat ttg gaa att acc tat gtg cag agg aat tat gat ctt tcc ttc        480
Gly Asn Leu Glu Ile Thr Tyr Val Gln Arg Asn Tyr Asp Leu Ser Phe
        65                  70                  75 tta aag acc atc cag gag gtg gct ggt tat gtc ctc att gcc ctc aac        528
Leu Lys Thr Ile Gln Glu Val Ala Gly Tyr Val Leu Ile Ala Leu Asn
    80                  85                  90
```

```
aca gtg gag cga att cct ttg gaa aac ctg cag atc atc aga gga aat      576
Thr Val Glu Arg Ile Pro Leu Glu Asn Leu Gln Ile Ile Arg Gly Asn
 95                 100                 105                 110 atg tac tac gaa aat tcc tat gcc tta gca gtc tta tct aac tat gat      624
Met Tyr Tyr Glu Asn Ser Tyr Ala Leu Ala Val Leu Ser Asn Tyr Asp
                115                 120                 125 gca aat aaa acc gga ctg aag gag ctg ccc atg aga aat tta cag gaa      672
Ala Asn Lys Thr Gly Leu Lys Glu Leu Pro Met Arg Asn Leu Gln Glu
            130                 135                 140 atc ctg cat ggc gcc gtg cgg ttc agc aac aac cct gcc ctg tgc aac      720
Ile Leu His Gly Ala Val Arg Phe Ser Asn Asn Pro Ala Leu Cys Asn
        145                 150                 155 gtg gag agc atc cag tgg cgg gac ata gtc agc agt gac ttt ctc agc      768
Val Glu Ser Ile Gln Trp Arg Asp Ile Val Ser Ser Asp Phe Leu Ser
    160                 165                 170 aac atg tcg atg gac ttc cag aac cac ctg ggc agc tgc caa aag tgt      816
Asn Met Ser Met Asp Phe Gln Asn His Leu Gly Ser Cys Gln Lys Cys
175                 180                 185                 190 gat cca agc tgt ccc aat ggg agc tgc tgg ggt gca gga gag gag aac      864
Asp Pro Ser Cys Pro Asn Gly Ser Cys Trp Gly Ala Gly Glu Glu Asn
                195                 200                 205 tgc cag aaa ctg acc aaa atc atc tgt gcc cag cag tgc tcc ggg cgc      912
Cys Gln Lys Leu Thr Lys Ile Ile Cys Ala Gln Gln Cys Ser Gly Arg
            210                 215                 220 tgc cgt ggc aag tcc ccc agt gac tgc tgc cac aac cag tgt gct gca      960
Cys Arg Gly Lys Ser Pro Ser Asp Cys Cys His Asn Gln Cys Ala Ala
        225                 230                 235 ggc tgc aca ggc ccc cgg gag agc gac tgc ctg gtc tgc cgc aaa ttc     1008
Gly Cys Thr Gly Pro Arg Glu Ser Asp Cys Leu Val Cys Arg Lys Phe
    240                 245                 250 cga gac gaa gcc acg tgc aag gac acc tgc ccc cca ctc atg ctc tac     1056
Arg Asp Glu Ala Thr Cys Lys Asp Thr Cys Pro Pro Leu Met Leu Tyr
255                 260                 265                 270 aac ccc acc acg tac cag atg gat gtg aac ccc gag ggc aaa tac agc     1104
Asn Pro Thr Thr Tyr Gln Met Asp Val Asn Pro Glu Gly Lys Tyr Ser
                275                 280                 285 ttt ggt gcc acc tgc gtg aag aag tgt ccc cgt aat tat gtg gtg aca     1152
Phe Gly Ala Thr Cys Val Lys Lys Cys Pro Arg Asn Tyr Val Val Thr
            290                 295                 300 gat cac ggc tcg tgc gtc cga gcc tgt ggg gcc gac agc tat gag atg     1200
Asp His Gly Ser Cys Val Arg Ala Cys Gly Ala Asp Ser Tyr Glu Met
        305                 310                 315 gag gaa gac ggc gtc cgc aag tgt aag aag tgc gaa ggg cct tgc cgc     1248
Glu Glu Asp Gly Val Arg Lys Cys Lys Lys Cys Glu Gly Pro Cys Arg
    320                 325                 330 aaa gtg tgt aac gga ata ggt att ggt gaa ttt aaa gac tca ctc tcc     1296
Lys Val Cys Asn Gly Ile Gly Ile Gly Glu Phe Lys Asp Ser Leu Ser
335                 340                 345                 350 ata aat gct acg aat att aaa cac ttc aaa aac tgc acc tcc atc agt     1344
Ile Asn Ala Thr Asn Ile Lys His Phe Lys Asn Cys Thr Ser Ile Ser
                355                 360                 365 ggc gat ctc cac atc ctg ccg gtg gca ttt agg ggt gac tcc ttc aca     1392
Gly Asp Leu His Ile Leu Pro Val Ala Phe Arg Gly Asp Ser Phe Thr
            370                 375                 380 cat act cct cct ctg gat cca cag gaa ctg gat att ctg aaa acc gta     1440
His Thr Pro Pro Leu Asp Pro Gln Glu Leu Asp Ile Leu Lys Thr Val
        385                 390                 395 aag gaa atc aca ggg ttt ttg ctg att cag gct tgg cct gaa aac agg     1488
Lys Glu Ile Thr Gly Phe Leu Leu Ile Gln Ala Trp Pro Glu Asn Arg
    400                 405                 410
```

-continued

| | | |
|---|---|---|
| acg gac ctc cat gcc ttt gag aac cta gaa atc ata cgc ggc agg acc<br>Thr Asp Leu His Ala Phe Glu Asn Leu Glu Ile Ile Arg Gly Arg Thr<br>415                    420                    425                    430 | 1536 |
| aag caa cat ggt cag ttt tct ctt gca gtc gtc agc ctg aac ata aca<br>Lys Gln His Gly Gln Phe Ser Leu Ala Val Val Ser Leu Asn Ile Thr<br>                435                    440                    445 | 1584 |
| tcc ttg gga tta cgc tcc ctc aag gag ata agt gat gga gat gtg ata<br>Ser Leu Gly Leu Arg Ser Leu Lys Glu Ile Ser Asp Gly Asp Val Ile<br>450                    455                    460 | 1632 |
| att tca gga aac aaa aat ttg tgc tat gca aat aca ata aac tgg aaa<br>Ile Ser Gly Asn Lys Asn Leu Cys Tyr Ala Asn Thr Ile Asn Trp Lys<br>        465                    470                    475 | 1680 |
| aaa ctg ttt ggg acc tcc ggt cag aaa acc aaa att ata agc aac aga<br>Lys Leu Phe Gly Thr Ser Gly Gln Lys Thr Lys Ile Ile Ser Asn Arg<br>480                    485                    490 | 1728 |
| ggt gaa aac agc tgc aag gcc aca ggc cag gtc tgc cat gcc ttg tgc<br>Gly Glu Asn Ser Cys Lys Ala Thr Gly Gln Val Cys His Ala Leu Cys<br>495                    500                    505                    510 | 1776 |
| tcc ccc gag ggc tgc tgg ggc ccg gag ccc agg gac tgc gtc tct tgc<br>Ser Pro Glu Gly Cys Trp Gly Pro Glu Pro Arg Asp Cys Val Ser Cys<br>                515                    520                    525 | 1824 |
| cgg aat gtc agc cga ggc agg gaa tgc gtg gac aag tgc aac ctt ctg<br>Arg Asn Val Ser Arg Gly Arg Glu Cys Val Asp Lys Cys Asn Leu Leu<br>530                    535                    540 | 1872 |
| gag ggt gag cca agg gag ttt gtg gag aac tct gag tgc ata cag tgc<br>Glu Gly Glu Pro Arg Glu Phe Val Glu Asn Ser Glu Cys Ile Gln Cys<br>        545                    550                    555 | 1920 |
| cac cca gag tgc ctg cct cag gcc atg aac atc acc tgc aca gga cgg<br>His Pro Glu Cys Leu Pro Gln Ala Met Asn Ile Thr Cys Thr Gly Arg<br>560                    565                    570 | 1968 |
| gga cca gac aac tgt atc cag tgt gcc cac tac att gac ggc ccc cac<br>Gly Pro Asp Asn Cys Ile Gln Cys Ala His Tyr Ile Asp Gly Pro His<br>575                    580                    585                    590 | 2016 |
| tgc gtc aag acc tgc ccg gca gga gtc atg gga gaa aac aac acc ctg<br>Cys Val Lys Thr Cys Pro Ala Gly Val Met Gly Glu Asn Asn Thr Leu<br>                    595                    600                    605 | 2064 |
| gtc tgg aag tac gca gac gcc ggc cat gtg tgc cac ctg tgc cat cca<br>Val Trp Lys Tyr Ala Asp Ala Gly His Val Cys His Leu Cys His Pro<br>610                    615                    620 | 2112 |
| aac tgc acc tac gga tgc act ggg cca ggt ctt gaa ggc tgt cca acg<br>Asn Cys Thr Tyr Gly Cys Thr Gly Pro Gly Leu Glu Gly Cys Pro Thr<br>        625                    630                    635 | 2160 |
| aat ggg cct aag atc ccg tcc atc gcc act ggg atg gtg ggg gcc ctc<br>Asn Gly Pro Lys Ile Pro Ser Ile Ala Thr Gly Met Val Gly Ala Leu<br>640                    645                    650 | 2208 |
| ctc ttg ctg ctg gtg gtg gcc ctg ggg atc ggc ctc ttc atg cga agg<br>Leu Leu Leu Leu Val Val Ala Leu Gly Ile Gly Leu Phe Met Arg Arg<br>655                    660                    665                    670 | 2256 |
| cgc cac atc gtt cgg aag cgc acg ctg cgg agg ctg ctg cag gag agg<br>Arg His Ile Val Arg Lys Arg Thr Leu Arg Arg Leu Leu Gln Glu Arg<br>                675                    680                    685 | 2304 |
| gag ctt gtg gag cct ctt aca ccc agt gga gaa gct ccc aac caa gct<br>Glu Leu Val Glu Pro Leu Thr Pro Ser Gly Glu Ala Pro Asn Gln Ala<br>690                    695                    700 | 2352 |
| ctc ttg agg atc ttg aag gaa act gaa ttc aaa aag atc aaa gtg ctg<br>Leu Leu Arg Ile Leu Lys Glu Thr Glu Phe Lys Lys Ile Lys Val Leu<br>705                    710                    715 | 2400 |
| ggc tcc ggt gcg ttc ggc acg gtg tat aag gga ctc tgg atc cca gaa<br>Gly Ser Gly Ala Phe Gly Thr Val Tyr Lys Gly Leu Trp Ile Pro Glu<br>720                    725                    730 | 2448 |

| | | |
|---|---|---|
| ggt gag aaa gtt aaa att ccc gtc gct atc aag gaa tta aga gaa gca<br>Gly Glu Lys Val Lys Ile Pro Val Ala Ile Lys Glu Leu Arg Glu Ala<br>735                    740                   745                  750 | 2496 |
| aca tct ccg aaa gcc aac aag gaa atc ctc gat gaa gcc tac gtg atg<br>Thr Ser Pro Lys Ala Asn Lys Glu Ile Leu Asp Glu Ala Tyr Val Met<br>                   755                   760                   765 | 2544 |
| gcc agc gtg gac aac ccc cac gtg tgc cgc ctg ctg ggc atc tgc ctc<br>Ala Ser Val Asp Asn Pro His Val Cys Arg Leu Leu Gly Ile Cys Leu<br>770                    775                   780 | 2592 |
| acc tcc acc gtg cag ctc atc acg cag ctc atg ccc ttc ggc tgc ctc<br>Thr Ser Thr Val Gln Leu Ile Thr Gln Leu Met Pro Phe Gly Cys Leu<br>                   785                   790                   795 | 2640 |
| ctg gac tat gtc cgg gaa cac aaa gac aat att ggc tcc cag tac ctg<br>Leu Asp Tyr Val Arg Glu His Lys Asp Asn Ile Gly Ser Gln Tyr Leu<br>800                    805                   810 | 2688 |
| ctc aac tgg tgt gtg cag atc gca aag ggc atg aac tac ttg gag gac<br>Leu Asn Trp Cys Val Gln Ile Ala Lys Gly Met Asn Tyr Leu Glu Asp<br>815                    820                   825                   830 | 2736 |
| cgt cgc ttg gtg cac cgc gac ctg gca gcc agg aac gta ctg gtg aaa<br>Arg Arg Leu Val His Arg Asp Leu Ala Ala Arg Asn Val Leu Val Lys<br>                   835                   840                   845 | 2784 |
| aca ccg cag cat gtc aag atc aca gat ttt ggg ctg gcc aaa ctg ctg<br>Thr Pro Gln His Val Lys Ile Thr Asp Phe Gly Leu Ala Lys Leu Leu<br>850                    855                   860 | 2832 |
| ggt gcg gaa gag aaa gaa tac cat gca gaa gga ggc aaa gtg cct atc<br>Gly Ala Glu Glu Lys Glu Tyr His Ala Glu Gly Gly Lys Val Pro Ile<br>                   865                   870                   875 | 2880 |
| aag tgg atg gca ttg gaa tca att tta cac aga atc tat acc cac cag<br>Lys Trp Met Ala Leu Glu Ser Ile Leu His Arg Ile Tyr Thr His Gln<br>880                    885                   890 | 2928 |
| agt gat gtc tgg agc tac ggg gtg acc gtt tgg gag ttg atg acc ttt<br>Ser Asp Val Trp Ser Tyr Gly Val Thr Val Trp Glu Leu Met Thr Phe<br>895                    900                   905                   910 | 2976 |
| gga tcc aag cca tat gac gga atc cct gcc agc gag atc tcc tcc atc<br>Gly Ser Lys Pro Tyr Asp Gly Ile Pro Ala Ser Glu Ile Ser Ser Ile<br>                   915                   920                   925 | 3024 |
| ctg gag aaa gga gaa cgc ctc cct cag cca ccc ata tgt acc atc gat<br>Leu Glu Lys Gly Glu Arg Leu Pro Gln Pro Pro Ile Cys Thr Ile Asp<br>930                    935                   940 | 3072 |
| gtc tac atg atc atg gtc aag tgc tgg atg ata gac gca gat agt cgc<br>Val Tyr Met Ile Met Val Lys Cys Trp Met Ile Asp Ala Asp Ser Arg<br>945                    950                   955 | 3120 |
| cca aag ttc cgt gag ttg atc atc gaa ttc tcc aaa atg gcc cga gac<br>Pro Lys Phe Arg Glu Leu Ile Ile Glu Phe Ser Lys Met Ala Arg Asp<br>960                    965                   970 | 3168 |
| ccc cag cgc tac ctt gtc att cag ggg gat gaa aga atg cat ttg cca<br>Pro Gln Arg Tyr Leu Val Ile Gln Gly Asp Glu Arg Met His Leu Pro<br>975                    980                   985                   990 | 3216 |
| agt cct aca gac tcc aac ttc tac cgt gcc  ctg atg gat gaa gaa  gac<br>Ser Pro Thr Asp Ser Asn Phe Tyr Arg Ala  Leu Met Asp Glu Glu  Asp<br>                   995                   1000                1005 | 3264 |
| atg gac gac gtg  gtg gat gcc gac gag  tac ctc atc cca cag  cag<br>Met Asp Asp Val  Val Asp Ala Asp Glu  Tyr Leu Ile Pro Gln  Gln<br>            1010                   1015                1020 | 3309 |
| ggc ttc ttc agc  agc ccc tcc acg tca  cgg act ccc ctc ctg  agc<br>Gly Phe Phe Ser  Ser Pro Ser Thr Ser  Arg Thr Pro Leu Leu  Ser<br>            1025                   1030                1035 | 3354 |
| tct ctg agt gca  acc agc aac aat tcc  acc gtg gct tgc att  gat<br>Ser Leu Ser Ala  Thr Ser Asn Asn Ser  Thr Val Ala Cys Ile  Asp<br>            1040                   1045                1050 | 3399 |

| | | | | | | | | | | | | |
|---|---|---|---|---|---|---|---|---|---|---|---|---|
| aga | aat | ggg | ctg | caa | agc | tgt | ccc | atc | aag | gaa | gac | agc | ttc | ttg | 3444 |
| Arg | Asn | Gly | Leu | Gln | Ser | Cys | Pro | Ile | Lys | Glu | Asp | Ser | Phe | Leu | |
| | | | 1055 | | | | 1060 | | | | 1065 | | | | |
| cag | cga | tac | agc | tca | gac | ccc | aca | ggc | gcc | ttg | act | gag | gac | agc | 3489 |
| Gln | Arg | Tyr | Ser | Ser | Asp | Pro | Thr | Gly | Ala | Leu | Thr | Glu | Asp | Ser | |
| | | | 1070 | | | | 1075 | | | | 1080 | | | | |
| ata | gac | gac | acc | ttc | ctc | cca | gtg | cct | gaa | tac | ata | aac | cag | tcc | 3534 |
| Ile | Asp | Asp | Thr | Phe | Leu | Pro | Val | Pro | Glu | Tyr | Ile | Asn | Gln | Ser | |
| | | | 1085 | | | | 1090 | | | | 1095 | | | | |
| gtt | ccc | aaa | agg | ccc | gct | ggc | tct | gtg | cag | aat | cct | gtc | tat | cac | 3579 |
| Val | Pro | Lys | Arg | Pro | Ala | Gly | Ser | Val | Gln | Asn | Pro | Val | Tyr | His | |
| | | | 1100 | | | | 1105 | | | | 1110 | | | | |
| aat | cag | cct | ctg | aac | ccc | gcg | ccc | agc | aga | gac | cca | cac | tac | cag | 3624 |
| Asn | Gln | Pro | Leu | Asn | Pro | Ala | Pro | Ser | Arg | Asp | Pro | His | Tyr | Gln | |
| | | | 1115 | | | | 1120 | | | | 1125 | | | | |
| gac | ccc | cac | agc | act | gca | gtg | ggc | aac | ccc | gag | tat | ctc | aac | act | 3669 |
| Asp | Pro | His | Ser | Thr | Ala | Val | Gly | Asn | Pro | Glu | Tyr | Leu | Asn | Thr | |
| | | | 1130 | | | | 1135 | | | | 1140 | | | | |
| gtc | cag | ccc | acc | tgt | gtc | aac | agc | aca | ttc | gac | agc | cct | gcc | cac | 3714 |
| Val | Gln | Pro | Thr | Cys | Val | Asn | Ser | Thr | Phe | Asp | Ser | Pro | Ala | His | |
| | | | 1145 | | | | 1150 | | | | 1155 | | | | |
| tgg | gcc | cag | aaa | ggc | agc | cac | caa | att | agc | ctg | gac | aac | cct | gac | 3759 |
| Trp | Ala | Gln | Lys | Gly | Ser | His | Gln | Ile | Ser | Leu | Asp | Asn | Pro | Asp | |
| | | | 1160 | | | | 1165 | | | | 1170 | | | | |
| tac | cag | cag | gac | ttc | ttt | ccc | aag | gaa | gcc | aag | cca | aat | ggc | atc | 3804 |
| Tyr | Gln | Gln | Asp | Phe | Phe | Pro | Lys | Glu | Ala | Lys | Pro | Asn | Gly | Ile | |
| | | | 1175 | | | | 1180 | | | | 1185 | | | | |
| ttt | aag | ggc | tcc | aca | gct | gaa | aat | gca | gaa | tac | cta | agg | gtc | gcg | 3849 |
| Phe | Lys | Gly | Ser | Thr | Ala | Glu | Asn | Ala | Glu | Tyr | Leu | Arg | Val | Ala | |
| | | | 1190 | | | | 1195 | | | | 1200 | | | | |
| cca | caa | agc | agt | gaa | ttt | att | gga | gca | tga | ccacggagga | tagtatgagc | | | | 3899 |
| Pro | Gln | Ser | Ser | Glu | Phe | Ile | Gly | Ala | | | | | | | |
| | | | 1205 | | | | 1210 | | | | | | | | |

| | |
|---|---|
| cctaaaaatc cagactctttt cgatacccag gaccaagcca cagcaggtcc tcatcccaa | 3959 |
| cagccatgcc cgcattagct cttagaccca cagactggtt ttgcaacgtt tacaccgact | 4019 |
| agccaggaag tacttccacc tcgggcacat tttgggaagt tgcattcctt tgtcttcaaa | 4079 |
| ctgtgaagca tttacagaaa cgcatccagc aagaatattg tcccttttgag cagaaattta | 4139 |
| tctttcaaag aggtatattt gaaaaaaaaa aaaagtatat gtgaggattt ttattgattg | 4199 |
| gggatcttgg agttttttcat tgtcgctatt gattttttact tcaatgggct cttccaacaa | 4259 |
| ggaagaagct tgctggtagc acttgctacc ctgagttcat ccaggcccaa ctgtgagcaa | 4319 |
| ggagcacaag ccacaagtct tccagaggat gcttgattcc agtggttctg cttcaaggct | 4379 |
| tccactgcaa aacactaaag atccaagaag gccttcatgg ccccagcagg ccggatcggt | 4439 |
| actgtatcaa gtcatggcag gtacagtagg ataagccact ctgtcccttc ctgggcaaag | 4499 |
| aagaaacgga ggggatggaa ttcttcctta gacttacttt tgtaaaaatg tccccacggt | 4559 |
| acttactccc cactgatgga ccagtggttt ccagtcatga gcgttagact gacttgtttg | 4619 |
| tcttccattc cattgtttttg aaactcagta tgctgcccct gtcttgctgt catgaaatca | 4679 |
| gcaagagagg atgacacatc aaataataac tcggattcca gcccacattg gattcatcag | 4739 |
| catttggacc aatagcccac agctgagaat gtggaatacc taaggatagc accgcttttg | 4799 |
| ttctcgcaaa aacgtatctc ctaatttgag gctcagatga aatgcatcag gtcctttggg | 4859 |
| gcatagatca gaagactaca aaaatgaagc tgctctgaaa tctcctttag ccatcacccc | 4919 |
| aacccccccaa aattagtttg tgttacttat ggaagatagt tttctccttt tacttcactt | 4979 |

-continued

```
caaaagcttt ttactcaaag agtatatgtt ccctccaggt cagctgcccc caaacccct      5039 ccttacgctt tgtcacacaa aaagtgtctc tgccttgagt catctattca agcacttaca      5099
gctctggcca caacagggca ttttacaggt gcgaatgaca gtagcattat gagtagtgtg      5159
gaattcaggt agtaaatatg aaactagggt ttgaaattga taatgctttc acaacatttg      5219
cagatgtttt agaaggaaaa aagttccttc ctaaaataat ttctctacaa ttggaagatt      5279
ggaagattca gctagttagg agcccacctt ttttcctaat ctgtgtgtgc cctgtaacct      5339
gactggttaa cagcagtcct ttgtaaacag tgttttaaac tctcctagtc aatatccacc      5399
ccatccaatt tatcaaggaa gaaatggttc agaaaatatt ttcagcctac agttatgttc      5459
agtcacacac acatacaaaa tgttcctttt gcttttaaag taattttga ctcccagatc       5519 agtcagagcc cctacagcat tgttaagaaa gtatttgatt tttgtctcaa tgaaaataaa      5579
actatattca tttccactct aaaaaaaaaa aaaaaa                                5616
```

<210> SEQ ID NO 2
<211> LENGTH: 1210
<212> TYPE: PRT
<213> ORGANISM: Homo sapiens

<400> SEQUENCE: 2

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
```

```
                    260                 265                 270
Thr Thr Tyr Gln Met Asp Val Asn Pro Glu Gly Lys Tyr Ser Phe Gly
            275                 280                 285
Ala Thr Cys Val Lys Lys Cys Pro Arg Asn Tyr Val Thr Asp His
            290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
            370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
            450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
                500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
            530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
            610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
```

Val Glu Pro Leu Thr Pro Ser Gly Glu Ala Pro Asn Gln Ala Leu Leu
690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
            725                 730                 735

Lys Val Lys Ile Pro Val Ala Ile Lys Glu Leu Arg Glu Ala Thr Ser
                740                 745                 750

Pro Lys Ala Asn Lys Glu Ile Leu Asp Glu Ala Tyr Val Met Ala Ser
            755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
                820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
                995                 1000                1005

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

```
Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 3
<211> LENGTH: 5992
<212> TYPE: DNA
<213> ORGANISM: Mus musculus
<220> FEATURE:
<221> NAME/KEY: CDS
<222> LOCATION: (281)..(3913)

<400> SEQUENCE: 3
ctcccccagt cccgacccga gctaactaga cgtctgggca gccccagcgc aacgcgcagc      60
agcctccctc ctcttcttcc cgcactgtgc gctcctcctg ggctagggcg tctggatcga     120
gtcccggagg ctaccgcctc ccagacagac gacaggtcac ctggacgcga gcctgtgtcc     180
gggtctcgtc gttgccggcg cagtcactgg gcacaaccgt gggactccgt ctgtctcgga     240
ttaatcccgg agagccagag ccaacctctc ccggtcagag atg cga ccc tca ggg       295
                                              Met Arg Pro Ser Gly
                                                1               5 acc gcg aga acc aca ctg ctg gtg ttg ctg acc gcg ctc tgc gcc gca       343
Thr Ala Arg Thr Thr Leu Leu Val Leu Leu Thr Ala Leu Cys Ala Ala
            10                  15                  20 ggt ggg gcg ttg gag gaa aag aaa gtc tgc caa ggc aca agt aac agg       391
Gly Gly Ala Leu Glu Glu Lys Lys Val Cys Gln Gly Thr Ser Asn Arg
        25                  30                  35 ctc acc caa ctg ggc act ttt gaa gac cac ttt ctg agc ctg cag agg       439
Leu Thr Gln Leu Gly Thr Phe Glu Asp His Phe Leu Ser Leu Gln Arg
    40                  45                  50 atg tac aac aac tgt gaa gtg gtc ctt ggg aac ttg gaa att acc tat       487
Met Tyr Asn Asn Cys Glu Val Val Leu Gly Asn Leu Glu Ile Thr Tyr
55                  60                  65 gtg caa agg aat tac gac ctt tcc ttc tta aag acc atc cag gag gtg       535
Val Gln Arg Asn Tyr Asp Leu Ser Phe Leu Lys Thr Ile Gln Glu Val
70                  75                  80                  85 gcc ggc tat gtc ctc att gcc ctc aac acc gtg gag aga atc cct ttg       583
Ala Gly Tyr Val Leu Ile Ala Leu Asn Thr Val Glu Arg Ile Pro Leu
                90                  95                 100 gag aac ctg cag atc atc agg gga aat gct ctt tat gaa aac acc tat       631
Glu Asn Leu Gln Ile Ile Arg Gly Asn Ala Leu Tyr Glu Asn Thr Tyr
            105                 110                 115 gcc tta gcc atc ctg tcc aac tat ggg aca aac aga act ggg ctt agg       679
Ala Leu Ala Ile Leu Ser Asn Tyr Gly Thr Asn Arg Thr Gly Leu Arg
        120                 125                 130 gaa ctg ccc atg cgg aac tta cag gaa atc ctg att ggt gct gtg cga       727
Glu Leu Pro Met Arg Asn Leu Gln Glu Ile Leu Ile Gly Ala Val Arg
    135                 140                 145
```

-continued

| | |
|---|---|
| ttc agc aac aac ccc atc ctc tgc aat atg gat act atc cag tgg agg<br>Phe Ser Asn Asn Pro Ile Leu Cys Asn Met Asp Thr Ile Gln Trp Arg<br>150                        155                      160                  165 | 775 |
| gac atc gtc caa aac gtc ttt atg agc aac atg tca atg gac tta cag<br>Asp Ile Val Gln Asn Val Phe Met Ser Asn Met Ser Met Asp Leu Gln<br>                  170                      175                      180 | 823 |
| agc cat ccg agc agt tgc ccc aaa tgt gat cca agc tgt ccc aat gga<br>Ser His Pro Ser Ser Cys Pro Lys Cys Asp Pro Ser Cys Pro Asn Gly<br>                185                      190                      195 | 871 |
| agc tgc tgg gga gga gga gag gag aac tgc cag aaa ttg acc aaa atc<br>Ser Cys Trp Gly Gly Gly Glu Glu Asn Cys Gln Lys Leu Thr Lys Ile<br>            200                      205                      210 | 919 |
| atc tgt gcc cag caa tgt tcc cat cgc tgt cgt ggc agg tcc ccc agt<br>Ile Cys Ala Gln Gln Cys Ser His Arg Cys Arg Gly Arg Ser Pro Ser<br>215                        220                      225 | 967 |
| gac tgc tgc cac aac caa tgt gct gcg ggg tgt aca ggg ccc cga gag<br>Asp Cys Cys His Asn Gln Cys Ala Ala Gly Cys Thr Gly Pro Arg Glu<br>230                        235                      240                      245 | 1015 |
| agt gac tgt ctg gtc tgc caa aag ttc caa gat gag gcc aca tgc aaa<br>Ser Asp Cys Leu Val Cys Gln Lys Phe Gln Asp Glu Ala Thr Cys Lys<br>                  250                      255                      260 | 1063 |
| gac acc tgc cca cca ctc atg ctg tac aac ccc acc acc tat cag atg<br>Asp Thr Cys Pro Pro Leu Met Leu Tyr Asn Pro Thr Thr Tyr Gln Met<br>                265                      270                      275 | 1111 |
| gat gtc aac cct gaa ggg aag tac agc ttt ggt gcc acc tgt gtg aag<br>Asp Val Asn Pro Glu Gly Lys Tyr Ser Phe Gly Ala Thr Cys Val Lys<br>            280                      285                      290 | 1159 |
| aag tgc ccc cga aac tac gtg gtg aca gat cat ggc tca tgt gtc cga<br>Lys Cys Pro Arg Asn Tyr Val Val Thr Asp His Gly Ser Cys Val Arg<br>295                        300                      305 | 1207 |
| gcc tgt ggg cct gac tac tac gaa gtg gaa gaa gat ggc atc cgc aag<br>Ala Cys Gly Pro Asp Tyr Tyr Glu Val Glu Glu Asp Gly Ile Arg Lys<br>310                        315                      320                      325 | 1255 |
| tgt aaa aaa tgt gat ggg ccc tgt cgc aaa gtt tgt aat ggc ata ggc<br>Cys Lys Lys Cys Asp Gly Pro Cys Arg Lys Val Cys Asn Gly Ile Gly<br>                  330                      335                      340 | 1303 |
| att ggt gaa ttt aaa gac aca ctc tcc ata aat gct aca aac atc aaa<br>Ile Gly Glu Phe Lys Asp Thr Leu Ser Ile Asn Ala Thr Asn Ile Lys<br>                  345                      350                      355 | 1351 |
| cac ttc aaa tac tgc act gcc atc agc ggg gac ctt cac atc ctg cca<br>His Phe Lys Tyr Cys Thr Ala Ile Ser Gly Asp Leu His Ile Leu Pro<br>                      360                      365                      370 | 1399 |
| gtg gcc ttt aag ggg gat tct ttc acg cgc act cct cct cta gac cca<br>Val Ala Phe Lys Gly Asp Ser Phe Thr Arg Thr Pro Pro Leu Asp Pro<br>375                        380                      385 | 1447 |
| cga gaa cta gaa att cta aaa acc gta aag gaa ata aca ggc ttt ttg<br>Arg Glu Leu Glu Ile Leu Lys Thr Val Lys Glu Ile Thr Gly Phe Leu<br>390                        395                      400                      405 | 1495 |
| ctg att cag gct tgg cct gat aac tgg act gac ctc cat gct ttc gag<br>Leu Ile Gln Ala Trp Pro Asp Asn Trp Thr Asp Leu His Ala Phe Glu<br>                      410                      415                      420 | 1543 |
| aac cta gaa ata ata cgt ggc aga aca aag caa cat ggt cag ttt tct<br>Asn Leu Glu Ile Ile Arg Gly Arg Thr Lys Gln His Gly Gln Phe Ser<br>                      425                      430                      435 | 1591 |
| ttg gcg gtc gtt ggc ctg aac atc aca tca ctg ggg ctg cgt tcc ctc<br>Leu Ala Val Val Gly Leu Asn Ile Thr Ser Leu Gly Leu Arg Ser Leu<br>                  440                      445                      450 | 1639 |
| aag gag atc agt gat ggg gat gtg atc att tct gga aac cga aat ttg<br>Lys Glu Ile Ser Asp Gly Asp Val Ile Ile Ser Gly Asn Arg Asn Leu<br>455                        460                      465 | 1687 |

| | | | | | | | | | | | | | | | |
|---|---|---|---|---|---|---|---|---|---|---|---|---|---|---|---|
| tgc | tac | gca | aac | aca | ata | aac | tgg | aaa | aaa | ctc | ttc | ggg | aca | ccc | aat | 1735 |
| Cys | Tyr | Ala | Asn | Thr | Ile | Asn | Trp | Lys | Lys | Leu | Phe | Gly | Thr | Pro | Asn | |
| 470 | | | | 475 | | | | | 480 | | | | | 485 | | |

| cag | aaa | acc | aaa | atc | atg | aac | aac | aga | gct | gag | aaa | gac | tgc | aag | gcc | 1783 |
| Gln | Lys | Thr | Lys | Ile | Met | Asn | Asn | Arg | Ala | Glu | Lys | Asp | Cys | Lys | Ala | |
| | | | | 490 | | | | | 495 | | | | | 500 | | |

| gtg | aac | cac | gtc | tgc | aat | cct | tta | tgc | tcc | tcg | gaa | ggc | tgc | tgg | ggc | 1831 |
| Val | Asn | His | Val | Cys | Asn | Pro | Leu | Cys | Ser | Ser | Glu | Gly | Cys | Trp | Gly | |
| | | | 505 | | | | | 510 | | | | | 515 | | | |

| cct | gag | ccc | agg | gac | tgt | gtc | tcc | tgc | cag | aat | gtg | agc | aga | ggc | agg | 1879 |
| Pro | Glu | Pro | Arg | Asp | Cys | Val | Ser | Cys | Gln | Asn | Val | Ser | Arg | Gly | Arg | |
| | | | 520 | | | | | 525 | | | | | 530 | | | |

| gag | tgc | gtg | gag | aaa | tgc | aac | atc | ctg | gag | ggg | gaa | cca | agg | gag | ttt | 1927 |
| Glu | Cys | Val | Glu | Lys | Cys | Asn | Ile | Leu | Glu | Gly | Glu | Pro | Arg | Glu | Phe | |
| | 535 | | | | | 540 | | | | | 545 | | | | | |

| gtg | gaa | aat | tct | gaa | tgc | atc | cag | tgc | cat | cca | gaa | tgt | ctg | ccc | cag | 1975 |
| Val | Glu | Asn | Ser | Glu | Cys | Ile | Gln | Cys | His | Pro | Glu | Cys | Leu | Pro | Gln | |
| 550 | | | | | 555 | | | | | 560 | | | | | 565 | |

| gcc | atg | aac | atc | acc | tgt | aca | ggc | agg | gga | cca | gac | aac | tgc | atc | cag | 2023 |
| Ala | Met | Asn | Ile | Thr | Cys | Thr | Gly | Arg | Gly | Pro | Asp | Asn | Cys | Ile | Gln | |
| | | | | 570 | | | | | 575 | | | | | 580 | | |

| tgt | gcc | cac | tac | att | gat | ggc | cca | cac | tgt | gtc | aag | acc | tgc | cca | gct | 2071 |
| Cys | Ala | His | Tyr | Ile | Asp | Gly | Pro | His | Cys | Val | Lys | Thr | Cys | Pro | Ala | |
| | | | 585 | | | | | 590 | | | | | 595 | | | |

| ggc | atc | atg | gga | gag | aac | aac | act | ctg | gtc | tgg | aag | tat | gca | gat | gcc | 2119 |
| Gly | Ile | Met | Gly | Glu | Asn | Asn | Thr | Leu | Val | Trp | Lys | Tyr | Ala | Asp | Ala | |
| | | | 600 | | | | | 605 | | | | | 610 | | | |

| aat | aat | gtc | tgc | cac | cta | tgc | cac | gcc | aac | tgt | acc | tat | gga | tgt | gct | 2167 |
| Asn | Asn | Val | Cys | His | Leu | Cys | His | Ala | Asn | Cys | Thr | Tyr | Gly | Cys | Ala | |
| | 615 | | | | | 620 | | | | | 625 | | | | | |

| ggg | cca | ggt | ctt | caa | gga | tgt | gaa | gtg | tgg | cca | tct | ggg | cca | aag | ata | 2215 |
| Gly | Pro | Gly | Leu | Gln | Gly | Cys | Glu | Val | Trp | Pro | Ser | Gly | Pro | Lys | Ile | |
| 630 | | | | | 635 | | | | | 640 | | | | | 645 | |

| cca | tct | att | gcc | act | ggg | att | gtg | ggt | ggc | ctc | ctc | ttc | ata | gtg | gtg | 2263 |
| Pro | Ser | Ile | Ala | Thr | Gly | Ile | Val | Gly | Gly | Leu | Leu | Phe | Ile | Val | Val | |
| | | | | 650 | | | | | 655 | | | | | 660 | | |

| gtg | gcc | ctt | ggg | att | ggc | cta | ttc | atg | cga | aga | cgt | cac | att | gtt | cga | 2311 |
| Val | Ala | Leu | Gly | Ile | Gly | Leu | Phe | Met | Arg | Arg | Arg | His | Ile | Val | Arg | |
| | | | 665 | | | | | 670 | | | | | 675 | | | |

| aag | cgt | aca | cta | cgc | cgc | ctg | ctt | caa | gag | aga | gag | ctc | gtg | gaa | cct | 2359 |
| Lys | Arg | Thr | Leu | Arg | Arg | Leu | Leu | Gln | Glu | Arg | Glu | Leu | Val | Glu | Pro | |
| | | | 680 | | | | | 685 | | | | | 690 | | | |

| ctc | aca | ccc | agc | gga | gaa | gct | cca | aac | caa | gcc | cac | ttg | agg | ata | tta | 2407 |
| Leu | Thr | Pro | Ser | Gly | Glu | Ala | Pro | Asn | Gln | Ala | His | Leu | Arg | Ile | Leu | |
| | 695 | | | | | 700 | | | | | 705 | | | | | |

| aag | gaa | aca | gaa | ttc | aaa | aag | atc | aaa | gtt | ctg | ggt | tcg | gga | gca | ttt | 2455 |
| Lys | Glu | Thr | Glu | Phe | Lys | Lys | Ile | Lys | Val | Leu | Gly | Ser | Gly | Ala | Phe | |
| 710 | | | | | 715 | | | | | 720 | | | | | 725 | |

| ggc | aca | gtg | tat | aag | ggt | ctc | tgg | atc | cca | gaa | ggt | gag | aaa | gta | aaa | 2503 |
| Gly | Thr | Val | Tyr | Lys | Gly | Leu | Trp | Ile | Pro | Glu | Gly | Glu | Lys | Val | Lys | |
| | | | | 730 | | | | | 735 | | | | | 740 | | |

| atc | ccg | gtg | gcc | atc | aag | gag | tta | aga | gaa | gcc | aca | tct | cca | aaa | gcc | 2551 |
| Ile | Pro | Val | Ala | Ile | Lys | Glu | Leu | Arg | Glu | Ala | Thr | Ser | Pro | Lys | Ala | |
| | | | | 745 | | | | | 750 | | | | | 755 | | |

| aac | aaa | gaa | atc | ctt | gac | gaa | gcc | tat | gtg | atg | gct | agt | gtg | gac | aac | 2599 |
| Asn | Lys | Glu | Ile | Leu | Asp | Glu | Ala | Tyr | Val | Met | Ala | Ser | Val | Asp | Asn | |
| | | | | 760 | | | | | 765 | | | | | 770 | | |

| cct | cat | gta | tgc | cgc | ctc | ctg | ggc | atc | tgt | ctg | acc | tcc | act | gtc | cag | 2647 |
| Pro | His | Val | Cys | Arg | Leu | Leu | Gly | Ile | Cys | Leu | Thr | Ser | Thr | Val | Gln | |
| | 775 | | | | | 780 | | | | | 785 | | | | | |

| | | |
|---|---|---|
| ctc att aca cag ctc atg ccc tac ggt tgc ctc ctg gac tac gtc cga | 2695 | |
| Leu Ile Thr Gln Leu Met Pro Tyr Gly Cys Leu Leu Asp Tyr Val Arg | | |
| 790 795 800 805 | | |
| gaa cac aag gac aac att ggc tcc cag tac ctc ctc aac tgg tgt gtg | 2743 | |
| Glu His Lys Asp Asn Ile Gly Ser Gln Tyr Leu Leu Asn Trp Cys Val | | |
| 810 815 820 | | |
| cag att gca aag ggc atg aac tac ctg gaa gat cgg cgt ttg gtg cac | 2791 | |
| Gln Ile Ala Lys Gly Met Asn Tyr Leu Glu Asp Arg Arg Leu Val His | | |
| 825 830 835 | | |
| cgt gac ttg gca gcc agg aat gta ctg gtg aag aca cca cag cat gtc | 2839 | |
| Arg Asp Leu Ala Ala Arg Asn Val Leu Val Lys Thr Pro Gln His Val | | |
| 840 845 850 | | |
| aag atc aca gat ttt ggg ctg gcc aaa ctg ctt ggt gct gaa gag aaa | 2887 | |
| Lys Ile Thr Asp Phe Gly Leu Ala Lys Leu Leu Gly Ala Glu Glu Lys | | |
| 855 860 865 | | |
| gaa tat cat gcc gag ggg ggc aaa gtg cct atc aag tgg atg gct ttg | 2935 | |
| Glu Tyr His Ala Glu Gly Gly Lys Val Pro Ile Lys Trp Met Ala Leu | | |
| 870 875 880 885 | | |
| gaa tca att tta cac cga att tat aca cac caa agt gat gtc tgg agc | 2983 | |
| Glu Ser Ile Leu His Arg Ile Tyr Thr His Gln Ser Asp Val Trp Ser | | |
| 890 895 900 | | |
| tat ggt gtc act gtg tgg gaa ctg atg acc ttt ggg tcc aag cct tat | 3031 | |
| Tyr Gly Val Thr Val Trp Glu Leu Met Thr Phe Gly Ser Lys Pro Tyr | | |
| 905 910 915 | | |
| gat gga atc cca gca agt gac atc tca tcc atc cta gag aaa gga gag | 3079 | |
| Asp Gly Ile Pro Ala Ser Asp Ile Ser Ser Ile Leu Glu Lys Gly Glu | | |
| 920 925 930 | | |
| cgc ctt cca cag cca cct atc tgc acc atc gat gtc tac atg atc atg | 3127 | |
| Arg Leu Pro Gln Pro Pro Ile Cys Thr Ile Asp Val Tyr Met Ile Met | | |
| 935 940 945 | | |
| gtc aag tgc tgg atg ata gat gct gat agc cgc cca aag ttc cga gag | 3175 | |
| Val Lys Cys Trp Met Ile Asp Ala Asp Ser Arg Pro Lys Phe Arg Glu | | |
| 950 955 960 965 | | |
| ttg att ctt gaa ttc tcc aaa atg gcc cga gac cca cag cgc tac ctt | 3223 | |
| Leu Ile Leu Glu Phe Ser Lys Met Ala Arg Asp Pro Gln Arg Tyr Leu | | |
| 970 975 980 | | |
| gtt atc cag ggg gat gaa aga atg cat ttg cca agc cct aca gac tcc | 3271 | |
| Val Ile Gln Gly Asp Glu Arg Met His Leu Pro Ser Pro Thr Asp Ser | | |
| 985 990 995 | | |
| aac ttt tac cga gcc ctg atg gat gaa gag gac atg gag gat gta | 3316 | |
| Asn Phe Tyr Arg Ala Leu Met Asp Glu Glu Asp Met Glu Asp Val | | |
| 1000 1005 1010 | | |
| gtt gat gct gat gag tat ctt atc cca cag caa ggc ttc ttc aac | 3361 | |
| Val Asp Ala Asp Glu Tyr Leu Ile Pro Gln Gln Gly Phe Phe Asn | | |
| 1015 1020 1025 | | |
| agc ccg tcc acg tcg agg act ccc ctc ttg agt tct ctg agt gca | 3406 | |
| Ser Pro Ser Thr Ser Arg Thr Pro Leu Leu Ser Ser Leu Ser Ala | | |
| 1030 1035 1040 | | |
| act agc aac aat tcc act gtg gct tgc att aat aga aat ggg agc | 3451 | |
| Thr Ser Asn Asn Ser Thr Val Ala Cys Ile Asn Arg Asn Gly Ser | | |
| 1045 1050 1055 | | |
| tgc cgt gtc aaa gaa gac gcc ttc ttg cag cgg tac agc tcc gac | 3496 | |
| Cys Arg Val Lys Glu Asp Ala Phe Leu Gln Arg Tyr Ser Ser Asp | | |
| 1060 1065 1070 | | |
| ccc aca ggt gct gta aca gag gac aac ata gat gac gca ttc ctc | 3541 | |
| Pro Thr Gly Ala Val Thr Glu Asp Asn Ile Asp Asp Ala Phe Leu | | |
| 1075 1080 1085 | | |
| cct gta cct gaa tat gta aac caa tct gtt ccc aag agg cca gca | 3586 | |
| Pro Val Pro Glu Tyr Val Asn Gln Ser Val Pro Lys Arg Pro Ala | | |
| 1090 1095 1100 | | |

| | | |
|---|---|---|
| ggc tct gtg cag aac cct gtc tat cac aat cag ccc ctg cat cca<br>Gly Ser Val Gln Asn Pro Val Tyr His Asn Gln Pro Leu His Pro<br>           1105                    1110                    1115 | 3631 | |
| gct cct gga aga gac ctg cat tat caa aat ccc cac agc aat gca<br>Ala Pro Gly Arg Asp Leu His Tyr Gln Asn Pro His Ser Asn Ala<br>           1120                    1125                    1130 | 3676 | |
| gtg ggc aac cct gag tat ctc aac act gcc cag cct acc tgt ctc<br>Val Gly Asn Pro Glu Tyr Leu Asn Thr Ala Gln Pro Thr Cys Leu<br>           1135                    1140                    1145 | 3721 | |
| agt agt ggg ttt aac agc cct gca ctc tgg atc cag aaa ggc agt<br>Ser Ser Gly Phe Asn Ser Pro Ala Leu Trp Ile Gln Lys Gly Ser<br>           1150                    1155                    1160 | 3766 | |
| cac caa atg agc cta gac aac cct gac tac cag cag gac ttc ttc<br>His Gln Met Ser Leu Asp Asn Pro Asp Tyr Gln Gln Asp Phe Phe<br>           1165                    1170                    1175 | 3811 | |
| ccc aag gaa acc aag cca aat ggc ata ttt aag ggc ccc aca gct<br>Pro Lys Glu Thr Lys Pro Asn Gly Ile Phe Lys Gly Pro Thr Ala<br>           1180                    1185                    1190 | 3856 | |
| gaa aat gca gag tac cta cgg gtg gca cct cca agc agt gag ttt<br>Glu Asn Ala Glu Tyr Leu Arg Val Ala Pro Pro Ser Ser Glu Phe<br>           1195                    1200                    1205 | 3901 | |
| att gga gca tga caagaagggg catcatacca gctataaaat gtctggactt<br>Ile Gly Ala<br>           1210 | 3953 | |
| tctagaatcc caggaccaac tatggcagca cctccacttc tggtagccat gcccacgctg | 4013 | |
| tgtcaaatgt cactcagact ggctttaaag cataactctg atgggctttg tcactgagcc | 4073 | |
| aagaagtggg cctctctcct gatgcacttt gggaagttga aggtacatca attgatcttc | 4133 | |
| gaactgtgaa gattccacaa aaaaggtatc catcgagaac attgtccatt ggaacagaag | 4193 | |
| tttgcctcat ggtgaggtac atatgggaaa aaaacagaca tatggagctt atatttaggg | 4253 | |
| aactttggga ttcttgtctt tattgatttg attgatgcac tcttgtagtc tggtacacag | 4313 | |
| agttgcctgg agccaactga ccagacagtt ggttccacca gctctgcatc aagacacttc | 4373 | |
| cgtggcaaga caactaaatg tataagaagt ccatggatgc cctgagcagg ccacacttgt | 4433 | |
| acagcattaa accatggcag atacaatagg ataagccact ttgttactta ctggggctgg | 4493 | |
| gagaagagga atgacggggt agaatttttcc ctcagacgta cttttttatat aaatatgtcc | 4553 | |
| ctggcaccta acacgcgcta gtttaccagt gttttctatt agacttcctt ctatgttttc | 4613 | |
| tgtttcattg ttttgagttg taaatatgtg ttcctgtctt catttcatga agtaaacaaa | 4673 | |
| caaacaaaaa acccagtatt aagtattatc aaagaacaac catgattcca cattcgaacc | 4733 | |
| cattcaaacc atcagtattg tgaccaaaag ccttttaacta agaaggagta accatgcaaa | 4793 | |
| aatccataga ggaatttaac ccaaaatttt agtctcagca ttgtgtctgc tgaggtgtgt | 4853 | |
| atatgagact acgaaagtga actactcttc aaatccactt tgccttcact cctctatacc | 4913 | |
| ctaaatctag tgtaaaccac acatggagga taacttttt ttttaatttt aaaagtgttt | 4973 | |
| attagatatg ttttttcttcc tggtaaactg cagccaaaca tcagttaaga gccattttg | 5033 | |
| ataaacacta tcacaatgat ctcgggatcc atcctttccg atttaccaag tgatggatag | 5093 | |
| acgtgaactc ataaacacta cccataagac aaaacaatga gtgccagaca agacatcagc | 5153 | |
| caggcaccag agcacagagc aggactgggc aatctgttgg agatatctag aaagttcaca | 5213 | |
| aaggaaacaa gattgtccac taccttgtga gatctagcag tcataaatac cagggaaatg | 5273 | |
| gaaagtgtgt ttccttacag caccaggtct tcgatcttcc taatgctgtg acccttaat | 5333 | |
| acagtttgcc atgttgtggt gacccccaac cataaaatta ttttgttgc tacttcataa | 5393 | |

-continued

```
ctgtaaattt gctactctta cagaccacaa tgtaaatatc tgatatgcta tctgatatgc    5453
aggctatctg acagaggtcg caacccgcag gttgagagcc actgccttca aggctttaat    5513
caagagagta gtgagctgag ggctttactg gtaagtcagg ggcaagtcca actcaatcat    5573
cctcacatac tggctgctcc ctcaggcctg agaatgaggc ttgcagcatc ctctggtttc    5633
ctaaccgtta tccatccctg actctcatct ctgaaaatag atgtcatcca tgaaattaag    5693
gagtgagaat attaagcagc atttatagag ctcaaaattc catgtcatca ccaggaagtg    5753
ccatgttgat cacagagaac acagaggaga catatagaca gggttttgct caaaattggg    5813
atatagaatg agcctgtcag gtacctatca ggagcggtaa tccgtgagag agaaccgttg    5873
caagccactc taactgtagc aatgaaaccc tagtattttt gtactttgaa atactttctt    5933
ataacaaaat aaagtagcaa aaaaactgtt caaaaaaaaa aaaaaaaaaa cccgaattc     5992
```

<210> SEQ ID NO 4
<211> LENGTH: 1210
<212> TYPE: PRT
<213> ORGANISM: Mus musculus

<400> SEQUENCE: 4

```
Met Arg Pro Ser Gly Thr Ala Arg Thr Thr Leu Leu Val Leu Leu Thr
1               5                   10                  15

Ala Leu Cys Ala Ala Gly Gly Ala Leu Glu Glu Lys Lys Val Cys Gln
                20                  25                  30

Gly Thr Ser Asn Arg Leu Thr Gln Leu Gly Thr Phe Glu Asp His Phe
            35                  40                  45

Leu Ser Leu Gln Arg Met Tyr Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Ala Leu
            100                 105                 110

Tyr Glu Asn Thr Tyr Ala Leu Ala Ile Leu Ser Asn Tyr Gly Thr Asn
        115                 120                 125

Arg Thr Gly Leu Arg Glu Leu Pro Met Arg Asn Leu Gln Glu Ile Leu
    130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
                165                 170                 175

Ser Met Asp Leu Gln Ser His Pro Ser Ser Cys Pro Lys Cys Asp Pro
            180                 185                 190

Ser Cys Pro Asn Gly Ser Cys Trp Gly Gly Glu Glu Asn Cys Gln
        195                 200                 205

Lys Leu Thr Lys Ile Ile Cys Ala Gln Gln Cys Ser His Arg Cys Arg
    210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
            260                 265                 270
```

-continued

```
Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Cys Asp Gly Pro Cys Arg Lys Val
                325                 330                 335

Cys Asn Gly Ile Gly Ile Gly Glu Phe Lys Asp Thr Leu Ser Ile Asn
                340                 345                 350

Ala Thr Asn Ile Lys His Phe Lys Tyr Cys Thr Ala Ile Ser Gly Asp
        355                 360                 365

Leu His Ile Leu Pro Val Ala Phe Lys Gly Asp Ser Phe Thr Arg Thr
370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Asp Asn Trp Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Gly Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Arg Asn Leu Cys Tyr Ala Asn Thr Ile Asn Trp Lys Lys Leu
465                 470                 475                 480

Phe Gly Thr Pro Asn Gln Lys Thr Lys Ile Met Asn Asn Arg Ala Glu
                485                 490                 495

Lys Asp Cys Lys Ala Val Asn His Val Cys Asn Pro Leu Cys Ser Ser
                500                 505                 510

Glu Gly Cys Trp Gly Pro Glu Pro Arg Asp Cys Val Ser Cys Gln Asn
        515                 520                 525

Val Ser Arg Gly Arg Glu Cys Val Glu Lys Cys Asn Ile Leu Glu Gly
530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Ile Met Gly Glu Asn Asn Thr Leu Val Trp
        595                 600                 605

Lys Tyr Ala Asp Ala Asn Asn Val Cys His Leu Cys His Ala Asn Cys
610                 615                 620

Thr Tyr Gly Cys Ala Gly Pro Gly Leu Gln Gly Cys Glu Val Trp Pro
625                 630                 635                 640

Ser Gly Pro Lys Ile Pro Ser Ile Ala Thr Gly Ile Val Gly Gly Leu
                645                 650                 655

Leu Phe Ile Val Val Val Ala Leu Gly Ile Gly Leu Phe Met Arg Arg
                660                 665                 670

Arg His Ile Val Arg Lys Arg Thr Leu Arg Arg Leu Leu Gln Glu Arg
        675                 680                 685

Glu Leu Val Glu Pro Leu Thr Pro Ser Gly Glu Ala Pro Asn Gln Ala
690                 695                 700
```

```
His Leu Arg Ile Leu Lys Glu Thr Glu Phe Lys Lys Ile Lys Val Leu
705                 710                 715                 720

Gly Ser Gly Ala Phe Gly Thr Val Tyr Lys Gly Leu Trp Ile Pro Glu
            725                 730                 735

Gly Glu Lys Val Lys Ile Pro Val Ala Ile Lys Glu Leu Arg Glu Ala
            740                 745                 750

Thr Ser Pro Lys Ala Asn Lys Glu Ile Leu Asp Glu Ala Tyr Val Met
            755                 760                 765

Ala Ser Val Asp Asn Pro His Val Cys Arg Leu Leu Gly Ile Cys Leu
        770                 775                 780

Thr Ser Thr Val Gln Leu Ile Thr Gln Leu Met Pro Tyr Gly Cys Leu
785                 790                 795                 800

Leu Asp Tyr Val Arg Glu His Lys Asp Asn Ile Gly Ser Gln Tyr Leu
                805                 810                 815

Leu Asn Trp Cys Val Gln Ile Ala Lys Gly Met Asn Tyr Leu Glu Asp
            820                 825                 830

Arg Arg Leu Val His Arg Asp Leu Ala Ala Arg Asn Val Leu Val Lys
            835                 840                 845

Thr Pro Gln His Val Lys Ile Thr Asp Phe Gly Leu Ala Lys Leu Leu
        850                 855                 860

Gly Ala Glu Glu Lys Glu Tyr His Ala Glu Gly Gly Lys Val Pro Ile
865                 870                 875                 880

Lys Trp Met Ala Leu Glu Ser Ile Leu His Arg Ile Tyr Thr His Gln
                885                 890                 895

Ser Asp Val Trp Ser Tyr Gly Val Thr Val Trp Glu Leu Met Thr Phe
            900                 905                 910

Gly Ser Lys Pro Tyr Asp Gly Ile Pro Ala Ser Asp Ile Ser Ser Ile
            915                 920                 925

Leu Glu Lys Gly Glu Arg Leu Pro Gln Pro Ile Cys Thr Ile Asp
930                 935                 940

Val Tyr Met Ile Met Val Lys Cys Trp Met Ile Asp Ala Asp Ser Arg
945                 950                 955                 960

Pro Lys Phe Arg Glu Leu Ile Leu Glu Phe Ser Lys Met Ala Arg Asp
                965                 970                 975

Pro Gln Arg Tyr Leu Val Ile Gln Gly Asp Glu Arg Met His Leu Pro
            980                 985                 990

Ser Pro Thr Asp Ser Asn Phe Tyr  Arg Ala Leu Met Asp  Glu Glu Asp
        995                 1000                1005

Met Glu  Asp Val Val  Asp Ala  Asp Glu Tyr Leu Ile  Pro Gln Gln
    1010                1015                1020

Gly Phe  Phe Asn Ser Pro  Ser  Thr Ser Arg Thr Pro  Leu Leu Ser
    1025                1030                1035

Ser Leu  Ser Ala Thr Ser Asn  Asn Ser Thr Val Ala  Cys Ile Asn
    1040                1045                1050

Arg Asn  Gly Ser Cys Arg Val  Lys Glu Asp Ala Phe  Leu Gln Arg
    1055                1060                1065

Tyr Ser  Ser Asp Pro Thr Gly  Ala Val Thr Glu Asp  Asn Ile Asp
    1070                1075                1080

Asp Ala  Phe Leu Pro Val Pro  Glu Tyr Val Asn Gln  Ser Val Pro
    1085                1090                1095

Lys Arg  Pro Ala Gly Ser Val  Gln Asn Pro Val Tyr  His Asn Gln
    1100                1105                1110

Pro Leu  His Pro Ala Pro Gly  Arg Asp Leu His Tyr  Gln Asn Pro
```

```
                   1115                1120                1125

His Ser  Asn Ala Val Gly Asn  Pro Glu Tyr Leu Asn  Thr Ala Gln
         1130                1135                1140

Pro Thr  Cys Leu Ser Ser Gly  Phe Asn Ser Pro Ala  Leu Trp Ile
         1145                1150                1155

Gln Lys  Gly Ser His Gln Met  Ser Leu Asp Asn Pro  Asp Tyr Gln
         1160                1165                1170

Gln Asp  Phe Phe Pro Lys Glu  Thr Lys Pro Asn Gly  Ile Phe Lys
         1175                1180                1185

Gly Pro  Thr Ala Glu Asn Ala  Glu Tyr Leu Arg Val  Ala Pro Pro
         1190                1195                1200

Ser Ser  Glu Phe Ile Gly Ala
         1205                1210

<210> SEQ ID NO 5
<211> LENGTH: 5992
<212> TYPE: DNA
<213> ORGANISM: Mus musculus
<220> FEATURE:
<221> NAME/KEY: CDS
<222> LOCATION: (281)..(3913)

<400> SEQUENCE: 5
ctcccccagt cccgacccga gctaactaga cgtctgggca gccccagcgc aacgcgcagc      60
agcctccctc ctcttcttcc cgcactgtgc gctcctcctg ggctagggcg tctggatcga     120
gtcccggagg ctaccgcctc ccagacagac gacaggtcac ctggacgcga gcctgtgtcc     180
gggtctcgtc gttgccggcg cagtcactgg gcacaaccgt gggactccgt ctgtctcgga     240
ttaatcccgg agagccagag ccaacctctc ccggtcagag atg cga ccc tca ggg      295
                                             Met Arg Pro Ser Gly
                                               1               5 acc gcg aga acc aca ctg ctg gtg ttg ctg acc gcg ctc tgc gcc gca      343
Thr Ala Arg Thr Thr Leu Leu Val Leu Leu Thr Ala Leu Cys Ala Ala
         10                  15                  20 ggt ggg gcg ttg gag gaa aag aaa gtc tgc caa ggc aca agt aac agg      391
Gly Gly Ala Leu Glu Glu Lys Lys Val Cys Gln Gly Thr Ser Asn Arg
     25                  30                  35 ctc acc caa ctg ggc act ttt gaa gac cac ttt ctg agc ctg cag agg      439
Leu Thr Gln Leu Gly Thr Phe Glu Asp His Phe Leu Ser Leu Gln Arg
 40                  45                  50 atg tac aac aac tgt gaa gtg gtc ctt ggg aac ttg gaa att acc tat      487
Met Tyr Asn Asn Cys Glu Val Val Leu Gly Asn Leu Glu Ile Thr Tyr
 55                  60                  65 gtg caa agg aat tac gac ctt tcc ttc tta aag acc atc cag gag gtg      535
Val Gln Arg Asn Tyr Asp Leu Ser Phe Leu Lys Thr Ile Gln Glu Val
 70                  75                  80                  85 gcc ggc tat gtc ctc att gcc ctc aac acc gtg gag aga atc cct ttg      583
Ala Gly Tyr Val Leu Ile Ala Leu Asn Thr Val Glu Arg Ile Pro Leu
                 90                  95                 100 gag aac ctg cag atc atc agg gga aat gct ctt tat gaa aac acc tat      631
Glu Asn Leu Gln Ile Ile Arg Gly Asn Ala Leu Tyr Glu Asn Thr Tyr
             105                 110                 115 gcc tta gcc atc ctg tcc aac tat ggg aca aac aga act ggg ctt agg      679
Ala Leu Ala Ile Leu Ser Asn Tyr Gly Thr Asn Arg Thr Gly Leu Arg
         120                 125                 130 gaa ctg ccc atg cgg aac tta cag gaa atc ctg att ggt gct gtg cga      727
Glu Leu Pro Met Arg Asn Leu Gln Glu Ile Leu Ile Gly Ala Val Arg
     135                 140                 145 ttc agc aac aac ccc atc ctc tgc aat atg gat act atc cag tgg agg      775
```

```
Phe Ser Asn Asn Pro Ile Leu Cys Asn Met Asp Thr Ile Gln Trp Arg
150                 155                 160                 165 gac atc gtc caa aac gtc ttt atg agc aac atg tca atg gac tta cag      823
Asp Ile Val Gln Asn Val Phe Met Ser Asn Met Ser Met Asp Leu Gln
            170                 175                 180 agc cat ccg agc agt tgc ccc aaa tgt gat cca agc tgt ccc aat gga      871
Ser His Pro Ser Ser Cys Pro Lys Cys Asp Pro Ser Cys Pro Asn Gly
                185                 190                 195 agc tgc tgg gga gga gga gag gag aac tgc cag aaa ttg acc aaa atc      919
Ser Cys Trp Gly Gly Gly Glu Glu Asn Cys Gln Lys Leu Thr Lys Ile
            200                 205                 210 atc tgt gcc cag caa tgt tcc cat cgc tgt cgt ggc agg tcc ccc agt      967
Ile Cys Ala Gln Gln Cys Ser His Arg Cys Arg Gly Arg Ser Pro Ser
215                 220                 225 gac tgc tgc cac aac caa tgt gct gcg ggg tgt aca ggg ccc cga gag     1015
Asp Cys Cys His Asn Gln Cys Ala Ala Gly Cys Thr Gly Pro Arg Glu
230                 235                 240                 245 agt gac tgt ctg gtc tgc caa aag ttc caa gat gag gcc aca tgc aaa     1063
Ser Asp Cys Leu Val Cys Gln Lys Phe Gln Asp Glu Ala Thr Cys Lys
                250                 255                 260 gac acc tgc cca cca ctc atg ctg tac aac ccc acc acc tat cag atg     1111
Asp Thr Cys Pro Pro Leu Met Leu Tyr Asn Pro Thr Thr Tyr Gln Met
            265                 270                 275 gat gtc aac cct gaa ggg aag tac agc ttt ggt gcc acc tgt gtg aag     1159
Asp Val Asn Pro Glu Gly Lys Tyr Ser Phe Gly Ala Thr Cys Val Lys
        280                 285                 290 aag tgc ccc cga aac tac gtg gtg aca gat cat ggc tca tgt gtc cga     1207
Lys Cys Pro Arg Asn Tyr Val Val Thr Asp His Gly Ser Cys Val Arg
295                 300                 305 gcc tgt ggg cct gac tac tac gaa gtg gaa gaa gat ggc atc cgc aag     1255
Ala Cys Gly Pro Asp Tyr Tyr Glu Val Glu Glu Asp Gly Ile Arg Lys
310                 315                 320                 325 tgt aaa aaa tgt gat ggg ccc tgt cgc aaa gtt tgt aat ggc ata ggc     1303
Cys Lys Lys Cys Asp Gly Pro Cys Arg Lys Val Cys Asn Gly Ile Gly
                330                 335                 340 att ggt gaa ttt aaa gac aca ctc tcc ata aat gct aca aac atc aaa     1351
Ile Gly Glu Phe Lys Asp Thr Leu Ser Ile Asn Ala Thr Asn Ile Lys
            345                 350                 355 cac ttc aaa tac tgc act gcc atc agc ggg gac ctt cac atc ctg cca     1399
His Phe Lys Tyr Cys Thr Ala Ile Ser Gly Asp Leu His Ile Leu Pro
        360                 365                 370 gtg gcc ttt aag ggg gat tct ttc acg cgc act cct cct cta gac cca     1447
Val Ala Phe Lys Gly Asp Ser Phe Thr Arg Thr Pro Pro Leu Asp Pro
375                 380                 385 cga gaa cta gaa att cta aaa acc gta aag gaa ata aca ggc ttt ttg     1495
Arg Glu Leu Glu Ile Leu Lys Thr Val Lys Glu Ile Thr Gly Phe Leu
390                 395                 400                 405 ctg att cag gct tgg cct gat aac tgg act gac ctc cat gct ttc gag     1543
Leu Ile Gln Ala Trp Pro Asp Asn Trp Thr Asp Leu His Ala Phe Glu
                410                 415                 420 aac cta gaa ata ata cgt ggc aga aca aag caa cat ggt cag ttt tct     1591
Asn Leu Glu Ile Ile Arg Gly Arg Thr Lys Gln His Gly Gln Phe Ser
            425                 430                 435 ttg gcg gtc gtt ggc ctg aac atc aca tca ctg ggg ctg cgt tcc ctc     1639
Leu Ala Val Val Gly Leu Asn Ile Thr Ser Leu Gly Leu Arg Ser Leu
        440                 445                 450 aag gag atc agt gat ggg gat gtg atc att tct gga aac cga aat ttg     1687
Lys Glu Ile Ser Asp Gly Asp Val Ile Ile Ser Gly Asn Arg Asn Leu
455                 460                 465 tgc tac gca aac aca ata aac tgg aaa aaa ctc ttc ggg aca ccc aat     1735
```

```
                                                    -continued

Cys Tyr Ala Asn Thr Ile Asn Trp Lys Lys Leu Phe Gly Thr Pro Asn
470             475                 480                 485 cag aaa acc aaa atc atg aac aac aga gct gag aaa gac tgc aag gcc     1783
Gln Lys Thr Lys Ile Met Asn Asn Arg Ala Glu Lys Asp Cys Lys Ala
                490                 495                 500 gtg aac cac gtc tgc aat cct tta tgc tcc tcg gaa ggc tgc tgg ggc     1831
Val Asn His Val Cys Asn Pro Leu Cys Ser Ser Glu Gly Cys Trp Gly
            505                 510                 515 cct gag ccc agg gac tgt gtc tcc tgc cag aat gtg agc aga ggc agg     1879
Pro Glu Pro Arg Asp Cys Val Ser Cys Gln Asn Val Ser Arg Gly Arg
        520                 525                 530 gag tgc gtg gag aaa tgc aac atc ctg gag ggg gaa cca agg gag ttt     1927
Glu Cys Val Glu Lys Cys Asn Ile Leu Glu Gly Glu Pro Arg Glu Phe
    535                 540                 545 gtg gaa aat tct gaa tgc atc cag tgc cat cca gaa tgt ctg ccc cag     1975
Val Glu Asn Ser Glu Cys Ile Gln Cys His Pro Glu Cys Leu Pro Gln
550                 555                 560                 565 gcc atg aac atc acc tgt aca ggc agg gga cca gac aac tgc atc cag     2023
Ala Met Asn Ile Thr Cys Thr Gly Arg Gly Pro Asp Asn Cys Ile Gln
                570                 575                 580 tgt gcc cac tac att gat ggc cca cac tgt gtc aag acc tgc cca gct     2071
Cys Ala His Tyr Ile Asp Gly Pro His Cys Val Lys Thr Cys Pro Ala
            585                 590                 595 ggc atc atg gga gag aac aac act ctg gtc tgg aag tat gca gat gcc     2119
Gly Ile Met Gly Glu Asn Asn Thr Leu Val Trp Lys Tyr Ala Asp Ala
        600                 605                 610 aat aat gtc tgc cac cta tgc cac gcc aac tgt acc tat gga tgt gct     2167
Asn Asn Val Cys His Leu Cys His Ala Asn Cys Thr Tyr Gly Cys Ala
    615                 620                 625 ggg cca ggt ctt caa gga tgt gaa gtg tgg cca tct ggg cca aag ata     2215
Gly Pro Gly Leu Gln Gly Cys Glu Val Trp Pro Ser Gly Pro Lys Ile
630                 635                 640                 645 cca tct att gcc act ggg att gtg ggt ggc ctc ctc ttc ata gtg gtg     2263
Pro Ser Ile Ala Thr Gly Ile Val Gly Gly Leu Leu Phe Ile Val Val
                650                 655                 660 gtg gcc ctt ggg att ggc cta ttc atg cga aga cgt cac att gtt cga     2311
Val Ala Leu Gly Ile Gly Leu Phe Met Arg Arg Arg His Ile Val Arg
            665                 670                 675 aag cgt aca cta cgc cgc ctg ctt caa gag aga gag ctc gtg gaa cct     2359
Lys Arg Thr Leu Arg Arg Leu Leu Gln Glu Arg Glu Leu Val Glu Pro
        680                 685                 690 ctc aca ccc agc gga gaa gct cca aac caa gcc cac ttg agg ata tta     2407
Leu Thr Pro Ser Gly Glu Ala Pro Asn Gln Ala His Leu Arg Ile Leu
    695                 700                 705 aag gaa aca gaa ttc aaa aag atc aaa gtt ctg ggt tcg gga gca ttt     2455
Lys Glu Thr Glu Phe Lys Lys Ile Lys Val Leu Gly Ser Gly Ala Phe
710                 715                 720                 725 ggc aca gtg tat aag ggt ctc tgg atc cca gaa ggt gag aaa gta aaa     2503
Gly Thr Val Tyr Lys Gly Leu Trp Ile Pro Glu Gly Glu Lys Val Lys
                730                 735                 740 atc ccg gtg gcc atc aag gag tta aga gaa gcc aca tct cca aaa gcc     2551
Ile Pro Val Ala Ile Lys Glu Leu Arg Glu Ala Thr Ser Pro Lys Ala
            745                 750                 755 aac aaa gaa atc ctt gac gaa gcc tat gtg atg gct agt gtg gac aac     2599
Asn Lys Glu Ile Leu Asp Glu Ala Tyr Val Met Ala Ser Val Asp Asn
        760                 765                 770 cct cat gta tgc cgc ctc ctg ggc atc tgt ctg acc tcc act gtc cag     2647
Pro His Val Cys Arg Leu Leu Gly Ile Cys Leu Thr Ser Thr Val Gln
    775                 780                 785 ctc att aca cag ctc atg ccc tac ggt tgc ctc ctg gac tac gtc cga     2695
```

```
                Leu Ile Thr Gln Leu Met Pro Tyr Gly Cys Leu Leu Asp Tyr Val Arg
                790             795                 800                 805 gaa cac aag gac aac att ggc tcc cag tac ctc ctc aac tgg tgt gtg         2743
Glu His Lys Asp Asn Ile Gly Ser Gln Tyr Leu Leu Asn Trp Cys Val
                    810                 815                 820 cag att gca aag ggc atg aac tac ctg gaa gat cgg cgt ttg gtg cac         2791
Gln Ile Ala Lys Gly Met Asn Tyr Leu Glu Asp Arg Arg Leu Val His
                825                 830                 835 cgt gac ttg gca gcc agg aat gta ctg gtg aag aca cca cag cat gtc         2839
Arg Asp Leu Ala Ala Arg Asn Val Leu Val Lys Thr Pro Gln His Val
            840                 845                 850 aag atc aca ggt ttt ggg ctg gcc aaa ctg ctt ggt gct gaa gag aaa         2887
Lys Ile Thr Gly Phe Gly Leu Ala Lys Leu Leu Gly Ala Glu Glu Lys
        855                 860                 865 gaa tat cat gcc gag ggg ggc aaa gtg cct atc aag tgg atg gct ttg         2935
Glu Tyr His Ala Glu Gly Gly Lys Val Pro Ile Lys Trp Met Ala Leu
870                 875                 880                 885 gaa tca att tta cac cga att tat aca cac caa agt gat gtc tgg agc         2983
Glu Ser Ile Leu His Arg Ile Tyr Thr His Gln Ser Asp Val Trp Ser
                    890                 895                 900 tat ggt gtc act gtg tgg gaa ctg atg acc ttt ggg tcc aag cct tat         3031
Tyr Gly Val Thr Val Trp Glu Leu Met Thr Phe Gly Ser Lys Pro Tyr
                905                 910                 915 gat gga atc cca gca agt gac atc tca tcc atc cta gag aaa gga gag         3079
Asp Gly Ile Pro Ala Ser Asp Ile Ser Ser Ile Leu Glu Lys Gly Glu
            920                 925                 930 cgc ctt cca cag cca cct atc tgc acc atc gat gtc tac atg atc atg         3127
Arg Leu Pro Gln Pro Pro Ile Cys Thr Ile Asp Val Tyr Met Ile Met
        935                 940                 945 gtc aag tgc tgg atg ata gat gct gat agc cgc cca aag ttc cga gag         3175
Val Lys Cys Trp Met Ile Asp Ala Asp Ser Arg Pro Lys Phe Arg Glu
950                 955                 960                 965 ttg att ctt gaa ttc tcc aaa atg gcc cga gac cca cag cgc tac ctt         3223
Leu Ile Leu Glu Phe Ser Lys Met Ala Arg Asp Pro Gln Arg Tyr Leu
                    970                 975                 980 gtt atc cag ggg gat gaa aga atg cat ttg cca agc cct aca gac tcc         3271
Val Ile Gln Gly Asp Glu Arg Met His Leu Pro Ser Pro Thr Asp Ser
                985                 990                 995 aac ttt tac cga gcc ctg atg gat gaa gag gac atg gag gat gta             3316
Asn Phe Tyr Arg Ala Leu Met Asp Glu Glu Asp Met Glu Asp Val
                    1000                1005                1010 gtt gat gct gat gag tat ctt atc cca cag caa ggc ttc ttc aac             3361
Val Asp Ala Asp Glu Tyr Leu Ile Pro Gln Gln Gly Phe Phe Asn
                1015                1020                1025 agc ccg tcc acg tcg agg act ccc ctc ttg agt tct ctg agt gca             3406
Ser Pro Ser Thr Ser Arg Thr Pro Leu Leu Ser Ser Leu Ser Ala
            1030                1035                1040 act agc aac aat tcc act gtg gct tgc att aat aga aat ggg agc             3451
Thr Ser Asn Asn Ser Thr Val Ala Cys Ile Asn Arg Asn Gly Ser
        1045                1050                1055 tgc cgt gtc aaa gaa gac gcc ttc ttg cag cgg tac agc tcc gac             3496
Cys Arg Val Lys Glu Asp Ala Phe Leu Gln Arg Tyr Ser Ser Asp
        1060                1065                1070 ccc aca ggt gct gta aca gag gac aac ata gat gac gca ttc ctc             3541
Pro Thr Gly Ala Val Thr Glu Asp Asn Ile Asp Asp Ala Phe Leu
    1075                1080                1085 cct gta cct gaa tat gta aac caa tct gtt ccc aag agg cca gca             3586
Pro Val Pro Glu Tyr Val Asn Gln Ser Val Pro Lys Arg Pro Ala
1090                1095                1100 ggc tct gtg cag aac cct gtc tat cac aat cag ccc ctg cat cca             3631
```

```
Gly Ser Val Gln Asn Pro Val Tyr His Asn Gln Pro Leu His Pro
        1105                1110                1115 gct cct gga aga gac ctg cat tat caa aat ccc cac agc aat gca      3676
Ala Pro Gly Arg Asp Leu His Tyr Gln Asn Pro His Ser Asn Ala
        1120                1125                1130 gtg ggc aac cct gag tat ctc aac act gcc cag cct acc tgt ctc      3721
Val Gly Asn Pro Glu Tyr Leu Asn Thr Ala Gln Pro Thr Cys Leu
        1135                1140                1145 agt agt ggg ttt aac agc cct gca ctc tgg atc cag aaa ggc agt      3766
Ser Ser Gly Phe Asn Ser Pro Ala Leu Trp Ile Gln Lys Gly Ser
        1150                1155                1160 cac caa atg agc cta gac aac cct gac tac cag cag gac ttc ttc      3811
His Gln Met Ser Leu Asp Asn Pro Asp Tyr Gln Gln Asp Phe Phe
        1165                1170                1175 ccc aag gaa acc aag cca aat ggc ata ttt aag ggc ccc aca gct      3856
Pro Lys Glu Thr Lys Pro Asn Gly Ile Phe Lys Gly Pro Thr Ala
        1180                1185                1190 gaa aat gca gag tac cta cgg gtg gca cct cca agc agt gag ttt      3901
Glu Asn Ala Glu Tyr Leu Arg Val Ala Pro Pro Ser Ser Glu Phe
        1195                1200                1205 att gga gca tga caagaagggg catcatacca gctataaaat gtctggactt      3953
Ile Gly Ala
        1210 tctagaatcc caggaccaac tatggcagca cctccacttc tggtagccat gcccacgctg   4013 tgtcaaatgt cactcagact ggctttaaag cataactctg atgggctttg tcactgagcc   4073 aagaagtggg cctctctcct gatgcacttt gggaagttga aggtacatca attgatcttc   4133 gaactgtgaa gattccacaa aaaaggtatc catcgagaac attgtccatt ggaacagaag   4193 tttgcctcat ggtgaggtac atatgggaaa aaacagaca tatggagctt atatttaggg    4253 aactttggga ttcttgtctt tattgatttg attgatgcac tcttgtagtc tggtacacag   4313 agttgcctgg agccaactga ccagacagtt ggttccacca gctctgcatc aagacacttc   4373 cgtggcaaga caactaaatg tataagaagt ccatggatgc cctgagcagg ccacacttgt   4433 acagcattaa accatggcag atacaatagg ataagccact tgttacttac tggggctgg    4493 gagaagagga atgacggggt agaattttcc ctcagacgta cttttttatat aaatatgtcc   4553 ctggcaccta cacgcgcta gtttaccagt gtttttctatt agacttcctt ctatgttttc    4613 tgtttcattg ttttgagttg taaatatgtg ttcctgtctt catttcatga agtaaacaaa   4673 caaacaaaaa acccagtatt aagtattatc aaagaacaac catgattcca cattcgaacc   4733 cattcaaacc atcagtattg tgaccaaaag cctttaacta agaaggagta accatgcaaa    4793 aatccataga ggaatttaac ccaaaatttt agtctcagca ttgtgtctgc tgaggtgtgt   4853 atatgagact acgaaagtga actactcttc aaatccactt tgccttcact cctctatacc    4913 ctaaatctag tgtaaaccac acatggagga taacttttt ttttaatttt aaaagtgttt    4973 attagatatg ttttcttcc tggtaaactg cagccaaaca tcagttaaga gccattttg     5033 ataaacacta tcacaatgat ctcgggatcc atcctttccg atttaccaag tgatggatag    5093 acgtgaactc ataaacacta cccataagac aaaacaatga gtgccagaca agacatcagc   5153 caggcaccag agcacagagc aggactgggc aatctgttgg agatatctag aaagttcaca    5213 aaggaaacaa gattgtccac taccttgtga gatctagcag tcataaatac cagggaaatg    5273 gaaagtgtgt ttccttacag caccaggtct tcgatcttcc taatgctgtg accctttaat   5333 acagtttgcc atgttgtggt gacccccaac cataaaatta ttttgttgc tacttcataa    5393 ctgtaaattt gctactctta cagaccacaa tgtaaatatc tgatatgcta tctgatatgc   5453
```

```
aggctatctg acagaggtcg caacccgcag gttgagagcc actgccttca aggctttaat    5513
caagagagta gtgagctgag ggctttactg gtaagtcagg ggcaagtcca actcaatcat    5573
cctcacatac tggctgctcc ctcaggcctg agaatgaggc ttgcagcatc ctctggtttc    5633
ctaaccgtta tccatccctg actctcatct ctgaaaatag atgtcatcca tgaaattaag    5693
gagtgagaat attaagcagc atttatagag ctcaaaattc catgtcatca ccaggaagtg    5753
ccatgttgat cacagagaac acagaggaga catatagaca gggttttgct caaaattggg    5813
atatagaatg agcctgtcag gtacctatca ggagcggtaa tccgtgagag agaaccgttg    5873
caagccactc taactgtagc aatgaaaccc tagtattttt gtactttgaa atactttctt    5933
ataacaaaat aaagtagcaa aaaaactgtt caaaaaaaaa aaaaaaaaaa cccgaattc     5992
```

<210> SEQ ID NO 6
<211> LENGTH: 1210
<212> TYPE: PRT
<213> ORGANISM: Mus musculus

<400> SEQUENCE: 6

```
Met Arg Pro Ser Gly Thr Ala Arg Thr Thr Leu Leu Val Leu Leu Thr
 1               5                  10                  15

Ala Leu Cys Ala Ala Gly Gly Ala Leu Glu Glu Lys Lys Val Cys Gln
             20                  25                  30

Gly Thr Ser Asn Arg Leu Thr Gln Leu Gly Thr Phe Glu Asp His Phe
         35                  40                  45

Leu Ser Leu Gln Arg Met Tyr Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Ala Leu
            100                 105                 110

Tyr Glu Asn Thr Tyr Ala Leu Ala Ile Leu Ser Asn Tyr Gly Thr Asn
        115                 120                 125

Arg Thr Gly Leu Arg Glu Leu Pro Met Arg Asn Leu Gln Glu Ile Leu
    130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
                165                 170                 175

Ser Met Asp Leu Gln Ser His Pro Ser Ser Cys Pro Lys Cys Asp Pro
            180                 185                 190

Ser Cys Pro Asn Gly Ser Cys Trp Gly Gly Glu Glu Asn Cys Gln
        195                 200                 205

Lys Leu Thr Lys Ile Ile Cys Ala Gln Gln Cys Ser His Arg Cys Arg
    210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285
```

```
Ala Thr Cys Val Lys Lys Cys Pro Arg Asn Tyr Val Thr Asp His
    290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Lys Cys Asp Gly Pro Cys Arg Lys Val
                    325                 330                 335

Cys Asn Gly Ile Gly Ile Gly Glu Phe Lys Asp Thr Leu Ser Ile Asn
                340                 345                 350

Ala Thr Asn Ile Lys His Phe Lys Tyr Cys Thr Ala Ile Ser Gly Asp
                355                 360                 365

Leu His Ile Leu Pro Val Ala Phe Lys Gly Asp Ser Phe Thr Arg Thr
    370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Asp Asn Trp Thr Asp
                    405                 410                 415

Leu His Ala Phe Glu Asn Leu Glu Ile Ile Arg Gly Arg Thr Lys Gln
                420                 425                 430

His Gly Gln Phe Ser Leu Ala Val Val Gly Leu Asn Ile Thr Ser Leu
                435                 440                 445

Gly Leu Arg Ser Leu Lys Glu Ile Ser Asp Gly Asp Val Ile Ile Ser
    450                 455                 460

Gly Asn Arg Asn Leu Cys Tyr Ala Asn Thr Ile Asn Trp Lys Lys Leu
465                 470                 475                 480

Phe Gly Thr Pro Asn Gln Lys Thr Lys Ile Met Asn Asn Arg Ala Glu
                    485                 490                 495

Lys Asp Cys Lys Ala Val Asn His Val Cys Asn Pro Leu Cys Ser Ser
                500                 505                 510

Glu Gly Cys Trp Gly Pro Glu Pro Arg Asp Cys Val Ser Cys Gln Asn
                515                 520                 525

Val Ser Arg Gly Arg Glu Cys Val Glu Lys Cys Asn Ile Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Ile Met Gly Glu Asn Asn Thr Leu Val Trp
    595                 600                 605

Lys Tyr Ala Asp Ala Asn Asn Val Cys His Leu Cys His Ala Asn Cys
    610                 615                 620

Thr Tyr Gly Cys Ala Gly Pro Gly Leu Gln Gly Cys Glu Val Trp Pro
625                 630                 635                 640

Ser Gly Pro Lys Ile Pro Ser Ile Ala Thr Gly Ile Val Gly Gly Leu
                645                 650                 655

Leu Phe Ile Val Val Ala Leu Gly Ile Gly Leu Phe Met Arg Arg
                660                 665                 670

Arg His Ile Val Arg Lys Arg Thr Leu Arg Arg Leu Leu Gln Glu Arg
                675                 680                 685

Glu Leu Val Glu Pro Leu Thr Pro Ser Gly Glu Ala Pro Asn Gln Ala
    690                 695                 700

His Leu Arg Ile Leu Lys Glu Thr Glu Phe Lys Lys Ile Lys Val Leu
```

-continued

Gly Ser Gly Ala Phe Gly Thr Val Tyr Lys Gly Leu Trp Ile Pro Glu
705                 710                 715                 720

Gly Glu Lys Val Lys Ile Pro Val Ala Ile Lys Glu Leu Arg Glu Ala
            725                 730                 735

Thr Ser Pro Lys Ala Asn Lys Glu Ile Leu Asp Glu Ala Tyr Val Met
            740                 745                 750

Ala Ser Val Asp Asn Pro His Val Cys Arg Leu Leu Gly Ile Cys Leu
        755                 760                 765

Thr Ser Thr Val Gln Leu Ile Thr Gln Leu Met Pro Tyr Gly Cys Leu
        770                 775                 780

Leu Asp Tyr Val Arg Glu His Lys Asp Asn Ile Gly Ser Gln Tyr Leu
785                 790                 795                 800

Leu Asn Trp Cys Val Gln Ile Ala Lys Gly Met Asn Tyr Leu Glu Asp
            805                 810                 815

Arg Arg Leu Val His Arg Asp Leu Ala Ala Arg Asn Val Leu Val Lys
            820                 825                 830

Thr Pro Gln His Val Lys Ile Thr Gly Phe Gly Leu Ala Lys Leu Leu
        835                 840                 845

Gly Ala Glu Glu Lys Glu Tyr His Ala Glu Gly Gly Lys Val Pro Ile
        850                 855                 860

Lys Trp Met Ala Leu Glu Ser Ile Leu His Arg Ile Tyr Thr His Gln
865                 870                 875                 880

Ser Asp Val Trp Ser Tyr Gly Val Thr Val Trp Glu Leu Met Thr Phe
            885                 890                 895

Gly Ser Lys Pro Tyr Asp Gly Ile Pro Ala Ser Asp Ile Ser Ser Ile
            900                 905                 910

Leu Glu Lys Gly Glu Arg Leu Pro Gln Pro Ile Cys Thr Ile Asp
        915                 920                 925

Val Tyr Met Ile Met Val Lys Cys Trp Met Ile Asp Ala Asp Ser Arg
        930                 935                 940

Pro Lys Phe Arg Glu Leu Ile Leu Glu Phe Ser Lys Met Ala Arg Asp
945                 950                 955                 960

Pro Gln Arg Tyr Leu Val Ile Gln Gly Asp Glu Arg Met His Leu Pro
            965                 970                 975

Ser Pro Thr Asp Ser Asn Phe Tyr Arg Ala Leu Met Asp Glu Glu Asp
            980                 985                 990

Met Glu Asp Val Val Asp Ala Asp Glu Tyr Leu Ile Pro Gln Gln
        995                 1000                1005

Gly Phe Phe Asn Ser Pro Ser Thr Ser Arg Thr Pro Leu Leu Ser
    1010                1015                1020

Ser Leu Ser Ala Thr Ser Asn Asn Ser Thr Val Ala Cys Ile Asn
    1025                1030                1035

Arg Asn Gly Ser Cys Arg Val Lys Glu Asp Ala Phe Leu Gln Arg
    1040                1045                1050

Tyr Ser Ser Asp Pro Thr Gly Ala Val Thr Glu Asp Asn Ile Asp
    1055                1060                1065

Asp Ala Phe Leu Pro Val Pro Glu Tyr Val Asn Gln Ser Val Pro
    1070                1075                1080

Lys Arg Pro Ala Gly Ser Val Gln Asn Pro Val Tyr His Asn Gln
    1085                1090                1095

Pro Leu His Pro Ala Pro Gly Arg Asp Leu His Tyr Gln Asn Pro
    1100                1105                1110
                        1115                1120                1125

-continued

```
His  Ser  Asn  Ala  Val  Gly  Asn  Pro  Glu  Tyr  Leu  Asn  Thr  Ala  Gln
     1130                1135                1140

Pro  Thr  Cys  Leu  Ser  Ser  Gly  Phe  Asn  Ser  Pro  Ala  Leu  Trp  Ile
     1145                1150                1155

Gln  Lys  Gly  Ser  His  Gln  Met  Ser  Leu  Asp  Asn  Pro  Asp  Tyr  Gln
     1160                1165                1170

Gln  Asp  Phe  Phe  Pro  Lys  Glu  Thr  Lys  Pro  Asn  Gly  Ile  Phe  Lys
     1175                1180                1185

Gly  Pro  Thr  Ala  Glu  Asn  Ala  Glu  Tyr  Leu  Arg  Val  Ala  Pro  Pro
     1190                1195                1200

Ser  Ser  Glu  Phe  Ile  Gly  Ala
     1205                1210

<210> SEQ ID NO 7
<211> LENGTH: 18
<212> TYPE: DNA
<213> ORGANISM: Mus musculus

<400> SEQUENCE: 7
gcatgtcaag atcacaga                                                    18

<210> SEQ ID NO 8
<211> LENGTH: 18
<212> TYPE: DNA
<213> ORGANISM: Mus musculus

<400> SEQUENCE: 8
gcatgtcaag atcacagg                                                    18

<210> SEQ ID NO 9
<211> LENGTH: 20
<212> TYPE: DNA
<213> ORGANISM: Mus musculus

<400> SEQUENCE: 9
tagagaatga ccctgacgag                                                  20

<210> SEQ ID NO 10
<211> LENGTH: 4624
<212> TYPE: DNA
<213> ORGANISM: Homo sapiens
<220> FEATURE:
<221> NAME/KEY: CDS
<222> LOCATION: (239)..(4006)

<400> SEQUENCE: 10
ggaggaggtg gaggaggagg gctgcttgag gaagtataag aatgaagttg tgaagctgag      60
attcccctcc attgggaccg gagaaaccag gggagccccc cgggcagccg cgcgcccctt     120 cccacgggc  cctttactgc gccgcgcgcc cggcccccac ccctcgcagc acccccgcgcc     180 ccgcgccctc ccagccgggt ccagccggag ccatggggcc ggagccgcag tgagcacc       238 atg gag ctg gcg gcc ttg tgc cgc tgg ggg ctc ctc ctc gcc ctc ttg       286
Met Glu Leu Ala Ala Leu Cys Arg Trp Gly Leu Leu Leu Ala Leu Leu
1               5                   10                  15 ccc ccc gga gcc gcg agc acc caa gtg tgc acc ggc aca gac atg aag       334
Pro Pro Gly Ala Ala Ser Thr Gln Val Cys Thr Gly Thr Asp Met Lys
                20                  25                  30 ctg cgg ctc cct gcc agt ccc gag acc cac ctg gac atg ctc cgc cac       382
Leu Arg Leu Pro Ala Ser Pro Glu Thr His Leu Asp Met Leu Arg His
            35                  40                  45 ctc tac cag ggc tgc cag gtg gtg cag gga aac ctg gaa ctc acc tac       430
Leu Tyr Gln Gly Cys Gln Val Val Gln Gly Asn Leu Glu Leu Thr Tyr
```

```
                Leu Tyr Gln Gly Cys Gln Val Val Gln Gly Asn Leu Glu Leu Thr Tyr
                     50                  55                  60 ctg ccc acc aat gcc agc ctg tcc ttc ctg cag gat atc cag gag gtg        478
Leu Pro Thr Asn Ala Ser Leu Ser Phe Leu Gln Asp Ile Gln Glu Val
 65                  70                  75                  80 cag ggc tac gtg ctc atc gct cac aac caa gtg agg cag gtc cca ctg        526
Gln Gly Tyr Val Leu Ile Ala His Asn Gln Val Arg Gln Val Pro Leu
                 85                  90                  95 cag agg ctg cgg att gtg cga ggc acc cag ctc ttt gag gac aac tat        574
Gln Arg Leu Arg Ile Val Arg Gly Thr Gln Leu Phe Glu Asp Asn Tyr
                100                 105                 110 gcc ctg gcc gtg cta gac aat gga gac ccg ctg aac aat acc acc cct        622
Ala Leu Ala Val Leu Asp Asn Gly Asp Pro Leu Asn Asn Thr Thr Pro
                    115                 120                 125 gtc aca ggg gcc tcc cca gga ggc ctg cgg gag ctg cag ctt cga agc        670
Val Thr Gly Ala Ser Pro Gly Gly Leu Arg Glu Leu Gln Leu Arg Ser
    130                 135                 140 ctc aca gag atc ttg aaa gga ggg gtc ttg atc cag cgg aac ccc cag        718
Leu Thr Glu Ile Leu Lys Gly Gly Val Leu Ile Gln Arg Asn Pro Gln
145                 150                 155                 160 ctc tgc tac cag gac acg att ttg tgg aag gac atc ttc cac aag aac        766
Leu Cys Tyr Gln Asp Thr Ile Leu Trp Lys Asp Ile Phe His Lys Asn
                    165                 170                 175 aac cag ctg gct ctc aca ctg ata gac acc aac cgc tct cgg gcc tgc        814
Asn Gln Leu Ala Leu Thr Leu Ile Asp Thr Asn Arg Ser Arg Ala Cys
                180                 185                 190 cac ccc tgt tct ccg atg tgt aag ggc tcc cgc tgc tgg gga gag agt        862
His Pro Cys Ser Pro Met Cys Lys Gly Ser Arg Cys Trp Gly Glu Ser
            195                 200                 205 tct gag gat tgt cag agc ctg acg cgc act gtc tgt gcc ggt ggc tgt        910
Ser Glu Asp Cys Gln Ser Leu Thr Arg Thr Val Cys Ala Gly Gly Cys
        210                 215                 220 gcc cgc tgc aag ggg cca ctg ccc act gac tgc tgc cat gag cag tgt        958
Ala Arg Cys Lys Gly Pro Leu Pro Thr Asp Cys Cys His Glu Gln Cys
225                 230                 235                 240 gct gcc ggc tgc acg ggc ccc aag cac tct gac tgc ctg gcc tgc ctc       1006
Ala Ala Gly Cys Thr Gly Pro Lys His Ser Asp Cys Leu Ala Cys Leu
                    245                 250                 255 cac ttc aac cac agt ggc atc tgt gag ctg cac tgc cca gcc ctg gtc       1054
His Phe Asn His Ser Gly Ile Cys Glu Leu His Cys Pro Ala Leu Val
                260                 265                 270 acc tac aac aca gac acg ttt gag tcc atg ccc aat ccc gag ggc cgg       1102
Thr Tyr Asn Thr Asp Thr Phe Glu Ser Met Pro Asn Pro Glu Gly Arg
            275                 280                 285 tat aca ttc ggc gcc agc tgt gtg act gcc tgt ccc tac aac tac ctt       1150
Tyr Thr Phe Gly Ala Ser Cys Val Thr Ala Cys Pro Tyr Asn Tyr Leu
        290                 295                 300 tct acg gac gtg gga tcc tgc acc ctc gtc tgc ccc ctg cac aac caa       1198
Ser Thr Asp Val Gly Ser Cys Thr Leu Val Cys Pro Leu His Asn Gln
305                 310                 315                 320 gag gtg aca gca gag gat gga aca cag cgg tgt gag aag tgc agc aag       1246
Glu Val Thr Ala Glu Asp Gly Thr Gln Arg Cys Glu Lys Cys Ser Lys
                    325                 330                 335 ccc tgt gcc cga gtg tgc tat ggt ctg ggc atg gag cac ttg cga gag       1294
Pro Cys Ala Arg Val Cys Tyr Gly Leu Gly Met Glu His Leu Arg Glu
                340                 345                 350 gtg agg gca gtt acc agt gcc aat atc cag gag ttt gct ggc tgc aag       1342
Val Arg Ala Val Thr Ser Ala Asn Ile Gln Glu Phe Ala Gly Cys Lys
            355                 360                 365 aag atc ttt ggg agc ctg gca ttt ctg ccg gag agc ttt gat ggg gac       1390
```

-continued

| | | | | | | | | | | | | | | |
|---|---|---|---|---|---|---|---|---|---|---|---|---|---|---|
| Lys | Ile | Phe | Gly | Ser | Leu | Ala | Phe | Leu | Pro | Glu | Ser | Phe | Asp | Gly | Asp |
| | 370 | | | | 375 | | | | 380 | | | | | | |

```
cca gcc tcc aac act gcc ccg ctc cag cca gag cag ctc caa gtg ttt          1438
Pro Ala Ser Asn Thr Ala Pro Leu Gln Pro Glu Gln Leu Gln Val Phe
385             390                 395                 400 gag act ctg gaa gag atc aca ggt tac cta tac atc tca gca tgg ccg          1486
Glu Thr Leu Glu Glu Ile Thr Gly Tyr Leu Tyr Ile Ser Ala Trp Pro
                405                 410                 415 gac agc ctg cct gac ctc agc gtc ttc cag aac ctg caa gta atc cgg          1534
Asp Ser Leu Pro Asp Leu Ser Val Phe Gln Asn Leu Gln Val Ile Arg
            420                 425                 430 gga cga att ctg cac aat ggc gcc tac tcg ctg acc ctg caa ggg ctg          1582
Gly Arg Ile Leu His Asn Gly Ala Tyr Ser Leu Thr Leu Gln Gly Leu
        435                 440                 445 ggc atc agc tgg ctg ggg ctg cgc tca ctg agg gaa ctg ggc agt gga          1630
Gly Ile Ser Trp Leu Gly Leu Arg Ser Leu Arg Glu Leu Gly Ser Gly
    450                 455                 460 ctg gcc ctc atc cac cat aac acc cac ctc tgc ttc gtg cac acg gtg          1678
Leu Ala Leu Ile His His Asn Thr His Leu Cys Phe Val His Thr Val
465                 470                 475                 480 ccc tgg gac cag ctc ttt cgg aac ccg cac caa gct ctg ctc cac act          1726
Pro Trp Asp Gln Leu Phe Arg Asn Pro His Gln Ala Leu Leu His Thr
                485                 490                 495 gcc aac cgg cca gag gac gag tgt gtg ggc gag ggc ctg gcc tgc cac          1774
Ala Asn Arg Pro Glu Asp Glu Cys Val Gly Glu Gly Leu Ala Cys His
            500                 505                 510 cag ctg tgc gcc cga ggg cac tgc tgg ggt cca ggg ccc acc cag tgt          1822
Gln Leu Cys Ala Arg Gly His Cys Trp Gly Pro Gly Pro Thr Gln Cys
        515                 520                 525 gtc aac tgc agc cag ttc ctt cgg ggc cag gag tgc gtg gag gaa tgc          1870
Val Asn Cys Ser Gln Phe Leu Arg Gly Gln Glu Cys Val Glu Glu Cys
    530                 535                 540 cga gta ctg cag ggg ctc ccc agg gag tat gtg aat gcc agg cac tgt          1918
Arg Val Leu Gln Gly Leu Pro Arg Glu Tyr Val Asn Ala Arg His Cys
545                 550                 555                 560 ttg ccg tgc cac cct gag tgt cag ccc cag aat ggc tca gtg acc tgt          1966
Leu Pro Cys His Pro Glu Cys Gln Pro Gln Asn Gly Ser Val Thr Cys
                565                 570                 575 ttt gga ccg gag gct gac cag tgt gtg gcc tgt gcc cac tat aag gac          2014
Phe Gly Pro Glu Ala Asp Gln Cys Val Ala Cys Ala His Tyr Lys Asp
            580                 585                 590 cct ccc ttc tgc gtg gcc cgc tgc ccc agc ggt gtg aaa cct gac ctc          2062
Pro Pro Phe Cys Val Ala Arg Cys Pro Ser Gly Val Lys Pro Asp Leu
        595                 600                 605 tcc tac atg ccc atc tgg aag ttt cca gat gag gag ggc gca tgc cag          2110
Ser Tyr Met Pro Ile Trp Lys Phe Pro Asp Glu Glu Gly Ala Cys Gln
    610                 615                 620 cct tgc ccc atc aac tgc acc cac tcc tgt gtg gac ctg gat gac aag          2158
Pro Cys Pro Ile Asn Cys Thr His Ser Cys Val Asp Leu Asp Asp Lys
625                 630                 635                 640 ggc tgc ccc gcc gag cag aga gcc agc cct ctg acg tcc atc atc tct          2206
Gly Cys Pro Ala Glu Gln Arg Ala Ser Pro Leu Thr Ser Ile Ile Ser
                645                 650                 655 gcg gtg gtt ggc att ctg ctg gtc gtg gtc ttg ggg gtg gtc ttt ggg          2254
Ala Val Val Gly Ile Leu Leu Val Val Val Leu Gly Val Val Phe Gly
            660                 665                 670 atc ctc atc aag cga cgg cag cag aag atc cgg aag tac acg atg cgg          2302
Ile Leu Ile Lys Arg Arg Gln Gln Lys Ile Arg Lys Tyr Thr Met Arg
        675                 680                 685 aga ctg ctg cag gaa acg gag ctg gtg gag ccg ctg aca cct agc gga          2350
```

```
                Arg Leu Leu Gln Glu Thr Glu Leu Val Glu Pro Leu Thr Pro Ser Gly
                690                 695                 700 gcg atg ccc aac cag gcg cag atg cgg atc ctg aaa gag acg gag ctg           2398
Ala Met Pro Asn Gln Ala Gln Met Arg Ile Leu Lys Glu Thr Glu Leu
705                 710                 715                 720 agg aag gtg aag gtg ctt gga tct ggc gct ttt ggc aca gtc tac aag           2446
Arg Lys Val Lys Val Leu Gly Ser Gly Ala Phe Gly Thr Val Tyr Lys
                725                 730                 735 ggc atc tgg atc cct gat ggg gag aat gtg aaa att cca gtg gcc atc           2494
Gly Ile Trp Ile Pro Asp Gly Glu Asn Val Lys Ile Pro Val Ala Ile
            740                 745                 750 aaa gtg ttg agg gaa aac aca tcc ccc aaa gcc aac aaa gaa atc tta           2542
Lys Val Leu Arg Glu Asn Thr Ser Pro Lys Ala Asn Lys Glu Ile Leu
        755                 760                 765 gac gaa gca tac gtg atg gct ggt gtg ggc tcc cca tat gtc tcc cgc           2590
Asp Glu Ala Tyr Val Met Ala Gly Val Gly Ser Pro Tyr Val Ser Arg
770                 775                 780 ctt ctg ggc atc tgc ctg aca tcc acg gtg cag ctg gtg aca cag ctt           2638
Leu Leu Gly Ile Cys Leu Thr Ser Thr Val Gln Leu Val Thr Gln Leu
785                 790                 795                 800 atg ccc tat ggc tgc ctc tta gac cat gtc cgg gaa aac cgc gga cgc           2686
Met Pro Tyr Gly Cys Leu Leu Asp His Val Arg Glu Asn Arg Gly Arg
                805                 810                 815 ctg ggc tcc cag gac ctg ctg aac tgg tgt atg cag att gcc aag ggg           2734
Leu Gly Ser Gln Asp Leu Leu Asn Trp Cys Met Gln Ile Ala Lys Gly
                820                 825                 830 atg agc tac ctg gag gat gtg cgg ctc gta cac agg gac ttg gcc gct           2782
Met Ser Tyr Leu Glu Asp Val Arg Leu Val His Arg Asp Leu Ala Ala
            835                 840                 845 cgg aac gtg ctg gtc aag agt ccc aac cat gtc aaa att aca gac ttc           2830
Arg Asn Val Leu Val Lys Ser Pro Asn His Val Lys Ile Thr Asp Phe
        850                 855                 860 ggg ctg gct cgg ctg ctg gac att gac gag aca gag tac cat gca gat           2878
Gly Leu Ala Arg Leu Leu Asp Ile Asp Glu Thr Glu Tyr His Ala Asp
865                 870                 875                 880 ggg ggc aag gtg ccc atc aag tgg atg gcg ctg gag tcc att ctc cgc           2926
Gly Gly Lys Val Pro Ile Lys Trp Met Ala Leu Glu Ser Ile Leu Arg
                885                 890                 895 cgg cgg ttc acc cac cag agt gat gtg tgg agt tat ggt gtg act gtg           2974
Arg Arg Phe Thr His Gln Ser Asp Val Trp Ser Tyr Gly Val Thr Val
                900                 905                 910 tgg gag ctg atg act ttt ggg gcc aaa cct tac gat ggg atc cca gcc           3022
Trp Glu Leu Met Thr Phe Gly Ala Lys Pro Tyr Asp Gly Ile Pro Ala
            915                 920                 925 cgg gag atc cct gac ctg ctg gaa aag ggg gag cgg ctg ccc cag ccc           3070
Arg Glu Ile Pro Asp Leu Leu Glu Lys Gly Glu Arg Leu Pro Gln Pro
        930                 935                 940 ccc atc tgc acc att gat gtc tac atg atc atg gtc aaa tgt tgg atg           3118
Pro Ile Cys Thr Ile Asp Val Tyr Met Ile Met Val Lys Cys Trp Met
945                 950                 955                 960 att gac tct gaa tgt cgg cca aga ttc cgg gag ttg gtg tct gaa ttc           3166
Ile Asp Ser Glu Cys Arg Pro Arg Phe Arg Glu Leu Val Ser Glu Phe
                965                 970                 975 tcc cgc atg gcc agg gac ccc cag cgc ttt gtg gtc atc cag aat gag           3214
Ser Arg Met Ala Arg Asp Pro Gln Arg Phe Val Val Ile Gln Asn Glu
                980                 985                 990 gac ttg ggc cca gcc agt ccc ttg  gac agc acc ttc tac  cgc tca ctg         3262
Asp Leu Gly Pro Ala Ser Pro Leu  Asp Ser Thr Phe Tyr  Arg Ser Leu
            995                 1000                1005 ctg gag  gac gat gac atg ggg  gac ctg gtg gat gct  gag gag tat           3307
```

```
Leu Glu Asp Asp Asp Met Gly Asp Leu Val Asp Ala Glu Glu Tyr
    1010            1015                1020 ctg gta ccc cag cag ggc ttc ttc tgt cca gac cct gcc ccg ggc    3352
Leu Val Pro Gln Gln Gly Phe Phe Cys Pro Asp Pro Ala Pro Gly
    1025            1030                1035 gct ggg ggc atg gtc cac cac agg cac cgc agc tca tct acc agg    3397
Ala Gly Gly Met Val His His Arg His Arg Ser Ser Ser Thr Arg
    1040            1045                1050 agt ggc ggt ggg gac ctg aca cta ggg ctg gag ccc tct gaa gag    3442
Ser Gly Gly Gly Asp Leu Thr Leu Gly Leu Glu Pro Ser Glu Glu
    1055            1060                1065 gag gcc ccc agg tct cca ctg gca ccc tcc gaa ggg gct ggc tcc    3487
Glu Ala Pro Arg Ser Pro Leu Ala Pro Ser Glu Gly Ala Gly Ser
    1070            1075                1080 gat gta ttt gat ggt gac ctg gga atg ggg gca gcc aag ggg ctg    3532
Asp Val Phe Asp Gly Asp Leu Gly Met Gly Ala Ala Lys Gly Leu
    1085            1090                1095 caa agc ctc ccc aca cat gac ccc agc cct cta cag cgg tac agt    3577
Gln Ser Leu Pro Thr His Asp Pro Ser Pro Leu Gln Arg Tyr Ser
    1100            1105                1110 gag gac ccc aca gta ccc ctg ccc tct gag act gat ggc tac gtt    3622
Glu Asp Pro Thr Val Pro Leu Pro Ser Glu Thr Asp Gly Tyr Val
    1115            1120                1125 gcc ccc ctg acc tgc agc ccc cag cct gaa tat gtg aac cag cca    3667
Ala Pro Leu Thr Cys Ser Pro Gln Pro Glu Tyr Val Asn Gln Pro
    1130            1135                1140 gat gtt cgg ccc cag ccc cct tcg ccc cga gag ggc cct ctg cct    3712
Asp Val Arg Pro Gln Pro Pro Ser Pro Arg Glu Gly Pro Leu Pro
    1145            1150                1155 gct gcc cga cct gct ggt gcc act ctg gaa agg ccc aag act ctc    3757
Ala Ala Arg Pro Ala Gly Ala Thr Leu Glu Arg Pro Lys Thr Leu
    1160            1165                1170 tcc cca ggg aag aat ggg gtc gtc aaa gac gtt ttt gcc ttt ggg    3802
Ser Pro Gly Lys Asn Gly Val Val Lys Asp Val Phe Ala Phe Gly
    1175            1180                1185 ggt gcc gtg gag aac ccc gag tac ttg aca ccc cag gga gga gct    3847
Gly Ala Val Glu Asn Pro Glu Tyr Leu Thr Pro Gln Gly Gly Ala
    1190            1195                1200 gcc cct cag ccc cac cct cct cct gcc ttc agc cca gcc ttc gac    3892
Ala Pro Gln Pro His Pro Pro Pro Ala Phe Ser Pro Ala Phe Asp
    1205            1210                1215 aac ctc tat tac tgg gac cag gac cca cca gag cgg ggg gct cca    3937
Asn Leu Tyr Tyr Trp Asp Gln Asp Pro Pro Glu Arg Gly Ala Pro
    1220            1225                1230 ccc agc acc ttc aaa ggg aca cct acg gca gag aac cca gag tac    3982
Pro Ser Thr Phe Lys Gly Thr Pro Thr Ala Glu Asn Pro Glu Tyr
    1235            1240                1245 ctg ggt ctg gac gtg cca gtg tga accagaaggc caagtccgca           4026
Leu Gly Leu Asp Val Pro Val
    1250            1255 gaagccctga tgtgtcctca gggagcaggg aaggcctgac ttctgctggc atcaagaggt    4086
gggagggccc tccgaccact tccagggGaa cctgccatgc aggaacctg tcctaaggaa     4146 ccttccttcc tgcttgagtt cccagatggc tggagggggt ccagcctcgt tggaagagga    4206
acagcactgg ggagtctttg tggattctga ggccctgccc aatgagactc tagggtccag    4266
tggatgccac agcccagctt ggcccttttcc ttccagatcc tgggtactga aagccttagg   4326
gaagctggcc tgagagggga agcggcccta agggagtgtc taagaacaaa agcgaccct    4386 tcagagactg tccctgaaac ctagtactgc ccccatgag gaaggaacag caatggtgtc    4446
```

```
agtatccagg ctttgtacag agtgcttttc tgtttagttt ttactttttt tgttttgttt    4506
ttttaaagat gaaataaaga cccagggggga gaatgggtgt tgtatgggga ggcaagtgtg    4566
gggggtcctt ctccacaccc actttgtcca tttgcaaata tattttggaa aacagcta      4624
```

<210> SEQ ID NO 11
<211> LENGTH: 1255
<212> TYPE: PRT
<213> ORGANISM: Homo sapiens

<400> SEQUENCE: 11

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350
```

-continued

```
Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
    370                 375                 380

Pro Ala Ser Asn Thr Ala Pro Leu Gln Pro Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
        500                 505                 510

Gln Leu Cys Ala Arg Gly His Cys Trp Gly Pro Gly Pro Thr Gln Cys
    515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
    610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
        660                 665                 670

Ile Leu Ile Lys Arg Arg Gln Gln Lys Ile Arg Lys Tyr Thr Met Arg
    675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
```

-continued

```
            770             775             780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
                820                 825                 830
Met Ser Tyr Leu Glu Asp Val Arg Leu Val His Arg Asp Leu Ala Ala
                835                 840                 845
Arg Asn Val Leu Val Lys Ser Pro Asn His Val Lys Ile Thr Asp Phe
            850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
                900                 905                 910
Trp Glu Leu Met Thr Phe Gly Ala Lys Pro Tyr Asp Gly Ile Pro Ala
                915                 920                 925
Arg Glu Ile Pro Asp Leu Leu Glu Lys Gly Glu Arg Leu Pro Gln Pro
            930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
                980                 985                 990
Asp Leu Gly Pro Ala Ser Pro Leu Asp Ser Thr Phe Tyr Arg Ser Leu
            995                 1000                1005
Leu Glu Asp Asp Asp Met Gly Asp Leu Val Asp Ala Glu Glu Tyr
       1010                1015                1020
Leu Val Pro Gln Gln Gly Phe Phe Cys Pro Asp Pro Ala Pro Gly
       1025                1030                1035
Ala Gly Gly Met Val His His Arg His Arg Ser Ser Ser Thr Arg
       1040                1045                1050
Ser Gly Gly Gly Asp Leu Thr Leu Gly Leu Glu Pro Ser Glu Glu
       1055                1060                1065
Glu Ala Pro Arg Ser Pro Leu Ala Pro Ser Glu Gly Ala Gly Ser
       1070                1075                1080
Asp Val Phe Asp Gly Asp Leu Gly Met Gly Ala Ala Lys Gly Leu
       1085                1090                1095
Gln Ser Leu Pro Thr His Asp Pro Ser Pro Leu Gln Arg Tyr Ser
       1100                1105                1110
Glu Asp Pro Thr Val Pro Leu Pro Ser Glu Thr Asp Gly Tyr Val
       1115                1120                1125
Ala Pro Leu Thr Cys Ser Pro Gln Pro Glu Tyr Val Asn Gln Pro
       1130                1135                1140
Asp Val Arg Pro Gln Pro Pro Ser Pro Arg Glu Gly Pro Leu Pro
       1145                1150                1155
Ala Ala Arg Pro Ala Gly Ala Thr Leu Glu Arg Pro Lys Thr Leu
       1160                1165                1170
Ser Pro Gly Lys Asn Gly Val Val Lys Asp Val Phe Ala Phe Gly
       1175                1180                1185
```

```
Gly Ala  Val Glu Asn Pro Glu  Tyr Leu Thr Pro Gln  Gly Gly Ala
    1190         1195              1200

Ala Pro  Gln Pro His Pro Pro  Ala Phe Ser Pro Ala  Phe Asp
1205              1210              1215

Asn Leu  Tyr Tyr Trp Asp Gln  Asp Pro Pro Glu Arg  Gly Ala Pro
    1220         1225              1230

Pro Ser  Thr Phe Lys Gly Thr  Pro Thr Ala Glu Asn  Pro Glu Tyr
    1235         1240              1245

Leu Gly  Leu Asp Val Pro Val
    1250         1255

<210> SEQ ID NO 12
<211> LENGTH: 4998
<212> TYPE: DNA
<213> ORGANISM: Mus musculus
<220> FEATURE:
<221> NAME/KEY: CDS
<222> LOCATION: (180)..(3950)

<400> SEQUENCE: 12
cgaggaagtg  cggcgtgaag  ttgtggagct  gagattgccc  gccgctgggg  acccggagcc      60
caggagcgcc  ccttcccagg  cggcccctt c  cggcgccgcg  cctgtgcctg  ccctcgccgc    120
gccccgcgcc  cgcagcctgg  tccagcctga  gccatgggc  cggagccgca  gtgatcatc     179 atg gag ctg gcg gcc tgg tgc cgt tgg ggg ttc ctc ctc gcc ctc ctg         227
Met Glu Leu Ala Ala Trp Cys Arg Trp Gly Phe Leu Leu Ala Leu Leu
1               5                   10                  15 tcc ccc gga gcc gcg ggt acc caa gtg tgt acc ggt acc gac atg aag         275
Ser Pro Gly Ala Ala Gly Thr Gln Val Cys Thr Gly Thr Asp Met Lys
            20                  25                  30 ttg cga ctc cct gcc agt cct gag acc cac ctg gac atg ctt cgc cac         323
Leu Arg Leu Pro Ala Ser Pro Glu Thr His Leu Asp Met Leu Arg His
        35                  40                  45 ctc tac cag ggc tgt cag gtg gtg cag ggc aat ttg gag ctt acc tac         371
Leu Tyr Gln Gly Cys Gln Val Val Gln Gly Asn Leu Glu Leu Thr Tyr
    50                  55                  60 ctg ccc gcc aat gcc agc ctc tca ttc ctg cag gac atc cag gaa gtc         419
Leu Pro Ala Asn Ala Ser Leu Ser Phe Leu Gln Asp Ile Gln Glu Val
65                  70                  75                  80 cag gga tac atg ctc atc gct cac aac cga gtg aaa cac gtc cca ctg         467
Gln Gly Tyr Met Leu Ile Ala His Asn Arg Val Lys His Val Pro Leu
                85                  90                  95 cag agg ttg cgc atc gtg aga ggg act cag ctc ttt gag gac aag tat         515
Gln Arg Leu Arg Ile Val Arg Gly Thr Gln Leu Phe Glu Asp Lys Tyr
            100                 105                 110 gcc ctg gct gtg cta gac aac cga gac cct ttg gac aac gtc acc acc         563
Ala Leu Ala Val Leu Asp Asn Arg Asp Pro Leu Asp Asn Val Thr Thr
        115                 120                 125 gcc gcc cca ggc aga acc cca gaa ggg ctg cgg gag ctg cag ctt cga         611
Ala Ala Pro Gly Arg Thr Pro Glu Gly Leu Arg Glu Leu Gln Leu Arg
    130                 135                 140 agt ctc aca gag atc ttg aag gga gga gtt ttg atc cgt ggg aac cct         659
Ser Leu Thr Glu Ile Leu Lys Gly Gly Val Leu Ile Arg Gly Asn Pro
145                 150                 155                 160 cag ctc tgc tac cag gac atg gtt ttg tgg aag gat gtc ctc cgt aag         707
Gln Leu Cys Tyr Gln Asp Met Val Leu Trp Lys Asp Val Leu Arg Lys
                165                 170                 175 aat aac cag ctg gct cct gtc gac atg gac acc aat cgt tcc cgg gcc         755
Asn Asn Gln Leu Ala Pro Val Asp Met Asp Thr Asn Arg Ser Arg Ala
            180                 185                 190
```

```
tgt cca cct tgt gcc cca acc tgc aaa gac aat cac tgt tgg ggt gag    803
Cys Pro Pro Cys Ala Pro Thr Cys Lys Asp Asn His Cys Trp Gly Glu
        195                 200                 205 agt cct gaa gac tgt cag atc ttg act ggc acc atc tgt act agt ggc    851
Ser Pro Glu Asp Cys Gln Ile Leu Thr Gly Thr Ile Cys Thr Ser Gly
    210                 215                 220 tgt gcc cgg tgc aag ggc cgg ctg ccc act gac tgt tgc cat gag cag    899
Cys Ala Arg Cys Lys Gly Arg Leu Pro Thr Asp Cys Cys His Glu Gln
225                 230                 235                 240 tgt gct gca ggc tgc acg ggt ccc aag cat tct gac tgc ctg gcc tgc    947
Cys Ala Ala Gly Cys Thr Gly Pro Lys His Ser Asp Cys Leu Ala Cys
                245                 250                 255 ctc cac ttc aat cat agt ggt atc tgt gag ctg cac tgc ccg gcc ctc    995
Leu His Phe Asn His Ser Gly Ile Cys Glu Leu His Cys Pro Ala Leu
            260                 265                 270 atc acc tac aac aca gac acc ttc gag tcc atg ctc aac cct gag ggt   1043
Ile Thr Tyr Asn Thr Asp Thr Phe Glu Ser Met Leu Asn Pro Glu Gly
        275                 280                 285 cgc tac acc ttt ggt gcc agc tgt gtg acc acc tgc ccc tac aac tac   1091
Arg Tyr Thr Phe Gly Ala Ser Cys Val Thr Thr Cys Pro Tyr Asn Tyr
    290                 295                 300 ctc tcc acg gaa gtg gga tcc tgc act ctg gtc tgt ccc ccg aac aac   1139
Leu Ser Thr Glu Val Gly Ser Cys Thr Leu Val Cys Pro Pro Asn Asn
305                 310                 315                 320 caa gag gtc aca gct gag gac gga aca cag cgg tgt gag aaa tgc agc   1187
Gln Glu Val Thr Ala Glu Asp Gly Thr Gln Arg Cys Glu Lys Cys Ser
                325                 330                 335 aag ccc tgt gct gga gta tgc tat ggt ctg ggc atg gag cac ctc cga   1235
Lys Pro Cys Ala Gly Val Cys Tyr Gly Leu Gly Met Glu His Leu Arg
            340                 345                 350 ggg gcg agg gcc atc acc agt gac aat atc cag gag ttt gct ggc tgc   1283
Gly Ala Arg Ala Ile Thr Ser Asp Asn Ile Gln Glu Phe Ala Gly Cys
        355                 360                 365 aag aag atc ttt ggg agc ctg gca ttt ttg ccg gag agc ttt gat ggg   1331
Lys Lys Ile Phe Gly Ser Leu Ala Phe Leu Pro Glu Ser Phe Asp Gly
    370                 375                 380 aac ccc tcc tcc ggc gtt gcc cca ctg aag cca gag cat ctc caa gtg   1379
Asn Pro Ser Ser Gly Val Ala Pro Leu Lys Pro Glu His Leu Gln Val
385                 390                 395                 400 ttc gaa acc ctg gag gag atc aca ggt tac cta tac att tca gca tgg   1427
Phe Glu Thr Leu Glu Glu Ile Thr Gly Tyr Leu Tyr Ile Ser Ala Trp
                405                 410                 415 cca gag agc ttc caa gac ctc agt gtc ttc cag aac ctt cgg gtc att   1475
Pro Glu Ser Phe Gln Asp Leu Ser Val Phe Gln Asn Leu Arg Val Ile
            420                 425                 430 cgg gga cgg att ctc cat gat ggt gct tac tca ttg acg ttg caa ggc   1523
Arg Gly Arg Ile Leu His Asp Gly Ala Tyr Ser Leu Thr Leu Gln Gly
        435                 440                 445 ctg ggg att cac tca ctg ggg cta cgc tca ctg cgg gag ctg ggc agt   1571
Leu Gly Ile His Ser Leu Gly Leu Arg Ser Leu Arg Glu Leu Gly Ser
    450                 455                 460 gga ttg gct ctc att cac cgc aac acc cat ctc tgc ttt gta aac act   1619
Gly Leu Ala Leu Ile His Arg Asn Thr His Leu Cys Phe Val Asn Thr
465                 470                 475                 480 gta cct tgg gac cag ctc ttc cgg aac ccg cac cag gcc cta ctc cac   1667
Val Pro Trp Asp Gln Leu Phe Arg Asn Pro His Gln Ala Leu Leu His
                485                 490                 495 agt ggg aac cgg cca gaa gag gca tgt ggt ctt gag ggc ttg gtc tgt   1715
Ser Gly Asn Arg Pro Glu Glu Ala Cys Gly Leu Glu Gly Leu Val Cys
            500                 505                 510
```

```
aac tca ctg tgt gcc cgt ggg cac tgc tgg ggg cca ggg ccc acc cag      1763
Asn Ser Leu Cys Ala Arg Gly His Cys Trp Gly Pro Gly Pro Thr Gln
        515                 520                 525 tgt gtc aac tgc agt cag ttc ctc cgg ggc cag gag tgt gtg gag gag      1811
Cys Val Asn Cys Ser Gln Phe Leu Arg Gly Gln Glu Cys Val Glu Glu
530                 535                 540 tgc cga gta tgg aag ggg ctc ccc agg gag tat gtg agg ggc aag cac      1859
Cys Arg Val Trp Lys Gly Leu Pro Arg Glu Tyr Val Arg Gly Lys His
545                 550                 555                 560 tgt ctg cca tgc cac ccc gag tgt cag cct caa aac agc tcg gag acc      1907
Cys Leu Pro Cys His Pro Glu Cys Gln Pro Gln Asn Ser Ser Glu Thr
                565                 570                 575 tgc tat gga tcg gag gct gac cag tgt gag gct tgt gcc cac tac aag      1955
Cys Tyr Gly Ser Glu Ala Asp Gln Cys Glu Ala Cys Ala His Tyr Lys
                580                 585                 590 gac tca tct tcc tgt gtg gct cgc tgc ccc agt ggt gtg aag cca gac      2003
Asp Ser Ser Ser Cys Val Ala Arg Cys Pro Ser Gly Val Lys Pro Asp
                595                 600                 605 ctc tcc tac atg cct atc tgg aag tac ccg gat gag gag ggc ata tgt      2051
Leu Ser Tyr Met Pro Ile Trp Lys Tyr Pro Asp Glu Glu Gly Ile Cys
    610                 615                 620 cag cca tgc ccc atc aac tgc acc cac tca tgt gtg gac ctg gac gaa      2099
Gln Pro Cys Pro Ile Asn Cys Thr His Ser Cys Val Asp Leu Asp Glu
625                 630                 635                 640 cga ggc tgc cca gca gag cag aga gcc agc cca gtg aca ttc atc att      2147
Arg Gly Cys Pro Ala Glu Gln Arg Ala Ser Pro Val Thr Phe Ile Ile
                645                 650                 655 gca act gtg gtg ggc gtc ctg ttg ttc ctg atc ata gtg gtg gtc att      2195
Ala Thr Val Val Gly Val Leu Leu Phe Leu Ile Ile Val Val Val Ile
                660                 665                 670 gga atc cta atc aaa cga agg cga cag aag atc cgg aag tat acc atg      2243
Gly Ile Leu Ile Lys Arg Arg Arg Gln Lys Ile Arg Lys Tyr Thr Met
            675                 680                 685 cgt agg ctg ctg cag gag acc gag ctg gtg gag ccg ctg acg ccc agt      2291
Arg Arg Leu Leu Gln Glu Thr Glu Leu Val Glu Pro Leu Thr Pro Ser
        690                 695                 700 gga gct gtg ccc aac cag gct cag atg cgg atc cta aag gag aca gag      2339
Gly Ala Val Pro Asn Gln Ala Gln Met Arg Ile Leu Lys Glu Thr Glu
705                 710                 715                 720 cta agg aag ctg aag gtg ctt ggg tca gga gcc ttc ggc act gtc tac      2387
Leu Arg Lys Leu Lys Val Leu Gly Ser Gly Ala Phe Gly Thr Val Tyr
                725                 730                 735 aag ggc atc tgg atc cca gat ggg gag aac gtg aaa atc ccc gtg gcc      2435
Lys Gly Ile Trp Ile Pro Asp Gly Glu Asn Val Lys Ile Pro Val Ala
                740                 745                 750 atc aag gtg ttg agg gaa aac aca tct cct aaa gct aac aaa gaa atc      2483
Ile Lys Val Leu Arg Glu Asn Thr Ser Pro Lys Ala Asn Lys Glu Ile
                755                 760                 765 cta gat gaa gcg tac gtc atg gct ggt gtg ggt tct cca tat gtg tcc      2531
Leu Asp Glu Ala Tyr Val Met Ala Gly Val Gly Ser Pro Tyr Val Ser
    770                 775                 780 cgc ctc ctg ggc atc tgc ctg aca tcc aca gtg cag ctg gtg aca cag      2579
Arg Leu Leu Gly Ile Cys Leu Thr Ser Thr Val Gln Leu Val Thr Gln
785                 790                 795                 800 ctt atg ccc tat ggc tgc ctt ctg gac cat gtc cga gaa cac cga ggt      2627
Leu Met Pro Tyr Gly Cys Leu Leu Asp His Val Arg Glu His Arg Gly
                805                 810                 815 cgc tta ggc tcc cag gac ctg ctc aac tgg tgt gtt cag att gcc aag      2675
Arg Leu Gly Ser Gln Asp Leu Leu Asn Trp Cys Val Gln Ile Ala Lys
                820                 825                 830
```

```
ggg atg agc tac ctg gag gaa gtt cgg ctt gtt cac agg gac cta gct       2723
Gly Met Ser Tyr Leu Glu Glu Val Arg Leu Val His Arg Asp Leu Ala
        835                 840                 845 gcc cga aac gtg cta gtc aag agt ccc aac cac gtc aag att acc gac       2771
Ala Arg Asn Val Leu Val Lys Ser Pro Asn His Val Lys Ile Thr Asp
850                 855                 860 ttc ggg ctg gca cgg ctg ctg gac att gat gag act gaa tac cat gca       2819
Phe Gly Leu Ala Arg Leu Leu Asp Ile Asp Glu Thr Glu Tyr His Ala
865                 870                 875                 880 gat ggg ggc aag gtg ccc atc aag tgg atg gca ttg gaa tct att ctc       2867
Asp Gly Gly Lys Val Pro Ile Lys Trp Met Ala Leu Glu Ser Ile Leu
                885                 890                 895 aga cgc cgg ttc acc cat cag agt gat gtg tgg agc tat ggt gtg act       2915
Arg Arg Arg Phe Thr His Gln Ser Asp Val Trp Ser Tyr Gly Val Thr
            900                 905                 910 gtg tgg gag ctg atg acc ttt ggg gcc aaa cct tac gat ggg atc cca       2963
Val Trp Glu Leu Met Thr Phe Gly Ala Lys Pro Tyr Asp Gly Ile Pro
915                 920                 925 gct cgg gag atc cct gat ttg ctg gag aag gga gaa cgc cta cct cag       3011
Ala Arg Glu Ile Pro Asp Leu Leu Glu Lys Gly Glu Arg Leu Pro Gln
930                 935                 940 cct cca atc tgc acc atc gac gtc tac atg atc atg gtc aaa tgt tgg       3059
Pro Pro Ile Cys Thr Ile Asp Val Tyr Met Ile Met Val Lys Cys Trp
945                 950                 955                 960 atg att gac tcc gaa tgt cgc ccg aga ttc cgg gag ttg gta tca gaa       3107
Met Ile Asp Ser Glu Cys Arg Pro Arg Phe Arg Glu Leu Val Ser Glu
                965                 970                 975 ttc tcc cgt atg gca agg gac ccc cag cgc ttt gtg gtc atc cag aac       3155
Phe Ser Arg Met Ala Arg Asp Pro Gln Arg Phe Val Val Ile Gln Asn
            980                 985                 990 gag gac tta ggc ccc tcc agc ccc atg gac agc acc ttc tac cgt tca       3203
Glu Asp Leu Gly Pro Ser Ser Pro Met Asp Ser Thr Phe Tyr Arg Ser
        995                 1000                1005 ctg ctg gag gat gat gac atg ggg gag ctg gtc gat gct gaa gag            3248
Leu Leu Glu Asp Asp Asp Met Gly Glu Leu Val Asp Ala Glu Glu
1010                1015                1020 tac ctg gta ccc cag cag gga ttc ttc tcc cca gac cct gcc cta            3293
Tyr Leu Val Pro Gln Gln Gly Phe Phe Ser Pro Asp Pro Ala Leu
    1025                1030                1035 ggt act ggg agc aca gcc cac cgc aga cac cgc agc tcg tcg gcc            3338
Gly Thr Gly Ser Thr Ala His Arg Arg His Arg Ser Ser Ser Ala
1040                1045                1050 agg agt ggc ggt ggt gag ctg aca ctg ggc ctg gag ccc tcg gaa            3383
Arg Ser Gly Gly Gly Glu Leu Thr Leu Gly Leu Glu Pro Ser Glu
    1055                1060                1065 gaa gag ccc ccc aga tct cca ctg gct ccc tcc gaa ggg gct ggc            3428
Glu Glu Pro Pro Arg Ser Pro Leu Ala Pro Ser Glu Gly Ala Gly
1070                1075                1080 tcc gat gtg ttt gat ggt gac ctg gca gtg ggg gta acc aaa gga            3473
Ser Asp Val Phe Asp Gly Asp Leu Ala Val Gly Val Thr Lys Gly
    1085                1090                1095 ctg cag agc ctc tct cca cat gac ctc agc cct cta cag cgg tac            3518
Leu Gln Ser Leu Ser Pro His Asp Leu Ser Pro Leu Gln Arg Tyr
1100                1105                1110 agt gag gat ccc aca tta cct ctg ccc ccc gag act gat ggc tac            3563
Ser Glu Asp Pro Thr Leu Pro Leu Pro Pro Glu Thr Asp Gly Tyr
    1115                1120                1125 gtt gct ccc ctg gcc tgc agc ccc cag ccc gag tat gtg aac cag            3608
Val Ala Pro Leu Ala Cys Ser Pro Gln Pro Glu Tyr Val Asn Gln
1130                1135                1140
```

```
cca gag gtt cgg cct cag tct ccc ttg acc cca gag ggt cct ccg      3653
Pro Glu Val Arg Pro Gln Ser Pro Leu Thr Pro Glu Gly Pro Pro
    1145            1150                1155 cct ccc atc cga cct gct ggt gct act cta gaa aga ccc aag act      3698
Pro Pro Ile Arg Pro Ala Gly Ala Thr Leu Glu Arg Pro Lys Thr
1160                1165                1170 ctc tct cct ggg aaa aat ggg gtt gtc aaa gac gtt ttt gcc ttt      3743
Leu Ser Pro Gly Lys Asn Gly Val Val Lys Asp Val Phe Ala Phe
    1175            1180                1185 ggg ggt gct gtg gag aac cct gaa tac tta gca ccc aga gca ggc      3788
Gly Gly Ala Val Glu Asn Pro Glu Tyr Leu Ala Pro Arg Ala Gly
1190                1195                1200 act gcc tct cag ccc cac cct tct cct gcc ttc agc cca gcc ttt      3833
Thr Ala Ser Gln Pro His Pro Ser Pro Ala Phe Ser Pro Ala Phe
    1205            1210                1215 gac aac ctc tat tac tgg gac cag aac tca tcg gag cag ggt cct      3878
Asp Asn Leu Tyr Tyr Trp Asp Gln Asn Ser Ser Glu Gln Gly Pro
1220                1225                1230 cca cca agt acc ttt gaa ggg acc ccc act gca gag aac cct gag      3923
Pro Pro Ser Thr Phe Glu Gly Thr Pro Thr Ala Glu Asn Pro Glu
    1235            1240                1245 tac cta ggc ctg gat gtg cca gta tga ggtcacatgt gcagacatcc        3970
Tyr Leu Gly Leu Asp Val Pro Val
1250                1255 tctgtcttca gagtggggaa ggaaggccta acttgtggtc tccatcgccc gccacaaagc   4030
agggagaagg tcctctggcc acatgacatc cagggcagcc ggctatgcca ggaacgtgcc   4090
ctgaggaacc tcgctcgatg cttcaatcct gagtggttaa gagggccccg cctggccgga   4150
agagacagca cactgttcag ccccagagga ttacagaccc tgactgccct gacagactgt   4210
agggtccagt gggtattcct tacctggcct ggctctcttg gttctgaaga ctgagggaag   4270
ctcagcctgc aagggaggag gccccaggtg aatatcctgg gagcaggaca ccccactagg   4330
actgaggcac gtgcatccca agaggggac agcacttgca cccagactgg tctttgtaca   4390
gagtttattt tgttctgttt ttacttttgt tttttgtttt tttttaaag atgaaataag   4450 gatacagtgg gagagtgggt gttatatgaa agtcgggggg tgctgtcccc tttctccatt   4510
tgcaatgaga tttgtaaaat aactggaccc cagcctatgt ctgagagtgg tcccgggccg   4570
ggtcaaaccg tattgctcat ctgacacaca gctcctcctg gagtgagtgt gtagagatct   4630
tccaaaagtt tgagacaatt tggctttggg cttgagggac tggggagtta ggattccttc   4690
tgaaggccct ttggcaacag ggtcattctc cgttggacac actcatacca aggctacccc   4750
cagaatactc cgttggacac actcattcca aggctacccc cagaatgaag tcctgtcctc   4810
ccagtgggag aggggagctt gtggagagca ttgccatgtg acttgttttc cttgccttag   4870
aaagaagtat ccatccagga aaacccccacc cactaggtgt tagtcccacc cactaggtgt   4930
tagcagggcc agactgacct gtgtgccccc cgcacaggct ggacataaac acacgccagt   4990
tgacacaa                                                          4998

<210> SEQ ID NO 13
<211> LENGTH: 1256
<212> TYPE: PRT
<213> ORGANISM: Mus musculus

<400> SEQUENCE: 13

Met Glu Leu Ala Ala Trp Cys Arg Trp Gly Phe Leu Leu Ala Leu Leu
1               5                   10                  15

Ser Pro Gly Ala Ala Gly Thr Gln Val Cys Thr Gly Thr Asp Met Lys
```

-continued

```
            20                  25                  30
Leu Arg Leu Pro Ala Ser Pro Glu Thr His Leu Asp Met Leu Arg His
         35                  40                  45

Leu Tyr Gln Gly Cys Gln Val Val Gln Gly Asn Leu Glu Leu Thr Tyr
 50                  55                  60

Leu Pro Ala Asn Ala Ser Leu Ser Phe Leu Gln Asp Ile Gln Glu Val
 65                  70                  75                  80

Gln Gly Tyr Met Leu Ile Ala His Asn Arg Val Lys His Val Pro Leu
                 85                  90                  95

Gln Arg Leu Arg Ile Val Arg Gly Thr Gln Leu Phe Glu Asp Lys Tyr
                100                 105                 110

Ala Leu Ala Val Leu Asp Asn Arg Asp Pro Leu Asp Asn Val Thr Thr
                115                 120                 125

Ala Ala Pro Gly Arg Thr Pro Glu Gly Leu Arg Glu Leu Gln Leu Arg
            130                 135                 140

Ser Leu Thr Glu Ile Leu Lys Gly Gly Val Leu Ile Arg Gly Asn Pro
145                 150                 155                 160

Gln Leu Cys Tyr Gln Asp Met Val Leu Trp Lys Asp Val Leu Arg Lys
                165                 170                 175

Asn Asn Gln Leu Ala Pro Val Asp Met Asp Thr Asn Arg Ser Arg Ala
                180                 185                 190

Cys Pro Pro Cys Ala Pro Thr Cys Lys Asp Asn His Cys Trp Gly Glu
            195                 200                 205

Ser Pro Glu Asp Cys Gln Ile Leu Thr Gly Thr Ile Cys Thr Ser Gly
        210                 215                 220

Cys Ala Arg Cys Lys Gly Arg Leu Pro Thr Asp Cys Cys His Glu Gln
225                 230                 235                 240

Cys Ala Ala Gly Cys Thr Gly Pro Lys His Ser Asp Cys Leu Ala Cys
                245                 250                 255

Leu His Phe Asn His Ser Gly Ile Cys Glu Leu His Cys Pro Ala Leu
                260                 265                 270

Ile Thr Tyr Asn Thr Asp Thr Phe Glu Ser Met Leu Asn Pro Glu Gly
            275                 280                 285

Arg Tyr Thr Phe Gly Ala Ser Cys Val Thr Cys Pro Tyr Asn Tyr
        290                 295                 300

Leu Ser Thr Glu Val Gly Ser Cys Thr Leu Val Cys Pro Pro Asn Asn
305                 310                 315                 320

Gln Glu Val Thr Ala Glu Asp Gly Thr Gln Arg Cys Glu Lys Cys Ser
                325                 330                 335

Lys Pro Cys Ala Gly Val Cys Tyr Gly Leu Gly Met Glu His Leu Arg
            340                 345                 350

Gly Ala Arg Ala Ile Thr Ser Asp Asn Ile Gln Glu Phe Ala Gly Cys
        355                 360                 365

Lys Lys Ile Phe Gly Ser Leu Ala Phe Leu Pro Glu Ser Phe Asp Gly
            370                 375                 380

Asn Pro Ser Ser Gly Val Ala Pro Leu Lys Pro Glu His Leu Gln Val
385                 390                 395                 400

Phe Glu Thr Leu Glu Glu Ile Thr Gly Tyr Leu Tyr Ile Ser Ala Trp
                405                 410                 415

Pro Glu Ser Phe Gln Asp Leu Ser Val Phe Gln Asn Leu Arg Val Ile
            420                 425                 430

Arg Gly Arg Ile Leu His Asp Gly Ala Tyr Ser Leu Thr Leu Gln Gly
        435                 440                 445
```

-continued

```
Leu Gly Ile His Ser Leu Gly Leu Arg Ser Leu Arg Glu Leu Gly Ser
        450                 455                 460
Gly Leu Ala Leu Ile His Arg Asn Thr His Leu Cys Phe Val Asn Thr
465                 470                 475                 480
Val Pro Trp Asp Gln Leu Phe Arg Asn Pro His Gln Ala Leu Leu His
                485                 490                 495
Ser Gly Asn Arg Pro Glu Glu Ala Cys Gly Leu Glu Gly Leu Val Cys
            500                 505                 510
Asn Ser Leu Cys Ala Arg Gly His Cys Trp Gly Pro Gly Pro Thr Gln
        515                 520                 525
Cys Val Asn Cys Ser Gln Phe Leu Arg Gly Gln Glu Cys Val Glu Glu
        530                 535                 540
Cys Arg Val Trp Lys Gly Leu Pro Arg Glu Tyr Val Arg Gly Lys His
545                 550                 555                 560
Cys Leu Pro Cys His Pro Glu Cys Gln Pro Gln Asn Ser Ser Glu Thr
                565                 570                 575
Cys Tyr Gly Ser Glu Ala Asp Gln Cys Glu Ala Cys Ala His Tyr Lys
            580                 585                 590
Asp Ser Ser Ser Cys Val Ala Arg Cys Pro Ser Gly Val Lys Pro Asp
        595                 600                 605
Leu Ser Tyr Met Pro Ile Trp Lys Tyr Pro Asp Glu Glu Gly Ile Cys
        610                 615                 620
Gln Pro Cys Pro Ile Asn Cys Thr His Ser Cys Val Asp Leu Asp Glu
625                 630                 635                 640
Arg Gly Cys Pro Ala Glu Gln Arg Ala Ser Pro Val Thr Phe Ile Ile
                645                 650                 655
Ala Thr Val Val Gly Val Leu Leu Phe Leu Ile Ile Val Val Val Ile
            660                 665                 670
Gly Ile Leu Ile Lys Arg Arg Gln Lys Ile Arg Lys Tyr Thr Met
        675                 680                 685
Arg Arg Leu Leu Gln Glu Thr Glu Leu Val Glu Pro Leu Thr Pro Ser
        690                 695                 700
Gly Ala Val Pro Asn Gln Ala Gln Met Arg Ile Leu Lys Glu Thr Glu
705                 710                 715                 720
Leu Arg Lys Leu Lys Val Leu Gly Ser Gly Ala Phe Gly Thr Val Tyr
                725                 730                 735
Lys Gly Ile Trp Ile Pro Asp Gly Glu Asn Val Lys Ile Pro Val Ala
            740                 745                 750
Ile Lys Val Leu Arg Glu Asn Thr Ser Pro Lys Ala Asn Lys Glu Ile
        755                 760                 765
Leu Asp Glu Ala Tyr Val Met Ala Gly Val Gly Ser Pro Tyr Val Ser
        770                 775                 780
Arg Leu Leu Gly Ile Cys Leu Thr Ser Thr Val Gln Leu Val Thr Gln
785                 790                 795                 800
Leu Met Pro Tyr Gly Cys Leu Leu Asp His Val Arg Glu His Arg Gly
                805                 810                 815
Arg Leu Gly Ser Gln Asp Leu Leu Asn Trp Cys Val Gln Ile Ala Lys
            820                 825                 830
Gly Met Ser Tyr Leu Glu Glu Val Arg Leu Val His Arg Asp Leu Ala
        835                 840                 845
Ala Arg Asn Val Leu Val Lys Ser Pro Asn His Val Lys Ile Thr Asp
        850                 855                 860
Phe Gly Leu Ala Arg Leu Leu Asp Ile Asp Glu Thr Glu Tyr His Ala
865                 870                 875                 880
```

```
Asp Gly Gly Lys Val Pro Ile Lys Trp Met Ala Leu Glu Ser Ile Leu
                885                 890                 895
Arg Arg Arg Phe Thr His Gln Ser Asp Val Trp Ser Tyr Gly Val Thr
            900                 905                 910
Val Trp Glu Leu Met Thr Phe Gly Ala Lys Pro Tyr Asp Gly Ile Pro
        915                 920                 925
Ala Arg Glu Ile Pro Asp Leu Leu Glu Lys Gly Glu Arg Leu Pro Gln
    930                 935                 940
Pro Pro Ile Cys Thr Ile Asp Val Tyr Met Ile Met Val Lys Cys Trp
945                 950                 955                 960
Met Ile Asp Ser Glu Cys Arg Pro Arg Phe Arg Glu Leu Val Ser Glu
                965                 970                 975
Phe Ser Arg Met Ala Arg Asp Pro Gln Arg Phe Val Val Ile Gln Asn
            980                 985                 990
Glu Asp Leu Gly Pro Ser Ser Pro Met Asp Ser Thr Phe Tyr Arg Ser
        995                 1000                1005
Leu Leu Glu Asp Asp Met Gly Glu Leu Val Asp Ala Glu Glu
    1010                1015                1020
Tyr Leu Val Pro Gln Gln Gly Phe Phe Ser Pro Asp Pro Ala Leu
    1025                1030                1035
Gly Thr Gly Ser Thr Ala His Arg Arg His Arg Ser Ser Ser Ala
    1040                1045                1050
Arg Ser Gly Gly Gly Glu Leu Thr Leu Gly Leu Glu Pro Ser Glu
    1055                1060                1065
Glu Glu Pro Pro Arg Ser Pro Leu Ala Pro Ser Glu Gly Ala Gly
    1070                1075                1080
Ser Asp Val Phe Asp Gly Asp Leu Ala Val Gly Val Thr Lys Gly
    1085                1090                1095
Leu Gln Ser Leu Ser Pro His Asp Leu Ser Pro Leu Gln Arg Tyr
    1100                1105                1110
Ser Glu Asp Pro Thr Leu Pro Leu Pro Pro Glu Thr Asp Gly Tyr
    1115                1120                1125
Val Ala Pro Leu Ala Cys Ser Pro Gln Pro Glu Tyr Val Asn Gln
    1130                1135                1140
Pro Glu Val Arg Pro Gln Ser Pro Leu Thr Pro Glu Gly Pro Pro
    1145                1150                1155
Pro Pro Ile Arg Pro Ala Gly Ala Thr Leu Glu Arg Pro Lys Thr
    1160                1165                1170
Leu Ser Pro Gly Lys Asn Gly Val Val Lys Asp Val Phe Ala Phe
    1175                1180                1185
Gly Gly Ala Val Glu Asn Pro Glu Tyr Leu Ala Pro Arg Ala Gly
    1190                1195                1200
Thr Ala Ser Gln Pro His Pro Ser Pro Ala Phe Ser Pro Ala Phe
    1205                1210                1215
Asp Asn Leu Tyr Tyr Trp Asp Gln Asn Ser Ser Glu Gln Gly Pro
    1220                1225                1230
Pro Pro Ser Thr Phe Glu Gly Thr Pro Thr Ala Glu Asn Pro Glu
    1235                1240                1245
Tyr Leu Gly Leu Asp Val Pro Val
    1250                1255

<210> SEQ ID NO 14
<211> LENGTH: 5511
<212> TYPE: DNA
```

```
<213> ORGANISM: Homo sapiens
<220> FEATURE:
<221> NAME/KEY: CDS
<222> LOCATION: (194)..(4222)

<400> SEQUENCE: 14
acacacacac acccctcccc tgccatccct ccccggactc cggctccggc tccgattgca      60
atttgcaacc tccgctgccg tcgccgcagc agccaccaat tcgccagcgg ttcaggtggc     120
tcttgcctcg atgtcctagc ctaggggccc ccgggccgga cttggctggg ctcccttcac     180
cctctgcgga gtc atg agg gcg aac gac gct ctg cag gtg ctg ggc ttg       229
            Met Arg Ala Asn Asp Ala Leu Gln Val Leu Gly Leu
              1               5                  10 ctt ttc agc ctg gcc cgg ggc tcc gag gtg ggc aac tct cag gca gtg       277
Leu Phe Ser Leu Ala Arg Gly Ser Glu Val Gly Asn Ser Gln Ala Val
         15                  20                  25 tgt cct ggg act ctg aat ggc ctg agt gtg acc ggc gat gct gag aac       325
Cys Pro Gly Thr Leu Asn Gly Leu Ser Val Thr Gly Asp Ala Glu Asn
 30                  35                  40 caa tac cag aca ctg tac aag ctc tac gag agg tgt gag gtg gtg atg       373
Gln Tyr Gln Thr Leu Tyr Lys Leu Tyr Glu Arg Cys Glu Val Val Met
45                  50                  55                  60 ggg aac ctt gag att gtg ctc acg gga cac aat gcc gac ctc tcc ttc       421
Gly Asn Leu Glu Ile Val Leu Thr Gly His Asn Ala Asp Leu Ser Phe
                 65                  70                  75 ctg cag tgg att cga gaa gtg aca ggc tat gtc ctc gtg gcc atg aat       469
Leu Gln Trp Ile Arg Glu Val Thr Gly Tyr Val Leu Val Ala Met Asn
         80                  85                  90 gaa ttc tct act cta cca ttg ccc aac ctc cgc gtg gtg cga ggg acc       517
Glu Phe Ser Thr Leu Pro Leu Pro Asn Leu Arg Val Val Arg Gly Thr
 95                 100                 105 cag gtc tac gat ggg aag ttt gcc atc ttc gtc atg ttg aac tat aac       565
Gln Val Tyr Asp Gly Lys Phe Ala Ile Phe Val Met Leu Asn Tyr Asn
    110                 115                 120 acc aac tcc agc cac gct ctg cgc cag ctc cgc ttg act cag ctc acc       613
Thr Asn Ser Ser His Ala Leu Arg Gln Leu Arg Leu Thr Gln Leu Thr
125                 130                 135                 140 gag att ctg tca ggg ggt gtt tat att gag aag aac gat aag ctt tgt       661
Glu Ile Leu Ser Gly Gly Val Tyr Ile Glu Lys Asn Asp Lys Leu Cys
                145                 150                 155 cac atg gac aca att gac tgg agg gac atc gtg agg gac cga gat gct       709
His Met Asp Thr Ile Asp Trp Arg Asp Ile Val Arg Asp Arg Asp Ala
        160                 165                 170 gag ata gtg gtg aag gac aat ggc aga agc tgt ccc ccc tgt cat gag       757
Glu Ile Val Val Lys Asp Asn Gly Arg Ser Cys Pro Pro Cys His Glu
    175                 180                 185 gtt tgc aag ggg cga tgc tgg ggt cct gga tca gaa gac tgc cag aca       805
Val Cys Lys Gly Arg Cys Trp Gly Pro Gly Ser Glu Asp Cys Gln Thr
190                 195                 200 ttg acc aag acc atc tgt gct cct cag tgt aat ggt cac tgc ttt ggg       853
Leu Thr Lys Thr Ile Cys Ala Pro Gln Cys Asn Gly His Cys Phe Gly
205                 210                 215                 220 ccc aac ccc aac cag tgc tgc cat gat gag tgt gcc ggg ggc tgc tca       901
Pro Asn Pro Asn Gln Cys Cys His Asp Glu Cys Ala Gly Gly Cys Ser
                225                 230                 235 ggc cct cag gac aca gac tgc ttt gcc tgc cgg cac ttc aat gac agt       949
Gly Pro Gln Asp Thr Asp Cys Phe Ala Cys Arg His Phe Asn Asp Ser
        240                 245                 250 gga gcc tgt gta cct cgc tgt cca cag cct ctt gtc tac aac aag cta       997
Gly Ala Cys Val Pro Arg Cys Pro Gln Pro Leu Val Tyr Asn Lys Leu
    255                 260                 265
```

```
act ttc cag ctg gaa ccc aat ccc cac acc aag tat cag tat gga gga    1045
Thr Phe Gln Leu Glu Pro Asn Pro His Thr Lys Tyr Gln Tyr Gly Gly
270                 275                 280 gtt tgt gta gcc agc tgt ccc cat aac ttt gtg gtg gat caa aca tcc    1093
Val Cys Val Ala Ser Cys Pro His Asn Phe Val Val Asp Gln Thr Ser
285                 290                 295                 300 tgt gtc agg gcc tgt cct cct gac aag atg gaa gta gat aaa aat ggg    1141
Cys Val Arg Ala Cys Pro Pro Asp Lys Met Glu Val Asp Lys Asn Gly
        305                 310                 315 ctc aag atg tgt gag cct tgt ggg gga cta tgt ccc aaa gcc tgt gag    1189
Leu Lys Met Cys Glu Pro Cys Gly Gly Leu Cys Pro Lys Ala Cys Glu
    320                 325                 330 gga aca ggc tct ggg agc cgc ttc cag act gtg gac tcg agc aac att    1237
Gly Thr Gly Ser Gly Ser Arg Phe Gln Thr Val Asp Ser Ser Asn Ile
        335                 340                 345 gat gga ttt gtg aac tgc acc aag atc ctg ggc aac ctg gac ttt ctg    1285
Asp Gly Phe Val Asn Cys Thr Lys Ile Leu Gly Asn Leu Asp Phe Leu
350                 355                 360 atc acc ggc ctc aat gga gac ccc tgg cac aag atc cct gcc ctg gac    1333
Ile Thr Gly Leu Asn Gly Asp Pro Trp His Lys Ile Pro Ala Leu Asp
365                 370                 375                 380 cca gag aag ctc aat gtc ttc cgg aca gta cgg gag atc aca ggt tac    1381
Pro Glu Lys Leu Asn Val Phe Arg Thr Val Arg Glu Ile Thr Gly Tyr
            385                 390                 395 ctg aac atc cag tcc tgg ccg ccc cac atg cac aac ttc agt gtt ttt    1429
Leu Asn Ile Gln Ser Trp Pro Pro His Met His Asn Phe Ser Val Phe
        400                 405                 410 tcc aat ttg aca acc att gga ggc aga agc ctc tac aac cgg ggc ttc    1477
Ser Asn Leu Thr Thr Ile Gly Gly Arg Ser Leu Tyr Asn Arg Gly Phe
        415                 420                 425 tca ttg ttg atc atg aag aac ttg aat gtc aca tct ctg ggc ttc cga    1525
Ser Leu Leu Ile Met Lys Asn Leu Asn Val Thr Ser Leu Gly Phe Arg
430                 435                 440 tcc ctg aag gaa att agt gct ggg cgt atc tat ata agt gcc aat agg    1573
Ser Leu Lys Glu Ile Ser Ala Gly Arg Ile Tyr Ile Ser Ala Asn Arg
445                 450                 455                 460 cag ctc tgc tac cac cac tct ttg aac tgg acc aag gtg ctt cgg ggg    1621
Gln Leu Cys Tyr His His Ser Leu Asn Trp Thr Lys Val Leu Arg Gly
            465                 470                 475 cct acg gaa gag cga cta gac atc aag cat aat cgg ccg cgc aga gac    1669
Pro Thr Glu Glu Arg Leu Asp Ile Lys His Asn Arg Pro Arg Arg Asp
        480                 485                 490 tgc gtg gca gag ggc aaa gtg tgt gac cca ctg tgc tcc tct ggg gga    1717
Cys Val Ala Glu Gly Lys Val Cys Asp Pro Leu Cys Ser Ser Gly Gly
        495                 500                 505 tgc tgg ggc cca ggc cct ggt cag tgc ttg tcc tgt cga aat tat agc    1765
Cys Trp Gly Pro Gly Pro Gly Gln Cys Leu Ser Cys Arg Asn Tyr Ser
    510                 515                 520 cga gga ggt gtc tgt gtg acc cac tgc aac ttt ctg aat ggg gag cct    1813
Arg Gly Gly Val Cys Val Thr His Cys Asn Phe Leu Asn Gly Glu Pro
525                 530                 535                 540 cga gaa ttt gcc cat gag gcc gaa tgc ttc tcc tgc cac ccg gaa tgc    1861
Arg Glu Phe Ala His Glu Ala Glu Cys Phe Ser Cys His Pro Glu Cys
            545                 550                 555 caa ccc atg gag ggc act gcc aca tgc aat ggc tcg ggc tct gat act    1909
Gln Pro Met Glu Gly Thr Ala Thr Cys Asn Gly Ser Gly Ser Asp Thr
        560                 565                 570 tgt gct caa tgt gcc cat ttt cga gat ggg ccc cac tgt gtg agc agc    1957
Cys Ala Gln Cys Ala His Phe Arg Asp Gly Pro His Cys Val Ser Ser
        575                 580                 585
```

| | | |
|---|---|---|
| tgc ccc cat gga gtc cta ggt gcc aag ggc cca atc tac aag tac cca<br>Cys Pro His Gly Val Leu Gly Ala Lys Gly Pro Ile Tyr Lys Tyr Pro<br>590                       595                        600 | 2005 |
| gat gtt cag aat gaa tgt cgg ccc tgc cat gag aac tgc acc cag ggg<br>Asp Val Gln Asn Glu Cys Arg Pro Cys His Glu Asn Cys Thr Gln Gly<br>605                       610                       615                 620 | 2053 |
| tgt aaa gga cca gag ctt caa gac tgt tta gga caa aca ctg gtg ctg<br>Cys Lys Gly Pro Glu Leu Gln Asp Cys Leu Gly Gln Thr Leu Val Leu<br>                     625                       630                     635 | 2101 |
| atc ggc aaa acc cat ctg aca atg gct ttg aca gtg ata gca gga ttg<br>Ile Gly Lys Thr His Leu Thr Met Ala Leu Thr Val Ile Ala Gly Leu<br>640                       645                       650 | 2149 |
| gta gtg att ttc atg atg ctg ggc ggc act ttt ctc tac tgg cgt ggg<br>Val Val Ile Phe Met Met Leu Gly Gly Thr Phe Leu Tyr Trp Arg Gly<br>               655                       660                     665 | 2197 |
| cgc cgg att cag aat aaa agg gct atg agg cga tac ttg gaa cgg ggt<br>Arg Arg Ile Gln Asn Lys Arg Ala Met Arg Arg Tyr Leu Glu Arg Gly<br>670                       675                       680 | 2245 |
| gag agc ata gag cct ctg gac ccc agt gag aag gct aac aaa gtc ttg<br>Glu Ser Ile Glu Pro Leu Asp Pro Ser Glu Lys Ala Asn Lys Val Leu<br>685                       690                       695                 700 | 2293 |
| gcc aga atc ttc aaa gag aca gag cta agg aag ctt aaa gtg ctt ggc<br>Ala Arg Ile Phe Lys Glu Thr Glu Leu Arg Lys Leu Lys Val Leu Gly<br>               705                       710                     715 | 2341 |
| tcg ggt gtc ttt gga act gtg cac aaa gga gtg tgg atc cct gag ggt<br>Ser Gly Val Phe Gly Thr Val His Lys Gly Val Trp Ile Pro Glu Gly<br>                   720                       725                     730 | 2389 |
| gaa tca atc aag att cca gtc tgc att aaa gtc att gag gac aag agt<br>Glu Ser Ile Lys Ile Pro Val Cys Ile Lys Val Ile Glu Asp Lys Ser<br>               735                       740                     745 | 2437 |
| gga cgg cag agt ttt caa gct gtg aca gat cat atg ctg gcc att ggc<br>Gly Arg Gln Ser Phe Gln Ala Val Thr Asp His Met Leu Ala Ile Gly<br>750                       755                       760 | 2485 |
| agc ctg gac cat gcc cac att gta agg ctg ctg gga cta tgc cca ggg<br>Ser Leu Asp His Ala His Ile Val Arg Leu Leu Gly Leu Cys Pro Gly<br>765                       770                       775                 780 | 2533 |
| tca tct ctg cag ctt gtc act caa tat ttg cct ctg ggt tct ctg ctg<br>Ser Ser Leu Gln Leu Val Thr Gln Tyr Leu Pro Leu Gly Ser Leu Leu<br>               785                       790                     795 | 2581 |
| gat cat gtg aga caa cac cgg ggg gca ctg ggg cca cag ctg ctg ctc<br>Asp His Val Arg Gln His Arg Gly Ala Leu Gly Pro Gln Leu Leu Leu<br>                   800                       805                     810 | 2629 |
| aac tgg gga gta caa att gcc aag gga atg tac tac ctt gag gaa cat<br>Asn Trp Gly Val Gln Ile Ala Lys Gly Met Tyr Tyr Leu Glu Glu His<br>               815                       820                     825 | 2677 |
| ggt atg gtg cat aga aac ctg gct gcc cga aac gtg cta ctc aag tca<br>Gly Met Val His Arg Asn Leu Ala Ala Arg Asn Val Leu Leu Lys Ser<br>830                       835                       840 | 2725 |
| ccc agt cag gtt cag gtg gca gat ttt ggt gtg gct gac ctg ctg cct<br>Pro Ser Gln Val Gln Val Ala Asp Phe Gly Val Ala Asp Leu Leu Pro<br>845                       850                       855                 860 | 2773 |
| cct gat gat aag cag ctg cta tac agt gag gcc aag act cca att aag<br>Pro Asp Asp Lys Gln Leu Leu Tyr Ser Glu Ala Lys Thr Pro Ile Lys<br>                   865                       870                     875 | 2821 |
| tgg atg gcc ctt gag agt atc cac ttt ggg aaa tac aca cac cag agt<br>Trp Met Ala Leu Glu Ser Ile His Phe Gly Lys Tyr Thr His Gln Ser<br>                   880                       885                     890 | 2869 |
| gat gtc tgg agc tat ggt gtg aca gtt tgg gag ttg atg acc ttc ggg<br>Asp Val Trp Ser Tyr Gly Val Thr Val Trp Glu Leu Met Thr Phe Gly<br>                   895                       900                     905 | 2917 |

| | | | | | | | | | | | | |
|---|---|---|---|---|---|---|---|---|---|---|---|---|
| gca | gag | ccc | tat | gca | ggg | cta | cga | ttg | gct | gaa | gta | cca gac ctg cta | 2965 |
| Ala | Glu | Pro | Tyr | Ala | Gly | Leu | Arg | Leu | Ala | Glu | Val | Pro Asp Leu Leu |
| | | 910 | | | 915 | | | | 920 | | | |

```
gca gag ccc tat gca ggg cta cga ttg gct gaa gta cca gac ctg cta     2965
Ala Glu Pro Tyr Ala Gly Leu Arg Leu Ala Glu Val Pro Asp Leu Leu
        910             915                 920 gag aag ggg gag cgg ttg gca cag ccc cag atc tgc aca att gat gtc     3013
Glu Lys Gly Glu Arg Leu Ala Gln Pro Gln Ile Cys Thr Ile Asp Val
925                 930                 935                 940 tac atg gtg atg gtc aag tgt tgg atg att gat gag aac att cgc cca     3061
Tyr Met Val Met Val Lys Cys Trp Met Ile Asp Glu Asn Ile Arg Pro
            945                 950                 955 acc ttt aaa gaa cta gcc aat gag ttc acc agg atg gcc cga gac cca     3109
Thr Phe Lys Glu Leu Ala Asn Glu Phe Thr Arg Met Ala Arg Asp Pro
        960                 965                 970 cca cgg tat ctg gtc ata aag aga gag agt ggg cct gga ata gcc cct     3157
Pro Arg Tyr Leu Val Ile Lys Arg Glu Ser Gly Pro Gly Ile Ala Pro
            975                 980                 985 ggg cca gag ccc cat ggt ctg aca aac aag aag cta  gag gaa gta gag    3205
Gly Pro Glu Pro His Gly Leu Thr Asn Lys Lys Leu  Glu Glu Val Glu
        990                 995                 1000 ctg gag cca gaa cta gac cta gac cta gac ttg  gaa gca gag gag        3250
Leu Glu Pro Glu Leu Asp Leu Asp Leu Asp Leu  Glu Ala Glu Glu
1005                1010                1015 gac aac ctg gca acc acc aca ctg ggc tcc gcc  ctc agc cta cca        3295
Asp Asn Leu Ala Thr Thr Thr Leu Gly Ser Ala  Leu Ser Leu Pro
1020                1025                1030 gtt gga aca ctt aat cgg cca cgt ggg agc cag  agc ctt tta agt        3340
Val Gly Thr Leu Asn Arg Pro Arg Gly Ser Gln  Ser Leu Leu Ser
1035                1040                1045 cca tca tct gga tac atg ccc atg aac cag ggt  aat ctt ggg gag        3385
Pro Ser Ser Gly Tyr Met Pro Met Asn Gln Gly  Asn Leu Gly Glu
1050                1055                1060 tct tgc cag gag tct gca gtt tct ggg agc agt  gaa cgg tgc ccc        3430
Ser Cys Gln Glu Ser Ala Val Ser Gly Ser Ser  Glu Arg Cys Pro
1065                1070                1075 cgt cca gtc tct cta cac cca atg cca cgg gga  tgc ctg gca tca        3475
Arg Pro Val Ser Leu His Pro Met Pro Arg Gly  Cys Leu Ala Ser
1080                1085                1090 gag tca tca gag ggg cat gta aca ggc tct gag  gct gag ctc cag        3520
Glu Ser Ser Glu Gly His Val Thr Gly Ser Glu  Ala Glu Leu Gln
1095                1100                1105 gag aaa gtg tca atg tgt agg agc cgg agc agg  agc cgg agc cca        3565
Glu Lys Val Ser Met Cys Arg Ser Arg Ser Arg  Ser Arg Ser Pro
1110                1115                1120 cgg cca cgc gga gat agc gcc tac cat tcc cag  cgc cac agt ctg        3610
Arg Pro Arg Gly Asp Ser Ala Tyr His Ser Gln  Arg His Ser Leu
1125                1130                1135 ctg act cct gtt acc cca ctc tcc cca ccc ggg  tta gag gaa gag        3655
Leu Thr Pro Val Thr Pro Leu Ser Pro Pro Gly  Leu Glu Glu Glu
1140                1145                1150 gat gtc aac ggt tat gtc atg cca gat aca cac  ctc aaa ggt act        3700
Asp Val Asn Gly Tyr Val Met Pro Asp Thr His  Leu Lys Gly Thr
1155                1160                1165 ccc tcc tcc cgg gaa ggc acc ctt tct tca gtg  ggt ctc agt tct        3745
Pro Ser Ser Arg Glu Gly Thr Leu Ser Ser Val  Gly Leu Ser Ser
1170                1175                1180 gtc ctg ggt act gaa gaa gaa gat gaa gat gag  gag tat gaa tac        3790
Val Leu Gly Thr Glu Glu Glu Asp Glu Asp Glu  Glu Tyr Glu Tyr
1185                1190                1195 atg aac cgg agg aga agg cac agt cca cct cat  ccc cct agg cca        3835
Met Asn Arg Arg Arg Arg His Ser Pro Pro His  Pro Pro Arg Pro
1200                1205                1210
```

| | | |
|---|---|---|
| agt tcc ctt gag gag ctg ggt tat gag tac atg gat gtg ggg tca<br>Ser Ser Leu Glu Glu Leu Gly Tyr Glu Tyr Met Asp Val Gly Ser<br>1215                      1220                      1225 | 3880 | |
| gac ctc agt gcc tct ctg ggc agc aca cag agt tgc cca ctc cac<br>Asp Leu Ser Ala Ser Leu Gly Ser Thr Gln Ser Cys Pro Leu His<br>1230                      1235                      1240 | 3925 | |
| cct gta ccc atc atg ccc act gca ggc aca act cca gat gaa gac<br>Pro Val Pro Ile Met Pro Thr Ala Gly Thr Thr Pro Asp Glu Asp<br>1245                      1250                      1255 | 3970 | |
| tat gaa tat atg aat cgg caa cga gat gga ggt ggt cct ggg ggt<br>Tyr Glu Tyr Met Asn Arg Gln Arg Asp Gly Gly Gly Pro Gly Gly<br>1260                      1265                      1270 | 4015 | |
| gat tat gca gcc atg ggg gcc tgc cca gca tct gag caa ggg tat<br>Asp Tyr Ala Ala Met Gly Ala Cys Pro Ala Ser Glu Gln Gly Tyr<br>1275                      1280                      1285 | 4060 | |
| gaa gag atg aga gct ttt cag ggg cct gga cat cag gcc ccc cat<br>Glu Glu Met Arg Ala Phe Gln Gly Pro Gly His Gln Ala Pro His<br>1290                      1295                      1300 | 4105 | |
| gtc cat tat gcc cgc cta aaa act cta cgt agc tta gag gct aca<br>Val His Tyr Ala Arg Leu Lys Thr Leu Arg Ser Leu Glu Ala Thr<br>1305                      1310                      1315 | 4150 | |
| gac tct gcc ttt gat aac cct gat tac tgg cat agc agg ctt ttc<br>Asp Ser Ala Phe Asp Asn Pro Asp Tyr Trp His Ser Arg Leu Phe<br>1320                      1325                      1330 | 4195 | |
| ccc aag gct aat gcc cag aga acg taa ctcctgctcc ctgtggcact<br>Pro Lys Ala Asn Ala Gln Arg Thr<br>1335                      1340 | 4242 | |
| cagggagcat ttaatggcag ctagtgcctt tagagggtac cgtcttctcc ctattccctc | 4302 | |
| tctctcccag gtcccagccc cttttcccca gtcccagaca attccattca atctttggag | 4362 | |
| gcttttaaac attttgacac aaaattctta tggtatgtag ccagctgtgc actttcttct | 4422 | |
| ctttcccaac cccaggaaag gttttcctta ttttgtgtgc tttcccagtc ccattcctca | 4482 | |
| gcttcttcac aggcactcct ggagatatga aggattactc tccatatccc ttcctctcag | 4542 | |
| gctcttgact acttggaact aggctcttat gtgtgccttt gtttcccatc agactgtcaa | 4602 | |
| gaagaggaaa gggaggaaac ctagcagagg aaagtgtaat tttggtttat gactcttaac | 4662 | |
| cccctagaaa gacagaagct taaaatctgt gaagaaagag gttaggagta gatattgatt | 4722 | |
| actatcataa ttcagcactt aactatgagc caggcatcat actaaacttc acctacatta | 4782 | |
| tctcacttag tcctttatca tccttaaaac aattctgtga catacatatt atctcatttt | 4842 | |
| acacaaaggg aagtcgggca tggtggctca tgcctgtaat ctcagcactt tgggaggctg | 4902 | |
| aggcagaagg attacctgag gcaaggagtt tgagaccagc ttagccaaca tagtaagacc | 4962 | |
| cccatctctt taaaaaaaaa aaaaaaaaaa aaaaaaaac tttagaactg ggtgcagtgg | 5022 | |
| ctcatgcctg taatcccagc cagcactttg ggaggctgag atgggaagat cacttgagcc | 5082 | |
| cagaattaga gataagccta tggaaacata gcaagacact gtctctacag ggaaaaaaa | 5142 | |
| aaaaagaaac tgagccttaa agagatgaaa taaattaagc agtagatcca ggatgcaaaa | 5202 | |
| tcctcccaat tcctgtgcat gtgctcttat tgtaaggtgc caagaaaaac tgatttaagt | 5262 | |
| tacagcccct gtttaagggg cactgttctt tgttttgtgca ctgaatcaag tctaacccca | 5322 | |
| acagccacat cctcctatac ctagacatct catctcagga agtggtggtg ggggtagtca | 5382 | |
| gaaggaaaaa taactggaca tcttgtgta accataatc cacatgtgcc gtaaatgatc | 5442 | |
| ttcactcctt atccgagggc aaattcacaa ggatccccaa gatccacttt tagaagccat | 5502 | |
| tctcatcca | 5511 | |

<210> SEQ ID NO 15
<211> LENGTH: 1342
<212> TYPE: PRT
<213> ORGANISM: Homo sapiens

<400> SEQUENCE: 15

```
Met Arg Ala Asn Asp Ala Leu Gln Val Leu Gly Leu Phe Ser Leu
1               5                   10                  15

Ala Arg Gly Ser Glu Val Gly Asn Ser Gln Ala Val Cys Pro Gly Thr
                20                  25                  30

Leu Asn Gly Leu Ser Val Thr Gly Asp Ala Glu Asn Gln Tyr Gln Thr
                35                  40                  45

Leu Tyr Lys Leu Tyr Glu Arg Cys Glu Val Val Met Gly Asn Leu Glu
    50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
                85                  90                  95

Leu Pro Leu Pro Asn Leu Arg Val Val Arg Gly Thr Gln Val Tyr Asp
                100                 105                 110

Gly Lys Phe Ala Ile Phe Val Met Leu Asn Tyr Asn Thr Asn Ser Ser
    115                 120                 125

His Ala Leu Arg Gln Leu Arg Leu Thr Gln Leu Thr Glu Ile Leu Ser
    130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
                180                 185                 190

Arg Cys Trp Gly Pro Gly Ser Glu Asp Cys Gln Thr Leu Thr Lys Thr
    195                 200                 205

Ile Cys Ala Pro Gln Cys Asn Gly His Cys Phe Gly Pro Asn Pro Asn
    210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
                260                 265                 270

Glu Pro Asn Pro His Thr Lys Tyr Gln Tyr Gly Gly Val Cys Val Ala
    275                 280                 285

Ser Cys Pro His Asn Phe Val Val Asp Gln Thr Ser Cys Val Arg Ala
    290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
                340                 345                 350

Asn Cys Thr Lys Ile Leu Gly Asn Leu Asp Phe Leu Ile Thr Gly Leu
    355                 360                 365

Asn Gly Asp Pro Trp His Lys Ile Pro Ala Leu Asp Pro Glu Lys Leu
    370                 375                 380
```

```
Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
        435                 440                 445

Ile Ser Ala Gly Arg Ile Tyr Ile Ser Ala Asn Arg Gln Leu Cys Tyr
    450                 455                 460

His His Ser Leu Asn Trp Thr Lys Val Leu Arg Gly Pro Thr Glu Glu
465                 470                 475                 480

Arg Leu Asp Ile Lys His Asn Arg Pro Arg Arg Asp Cys Val Ala Glu
                485                 490                 495

Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Gly Gly Val
        515                 520                 525

Cys Val Thr His Cys Asn Phe Leu Asn Gly Glu Pro Arg Glu Phe Ala
    530                 535                 540

His Glu Ala Glu Cys Phe Ser Cys His Pro Glu Cys Gln Pro Met Glu
545                 550                 555                 560

Gly Thr Ala Thr Cys Asn Gly Ser Gly Ser Asp Thr Cys Ala Gln Cys
                565                 570                 575

Ala His Phe Arg Asp Gly Pro His Cys Val Ser Ser Cys Pro His Gly
            580                 585                 590

Val Leu Gly Ala Lys Gly Pro Ile Tyr Lys Tyr Pro Asp Val Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Thr Leu Val Leu Ile Gly Lys Thr
625                 630                 635                 640

His Leu Thr Met Ala Leu Thr Val Ile Ala Gly Leu Val Val Ile Phe
                645                 650                 655

Met Met Leu Gly Gly Thr Phe Leu Tyr Trp Arg Gly Arg Arg Ile Gln
            660                 665                 670

Asn Lys Arg Ala Met Arg Arg Tyr Leu Glu Arg Gly Glu Ser Ile Glu
        675                 680                 685

Pro Leu Asp Pro Ser Glu Lys Ala Asn Lys Val Leu Ala Arg Ile Phe
    690                 695                 700

Lys Glu Thr Glu Leu Arg Lys Leu Lys Val Leu Gly Ser Gly Val Phe
705                 710                 715                 720

Gly Thr Val His Lys Gly Val Trp Ile Pro Glu Gly Glu Ser Ile Lys
                725                 730                 735

Ile Pro Val Cys Ile Lys Val Ile Glu Asp Lys Ser Gly Arg Gln Ser
            740                 745                 750

Phe Gln Ala Val Thr Asp His Met Leu Ala Ile Gly Ser Leu Asp His
        755                 760                 765

Ala His Ile Val Arg Leu Leu Gly Leu Cys Pro Gly Ser Ser Leu Gln
    770                 775                 780

Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
```

```
                    805                 810                 815
Gln Ile Ala Lys Gly Met Tyr Tyr Leu Glu Glu His Gly Met Val His
            820                 825                 830

Arg Asn Leu Ala Ala Arg Asn Val Leu Leu Lys Ser Pro Ser Gln Val
            835                 840                 845

Gln Val Ala Asp Phe Gly Val Ala Asp Leu Leu Pro Pro Asp Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
            930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
            995                 1000                1005

Leu Asp Leu Asp Leu Asp Leu Glu Ala Glu Glu Asp Asn Leu Ala
    1010                1015                1020

Thr Thr Thr Leu Gly Ser Ala Leu Ser Leu Pro Val Gly Thr Leu
    1025                1030                1035

Asn Arg Pro Arg Gly Ser Gln Ser Leu Leu Ser Pro Ser Ser Gly
    1040                1045                1050

Tyr Met Pro Met Asn Gln Gly Asn Leu Gly Glu Ser Cys Gln Glu
    1055                1060                1065

Ser Ala Val Ser Gly Ser Ser Glu Arg Cys Pro Arg Pro Val Ser
    1070                1075                1080

Leu His Pro Met Pro Arg Gly Cys Leu Ala Ser Glu Ser Ser Glu
    1085                1090                1095

Gly His Val Thr Gly Ser Glu Ala Glu Leu Gln Glu Lys Val Ser
    1100                1105                1110

Met Cys Arg Ser Arg Ser Arg Ser Arg Ser Pro Arg Pro Arg Gly
    1115                1120                1125

Asp Ser Ala Tyr His Ser Gln Arg His Ser Leu Leu Thr Pro Val
    1130                1135                1140

Thr Pro Leu Ser Pro Pro Gly Leu Glu Glu Glu Asp Val Asn Gly
    1145                1150                1155

Tyr Val Met Pro Asp Thr His Leu Lys Gly Thr Pro Ser Ser Arg
    1160                1165                1170

Glu Gly Thr Leu Ser Ser Val Gly Leu Ser Ser Val Leu Gly Thr
    1175                1180                1185

Glu Glu Glu Asp Glu Asp Glu Glu Tyr Glu Tyr Met Asn Arg Arg
    1190                1195                1200

Arg Arg His Ser Pro Pro His Pro Pro Arg Pro Ser Ser Leu Glu
    1205                1210                1215
```

```
Glu  Leu  Gly  Tyr  Glu  Tyr  Met  Asp  Val  Gly  Ser  Asp  Leu  Ser  Ala
     1220                1225                1230

Ser  Leu  Gly  Ser  Thr  Gln  Ser  Cys  Pro  Leu  His  Pro  Val  Pro  Ile
     1235                1240                1245

Met  Pro  Thr  Ala  Gly  Thr  Thr  Pro  Asp  Glu  Asp  Tyr  Glu  Tyr  Met
     1250                1255                1260

Asn  Arg  Gln  Arg  Asp  Gly  Gly  Pro  Gly  Gly  Asp  Tyr  Ala  Ala
     1265                1270                1275

Met  Gly  Ala  Cys  Pro  Ala  Ser  Glu  Gln  Gly  Tyr  Glu  Glu  Met  Arg
     1280                1285                1290

Ala  Phe  Gln  Gly  Pro  Gly  His  Gln  Ala  Pro  His  Val  His  Tyr  Ala
     1295                1300                1305

Arg  Leu  Lys  Thr  Leu  Arg  Ser  Leu  Glu  Ala  Thr  Asp  Ser  Ala  Phe
     1310                1315                1320

Asp  Asn  Pro  Asp  Tyr  Trp  His  Ser  Arg  Leu  Phe  Pro  Lys  Ala  Asn
     1325                1330                1335

Ala  Gln  Arg  Thr
     1340
```

<210> SEQ ID NO 16
<211> LENGTH: 4020
<212> TYPE: DNA
<213> ORGANISM: Mus musculus
<220> FEATURE:
<221> NAME/KEY: CDS
<222> LOCATION: (1)..(4020)

<400> SEQUENCE: 16

```
atg agt gcg att ggg act ctg cag gtg ctg ggt ttc ctt ctc agc ctg      48
Met Ser Ala Ile Gly Thr Leu Gln Val Leu Gly Phe Leu Leu Ser Leu
 1               5                  10                  15 gcc cgg ggt tcc gag atg ggc aac tct cag gca gta tgt cct ggg act      96
Ala Arg Gly Ser Glu Met Gly Asn Ser Gln Ala Val Cys Pro Gly Thr
             20                  25                  30 cta aac ggg ctg agt gtg acc ggc gat gct gac aac cag tac cag aca     144
Leu Asn Gly Leu Ser Val Thr Gly Asp Ala Asp Asn Gln Tyr Gln Thr
         35                  40                  45 ctg tac aaa ctc tat gag aag tgt gag gtg gtc atg ggt aac ctg gag     192
Leu Tyr Lys Leu Tyr Glu Lys Cys Glu Val Val Met Gly Asn Leu Glu
     50                  55                  60 att gtg ctt acg gga cac aat gct gat ctt tcc ttc ctg caa tgg atc     240
Ile Val Leu Thr Gly His Asn Ala Asp Leu Ser Phe Leu Gln Trp Ile
 65                  70                  75                  80 cga gaa gtg aca ggc tat gta ctg gtg gcc atg aat gaa ttc tct gta     288
Arg Glu Val Thr Gly Tyr Val Leu Val Ala Met Asn Glu Phe Ser Val
                 85                  90                  95 ctg ccc tta cct aac ctc cga gtg gtc cgg gga acc cag gtc tac gat     336
Leu Pro Leu Pro Asn Leu Arg Val Val Arg Gly Thr Gln Val Tyr Asp
            100                 105                 110 ggg aag ttt gcc atc ttt gtc atg ttg aac tac aat acc aac tcc agc     384
Gly Lys Phe Ala Ile Phe Val Met Leu Asn Tyr Asn Thr Asn Ser Ser
        115                 120                 125 cat gct ctg cgc cag ctc cgg ttc act cag ctt act gag att ctg tta     432
His Ala Leu Arg Gln Leu Arg Phe Thr Gln Leu Thr Glu Ile Leu Leu
    130                 135                 140 ggg ggc gtt tac att gag aag aat gac aaa ctt tgc cac atg gat aca     480
Gly Gly Val Tyr Ile Glu Lys Asn Asp Lys Leu Cys His Met Asp Thr
145                 150                 155                 160 att gac tgg agg gac atc gtg agg gtt cca gac gct gag ata gtg gtg     528
Ile Asp Trp Arg Asp Ile Val Arg Val Pro Asp Ala Glu Ile Val Val
```

-continued

```
                        165                     170                     175
aag aac aac ggg ggg aac tgt cca ccc tgt cac gaa gtc tgc aag ggg        576
Lys Asn Asn Gly Gly Asn Cys Pro Pro Cys His Glu Val Cys Lys Gly
            180                     185                     190 cga tgc tgg ggg cct gga cca gaa gac tgc cag ata ttg acc aag acc        624
Arg Cys Trp Gly Pro Gly Pro Glu Asp Cys Gln Ile Leu Thr Lys Thr
            195                     200                     205 atc tgt gcc cct cag tgt aac ggt cgc tgc ttc ggg ccc aat cct aac        672
Ile Cys Ala Pro Gln Cys Asn Gly Arg Cys Phe Gly Pro Asn Pro Asn
210                     215                     220 cag tgc tgc cac gat gaa tgt gca ggt ggc tgt tct gga ccc cag gac        720
Gln Cys Cys His Asp Glu Cys Ala Gly Gly Cys Ser Gly Pro Gln Asp
225                     230                     235                     240 aca gat tgc ttc gcc tgc cga cac ttc aat gac agt ggt gcc tgt gtg        768
Thr Asp Cys Phe Ala Cys Arg His Phe Asn Asp Ser Gly Ala Cys Val
                245                     250                     255 ccc agg tgt cca gcg ccc ctt gtg tac aac aag cta acg ttc cag ctt        816
Pro Arg Cys Pro Ala Pro Leu Val Tyr Asn Lys Leu Thr Phe Gln Leu
                260                     265                     270 gag ccc aac ccc cat atc aag tat cag tac gga gga gtc tgt gtt gcc        864
Glu Pro Asn Pro His Ile Lys Tyr Gln Tyr Gly Gly Val Cys Val Ala
            275                     280                     285 agt tgt ccc cat aac ttt gtg gtg gat cag aca ttt tgt gtc agg gct        912
Ser Cys Pro His Asn Phe Val Val Asp Gln Thr Phe Cys Val Arg Ala
        290                     295                     300 tgt cct gct gac aag atg gaa gta gat aag aat gga ctc aag atg tgt        960
Cys Pro Ala Asp Lys Met Glu Val Asp Lys Asn Gly Leu Lys Met Cys
305                     310                     315                     320 gag cct tgc aga ggg ctg tgc cca aaa gcc tgt gag ggg acg ggc tct       1008
Glu Pro Cys Arg Gly Leu Cys Pro Lys Ala Cys Glu Gly Thr Gly Ser
                325                     330                     335 gga agc cgc tac cag acc gtg gac tct agc aat atc gat ggg ttc gtg       1056
Gly Ser Arg Tyr Gln Thr Val Asp Ser Ser Asn Ile Asp Gly Phe Val
            340                     345                     350 aac tgt acc aag atc ctg ggc aac ctg gac ttc ctc atc act ggc ctc       1104
Asn Cys Thr Lys Ile Leu Gly Asn Leu Asp Phe Leu Ile Thr Gly Leu
        355                     360                     365 aat ggt gac ccc tgg cac aag atc cct gca ctg gac ccg gaa aag ctc       1152
Asn Gly Asp Pro Trp His Lys Ile Pro Ala Leu Asp Pro Glu Lys Leu
370                     375                     380 aat gtt ttc agg aca gtc cgg gag att aca ggc tac cta aac atc cag       1200
Asn Val Phe Arg Thr Val Arg Glu Ile Thr Gly Tyr Leu Asn Ile Gln
385                     390                     395                     400 tcc tgg ccc cct cac atg cac aac ttc agt gtt ttt tcc aac ctg acg       1248
Ser Trp Pro Pro His Met His Asn Phe Ser Val Phe Ser Asn Leu Thr
                405                     410                     415 acc atc ggg ggc aga agc ctc tac aat cgg ggc ttc tcc ttg ttg atc       1296
Thr Ile Gly Gly Arg Ser Leu Tyr Asn Arg Gly Phe Ser Leu Leu Ile
            420                     425                     430 atg aag aac ttg aat gtc acg tct ctg ggc ttc cgg tcc ctg aag gaa       1344
Met Lys Asn Leu Asn Val Thr Ser Leu Gly Phe Arg Ser Leu Lys Glu
        435                     440                     445 att agt gct ggg cgt gtc tac ata agt gcc aat cag caa ctt tgt tac       1392
Ile Ser Ala Gly Arg Val Tyr Ile Ser Ala Asn Gln Gln Leu Cys Tyr
450                     455                     460 cac cac tct ctg aac tgg acc aga ctt ctg cgg ggg ccc gca gag gag       1440
His His Ser Leu Asn Trp Thr Arg Leu Leu Arg Gly Pro Ala Glu Glu
465                     470                     475                     480 aga ctt gac atc aag tac aac cgg cct ctg gga gaa tgc gtg gca gag       1488
Arg Leu Asp Ile Lys Tyr Asn Arg Pro Leu Gly Glu Cys Val Ala Glu
```

-continued

```
                485                 490                 495
ggc aaa gtg tgt gat cca ctg tgc tcc tct ggg gga tgc tgg ggc cca     1536
Gly Lys Val Cys Asp Pro Leu Cys Ser Ser Gly Gly Cys Trp Gly Pro
        500                 505                 510 ggc cct ggt cag tgc ttg tct tgt cga aac tac agc cgg gaa ggt gtc     1584
Gly Pro Gly Gln Cys Leu Ser Cys Arg Asn Tyr Ser Arg Glu Gly Val
        515                 520                 525 tgt gtg act cac tgc aac gtt ctg caa ggg gaa ccc cga gag ttt gtt     1632
Cys Val Thr His Cys Asn Val Leu Gln Gly Glu Pro Arg Glu Phe Val
530                 535                 540 cat gag gct cat tgc ttc tcc tgc cat cca gaa tgc cag ccc atg gag     1680
His Glu Ala His Cys Phe Ser Cys His Pro Glu Cys Gln Pro Met Glu
545                 550                 555                 560 ggc acc agc acg tgc aat ggc tcg ggc tcc gac gct tgt gct cga tgc     1728
Gly Thr Ser Thr Cys Asn Gly Ser Gly Ser Asp Ala Cys Ala Arg Cys
        565                 570                 575 gcc cat ttt cgt gat ggg ccc cac tgt gtg aac agc tgc ccc cat gga     1776
Ala His Phe Arg Asp Gly Pro His Cys Val Asn Ser Cys Pro His Gly
        580                 585                 590 atc cta ggt gcc aaa ggt cca atc tac aaa tat cca gat gct cag aat     1824
Ile Leu Gly Ala Lys Gly Pro Ile Tyr Lys Tyr Pro Asp Ala Gln Asn
        595                 600                 605 gag tgc cgg ccc tgc cac gag aac tgc acc caa ggg tgt aag gga cca     1872
Glu Cys Arg Pro Cys His Glu Asn Cys Thr Gln Gly Cys Lys Gly Pro
        610                 615                 620 gaa cta caa gac tgt tta ggc caa gca gag gta tta atg agc aaa cca     1920
Glu Leu Gln Asp Cys Leu Gly Gln Ala Glu Val Leu Met Ser Lys Pro
625                 630                 635                 640 cac ctg gtc ata gcg gtg aca gta gga ctg act gtg atc ttc ctg att     1968
His Leu Val Ile Ala Val Thr Val Gly Leu Thr Val Ile Phe Leu Ile
        645                 650                 655 ctg gga ggc tct ttt ctc tat tgg cgt gga cgc agg att cag aat aaa     2016
Leu Gly Gly Ser Phe Leu Tyr Trp Arg Gly Arg Arg Ile Gln Asn Lys
        660                 665                 670 agg gct atg aga cgc tac ttg gag cgg ggt gag agc atc gag cct ctg     2064
Arg Ala Met Arg Arg Tyr Leu Glu Arg Gly Glu Ser Ile Glu Pro Leu
        675                 680                 685 gac cca agc gag aag gca aac aaa gtc ttg gct aga atc ttc aaa gag     2112
Asp Pro Ser Glu Lys Ala Asn Lys Val Leu Ala Arg Ile Phe Lys Glu
690                 695                 700 aca gag ctg agg aaa ctt aag gtg ctt ggc tct ggt gtc ttt gga act     2160
Thr Glu Leu Arg Lys Leu Lys Val Leu Gly Ser Gly Val Phe Gly Thr
705                 710                 715                 720 gta cac aag ggg att tgg att ccc gag ggt gaa tcc atc aag att cca     2208
Val His Lys Gly Ile Trp Ile Pro Glu Gly Glu Ser Ile Lys Ile Pro
        725                 730                 735 gtc tgc att aaa gtc atc gag gac aag agt ggg cgg cag agt ttt cag     2256
Val Cys Ile Lys Val Ile Glu Asp Lys Ser Gly Arg Gln Ser Phe Gln
        740                 745                 750 gct gtg act gat cac atg ctg gcc gtc ggc agc ctg gac cat gcc cac     2304
Ala Val Thr Asp His Met Leu Ala Val Gly Ser Leu Asp His Ala His
        755                 760                 765 att gta cgg ctg ctg gga ctg tgc cca ggg tca tct ctg cag ctt gtc     2352
Ile Val Arg Leu Leu Gly Leu Cys Pro Gly Ser Ser Leu Gln Leu Val
770                 775                 780 act cag tac ttg cct ctg ggc tct ctc ctt gat cat gta aga cag cac     2400
Thr Gln Tyr Leu Pro Leu Gly Ser Leu Leu Asp His Val Arg Gln His
785                 790                 795                 800 cgt gag aca ctg gga cca cag ctg ctg ctc aac tgg gga gta caa att     2448
Arg Glu Thr Leu Gly Pro Gln Leu Leu Leu Asn Trp Gly Val Gln Ile
```

|  |  |
|---|---|
| 805 810 815 | |
| gcc aag ggt atg tat tac ctc gag gaa cac agc atg gtg cat agg gac<br>Ala Lys Gly Met Tyr Tyr Leu Glu Glu His Ser Met Val His Arg Asp<br>820 825 830 | 2496 |
| ctt gcg ctc cgg aat gtg atg ctt aag tca ccg agt caa gtc cag gtg<br>Leu Ala Leu Arg Asn Val Met Leu Lys Ser Pro Ser Gln Val Gln Val<br>835 840 845 | 2544 |
| gca gat ttt ggt gtg gct gac ttg ctg ccg cca gat gac aag cag tta<br>Ala Asp Phe Gly Val Ala Asp Leu Leu Pro Pro Asp Asp Lys Gln Leu<br>850 855 860 | 2592 |
| cta cac agt gag gcc aag act cca att aaa tgg atg gcc ctt gag agt<br>Leu His Ser Glu Ala Lys Thr Pro Ile Lys Trp Met Ala Leu Glu Ser<br>865 870 875 880 | 2640 |
| atc cac ttt ggg aaa tac aca cac cag agt gat gtc tgg agt tac ggt<br>Ile His Phe Gly Lys Tyr Thr His Gln Ser Asp Val Trp Ser Tyr Gly<br>885 890 895 | 2688 |
| gta acc gtt tgg gag ttg atg acc ttc ggg gca gag ccc tac gca ggg<br>Val Thr Val Trp Glu Leu Met Thr Phe Gly Ala Glu Pro Tyr Ala Gly<br>900 905 910 | 2736 |
| cta cga ctg gct gaa ata cca gac ctg ctg gag aag gga gag cgg tta<br>Leu Arg Leu Ala Glu Ile Pro Asp Leu Leu Glu Lys Gly Glu Arg Leu<br>915 920 925 | 2784 |
| gca cag ccc cag atc tgc acc att gac gtc tac atg gtc atg gtc aag<br>Ala Gln Pro Gln Ile Cys Thr Ile Asp Val Tyr Met Val Met Val Lys<br>930 935 940 | 2832 |
| tgt tgg atg att gac gag aat att cgc cca acc ttt aaa gaa ctg gcc<br>Cys Trp Met Ile Asp Glu Asn Ile Arg Pro Thr Phe Lys Glu Leu Ala<br>945 950 955 960 | 2880 |
| aat gag ttt acc agg atg gcc cgg gac cca cca agg tat ctg gtc atc<br>Asn Glu Phe Thr Arg Met Ala Arg Asp Pro Pro Arg Tyr Leu Val Ile<br>965 970 975 | 2928 |
| aag aga gcg agt ggg cct gga ata cct cct gca gca gag cca tct gct<br>Lys Arg Ala Ser Gly Pro Gly Ile Pro Pro Ala Ala Glu Pro Ser Ala<br>980 985 990 | 2976 |
| ctg agc acc aaa gag ttg cag gat gca gag ctg gag cca gac ctg gac<br>Leu Ser Thr Lys Glu Leu Gln Asp Ala Glu Leu Glu Pro Asp Leu Asp<br>995 1000 1005 | 3024 |
| ctc gac cta gac gtg gag gta gaa gag gag ggc ctg gcg acc aca<br>Leu Asp Leu Asp Val Glu Val Glu Glu Glu Gly Leu Ala Thr Thr<br>1010 1015 1020 | 3069 |
| ctg ggt tct gcc ctc agc ttg cct aca gga acg ctt acc cgg cca<br>Leu Gly Ser Ala Leu Ser Leu Pro Thr Gly Thr Leu Thr Arg Pro<br>1025 1030 1035 | 3114 |
| cgt ggg agc cag agt ctt tta agt cct tcg tct gga tac atg ccc<br>Arg Gly Ser Gln Ser Leu Leu Ser Pro Ser Ser Gly Tyr Met Pro<br>1040 1045 1050 | 3159 |
| atg aac cag agc aac ctt ggg gag gct tgt ctg gat tct gcg gtt<br>Met Asn Gln Ser Asn Leu Gly Glu Ala Cys Leu Asp Ser Ala Val<br>1055 1060 1065 | 3204 |
| ttg ggg ggt cgc gaa cag ttc tcc cgt ccc atc tct ctg cac ccg<br>Leu Gly Gly Arg Glu Gln Phe Ser Arg Pro Ile Ser Leu His Pro<br>1070 1075 1080 | 3249 |
| atc cca cgg ggg cgt caa acg tca gag tca tca gag ggc cat gtg<br>Ile Pro Arg Gly Arg Gln Thr Ser Glu Ser Ser Glu Gly His Val<br>1085 1090 1095 | 3294 |
| acg ggc tct gag gct gaa ctc caa gag aga gta tca atg tgt agg<br>Thr Gly Ser Glu Ala Glu Leu Gln Glu Arg Val Ser Met Cys Arg<br>1100 1105 1110 | 3339 |
| agc cgg agc cgg agc cgg agc cca cgg cca cgt ggg gac agt gcc<br>Ser Arg Ser Arg Ser Arg Ser Pro Arg Pro Arg Gly Asp Ser Ala | 3384 |

| | | |
|---|---|---|
| tac cat tcg cag cga cac agc ctg ctt act ccc gtc acc ccg ctc<br>Tyr His Ser Gln Arg His Ser Leu Leu Thr Pro Val Thr Pro Leu<br>                  1130                        1135                      1140 | 3429 |
| tcc cca cca ggg tta gag gaa gag gat ggc aat ggt tat gtc atg<br>Ser Pro Pro Gly Leu Glu Glu Glu Asp Gly Asn Gly Tyr Val Met<br>1145                      1150                      1155 | 3474 |
| cca gat acg cac ctc aga ggt aca tcc tct tcc cgg gaa ggc acc<br>Pro Asp Thr His Leu Arg Gly Thr Ser Ser Ser Arg Glu Gly Thr<br>1160                      1165                      1170 | 3519 |
| ctt tcg tca gta ggt ctc agt tct gtg ctg ggt acc gaa gag gaa<br>Leu Ser Ser Val Gly Leu Ser Ser Val Leu Gly Thr Glu Glu Glu<br>1175                      1180                      1185 | 3564 |
| gat gaa gat gag gag tat gaa tac atg aac cgg aag agg agg ggt<br>Asp Glu Asp Glu Glu Tyr Glu Tyr Met Asn Arg Lys Arg Arg Gly<br>1190                      1195                      1200 | 3609 |
| agc ccg gct cgg ccc ccc aga cct ggt tcc ctg gaa gag ctg ggc<br>Ser Pro Ala Arg Pro Pro Arg Pro Gly Ser Leu Glu Glu Leu Gly<br>1205                      1210                      1215 | 3654 |
| tat gag tac atg gat gtg ggt tca gac ctc agt gct tct ctg ggc<br>Tyr Glu Tyr Met Asp Val Gly Ser Asp Leu Ser Ala Ser Leu Gly<br>1220                      1225                      1230 | 3699 |
| agt acg cag agt tgc cca ctc cat ccc atg gcc atc gtg ccc tct<br>Ser Thr Gln Ser Cys Pro Leu His Pro Met Ala Ile Val Pro Ser<br>1235                      1240                      1245 | 3744 |
| gct ggc acg act cca gat gag gac tat gaa tac atg aac cgc agg<br>Ala Gly Thr Thr Pro Asp Glu Asp Tyr Glu Tyr Met Asn Arg Arg<br>1250                      1255                      1260 | 3789 |
| cgt ggt gcg ggc ggt tcc gga ggg gat tat gca gct atg ggg gcc<br>Arg Gly Ala Gly Gly Ser Gly Gly Asp Tyr Ala Ala Met Gly Ala<br>1265                      1270                      1275 | 3834 |
| tgc cca gca gct gaa caa ggg tat gag gaa atg cga gct ttc cag<br>Cys Pro Ala Ala Glu Gln Gly Tyr Glu Glu Met Arg Ala Phe Gln<br>1280                      1285                      1290 | 3879 |
| ggg cct gga cat caa gcc ccc cat gtt cgt tat gcc cgc ctc aaa<br>Gly Pro Gly His Gln Ala Pro His Val Arg Tyr Ala Arg Leu Lys<br>1295                      1300                      1305 | 3924 |
| act ctg cgt agt tta gaa gcc act gac tcc gcc ttt gac aac ccc<br>Thr Leu Arg Ser Leu Glu Ala Thr Asp Ser Ala Phe Asp Asn Pro<br>1310                      1315                      1320 | 3969 |
| gat tac tgg cat agc agg ctt ttc cct aag gct aac gcc cag aga<br>Asp Tyr Trp His Ser Arg Leu Phe Pro Lys Ala Asn Ala Gln Arg<br>1325                      1330                      1335 | 4014 |
| att tga<br>Ile | 4020 |

<210> SEQ ID NO 17
<211> LENGTH: 1339
<212> TYPE: PRT
<213> ORGANISM: Mus musculus

<400> SEQUENCE: 17

Met Ser Ala Ile Gly Thr Leu Gln Val Leu Gly Phe Leu Leu Ser Leu
1                  5                      10                    15

Ala Arg Gly Ser Glu Met Gly Asn Ser Gln Ala Val Cys Pro Gly Thr
                20                    25                    30

Leu Asn Gly Leu Ser Val Thr Gly Asp Ala Asp Asn Gln Tyr Gln Thr
          35                    40                    45

Leu Tyr Lys Leu Tyr Glu Lys Cys Glu Val Val Met Gly Asn Leu Glu
50                    55                    60

```
Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Val
                85                  90                  95

Leu Pro Leu Pro Asn Leu Arg Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Phe Thr Gln Leu Thr Glu Ile Leu Leu
            130                 135                 140

Gly Gly Val Tyr Ile Glu Lys Asn Asp Lys Leu Cys His Met Asp Thr
145                 150                 155                 160

Ile Asp Trp Arg Asp Ile Val Arg Val Pro Asp Ala Glu Ile Val Val
                165                 170                 175

Lys Asn Asn Gly Gly Asn Cys Pro Pro Cys His Glu Val Cys Lys Gly
            180                 185                 190

Arg Cys Trp Gly Pro Gly Pro Glu Asp Cys Gln Ile Leu Thr Lys Thr
            195                 200                 205

Ile Cys Ala Pro Gln Cys Asn Gly Arg Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Ala Pro Leu Val Tyr Asn Lys Leu Thr Phe Gln Leu
            260                 265                 270

Glu Pro Asn Pro His Ile Lys Tyr Gln Tyr Gly Gly Val Cys Val Ala
            275                 280                 285

Ser Cys Pro His Asn Phe Val Val Asp Gln Thr Phe Cys Val Arg Ala
            290                 295                 300

Cys Pro Ala Asp Lys Met Glu Val Asp Lys Asn Gly Leu Lys Met Cys
305                 310                 315                 320

Glu Pro Cys Arg Gly Leu Cys Pro Lys Ala Cys Glu Gly Thr Gly Ser
                325                 330                 335

Gly Ser Arg Tyr Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
                405                 410                 415

Thr Ile Gly Gly Arg Ser Leu Tyr Asn Arg Gly Phe Ser Leu Leu Ile
            420                 425                 430

Met Lys Asn Leu Asn Val Thr Ser Leu Gly Phe Arg Ser Leu Lys Glu
            435                 440                 445

Ile Ser Ala Gly Arg Val Tyr Ile Ser Ala Asn Gln Gln Leu Cys Tyr
            450                 455                 460

His His Ser Leu Asn Trp Thr Arg Leu Leu Arg Gly Pro Ala Glu Glu
465                 470                 475                 480

Arg Leu Asp Ile Lys Tyr Asn Arg Pro Leu Gly Glu Cys Val Ala Glu
```

```
                485                 490                 495
Gly Lys Val Cys Asp Pro Leu Cys Ser Ser Gly Gly Cys Trp Gly Pro
            500                 505                 510

Gly Pro Gly Gln Cys Leu Ser Cys Arg Asn Tyr Ser Arg Glu Gly Val
        515                 520                 525

Cys Val Thr His Cys Asn Val Leu Gln Gly Glu Pro Arg Glu Phe Val
    530                 535                 540

His Glu Ala His Cys Phe Ser Cys His Pro Glu Cys Gln Pro Met Glu
545                 550                 555                 560

Gly Thr Ser Thr Cys Asn Gly Ser Gly Ser Asp Ala Cys Ala Arg Cys
                565                 570                 575

Ala His Phe Arg Asp Gly Pro His Cys Val Asn Ser Cys Pro His Gly
            580                 585                 590

Ile Leu Gly Ala Lys Gly Pro Ile Tyr Lys Tyr Pro Asp Ala Gln Asn
        595                 600                 605

Glu Cys Arg Pro Cys His Glu Asn Cys Thr Gln Gly Cys Lys Gly Pro
    610                 615                 620

Glu Leu Gln Asp Cys Leu Gly Gln Ala Glu Val Leu Met Ser Lys Pro
625                 630                 635                 640

His Leu Val Ile Ala Val Thr Val Gly Leu Thr Val Ile Phe Leu Ile
                645                 650                 655

Leu Gly Gly Ser Phe Leu Tyr Trp Arg Gly Arg Arg Ile Gln Asn Lys
            660                 665                 670

Arg Ala Met Arg Arg Tyr Leu Glu Arg Gly Glu Ser Ile Glu Pro Leu
        675                 680                 685

Asp Pro Ser Glu Lys Ala Asn Lys Val Leu Ala Arg Ile Phe Lys Glu
    690                 695                 700

Thr Glu Leu Arg Lys Leu Lys Val Leu Gly Ser Gly Val Phe Gly Thr
705                 710                 715                 720

Val His Lys Gly Ile Trp Ile Pro Glu Gly Glu Ser Ile Lys Ile Pro
                725                 730                 735

Val Cys Ile Lys Val Ile Glu Asp Lys Ser Gly Arg Gln Ser Phe Gln
            740                 745                 750

Ala Val Thr Asp His Met Leu Ala Val Gly Ser Leu Asp His Ala His
        755                 760                 765

Ile Val Arg Leu Leu Gly Leu Cys Pro Gly Ser Ser Leu Gln Leu Val
    770                 775                 780

Thr Gln Tyr Leu Pro Leu Gly Ser Leu Leu Asp His Val Arg Gln His
785                 790                 795                 800

Arg Glu Thr Leu Gly Pro Gln Leu Leu Leu Asn Trp Gly Val Gln Ile
                805                 810                 815

Ala Lys Gly Met Tyr Tyr Leu Glu Glu His Ser Met Val His Arg Asp
            820                 825                 830

Leu Ala Leu Arg Asn Val Met Leu Lys Ser Pro Ser Gln Val Gln Val
        835                 840                 845

Ala Asp Phe Gly Val Ala Asp Leu Leu Pro Pro Asp Lys Gln Leu
    850                 855                 860

Leu His Ser Glu Ala Lys Thr Pro Ile Lys Trp Met Ala Leu Glu Ser
865                 870                 875                 880

Ile His Phe Gly Lys Tyr Thr His Gln Ser Asp Val Trp Ser Tyr Gly
                885                 890                 895

Val Thr Val Trp Glu Leu Met Thr Phe Gly Ala Glu Pro Tyr Ala Gly
            900                 905                 910
```

-continued

```
Leu Arg Leu Ala Glu Ile Pro Asp Leu Leu Glu Lys Gly Glu Arg Leu
        915                 920                 925

Ala Gln Pro Gln Ile Cys Thr Ile Asp Val Tyr Met Val Met Val Lys
    930                 935                 940

Cys Trp Met Ile Asp Glu Asn Ile Arg Pro Thr Phe Lys Glu Leu Ala
945                 950                 955                 960

Asn Glu Phe Thr Arg Met Ala Arg Asp Pro Pro Arg Tyr Leu Val Ile
                965                 970                 975

Lys Arg Ala Ser Gly Pro Gly Ile Pro Pro Ala Ala Glu Pro Ser Ala
            980                 985                 990

Leu Ser Thr Lys Glu Leu Gln Asp Ala Glu Leu Glu Pro Asp Leu Asp
        995                1000                1005

Leu Asp Leu Asp Val Glu Val Glu Glu Glu Gly Leu Ala Thr Thr
    1010                1015                1020

Leu Gly Ser Ala Leu Ser Leu Pro Thr Gly Thr Leu Thr Arg Pro
    1025                1030                1035

Arg Gly Ser Gln Ser Leu Leu Ser Pro Ser Ser Gly Tyr Met Pro
    1040                1045                1050

Met Asn Gln Ser Asn Leu Gly Glu Ala Cys Leu Asp Ser Ala Val
    1055                1060                1065

Leu Gly Gly Arg Glu Gln Phe Ser Arg Pro Ile Ser Leu His Pro
    1070                1075                1080

Ile Pro Arg Gly Arg Gln Thr Ser Glu Ser Ser Glu Gly His Val
    1085                1090                1095

Thr Gly Ser Glu Ala Glu Leu Gln Glu Arg Val Ser Met Cys Arg
    1100                1105                1110

Ser Arg Ser Arg Ser Arg Ser Pro Arg Pro Arg Gly Asp Ser Ala
    1115                1120                1125

Tyr His Ser Gln Arg His Ser Leu Leu Thr Pro Val Thr Pro Leu
    1130                1135                1140

Ser Pro Pro Gly Leu Glu Glu Glu Asp Gly Asn Gly Tyr Val Met
    1145                1150                1155

Pro Asp Thr His Leu Arg Gly Thr Ser Ser Ser Arg Glu Gly Thr
    1160                1165                1170

Leu Ser Ser Val Gly Leu Ser Ser Val Leu Gly Thr Glu Glu Glu
    1175                1180                1185

Asp Glu Asp Glu Glu Tyr Glu Tyr Met Asn Arg Lys Arg Arg Gly
    1190                1195                1200

Ser Pro Ala Arg Pro Arg Pro Gly Ser Leu Glu Glu Leu Gly
    1205                1210                1215

Tyr Glu Tyr Met Asp Val Gly Ser Asp Leu Ser Ala Ser Leu Gly
    1220                1225                1230

Ser Thr Gln Ser Cys Pro Leu His Pro Met Ala Ile Val Pro Ser
    1235                1240                1245

Ala Gly Thr Thr Pro Asp Glu Asp Tyr Glu Tyr Met Asn Arg Arg
    1250                1255                1260

Arg Gly Ala Gly Gly Ser Gly Gly Asp Tyr Ala Ala Met Gly Ala
    1265                1270                1275

Cys Pro Ala Ala Glu Gln Gly Tyr Glu Glu Met Arg Ala Phe Gln
    1280                1285                1290

Gly Pro Gly His Gln Ala Pro His Val Arg Tyr Ala Arg Leu Lys
    1295                1300                1305

Thr Leu Arg Ser Leu Glu Ala Thr Asp Ser Ala Phe Asp Asn Pro
    1310                1315                1320
```

```
Asp Tyr Trp His Ser Arg Leu Phe Pro Lys Ala Asn Ala Gln Arg
    1325            1330                1335

Ile

<210> SEQ ID NO 18
<211> LENGTH: 5484
<212> TYPE: DNA
<213> ORGANISM: Homo sapiens
<220> FEATURE:
<221> NAME/KEY: CDS
<222> LOCATION: (34)..(3960)

<400> SEQUENCE: 18
aattgtcagc acgggatctg agacttccaa aaa atg aag ccg gcg aca gga ctt       54
                                   Met Lys Pro Ala Thr Gly Leu
                                     1               5 tgg gtc tgg gtg agc ctt ctc gtg gcg gcg ggg acc gtc cag ccc agc      102
Trp Val Trp Val Ser Leu Leu Val Ala Ala Gly Thr Val Gln Pro Ser
         10                  15                  20 gat tct cag tca gtg tgt gca gga acg gag aat aaa ctg agc tct ctc      150
Asp Ser Gln Ser Val Cys Ala Gly Thr Glu Asn Lys Leu Ser Ser Leu
     25                  30                  35 tct gac ctg gaa cag cag tac cga gcc ttg cgc aag tac tat gaa aac      198
Ser Asp Leu Glu Gln Gln Tyr Arg Ala Leu Arg Lys Tyr Tyr Glu Asn
 40                  45                  50                  55 tgt gag gtt gtc atg ggc aac ctg gag ata acc agc att gag cac aac      246
Cys Glu Val Val Met Gly Asn Leu Glu Ile Thr Ser Ile Glu His Asn
                 60                  65                  70 cgg gac ctc tcc ttc ctg cgg tct gtt cga gaa gtc aca ggc tac gtg      294
Arg Asp Leu Ser Phe Leu Arg Ser Val Arg Glu Val Thr Gly Tyr Val
             75                  80                  85 tta gtg gct ctt aat cag ttt cgt tac ctg cct ctg gag aat tta cgc      342
Leu Val Ala Leu Asn Gln Phe Arg Tyr Leu Pro Leu Glu Asn Leu Arg
         90                  95                 100 att att cgt ggg aca aaa ctt tat gag gat cga tat gcc ttg gca ata      390
Ile Ile Arg Gly Thr Lys Leu Tyr Glu Asp Arg Tyr Ala Leu Ala Ile
     105                 110                 115 ttt tta aac tac aga aaa gat gga aac ttt gga ctt caa gaa ctt gga      438
Phe Leu Asn Tyr Arg Lys Asp Gly Asn Phe Gly Leu Gln Glu Leu Gly
120                 125                 130                 135 tta aag aac ttg aca gaa atc cta aat ggt gga gtc tat gta gac cag      486
Leu Lys Asn Leu Thr Glu Ile Leu Asn Gly Gly Val Tyr Val Asp Gln
                 140                 145                 150 aac aaa ttc ctt tgt tat gca gac acc att cat tgg caa gat att gtt      534
Asn Lys Phe Leu Cys Tyr Ala Asp Thr Ile His Trp Gln Asp Ile Val
             155                 160                 165 cgg aac cca tgg cct tcc aac ttg act ctt gtg tca aca aat ggt agt      582
Arg Asn Pro Trp Pro Ser Asn Leu Thr Leu Val Ser Thr Asn Gly Ser
         170                 175                 180 tca gga tgt gga cgt tgc cat aag tcc tgt act ggc cgt tgc tgg gga      630
Ser Gly Cys Gly Arg Cys His Lys Ser Cys Thr Gly Arg Cys Trp Gly
     185                 190                 195 ccc aca gaa aat cat tgc cag act ttg aca agg acg gtg tgt gca gaa      678
Pro Thr Glu Asn His Cys Gln Thr Leu Thr Arg Thr Val Cys Ala Glu
200                 205                 210                 215 caa tgt gac ggc aga tgc tac gga cct tac gtc agt gac tgc tgc cat      726
Gln Cys Asp Gly Arg Cys Tyr Gly Pro Tyr Val Ser Asp Cys Cys His
                 220                 225                 230 cga gaa tgt gct gga ggc tgc tca gga cct aag gac aca gac tgc ttt      774
Arg Glu Cys Ala Gly Gly Cys Ser Gly Pro Lys Asp Thr Asp Cys Phe
             235                 240                 245
```

```
gcc tgc atg aat ttc aat gac agt gga gca tgt gtt act cag tgt ccc      822
Ala Cys Met Asn Phe Asn Asp Ser Gly Ala Cys Val Thr Gln Cys Pro
        250                 255                 260 caa acc ttt gtc tac aat cca acc acc ttt caa ctg gag cac aat ttc      870
Gln Thr Phe Val Tyr Asn Pro Thr Thr Phe Gln Leu Glu His Asn Phe
265                 270                 275 aat gca aag tac aca tat gga gca ttc tgt gtc aag aaa tgt cca cat      918
Asn Ala Lys Tyr Thr Tyr Gly Ala Phe Cys Val Lys Lys Cys Pro His
280                 285                 290                 295 aac ttt gtg gta gat tcc agt tct tgt gtg cgt gcc tgc cct agt tcc      966
Asn Phe Val Val Asp Ser Ser Ser Cys Val Arg Ala Cys Pro Ser Ser
                300                 305                 310 aag atg gaa gta gaa gaa aat ggg att aaa atg tgt aaa cct tgc act     1014
Lys Met Glu Val Glu Glu Asn Gly Ile Lys Met Cys Lys Pro Cys Thr
            315                 320                 325 gac att tgc cca aaa gct tgt gat ggc att ggc aca gga tca ttg atg     1062
Asp Ile Cys Pro Lys Ala Cys Asp Gly Ile Gly Thr Gly Ser Leu Met
        330                 335                 340 tca gct cag act gtg gat tcc agt aac att gac aaa ttc ata aac tgt     1110
Ser Ala Gln Thr Val Asp Ser Ser Asn Ile Asp Lys Phe Ile Asn Cys
345                 350                 355 acc aag atc aat ggg aat ttg atc ttt cta gtc act ggt att cat ggg     1158
Thr Lys Ile Asn Gly Asn Leu Ile Phe Leu Val Thr Gly Ile His Gly
360                 365                 370                 375 gac cct tac aat gca att gaa gcc ata gac cca gag aaa ctg aac gtc     1206
Asp Pro Tyr Asn Ala Ile Glu Ala Ile Asp Pro Glu Lys Leu Asn Val
                380                 385                 390 ttt cgg aca gtc aga gag ata aca ggt ttc ctg aac ata cag tca tgg     1254
Phe Arg Thr Val Arg Glu Ile Thr Gly Phe Leu Asn Ile Gln Ser Trp
            395                 400                 405 cca cca aac atg act gac ttc agt gtt ttt tct aac ctg gtg acc att     1302
Pro Pro Asn Met Thr Asp Phe Ser Val Phe Ser Asn Leu Val Thr Ile
        410                 415                 420 ggt gga aga gta ctc tat agt ggc ctg tcc ttg ctt atc ctc aag caa     1350
Gly Gly Arg Val Leu Tyr Ser Gly Leu Ser Leu Leu Ile Leu Lys Gln
425                 430                 435 cag ggc atc acc tct cta cag ttc cag tcc ctg aag gaa atc agc gca     1398
Gln Gly Ile Thr Ser Leu Gln Phe Gln Ser Leu Lys Glu Ile Ser Ala
440                 445                 450                 455 gga aac atc tat att act gac aac agc aac ctg tgt tat tat cat acc     1446
Gly Asn Ile Tyr Ile Thr Asp Asn Ser Asn Leu Cys Tyr Tyr His Thr
                460                 465                 470 att aac tgg aca aca ctc ttc agc aca atc aac cag aga ata gta atc     1494
Ile Asn Trp Thr Thr Leu Phe Ser Thr Ile Asn Gln Arg Ile Val Ile
            475                 480                 485 cgg gac aac aga aaa gct gaa aat tgt act gct gaa gga atg gtg tgc     1542
Arg Asp Asn Arg Lys Ala Glu Asn Cys Thr Ala Glu Gly Met Val Cys
        490                 495                 500 aac cat ctg tgt tcc agt gat ggc tgt tgg gga cct ggg cca gac caa     1590
Asn His Leu Cys Ser Ser Asp Gly Cys Trp Gly Pro Gly Pro Asp Gln
505                 510                 515 tgt ctg tcg tgt cgc cgc ttc agt aga gga agg atc tgc ata gag tct     1638
Cys Leu Ser Cys Arg Arg Phe Ser Arg Gly Arg Ile Cys Ile Glu Ser
520                 525                 530                 535 tgt aac ctc tat gat ggt gaa ttt cgg gag ttt gag aat ggc tcc atc     1686
Cys Asn Leu Tyr Asp Gly Glu Phe Arg Glu Phe Glu Asn Gly Ser Ile
                540                 545                 550 tgt gtg gag tgt gac ccc cag tgt gag aag atg gaa gat ggc ctc ctc     1734
Cys Val Glu Cys Asp Pro Gln Cys Glu Lys Met Glu Asp Gly Leu Leu
            555                 560                 565
```

```
aca tgc cat gga ccg ggt cct gac aac tgt aca aag tgc tct cat ttt      1782
Thr Cys His Gly Pro Gly Pro Asp Asn Cys Thr Lys Cys Ser His Phe
            570                 575                 580 aaa gat ggc cca aac tgt gtg gaa aaa tgt cca gat ggc tta cag ggg      1830
Lys Asp Gly Pro Asn Cys Val Glu Lys Cys Pro Asp Gly Leu Gln Gly
585                 590                 595 gca aac agt ttc att ttc aag tat gct gat cca gat cgg gag tgc cac      1878
Ala Asn Ser Phe Ile Phe Lys Tyr Ala Asp Pro Asp Arg Glu Cys His
600                 605                 610                 615 cca tgc cat cca aac tgc acc caa ggg tgt aac ggt ccc act agt cat      1926
Pro Cys His Pro Asn Cys Thr Gln Gly Cys Asn Gly Pro Thr Ser His
            620                 625                 630 gac tgc att tac tac cca tgg acg ggc cat tcc act tta cca caa cat      1974
Asp Cys Ile Tyr Tyr Pro Trp Thr Gly His Ser Thr Leu Pro Gln His
            635                 640                 645 gct aga act ccc ctg att gca gct gga gta att ggt ggg ctc ttc att      2022
Ala Arg Thr Pro Leu Ile Ala Ala Gly Val Ile Gly Gly Leu Phe Ile
            650                 655                 660 ctg gtc att gtg ggt ctg aca ttt gct gtt tat gtt aga agg aag agc      2070
Leu Val Ile Val Gly Leu Thr Phe Ala Val Tyr Val Arg Arg Lys Ser
665                 670                 675 atc aaa aag aaa aga gcc ttg aga aga ttc ttg gaa aca gag ttg gtg      2118
Ile Lys Lys Lys Arg Ala Leu Arg Arg Phe Leu Glu Thr Glu Leu Val
680                 685                 690                 695 gaa cca tta act ccc agt ggc aca gca ccc aat caa gct caa ctt cgt      2166
Glu Pro Leu Thr Pro Ser Gly Thr Ala Pro Asn Gln Ala Gln Leu Arg
            700                 705                 710 att ttg aaa gaa act gag ctg aag agg gta aaa gtc ctt ggc tca ggt      2214
Ile Leu Lys Glu Thr Glu Leu Lys Arg Val Lys Val Leu Gly Ser Gly
            715                 720                 725 gct ttt gga acg gtt tat aaa ggt att tgg gta cct gaa gga gaa act      2262
Ala Phe Gly Thr Val Tyr Lys Gly Ile Trp Val Pro Glu Gly Glu Thr
            730                 735                 740 gtg aag att cct gtg gct att aag att ctt aat gag aca act ggt ccc      2310
Val Lys Ile Pro Val Ala Ile Lys Ile Leu Asn Glu Thr Thr Gly Pro
745                 750                 755 aag gca aat gtg gag ttc atg gat gaa gct ctg atc atg gca agt atg      2358
Lys Ala Asn Val Glu Phe Met Asp Glu Ala Leu Ile Met Ala Ser Met
760                 765                 770                 775 gat cat cca cac cta gtc cgg ttg ctg ggt gtg tgt ctg agc cca acc      2406
Asp His Pro His Leu Val Arg Leu Leu Gly Val Cys Leu Ser Pro Thr
            780                 785                 790 atc cag ctg gtt act caa ctt atg ccc cat ggc tgc ctg ttg gag tat      2454
Ile Gln Leu Val Thr Gln Leu Met Pro His Gly Cys Leu Leu Glu Tyr
            795                 800                 805 gtc cac gag cac aag gat aac att gga tca caa ctg ctg ctt aac tgg      2502
Val His Glu His Lys Asp Asn Ile Gly Ser Gln Leu Leu Leu Asn Trp
            810                 815                 820 tgt gtc cag ata gct aag gga atg atg tac ctg gaa gaa aga cga ctc      2550
Cys Val Gln Ile Ala Lys Gly Met Met Tyr Leu Glu Glu Arg Arg Leu
825                 830                 835 gtt cat cgg gat ttg gca gcc cgt aat gtc tta gtg aaa tct cca aac      2598
Val His Arg Asp Leu Ala Ala Arg Asn Val Leu Val Lys Ser Pro Asn
840                 845                 850                 855 cat gtg aaa atc aca gat ttt ggg cta gcc aga ctc ttg gaa gga gat      2646
His Val Lys Ile Thr Asp Phe Gly Leu Ala Arg Leu Leu Glu Gly Asp
            860                 865                 870 gaa aaa gag tac aat gct gat gga gga aag atg cca att aaa tgg atg      2694
Glu Lys Glu Tyr Asn Ala Asp Gly Gly Lys Met Pro Ile Lys Trp Met
            875                 880                 885
```

```
gct ctg gag tgt ata cat tac agg aaa ttc acc cat cag agt gac gtt      2742
Ala Leu Glu Cys Ile His Tyr Arg Lys Phe Thr His Gln Ser Asp Val
        890                 895                 900 tgg agc tat gga gtt act ata tgg gaa ctg atg acc ttt gga gga aaa      2790
Trp Ser Tyr Gly Val Thr Ile Trp Glu Leu Met Thr Phe Gly Gly Lys
    905                 910                 915 ccc tat gat gga att cca acg cga gaa atc cct gat tta tta gag aaa      2838
Pro Tyr Asp Gly Ile Pro Thr Arg Glu Ile Pro Asp Leu Leu Glu Lys
920                 925                 930                 935 gga gaa cgt ttg cct cag cct ccc atc tgc act att gac gtt tac atg      2886
Gly Glu Arg Leu Pro Gln Pro Pro Ile Cys Thr Ile Asp Val Tyr Met
                940                 945                 950 gtc atg gtc aaa tgt tgg atg att gat gct gac agt aga cct aaa ttt      2934
Val Met Val Lys Cys Trp Met Ile Asp Ala Asp Ser Arg Pro Lys Phe
            955                 960                 965 aag gaa ctg gct gct gag ttt tca agg atg gct cga gac cct caa aga      2982
Lys Glu Leu Ala Ala Glu Phe Ser Arg Met Ala Arg Asp Pro Gln Arg
        970                 975                 980 tac cta gtt att cag ggt gat gat cgt atg aag ctt ccc agt cca aat      3030
Tyr Leu Val Ile Gln Gly Asp Asp Arg Met Lys Leu Pro Ser Pro Asn
    985                 990                 995 gac agc aag ttc ttt cag aat ctc ttg gat gaa gag gat ttg gaa           3075
Asp Ser Lys Phe Phe Gln Asn Leu Leu Asp Glu Glu Asp Leu Glu
1000                1005                1010 gat atg atg gat gct gag gag tac ttg gtc cct cag gct ttc aac           3120
Asp Met Met Asp Ala Glu Glu Tyr Leu Val Pro Gln Ala Phe Asn
        1015                1020                1025 atc cca cct ccc atc tat act tcc aga gca aga att gac tcg aat           3165
Ile Pro Pro Pro Ile Tyr Thr Ser Arg Ala Arg Ile Asp Ser Asn
1030                1035                1040 agg agt gaa att gga cac agc cct cct cct gcc tac acc ccc atg           3210
Arg Ser Glu Ile Gly His Ser Pro Pro Pro Ala Tyr Thr Pro Met
1045                1050                1055 tca gga aac cag ttt gta tac cga gat gga ggt ttt gct gct gaa           3255
Ser Gly Asn Gln Phe Val Tyr Arg Asp Gly Gly Phe Ala Ala Glu
1060                1065                1070 caa gga gtg tct gtg ccc tac aga gcc cca act agc aca att cca           3300
Gln Gly Val Ser Val Pro Tyr Arg Ala Pro Thr Ser Thr Ile Pro
1075                1080                1085 gaa gct cct gtg gca cag ggt gct act gct gag att ttt gat gac           3345
Glu Ala Pro Val Ala Gln Gly Ala Thr Ala Glu Ile Phe Asp Asp
1090                1095                1100 tcc tgc tgt aat ggc acc cta cgc aag cca gtg gca ccc cat gtc           3390
Ser Cys Cys Asn Gly Thr Leu Arg Lys Pro Val Ala Pro His Val
1105                1110                1115 caa gag gac agt agc acc cag agg tac agt gct gac ccc acc gtg           3435
Gln Glu Asp Ser Ser Thr Gln Arg Tyr Ser Ala Asp Pro Thr Val
1120                1125                1130 ttt gcc cca gaa cgg agc cca cga gga gag ctg gat gag gaa ggt           3480
Phe Ala Pro Glu Arg Ser Pro Arg Gly Glu Leu Asp Glu Glu Gly
1135                1140                1145 tac atg act cct atg cga gac aaa ccc aaa caa gaa tac ctg aat           3525
Tyr Met Thr Pro Met Arg Asp Lys Pro Lys Gln Glu Tyr Leu Asn
1150                1155                1160 cca gtg gag gag aac cct ttt gtt tct cgg aga aaa aat gga gac           3570
Pro Val Glu Glu Asn Pro Phe Val Ser Arg Arg Lys Asn Gly Asp
1165                1170                1175 ctt caa gca ttg gat aat ccc gaa tat cac aat gca tcc aat ggt           3615
Leu Gln Ala Leu Asp Asn Pro Glu Tyr His Asn Ala Ser Asn Gly
1180                1185                1190
```

| | | | | | | | | | | | | | | |
|---|---|---|---|---|---|---|---|---|---|---|---|---|---|---|
| cca | ccc | aag | gcc | gag | gat | gag | tat | gtg | aat | gag | cca | ctg | tac | ctc | 3660 |
| Pro | Pro | Lys | Ala | Glu | Asp | Glu | Tyr | Val | Asn | Glu | Pro | Leu | Tyr | Leu | |
| 1195 | | | | 1200 | | | | | 1205 | | | | | | |
| aac | acc | ttt | gcc | aac | acc | ttg | gga | aaa | gct | gag | tac | ctg | aag | aac | 3705 |
| Asn | Thr | Phe | Ala | Asn | Thr | Leu | Gly | Lys | Ala | Glu | Tyr | Leu | Lys | Asn | |
| 1210 | | | | 1215 | | | | | 1220 | | | | | | |
| aac | ata | ctg | tca | atg | cca | gag | aag | gcc | aag | aaa | gcg | ttt | gac | aac | 3750 |
| Asn | Ile | Leu | Ser | Met | Pro | Glu | Lys | Ala | Lys | Lys | Ala | Phe | Asp | Asn | |
| 1225 | | | | 1230 | | | | | 1235 | | | | | | |
| cct | gac | tac | tgg | aac | cac | agc | ctg | cca | cct | cgg | agc | acc | ctt | cag | 3795 |
| Pro | Asp | Tyr | Trp | Asn | His | Ser | Leu | Pro | Pro | Arg | Ser | Thr | Leu | Gln | |
| 1240 | | | | 1245 | | | | | 1250 | | | | | | |
| cac | cca | gac | tac | ctg | cag | gag | tac | agc | aca | aaa | tat | ttt | tat | aaa | 3840 |
| His | Pro | Asp | Tyr | Leu | Gln | Glu | Tyr | Ser | Thr | Lys | Tyr | Phe | Tyr | Lys | |
| 1255 | | | | 1260 | | | | | 1265 | | | | | | |
| cag | aat | ggg | cgg | atc | cgg | cct | att | gtg | gca | gag | aat | cct | gaa | tac | 3885 |
| Gln | Asn | Gly | Arg | Ile | Arg | Pro | Ile | Val | Ala | Glu | Asn | Pro | Glu | Tyr | |
| 1270 | | | | 1275 | | | | | 1280 | | | | | | |
| ctc | tct | gag | ttc | tcc | ctg | aag | cca | ggc | act | gtg | ctg | ccg | cct | cca | 3930 |
| Leu | Ser | Glu | Phe | Ser | Leu | Lys | Pro | Gly | Thr | Val | Leu | Pro | Pro | Pro | |
| 1285 | | | | 1290 | | | | | 1295 | | | | | | |

| | | | | | | | | |
|---|---|---|---|---|---|---|---|---|
| cct | tac | aga | cac | cgg | aat | act | gtg | gtg taa gctcagttgt ggttttttag | 3980 |
| Pro | Tyr | Arg | His | Arg | Asn | Thr | Val | Val | |
| 1300 | | | | | 1305 | | | | |

| | |
|---|---|
| gtggagagac acacctgctc caatttcccc accccctct ctttctctgg tggtcttcct | 4040 |
| tctaccccaa ggccagtagt tttgacactt cccagtggaa gatacagaga tgcaatgata | 4100 |
| gttatgtgct tacctaactt gaacattaga gggaaagact gaaagagaaa gataggagga | 4160 |
| accacaatgt ttcttcattt ctctgcatgg gttggtcagg agaatgaaac agctagaaa | 4220 |
| ggaccagaaa atgtaaggca atgctgccta ctatcaaact agctgtcact tttttctttt | 4280 |
| ttcttttttct ttcttttgttt cttctttcct cttcttttt tttttttttt taaagcagat | 4340 |
| ggttgaaaca cccatgctat ctgttcctat ctgcaggaac tgatgtgtgc atatttagca | 4400 |
| tccctggaaa tcataataaa gtttccatta gaacaaaaga ataacatttt ctataacata | 4460 |
| tgatagtgtc tgaaattgag aatccagttt ctttccccag cagtttctgt cctagcaagt | 4520 |
| aagaatggcc aactcaactt tcataattta aaaatctcca ttaaagttat aactagtaat | 4580 |
| tatgttttca acactttttg gttttttttca ttttgttttg ctctgaccga ttcctttata | 4640 |
| tttgctcccc tattttttggc tttaattttct aattgcaaag atgtttacat caaagcttct | 4700 |
| tcacagaatt taagcaagaa atatttttaat atagtgaaat ggccactact ttaagtatac | 4760 |
| aatctttaaa ataagaaagg gaggctaata ttttttcatgc tatcaaatta tcttcacct | 4820 |
| catcctttac attttttcaac attttttttt ctccataaat gacactactt gataggccgt | 4880 |
| tggttgtctg aagagtagaa gggaaactaa gagacagttc tctgtggttc aggaaaacta | 4940 |
| ctgatacttt cagggggtggc ccaatgaggg aatccattga actggaagaa acacactgga | 5000 |
| ttgggtatgt ctacctggca gatactcaga aatgtagttt gcacttaagc tgtaatttta | 5060 |
| tttgttcttt ttctgaactc catttttggat tttgaatcaa gcaatatgga agcaaccagc | 5120 |
| aaattaacta atttaagtac attttttaaaa aaagagctaa gataaagact gtggaaatgc | 5180 |
| caaaccaagc aaattaggaa ccttgcaacg gtatccaggg actatgatga gaggccagca | 5240 |
| cattatcttc atatgtcacc tttgctacgc aaggaaattt gttcagttcg tatacttcgt | 5300 |
| aagaaggaat gcgagtaagg attggcttga attccatgga atttctagta tgagactatt | 5360 |
| tatatgaagt agaaggtaac tctttgcaca taaattggta taataaaaag aaaaacacaa | 5420 |

```
acattcaaag cttagggata ggtccttggg tcaaaagttg taaataaatg tgaaacatct    5480
tctc                                                                 5484
```

<210> SEQ ID NO 19
<211> LENGTH: 1308
<212> TYPE: PRT
<213> ORGANISM: Homo sapiens

<400> SEQUENCE: 19

```
Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
    290                 295                 300

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
```

```
                    355                 360                 365
Leu Val Thr Gly Ile His Gly Asp Pro Tyr Asn Ala Ile Glu Ala Ile
            370                 375                 380
Asp Pro Glu Lys Leu Asn Val Phe Arg Thr Val Arg Glu Ile Thr Gly
385                 390                 395                 400
Phe Leu Asn Ile Gln Ser Trp Pro Pro Asn Met Thr Asp Phe Ser Val
                405                 410                 415
Phe Ser Asn Leu Val Thr Ile Gly Gly Arg Val Leu Tyr Ser Gly Leu
                420                 425                 430
Ser Leu Leu Ile Leu Lys Gln Gln Gly Ile Thr Ser Leu Gln Phe Gln
                435                 440                 445
Ser Leu Lys Glu Ile Ser Ala Gly Asn Ile Tyr Ile Thr Asp Asn Ser
            450                 455                 460
Asn Leu Cys Tyr Tyr His Thr Ile Asn Trp Thr Thr Leu Phe Ser Thr
465                 470                 475                 480
Ile Asn Gln Arg Ile Val Ile Arg Asp Asn Arg Lys Ala Glu Asn Cys
                485                 490                 495
Thr Ala Glu Gly Met Val Cys Asn His Leu Cys Ser Ser Asp Gly Cys
            500                 505                 510
Trp Gly Pro Gly Pro Asp Gln Cys Leu Ser Cys Arg Arg Phe Ser Arg
            515                 520                 525
Gly Arg Ile Cys Ile Glu Ser Cys Asn Leu Tyr Asp Gly Glu Phe Arg
            530                 535                 540
Glu Phe Glu Asn Gly Ser Ile Cys Val Glu Cys Asp Pro Gln Cys Glu
545                 550                 555                 560
Lys Met Glu Asp Gly Leu Leu Thr Cys His Gly Pro Gly Pro Asp Asn
                565                 570                 575
Cys Thr Lys Cys Ser His Phe Lys Asp Gly Pro Asn Cys Val Glu Lys
                580                 585                 590
Cys Pro Asp Gly Leu Gln Gly Ala Asn Ser Phe Ile Phe Lys Tyr Ala
            595                 600                 605
Asp Pro Asp Arg Glu Cys His Pro Cys His Pro Asn Cys Thr Gln Gly
610                 615                 620
Cys Asn Gly Pro Thr Ser His Asp Cys Ile Tyr Tyr Pro Trp Thr Gly
625                 630                 635                 640
His Ser Thr Leu Pro Gln His Ala Arg Thr Pro Leu Ile Ala Ala Gly
                645                 650                 655
Val Ile Gly Gly Leu Phe Ile Leu Val Ile Val Gly Leu Thr Phe Ala
            660                 665                 670
Val Tyr Val Arg Arg Lys Ser Ile Lys Lys Lys Arg Ala Leu Arg Arg
            675                 680                 685
Phe Leu Glu Thr Glu Leu Val Glu Pro Leu Thr Pro Ser Gly Thr Ala
            690                 695                 700
Pro Asn Gln Ala Gln Leu Arg Ile Leu Lys Glu Thr Glu Leu Lys Arg
705                 710                 715                 720
Val Lys Val Leu Gly Ser Gly Ala Phe Gly Thr Val Tyr Lys Gly Ile
                725                 730                 735
Trp Val Pro Glu Gly Glu Thr Val Lys Ile Pro Val Ala Ile Lys Ile
            740                 745                 750
Leu Asn Glu Thr Thr Gly Pro Lys Ala Asn Val Glu Phe Met Asp Glu
            755                 760                 765
Ala Leu Ile Met Ala Ser Met Asp His Pro His Leu Val Arg Leu Leu
            770                 775                 780
```

-continued

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
            805                 810                 815

Ser Gln Leu Leu Leu Asn Trp Cys Val Gln Ile Ala Lys Gly Met Met
        820                 825                 830

Tyr Leu Glu Glu Arg Arg Leu Val His Arg Asp Leu Ala Ala Arg Asn
    835                 840                 845

Val Leu Val Lys Ser Pro Asn His Val Lys Ile Thr Asp Phe Gly Leu
850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
            885                 890                 895

Phe Thr His Gln Ser Asp Val Trp Ser Tyr Gly Val Thr Ile Trp Glu
        900                 905                 910

Leu Met Thr Phe Gly Gly Lys Pro Tyr Asp Gly Ile Pro Thr Arg Glu
    915                 920                 925

Ile Pro Asp Leu Leu Glu Lys Gly Glu Arg Leu Pro Gln Pro Pro Ile
930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
            965                 970                 975

Met Ala Arg Asp Pro Gln Arg Tyr Leu Val Ile Gln Gly Asp Asp Arg
        980                 985                 990

Met Lys Leu Pro Ser Pro Asn Asp Ser Lys Phe Phe Gln Asn Leu Leu
    995                 1000                1005

Asp Glu Glu Asp Leu Glu Asp Met Met Asp Ala Glu Glu Tyr Leu
    1010                1015                1020

Val Pro Gln Ala Phe Asn Ile Pro Pro Pro Ile Tyr Thr Ser Arg
    1025                1030                1035

Ala Arg Ile Asp Ser Asn Arg Ser Glu Ile Gly His Ser Pro Pro
    1040                1045                1050

Pro Ala Tyr Thr Pro Met Ser Gly Asn Gln Phe Val Tyr Arg Asp
    1055                1060                1065

Gly Gly Phe Ala Ala Glu Gln Gly Val Ser Val Pro Tyr Arg Ala
    1070                1075                1080

Pro Thr Ser Thr Ile Pro Glu Ala Pro Val Ala Gln Gly Ala Thr
    1085                1090                1095

Ala Glu Ile Phe Asp Asp Ser Cys Cys Asn Gly Thr Leu Arg Lys
    1100                1105                1110

Pro Val Ala Pro His Val Gln Glu Asp Ser Ser Thr Gln Arg Tyr
    1115                1120                1125

Ser Ala Asp Pro Thr Val Phe Ala Pro Glu Arg Ser Pro Arg Gly
    1130                1135                1140

Glu Leu Asp Glu Glu Gly Tyr Met Thr Pro Met Arg Asp Lys Pro
    1145                1150                1155

Lys Gln Glu Tyr Leu Asn Pro Val Glu Glu Asn Pro Phe Val Ser
    1160                1165                1170

Arg Arg Lys Asn Gly Asp Leu Gln Ala Leu Asp Asn Pro Glu Tyr
    1175                1180                1185

His Asn Ala Ser Asn Gly Pro Pro Lys Ala Glu Asp Glu Tyr Val
    1190                1195                1200

```
Asn Glu Pro Leu Tyr Leu Asn Thr Phe Ala Asn Thr Leu Gly Lys
    1205            1210                1215

Ala Glu Tyr Leu Lys Asn Asn Ile Leu Ser Met Pro Glu Lys Ala
    1220            1225                1230

Lys Lys Ala Phe Asp Asn Pro Asp Tyr Trp Asn His Ser Leu Pro
    1235            1240                1245

Pro Arg Ser Thr Leu Gln His Pro Asp Tyr Leu Gln Glu Tyr Ser
    1250            1255                1260

Thr Lys Tyr Phe Tyr Lys Gln Asn Gly Arg Ile Arg Pro Ile Val
    1265            1270                1275

Ala Glu Asn Pro Glu Tyr Leu Ser Glu Phe Ser Leu Lys Pro Gly
    1280            1285                1290

Thr Val Leu Pro Pro Pro Pro Tyr Arg His Arg Asn Thr Val Val
    1295            1300                1305

<210> SEQ ID NO 20
<211> LENGTH: 3897
<212> TYPE: DNA
<213> ORGANISM: Mus musculus
<220> FEATURE:
<221> NAME/KEY: CDS
<222> LOCATION: (1)..(3897)

<400> SEQUENCE: 20 atg gca ata cca tca aga cgc aag gac tat cca aaa cta tct gaa atc        48
Met Ala Ile Pro Ser Arg Arg Lys Asp Tyr Pro Lys Leu Ser Glu Ile
1               5                   10                  15 aca gtg tgc gca gga aca gag aac aaa ctg agc tct ctc tct gac ctg        96
Thr Val Cys Ala Gly Thr Glu Asn Lys Leu Ser Ser Leu Ser Asp Leu
            20                  25                  30 gaa cag cag tac cga gcc ttg cgc aaa tac tat gaa aac tgc gag gta       144
Glu Gln Gln Tyr Arg Ala Leu Arg Lys Tyr Tyr Glu Asn Cys Glu Val
        35                  40                  45 gtc atg ggc aac ctg gag atc acc agc atc gag cac aac cgg gac ctc       192
Val Met Gly Asn Leu Glu Ile Thr Ser Ile Glu His Asn Arg Asp Leu
    50                  55                  60 tcc ttc ctg cgg tct atc cga gaa gtc aca ggc tac gtc ctg gtg gcc       240
Ser Phe Leu Arg Ser Ile Arg Glu Val Thr Gly Tyr Val Leu Val Ala
65                  70                  75                  80 ctc aac cag ttt cgt tac ttg cct ctg gag aat tta cgc att att cgt       288
Leu Asn Gln Phe Arg Tyr Leu Pro Leu Glu Asn Leu Arg Ile Ile Arg
                85                  90                  95 ggg aca aaa cta tat gaa gat cgc tat gcc tta gcg ata ttc tta aac       336
Gly Thr Lys Leu Tyr Glu Asp Arg Tyr Ala Leu Ala Ile Phe Leu Asn
            100                 105                 110 tac agg aaa gat ggc aac ttt gga ctc caa gaa ctt gga tta aag aac       384
Tyr Arg Lys Asp Gly Asn Phe Gly Leu Gln Glu Leu Gly Leu Lys Asn
        115                 120                 125 ctg acc gaa ata cta aat ggt gga gtc tat gta gac cag aac aaa ttc       432
Leu Thr Glu Ile Leu Asn Gly Gly Val Tyr Val Asp Gln Asn Lys Phe
    130                 135                 140 cta tgt tat gct gac act ata cac tgg caa gat att gtt cgg aat cca       480
Leu Cys Tyr Ala Asp Thr Ile His Trp Gln Asp Ile Val Arg Asn Pro
145                 150                 155                 160 tgg cct tcc aac atg act ctg gtg tca aca aat gga agt tct gga tgt       528
Trp Pro Ser Asn Met Thr Leu Val Ser Thr Asn Gly Ser Ser Gly Cys
                165                 170                 175 gga aga tgc cat aag tct tgc act ggc cga tgc tgg gga ccc aca gaa       576
Gly Arg Cys His Lys Ser Cys Thr Gly Arg Cys Trp Gly Pro Thr Glu
            180                 185                 190
```

```
aat cac tgc cag acc ttg acc aga act gtg tgt gct gaa caa tgt gat      624
Asn His Cys Gln Thr Leu Thr Arg Thr Val Cys Ala Glu Gln Cys Asp
        195                 200                 205 ggc agg tgc tat gga ccc tac gtt agt gac tgc tgc cat cga gaa tgt      672
Gly Arg Cys Tyr Gly Pro Tyr Val Ser Asp Cys Cys His Arg Glu Cys
    210                 215                 220 gct gga ggc tgc tca gga cca aag gac act gac tgc ttt gcc tgc atg      720
Ala Gly Gly Cys Ser Gly Pro Lys Asp Thr Asp Cys Phe Ala Cys Met
225                 230                 235                 240 aac ttc aat gac agt gga gcc tgc gtt act caa tgt ccc caa aca ttt      768
Asn Phe Asn Asp Ser Gly Ala Cys Val Thr Gln Cys Pro Gln Thr Phe
                245                 250                 255 gtc tac aat cca acc acc ttt caa ctg gaa cac aac ttc aat gca aag      816
Val Tyr Asn Pro Thr Thr Phe Gln Leu Glu His Asn Phe Asn Ala Lys
            260                 265                 270 tac acg tat gga gca ttc tgt gtt aag aaa tgt cca cat aac ttc gtg      864
Tyr Thr Tyr Gly Ala Phe Cys Val Lys Lys Cys Pro His Asn Phe Val
        275                 280                 285 gta gat tcc agt tct tgt gta cga gcc tgc cct agt tct aag atg gaa      912
Val Asp Ser Ser Ser Cys Val Arg Ala Cys Pro Ser Ser Lys Met Glu
290                 295                 300 gta gaa gaa aat ggg att aaa atg tgt aag cct tgc acc gat att tgc      960
Val Glu Glu Asn Gly Ile Lys Met Cys Lys Pro Cys Thr Asp Ile Cys
305                 310                 315                 320 ccc aaa gca tgt gat gga atc ggc acg gga tca ctg atg tct gct cag     1008
Pro Lys Ala Cys Asp Gly Ile Gly Thr Gly Ser Leu Met Ser Ala Gln
                325                 330                 335 act gtg gat tca agt aac att gac aaa ttc ata aac tgc aca aag atc     1056
Thr Val Asp Ser Ser Asn Ile Asp Lys Phe Ile Asn Cys Thr Lys Ile
            340                 345                 350 aat ggc aat ctc atc ttt ctt gtc act ggc att cat gga gac cct tac     1104
Asn Gly Asn Leu Ile Phe Leu Val Thr Gly Ile His Gly Asp Pro Tyr
        355                 360                 365 aat gct att gac gcc ata gat cca gag aaa ctg aat gtc ttt cgg act     1152
Asn Ala Ile Asp Ala Ile Asp Pro Glu Lys Leu Asn Val Phe Arg Thr
    370                 375                 380 gtc aga gaa ata aca ggt ttc ctg aac ata cag tct tgg ccc cca aat     1200
Val Arg Glu Ile Thr Gly Phe Leu Asn Ile Gln Ser Trp Pro Pro Asn
385                 390                 395                 400 atg aca gat ttc agt gtt ttc tcc aac ctc gtc aca att gga gga aga     1248
Met Thr Asp Phe Ser Val Phe Ser Asn Leu Val Thr Ile Gly Gly Arg
                405                 410                 415 gtc ctc tac agt ggt ctc tca ttg ctg atc ctc aaa caa caa ggt atc     1296
Val Leu Tyr Ser Gly Leu Ser Leu Leu Ile Leu Lys Gln Gln Gly Ile
            420                 425                 430 act tcc cta cag ttc cag tct ctg aag gaa atc agt gcg ggc aat atc     1344
Thr Ser Leu Gln Phe Gln Ser Leu Lys Glu Ile Ser Ala Gly Asn Ile
        435                 440                 445 tac atc act gac aac agc aac ctg tgt tat tac cat acc att aac tgg     1392
Tyr Ile Thr Asp Asn Ser Asn Leu Cys Tyr Tyr His Thr Ile Asn Trp
    450                 455                 460 aca aca ctc ttc agc acc att aac cag aga ata gtg atc cga gat aac     1440
Thr Thr Leu Phe Ser Thr Ile Asn Gln Arg Ile Val Ile Arg Asp Asn
465                 470                 475                 480 aga aga gct gag aat tgt act gct gaa ggc atg gta tgc aac cac ctg     1488
Arg Arg Ala Glu Asn Cys Thr Ala Glu Gly Met Val Cys Asn His Leu
                485                 490                 495 tgt tca aat gat ggt tgt tgg gga cct ggg ccg gac cag tgc ctg tca     1536
Cys Ser Asn Asp Gly Cys Trp Gly Pro Gly Pro Asp Gln Cys Leu Ser
            500                 505                 510
```

```
tgt cgg cgc ttc agc agg gga aag atc tgc ata gag tct tgc aac ctt      1584
Cys Arg Arg Phe Ser Arg Gly Lys Ile Cys Ile Glu Ser Cys Asn Leu
515                 520                 525 tat gat ggg gaa ttt cga gag ttt gaa aac ggc tcc atc tgt gtt gag      1632
Tyr Asp Gly Glu Phe Arg Glu Phe Glu Asn Gly Ser Ile Cys Val Glu
530                 535                 540 tgt gac tcc cag tgt gag aaa atg gaa gat gga ctc ctc aca tgc cat      1680
Cys Asp Ser Gln Cys Glu Lys Met Glu Asp Gly Leu Leu Thr Cys His
545                 550                 555                 560 gga ccg gga cct gac aac tgc aca aag tgc tct cat ttt aag gat ggt      1728
Gly Pro Gly Pro Asp Asn Cys Thr Lys Cys Ser His Phe Lys Asp Gly
                565                 570                 575 cca aac tgt gtg gag aaa tgt cca gat ggc cta cag gga gca aac agt      1776
Pro Asn Cys Val Glu Lys Cys Pro Asp Gly Leu Gln Gly Ala Asn Ser
            580                 585                 590 ttc att ttt aag tat gca gat cag gat cgg gag tgc cac cct tgc cat      1824
Phe Ile Phe Lys Tyr Ala Asp Gln Asp Arg Glu Cys His Pro Cys His
        595                 600                 605 cca aac tgc acc cag ggg tgt aac ggt ccc act agt cat gac tgc att      1872
Pro Asn Cys Thr Gln Gly Cys Asn Gly Pro Thr Ser His Asp Cys Ile
610                 615                 620 tac tac cca tgg acg ggc cat tcc act tta cca caa cac gct aga act      1920
Tyr Tyr Pro Trp Thr Gly His Ser Thr Leu Pro Gln His Ala Arg Thr
625                 630                 635                 640 cca ctg att gca gcc gga gtc att gga ggc ctc ttc atc ctg gtg atc      1968
Pro Leu Ile Ala Ala Gly Val Ile Gly Gly Leu Phe Ile Leu Val Ile
                645                 650                 655 atg gct ttg aca ttt gct gtc tat gtc aga aga aag agc atc aaa aag      2016
Met Ala Leu Thr Phe Ala Val Tyr Val Arg Arg Lys Ser Ile Lys Lys
            660                 665                 670 aaa cgt gct ttg agg aga ttc ctg gag aca gag ctg gta gag ccc tta      2064
Lys Arg Ala Leu Arg Arg Phe Leu Glu Thr Glu Leu Val Glu Pro Leu
        675                 680                 685 act ccc agt ggc acg gca ccc aat caa gct caa ctt cgc att ttg aag      2112
Thr Pro Ser Gly Thr Ala Pro Asn Gln Ala Gln Leu Arg Ile Leu Lys
690                 695                 700 gaa acc gaa cta aag agg gta aag gtc ctt ggc tcg gga gct ttt gga      2160
Glu Thr Glu Leu Lys Arg Val Lys Val Leu Gly Ser Gly Ala Phe Gly
705                 710                 715                 720 acc gtt tat aaa ggt att tgg gtg cct gaa ggt gaa aca gtg aaa atc      2208
Thr Val Tyr Lys Gly Ile Trp Val Pro Glu Gly Glu Thr Val Lys Ile
                725                 730                 735 cct gtg gct ata aag atc ctc aat gaa aca act ggc ccc aaa gcc aac      2256
Pro Val Ala Ile Lys Ile Leu Asn Glu Thr Thr Gly Pro Lys Ala Asn
            740                 745                 750 gtg gag ttc atg gat gag gct ctg atc atg gca agt atg gat cac cca      2304
Val Glu Phe Met Asp Glu Ala Leu Ile Met Ala Ser Met Asp His Pro
        755                 760                 765 cac cta gtt cgc cta ttg gga gtg tgt ctg agt ccc act atc cag ttg      2352
His Leu Val Arg Leu Leu Gly Val Cys Leu Ser Pro Thr Ile Gln Leu
770                 775                 780 gtt acg cag ctg atg ccg cat ggc tgc cta ctg gac tat gtt cat gaa      2400
Val Thr Gln Leu Met Pro His Gly Cys Leu Leu Asp Tyr Val His Glu
785                 790                 795                 800 cac aag gat aac att gga tca cag ctg ctg ttg aac tgg tgt gtc cag      2448
His Lys Asp Asn Ile Gly Ser Gln Leu Leu Leu Asn Trp Cys Val Gln
                805                 810                 815 att gct aag gga atg atg tac cta gaa gaa aga cgg ctt gtt cat cgg      2496
Ile Ala Lys Gly Met Met Tyr Leu Glu Glu Arg Arg Leu Val His Arg
            820                 825                 830
```

```
gat ctg gca gcc cgc aat gtc tta gtg aaa tct cca aat cat gtt aaa    2544
Asp Leu Ala Ala Arg Asn Val Leu Val Lys Ser Pro Asn His Val Lys
            835                 840                 845 atc aca gat ttt gga ctg gcc cgg ctc ttg gaa gga gat gaa aaa gaa    2592
Ile Thr Asp Phe Gly Leu Ala Arg Leu Leu Glu Gly Asp Glu Lys Glu
850                 855                 860 tac aat gct gat ggt ggc aag atg cca att aaa tgg atg gct ctg gaa    2640
Tyr Asn Ala Asp Gly Gly Lys Met Pro Ile Lys Trp Met Ala Leu Glu
865                 870                 875                 880 tgt ata cat tat agg aaa ttc aca cat caa agt gat gtt tgg agc tat    2688
Cys Ile His Tyr Arg Lys Phe Thr His Gln Ser Asp Val Trp Ser Tyr
                885                 890                 895 ggc gtc act ata tgg gaa ctg atg acc ttt gga gga aag ccc tat gat    2736
Gly Val Thr Ile Trp Glu Leu Met Thr Phe Gly Gly Lys Pro Tyr Asp
            900                 905                 910 gga att cca acc cga gaa atc ccc gat tta ctg gag aaa gga gag cgt    2784
Gly Ile Pro Thr Arg Glu Ile Pro Asp Leu Leu Glu Lys Gly Glu Arg
        915                 920                 925 ctg cct cag cct ccc atc tgc act att gat gtt tac atg gtc atg gtc    2832
Leu Pro Gln Pro Pro Ile Cys Thr Ile Asp Val Tyr Met Val Met Val
930                 935                 940 aaa tgt tgg atg atc gat gct gac agc aga cct aaa ttc aaa gaa ctg    2880
Lys Cys Trp Met Ile Asp Ala Asp Ser Arg Pro Lys Phe Lys Glu Leu
945                 950                 955                 960 gct gct gag ttt tca aga atg gct aga gac cct caa aga tac cta gtt    2928
Ala Ala Glu Phe Ser Arg Met Ala Arg Asp Pro Gln Arg Tyr Leu Val
                965                 970                 975 att cag ggt gat gat cgt atg aag ctt ccc agt cca aat gac agc aaa    2976
Ile Gln Gly Asp Asp Arg Met Lys Leu Pro Ser Pro Asn Asp Ser Lys
            980                 985                 990 ttc ttc cag aat ctc ttg gat gaa gag gat ttg gaa gac atg atg gat    3024
Phe Phe Gln Asn Leu Leu Asp Glu Glu Asp Leu Glu Asp Met Met Asp
        995                 1000                1005 gct gag gaa tat ttg gtc ccc cag gct ttc aac ata cct cct ccc       3069
Ala Glu Glu Tyr Leu Val Pro Gln Ala Phe Asn Ile Pro Pro Pro
1010                1015                1020 atc tac aca tcc aga aca aga att gac tcc aat agg agt gaa att       3114
Ile Tyr Thr Ser Arg Thr Arg Ile Asp Ser Asn Arg Ser Glu Ile
1025                1030                1035 gga cac agc cct cct cct gcc tac acc ccc atg tcg gga aat cag       3159
Gly His Ser Pro Pro Pro Ala Tyr Thr Pro Met Ser Gly Asn Gln
1040                1045                1050 ttt gtg tac caa gat ggg ggc ttt gct aca caa caa gga atg ccc       3204
Phe Val Tyr Gln Asp Gly Gly Phe Ala Thr Gln Gln Gly Met Pro
1055                1060                1065 atg ccc tac aga gcc aca acc agc acc ata cca gag gct cca gta       3249
Met Pro Tyr Arg Ala Thr Thr Ser Thr Ile Pro Glu Ala Pro Val
1070                1075                1080 gct cag ggt gca acg gct gag atg ttt gat gac tcc tgc tgt aat       3294
Ala Gln Gly Ala Thr Ala Glu Met Phe Asp Asp Ser Cys Cys Asn
1085                1090                1095 ggt acc cta cga aag cca gtg gca ccc cat gtc caa gag gac agt       3339
Gly Thr Leu Arg Lys Pro Val Ala Pro His Val Gln Glu Asp Ser
1100                1105                1110 agc act cag agg tat agt gct gat ccc aca gtg ttc gcc cca gaa       3384
Ser Thr Gln Arg Tyr Ser Ala Asp Pro Thr Val Phe Ala Pro Glu
1115                1120                1125 cgg aat cct cga gga gaa ctg gat gaa gaa ggc tac atg act cca       3429
Arg Asn Pro Arg Gly Glu Leu Asp Glu Glu Gly Tyr Met Thr Pro
1130                1135                1140
```

```
atg cat gac aag ccc aaa caa gaa tat ctg aat cct gtg gaa gag     3474
Met His Asp Lys Pro Lys Gln Glu Tyr Leu Asn Pro Val Glu Glu
    1145                1150                1155 aac cct ttt gtg tcc cga agg aag aat gga gat ctt caa gct tta     3519
Asn Pro Phe Val Ser Arg Arg Lys Asn Gly Asp Leu Gln Ala Leu
1160                1165                1170 gat aat ccg gag tat cac agt gct tcc agc ggt cca ccc aag gcg     3564
Asp Asn Pro Glu Tyr His Ser Ala Ser Ser Gly Pro Pro Lys Ala
    1175                1180                1185 gag gat gaa tac gtg aat gag cct cta tac ctc aac acc ttc gcc     3609
Glu Asp Glu Tyr Val Asn Glu Pro Leu Tyr Leu Asn Thr Phe Ala
1190                1195                1200 aat gcc ttg ggg agt gca gag tac atg aaa aac agt gta ctg tct     3654
Asn Ala Leu Gly Ser Ala Glu Tyr Met Lys Asn Ser Val Leu Ser
    1205                1210                1215 gtg cca gag aaa gcc aag aaa gca ttt gac aac ccc gac tac tgg     3699
Val Pro Glu Lys Ala Lys Lys Ala Phe Asp Asn Pro Asp Tyr Trp
1220                1225                1230 aac cac agc ctg cca ccc cgg agc acc ctt cag cac cca gac tac     3744
Asn His Ser Leu Pro Pro Arg Ser Thr Leu Gln His Pro Asp Tyr
    1235                1240                1245 ctg cag gaa tac agc aca aaa tat ttt tat aaa cag aat gga cgg     3789
Leu Gln Glu Tyr Ser Thr Lys Tyr Phe Tyr Lys Gln Asn Gly Arg
1250                1255                1260 atc cgc ccc att gtg gca gag aat cct gag tac ctc tcg gag ttc     3834
Ile Arg Pro Ile Val Ala Glu Asn Pro Glu Tyr Leu Ser Glu Phe
    1265                1270                1275 tcg ctg aag cct ggc act atg ctg ccc cct ccg ccc tac aga cac     3879
Ser Leu Lys Pro Gly Thr Met Leu Pro Pro Pro Pro Tyr Arg His
1280                1285                1290 cgg aat act gtg gtg tga                                         3897
Arg Asn Thr Val Val
    1295

<210> SEQ ID NO 21
<211> LENGTH: 1298
<212> TYPE: PRT
<213> ORGANISM: Mus musculus

<400> SEQUENCE: 21

Met Ala Ile Pro Ser Arg Arg Lys Asp Tyr Pro Lys Leu Ser Glu Ile
1               5                   10                  15

Thr Val Cys Ala Gly Thr Glu Asn Lys Leu Ser Ser Leu Ser Asp Leu
            20                  25                  30

Glu Gln Gln Tyr Arg Ala Leu Arg Lys Tyr Tyr Glu Asn Cys Glu Val
        35                  40                  45

Val Met Gly Asn Leu Glu Ile Thr Ser Ile Glu His Asn Arg Asp Leu
    50                  55                  60

Ser Phe Leu Arg Ser Ile Arg Glu Val Thr Gly Tyr Val Leu Val Ala
65                  70                  75                  80

Leu Asn Gln Phe Arg Tyr Leu Pro Leu Glu Asn Leu Arg Ile Ile Arg
                85                  90                  95

Gly Thr Lys Leu Tyr Glu Asp Arg Tyr Ala Leu Ala Ile Phe Leu Asn
            100                 105                 110

Tyr Arg Lys Asp Gly Asn Phe Gly Leu Gln Glu Leu Gly Leu Lys Asn
        115                 120                 125

Leu Thr Glu Ile Leu Asn Gly Gly Val Tyr Val Asp Gln Asn Lys Phe
    130                 135                 140
```

```
Leu Cys Tyr Ala Asp Thr Ile His Trp Gln Asp Ile Val Arg Asn Pro
145                 150                 155                 160

Trp Pro Ser Asn Met Thr Leu Val Ser Thr Asn Gly Ser Ser Gly Cys
                165                 170                 175

Gly Arg Cys His Lys Ser Cys Thr Gly Arg Cys Trp Gly Pro Thr Glu
            180                 185                 190

Asn His Cys Gln Thr Leu Thr Arg Thr Val Cys Ala Glu Gln Cys Asp
        195                 200                 205

Gly Arg Cys Tyr Gly Pro Tyr Val Ser Asp Cys Cys His Arg Glu Cys
    210                 215                 220

Ala Gly Gly Cys Ser Gly Pro Lys Asp Thr Asp Cys Phe Ala Cys Met
225                 230                 235                 240

Asn Phe Asn Asp Ser Gly Ala Cys Val Thr Gln Cys Pro Gln Thr Phe
                245                 250                 255

Val Tyr Asn Pro Thr Thr Phe Gln Leu Glu His Asn Phe Asn Ala Lys
                260                 265                 270

Tyr Thr Tyr Gly Ala Phe Cys Val Lys Lys Cys Pro His Asn Phe Val
            275                 280                 285

Val Asp Ser Ser Ser Cys Val Arg Ala Cys Pro Ser Ser Lys Met Glu
290                 295                 300

Val Glu Glu Asn Gly Ile Lys Met Cys Lys Pro Cys Thr Asp Ile Cys
305                 310                 315                 320

Pro Lys Ala Cys Asp Gly Ile Gly Thr Gly Ser Leu Met Ser Ala Gln
                325                 330                 335

Thr Val Asp Ser Ser Asn Ile Asp Lys Phe Ile Asn Cys Thr Lys Ile
            340                 345                 350

Asn Gly Asn Leu Ile Phe Leu Val Thr Gly Ile His Gly Asp Pro Tyr
        355                 360                 365

Asn Ala Ile Asp Ala Ile Asp Pro Glu Lys Leu Asn Val Phe Arg Thr
    370                 375                 380

Val Arg Glu Ile Thr Gly Phe Leu Asn Ile Gln Ser Trp Pro Pro Asn
385                 390                 395                 400

Met Thr Asp Phe Ser Val Phe Ser Asn Leu Val Thr Ile Gly Gly Arg
                405                 410                 415

Val Leu Tyr Ser Gly Leu Ser Leu Leu Ile Leu Lys Gln Gln Gly Ile
                420                 425                 430

Thr Ser Leu Gln Phe Gln Ser Leu Lys Glu Ile Ser Ala Gly Asn Ile
            435                 440                 445

Tyr Ile Thr Asp Asn Ser Asn Leu Cys Tyr Tyr His Thr Ile Asn Trp
        450                 455                 460

Thr Thr Leu Phe Ser Thr Ile Asn Gln Arg Ile Val Ile Arg Asp Asn
465                 470                 475                 480

Arg Arg Ala Glu Asn Cys Thr Ala Glu Gly Met Val Cys Asn His Leu
                485                 490                 495

Cys Ser Asn Asp Gly Cys Trp Gly Pro Gly Pro Asp Gln Cys Leu Ser
                500                 505                 510

Cys Arg Arg Phe Ser Arg Gly Lys Ile Cys Ile Glu Ser Cys Asn Leu
            515                 520                 525

Tyr Asp Gly Glu Phe Arg Glu Phe Glu Asn Gly Ser Ile Cys Val Glu
        530                 535                 540

Cys Asp Ser Gln Cys Glu Lys Met Glu Asp Gly Leu Leu Thr Cys His
545                 550                 555                 560

Gly Pro Gly Pro Asp Asn Cys Thr Lys Cys Ser His Phe Lys Asp Gly
                565                 570                 575
```

-continued

```
Pro Asn Cys Val Glu Lys Cys Pro Asp Gly Leu Gln Gly Ala Asn Ser
        580                 585                 590
Phe Ile Phe Lys Tyr Ala Asp Gln Asp Arg Glu Cys His Pro Cys His
        595                 600                 605
Pro Asn Cys Thr Gln Gly Cys Asn Gly Pro Thr Ser His Asp Cys Ile
    610                 615                 620
Tyr Tyr Pro Trp Thr Gly His Ser Thr Leu Pro Gln His Ala Arg Thr
625                 630                 635                 640
Pro Leu Ile Ala Ala Gly Val Ile Gly Gly Leu Phe Ile Leu Val Ile
                645                 650                 655
Met Ala Leu Thr Phe Ala Val Tyr Val Arg Arg Lys Ser Ile Lys Lys
                660                 665                 670
Lys Arg Ala Leu Arg Arg Phe Leu Glu Thr Glu Leu Val Glu Pro Leu
                675                 680                 685
Thr Pro Ser Gly Thr Ala Pro Asn Gln Ala Gln Leu Arg Ile Leu Lys
        690                 695                 700
Glu Thr Glu Leu Lys Arg Val Lys Val Leu Gly Ser Gly Ala Phe Gly
705                 710                 715                 720
Thr Val Tyr Lys Gly Ile Trp Val Pro Glu Gly Glu Thr Val Lys Ile
                725                 730                 735
Pro Val Ala Ile Lys Ile Leu Asn Glu Thr Thr Gly Pro Lys Ala Asn
                740                 745                 750
Val Glu Phe Met Asp Glu Ala Leu Ile Met Ala Ser Met Asp His Pro
                755                 760                 765
His Leu Val Arg Leu Leu Gly Val Cys Leu Ser Pro Thr Ile Gln Leu
        770                 775                 780
Val Thr Gln Leu Met Pro His Gly Cys Leu Leu Asp Tyr Val His Glu
785                 790                 795                 800
His Lys Asp Asn Ile Gly Ser Gln Leu Leu Leu Asn Trp Cys Val Gln
                805                 810                 815
Ile Ala Lys Gly Met Met Tyr Leu Glu Glu Arg Arg Leu Val His Arg
                820                 825                 830
Asp Leu Ala Ala Arg Asn Val Leu Val Lys Ser Pro Asn His Val Lys
                835                 840                 845
Ile Thr Asp Phe Gly Leu Ala Arg Leu Leu Glu Gly Asp Glu Lys Glu
        850                 855                 860
Tyr Asn Ala Asp Gly Gly Lys Met Pro Ile Lys Trp Met Ala Leu Glu
865                 870                 875                 880
Cys Ile His Tyr Arg Lys Phe Thr His Gln Ser Asp Val Trp Ser Tyr
                885                 890                 895
Gly Val Thr Ile Trp Glu Leu Met Thr Phe Gly Gly Lys Pro Tyr Asp
                900                 905                 910
Gly Ile Pro Thr Arg Glu Ile Pro Asp Leu Leu Glu Lys Gly Glu Arg
        915                 920                 925
Leu Pro Gln Pro Pro Ile Cys Thr Ile Asp Val Tyr Met Val Met Val
        930                 935                 940
Lys Cys Trp Met Ile Asp Ala Asp Ser Arg Pro Lys Phe Lys Glu Leu
945                 950                 955                 960
Ala Ala Glu Phe Ser Arg Met Ala Arg Asp Pro Gln Arg Tyr Leu Val
                965                 970                 975
Ile Gln Gly Asp Asp Arg Met Lys Leu Pro Ser Pro Asn Asp Ser Lys
        980                 985                 990
Phe Phe Gln Asn Leu Leu Asp Glu  Glu Asp Leu Glu Asp  Met Met Asp
```

-continued

```
        995                1000               1005
Ala Glu Glu Tyr Leu Val Pro Gln Ala Phe Asn Ile Pro Pro Pro
        1010               1015               1020
Ile Tyr Thr Ser Arg Thr Arg Ile Asp Ser Asn Arg Ser Glu Ile
        1025               1030               1035
Gly His Ser Pro Pro Pro Ala Tyr Thr Pro Met Ser Gly Asn Gln
        1040               1045               1050
Phe Val Tyr Gln Asp Gly Gly Phe Ala Thr Gln Gln Gly Met Pro
        1055               1060               1065
Met Pro Tyr Arg Ala Thr Thr Ser Thr Ile Pro Glu Ala Pro Val
        1070               1075               1080
Ala Gln Gly Ala Thr Ala Glu Met Phe Asp Asp Ser Cys Cys Asn
        1085               1090               1095
Gly Thr Leu Arg Lys Pro Val Ala Pro His Val Gln Glu Asp Ser
        1100               1105               1110
Ser Thr Gln Arg Tyr Ser Ala Asp Pro Thr Val Phe Ala Pro Glu
        1115               1120               1125
Arg Asn Pro Arg Gly Glu Leu Asp Glu Glu Gly Tyr Met Thr Pro
        1130               1135               1140
Met His Asp Lys Pro Lys Gln Glu Tyr Leu Asn Pro Val Glu Glu
        1145               1150               1155
Asn Pro Phe Val Ser Arg Arg Lys Asn Gly Asp Leu Gln Ala Leu
        1160               1165               1170
Asp Asn Pro Glu Tyr His Ser Ala Ser Ser Gly Pro Pro Lys Ala
        1175               1180               1185
Glu Asp Glu Tyr Val Asn Glu Pro Leu Tyr Leu Asn Thr Phe Ala
        1190               1195               1200
Asn Ala Leu Gly Ser Ala Glu Tyr Met Lys Asn Ser Val Leu Ser
        1205               1210               1215
Val Pro Glu Lys Ala Lys Lys Ala Phe Asp Asn Pro Asp Tyr Trp
        1220               1225               1230
Asn His Ser Leu Pro Pro Arg Ser Thr Leu Gln His Pro Asp Tyr
        1235               1240               1245
Leu Gln Glu Tyr Ser Thr Lys Tyr Phe Tyr Lys Gln Asn Gly Arg
        1250               1255               1260
Ile Arg Pro Ile Val Ala Glu Asn Pro Glu Tyr Leu Ser Glu Phe
        1265               1270               1275
Ser Leu Lys Pro Gly Thr Met Leu Pro Pro Pro Tyr Arg His
        1280               1285               1290
Arg Asn Thr Val Val
        1295
```

MODULATION OF EPIDERMAL GROWTH FACTOR HETERODIMER ACTIVITY

CROSS REFERENCE TO RELATED APPLICATIONS

This application claims the benefit of U.S. Provisional Patent Application Ser. No. 60/545,185, filed Feb. 17, 2004, the contents of which is herein incorporated by reference in its entirety.

GRANT STATEMENT

This work was supported by grants CA092479, CA084239, and HD039896 from the National Institutes of Health. Thus, the United States government has certain rights in the presently disclosed subject matter.

TECHNICAL FIELD

The presently disclosed subject matter relates generally to the modulation of the activity of a heterodimer of an epidermal growth factor receptor (EGFR) with other members of the ERBB family in the regulation of cellular proliferation, differentiation, and survival. More particularly, the presently disclosed subject matter relates to the modulation of the activity of EGFR/ERBB2, EGFR/ERBB3, and/or EGFR/ERBB4 heterodimers in the regulation of cellular proliferation, differentiation, and survival.

BACKGROUND ART

The epidermal growth factor receptor (EGFR) is the prototypical type-I receptor tyrosine kinase and the first member of the ERBB family of receptors to be identified (Coussens et al., 1985; Kraus et al., 1989; Carpenter & Wahl, 1990; Plowman et al., 1990; Plowman et al., 1993; Gullick, 1998). It is a member of the ERBB family of receptor tyrosine kinases, and is also known as HER1 and ERBB1. Other members of the family include HER2/NEU/ERBB2, HER3/ERBB3, and HER4/ERBB4.

The ERBB receptors have similar structures, with extracellular ligand-binding domains, a single membrane-spanning region, and a cytoplasmic protein tyrosine kinase domain. Under normal physiological conditions, the activity of the ERBB receptors is controlled by the availability of their ligands, which are members of the EGF-related growth factor family. The binding of EGF to EGFR causes dimerization of the receptor, leading to autophosphorylation and the recruitment of various molecules associated with signal transduction. Ligand binding to EGFR also results in the formation of heterodimers of EGFR and other members of the ERBB family.

EGFR, like other ERBB receptors, is required for normal mammalian development (Threadgill et al., 1995). However, inappropriate expression and/or activity of the ERBB receptors has been associated with various tumors, including tumors of the breast, colon, lung, ovary, and head and neck, and also in glioma (Rasheed et al., 1999; Wong et al., 1992; Moscatello et al., 1995). For example, there is some indication that the activity of heterodimers between EGFR and other ERBB family members (for example, ERBB2) is associated with cellular transformation and poor prognosis. Additionally, ERBB2 must heterodimerize with another ERBB family member in order to become activated, and given the role that ERBB2 appears to play in metastatic breast cancer, an ability to modulate the formation of ERBB2-containing heterodimers would be a possible strategy for treating and/or preventing this disease.

As such, there is considerable effort in the medical community to identify modulators of the ERBB family. Several such modulators are in clinical development or are already available, including the anti-EGFR antibodies ERBITUX® (cetuximab; ImClone Systems Incorporated, New York, N.Y., United States of America) and ABX-EGF (panitumumab; Abgenix, Inc., Fremont, Calif., United States of America). HERCEPTIN® (trastuzumab; Genentech, Inc., South San Francisco, Calif., United States of America) is a monoclonal antibody directed against ERBB2/HER2 that has been approved by the Food and Drug Administration for the treatment of ERBB2/HER2 positive metastatic breast cancer. Each of these antibodies is believed to modulate receptor activity by blocking ligand binding and/or enhancing endocytosis of the receptor, thus limiting its availability to become activated by ligand binding.

Small molecule inhibitors of EGFR, including IRESSA® (gefitinib/ZD1839; AstraZeneca PLC, London, United Kingdom) and TARCEVA™ (erlotinib; (OSI)™ Pharmaceuticals, Melville, N.Y., United States of America), have also been produced. These small molecules are thought to inhibit the kinase activity of EGFR. However, they are likely to be non-specific for EGFR, with significant activity on other tyrosine kinases.

Despite these advances, current methods for modulating EGFR heterodimer activity are hindered by their reliance on modulators that also modulate the activity of homodimers of the ERBB family and/or other tyrosine kinases. Ideally, a modulator should modulate the activity of EGFR heterodimers without affecting the activity of homodimeric forms of the ERBB family or ERBB family heterodimers that do not include EGFR. Thus, there exists a long-felt need in the art for modulators that are specific for heterodimers that contain EGFR.

To meet this need, the presently disclosed subject matter provides in some embodiments a method for identifying modulators that specifically bind to EGFR heterodimers. Such modulators are useful for treating disorders associated with undesirable EGFR heterodimer activity, among other applications.

SUMMARY

The presently disclosed subject matter provides a method for screening a plurality of compounds for an ability to bind to a heterodimer of EGFR and another ERBB family member. In some embodiments, the method comprises (a) contacting a first structure comprising an EGFR/ERBB heterodimer with a first solution, the first solution comprising the plurality of compounds; (b) removing any compounds bound to the first structure to produce a second solution; (c) contacting a second structure comprising an EGFR homodimer with the second solution, wherein the first structure and the second structure are identical except that the second structure does not contain an ERBB family member other than EGFR; and (d) recovering any unbound compounds to produce a third solution, whereby a compound that binds to a heterodimer of EGFR and another ERBB family member is identified. In some embodiments, the plurality of compounds comprises a plurality of antibodies. In some embodiments, the plurality of compounds comprises phage-displayed antibodies. In some embodiments, the plurality of compounds comprises a phage-displayed antibody library. In some embodiments, the phage-displayed antibody library comprises a phage-displayed single chain variable fragment (scFv) library or a phage-displayed Fab library. In some embodiments, the phage-displayed antibodies are humanized.

In some embodiments of the present method, the first structure and the third structure comprise a cell that expresses EGRF and another ERBB family member, or an isolated membrane fraction of said cell. In some embodiments, the cell is a recombinant cell that does not normally express any ERBB family member or ErbB ligand, but has been engineered to express a human EGFR and at least one other human ERBB family member. In still another embodiments, the second structure comprises a cell that expresses EGRF but no other ERBB family member, or an isolated membrane fraction of said cell. In some embodiments, the cell is a recombinant cell that does not normally express any ERBB family member or ErbB ligand, but has been engineered to express a human EGFR.

In some embodiments, the method further comprises contacting a third structure comprising an EGFR/ERBB heterodimer with the third solution; and detecting binding of a compound to the EGFR/ERBB heterodimer on the third structure. In some embodiments, the method further comprises negatively selecting the plurality of compounds by contacting the plurality of compounds with a structure that is identical to the first and second structures except that it does not contain any ERBB family members.

The presently disclosed subject matter also provides a compound identified by the disclosed methods. Such compounds can be employed for treating any disorder associated with undesirable EGFR heterodimer activity, for example, a tumor associated with EGFR heterodimer activity. Thus, the presently disclosed subject matter also provides a method for suppressing the growth of a tumor associated with EGFR heterodimer activity in a subject. In some embodiments, the method comprises administering to the subject bearing the tumor associated with EGFR heterodimer activity an effective amount of a compound identified by the disclosed methods, whereby growth of the tumor is suppressed. In some embodiments, the compound comprises an antibody or antibody fragment. In some embodiments, the antibody or antibody fragment is a single chain fragment variable (scFv) antibody or an Fab antibody. In some embodiments, the tumor is selected from the group consisting of benign intracranial meningiomas, arteriovenous malformation, angioma, macular degeneration, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, solid tumors, solid tumor metastases, angiofibromas, retrolental fibroplasia, hemangiomas, Karposi's sarcoma, head and neck carcinomas, and combinations thereof.

The present method can be employed to suppress the growth of a tumor in any organism. In some embodiments, the subject is a mammal. In some embodiments, the mammal is a human.

The presently disclosed subject matter also provides a method for identifying an antibody that specifically binds to an EGFR heterodimer. In some embodiments, the method comprises (a) isolating a membrane fraction of a cell, wherein the membrane fraction of the cell comprises EGFR and at least one of ERBB2, ERBB3, and ERBB4; (b) immunizing a mammalian subject with the membrane fraction; and (c) purifying an antibody from the antisera that specifically binds to an EGFR heterodimer. In some embodiments, (i) the cell is a mammalian cell that does not normally express any member of the ERBB family; and (ii) the mammalian cell has been transformed with one or more expression constructs that encode one or more ERBB family members selected from the group consisting of EGFR, ERBB2, ERBB3, and ERBB4, wherein the transforming results in the mammalian cell expressing EGFR and at least one of ERBB2, ERBB3, and ERBB4 in a membrane of the cell. In some embodiments, the present method further comprises isolating spleen cells from the mouse immunized with the membrane fraction; generating hybridomas using the spleen cells; and identifying a hybridoma that produces a monoclonal antibody that specifically binds to an EGFR heterodimer.

The presently disclosed subject matter also provides a method for identifying a compound that inhibits formation of a heterodimer between EGFR and another ERBB family member. In some embodiments, the method comprises (a) producing a first solution comprising a plurality of molecules that bind to EGFR; (b) producing a second solution comprising a plurality of molecules that bind to the other ERBB family member; (c) contacting the first solution with a first structure comprising a plurality of EGFR homodimers under conditions sufficient to allow any of the plurality of molecules to bind to the EGFR homodimers; (d) contacting the second solution with a second structure comprising a plurality of homodimers of the other ERBB family member under conditions sufficient to allow any of the plurality of molecules to bind to the homodimers of the other ERBB family member; (e) pooling any unbound compounds from the first and second solutions to produce a third solution; and (f) testing the unbound compounds in the third solution for an ability to inhibit formation of a heterodimer between EGFR and the other ERBB family member, whereby a compound that inhibits formation of a heterodimer between EGFR and the other ERBB family member is identified. In some embodiments, the first solution and the second solution comprise polyclonal antisera produced by immunizing an animal with purified EGFR, the other ERBB family member, or combinations thereof. In some embodiments, the first solution and the second solution comprise pooled monoclonal antibodies produced by hybridomas generated from an animal that had been immunized with purified EGFR, the other ERBB family member, or combinations thereof. In some embodiments, the first solution and the second solution are the same.

In some embodiments of the present method, the EGFR is human EGFR and the other ERBB family member is human ERBB2.

In some embodiments of the present method, the first structure and the second structure each comprises a cell that has been engineered to express either EGFR or the other ERBB family member.

Accordingly, it is an object of the presently disclosed subject matter to provide a method for screening modulators for an ability to specifically bind to an EGFR heterodimer. This and other objects are achieved in whole or in part by the presently disclosed subject matter.

An object of the presently disclosed subject matter having been stated above, other objects and advantages of the presently disclosed subject matter will become apparent to those of ordinary skill in the art after a study of the following description and non-limiting Examples.

BRIEF DESCRIPTION OF THE DRAWINGS

In FIG. 1A, the top panel depicts DNA and amino acid sequence comparisons of the $Egfr^{Wa5}$ (Wa5) kinase region containing the ENU-induced mutation with wild type Egfr (+). The bottom panel depicts the amino acid sequence similarity between highly divergent human Ser/Thr and Tyr kinases. All DFG-containing kinases listed have a functional kinase, whereas those lacking the DFG motif (shown below the dotted line) are kinase dead.

FIG. 1B depicts a ribbon structure of the human EGFR kinase domain (Protein Data Bank Identification No. 1M14) displayed with RasMol showing positions of amino acids altered in different Egfr mutations. Lys723 and Asp815 have been proven to be essential for kinase activity in vitro. Sites of existing Egfr mutations in mice (and their alleles) are indicated. The amino acid numbering is based upon the mature mouse Egfr sequence (i.e., the protein without the 24 amino acid signal sequence).

FIG. 2A depicts the number of polyps in $Apc^{Min}/+$ mice with and without an $Egfr^{Wa5}$ allele. Each dot represents the total number of polyps (>0.3 mm in diameter) from individual three-month-old mice. Horizontal lines are means for each genotype. n=20 for Egfr wild type and n=22 for $Egfr^{Wa5}/+$.

FIG. 2B depicts the sizes of polyps (diameter) from the tumor-bearing mice summarized in FIG. 2A. Each dot represents the mean size of all polyps from a single mouse. Horizontal lines are means for each group.

FIG. 3A depicts EGF-induced tyrosine phosphorylation in vivo in liver and skin extracts from two-day-old pups. FIG. 3B depicts EGF-induced tyrosine phosphorylation in vivo in liver extract from seven-day-old pups. Wild type Egfr (+/+) and $Egfr^{Wa5}/+$ (Wa5/+) pups were injected subcutaneously with either PBS (P) or EGF ($E_{0.5}$, $E_{1.0}$, and $E_{10}$ refer to 0.5, 1.0, and 10 µg/g of body weight) before euthanizing 10 minutes later. Extracts were prepared and equal amounts (15 µg) were analyzed by western blot analysis using either anti-phosphotyrosine antibody (pY) or anti-EGFR antibody (EGFR). kD, molecular weight markers; arrowheads, EGFR; arrows, p120 and p55 phosphorylation targets.

FIG. 4A depicts levels of total EGFR (EGFR) and phosphorylated EGFR (pY) protein in extracts from wild type EGFR (Wt), $EGFR^{kd}$ (a kinase-dead EGFR; kd; Honegger et al., 1987), or $EGFR^{Wa5}$ transfected CHO cells. Cells were transfected with 0.1, 0.2, or 0.5 µg of the respective expression vector. FIG. 4B depicts dimerization complexes of Wt, kd, and Wa5 in extracts from CHO cells transiently transfected with 0.5 µg of respective expression vector followed by chemical cross-linking. Arrowheads, monomers; arrows, dimers. FIG. 4C depicts levels of total and phosphorylated EGFR in extracts from CHO cells transiently co-transfected with 0.2 µg of wild type EGFR expression vector and 0.1 or 0.2 µg of Wt, kd, or Wa5 EGFR expression vectors. FIG. 4D depicts immunoprecipitation-western blot analysis of extracts from CHO cells transiently co-transfected with wild type EGFR expression vector and FLAG-tagged (f) Wt, kd, or Wa5 EGFR expression vectors. After immunoprecipitation with anti-FLAG antibody, immune complexes were divided equally before electrophoresis and blotting to three different membranes for detection of EGFR, FLAG, and pY. FIG. 4E depicts levels of total and phosphorylated EGFR in extracts from CHO cells transiently co-transfected with 0.25 µg of $EGFR^{Dsk5}$ expression vector and 0.05, 0.1, or 0.25 µg of $EGFR^{Wa5}$ expression vector or vice versa. C, extracts from non-transfected CHO cells; EGFR, anti-EGFR antibody; pY, anti-phosphotyrosine antibody; FLAG, anti-FLAG antibody; triangles, dilution series of co-transfected constructs.

FIG. 5A depicts levels of total EGFR (EGFR), total ERBB2 (B2) and phosphorylated EGFR or ERBB2 (pY) in extracts from cells co-transfected with 0.1 µg ERBB2 (B2) expression vector alone or with 0.1, 0.3, or 0.5 µg of wild type EGFR (Wt), $EGFR^{kd}$ (kd), or $EGFR^{Wa5}$ (Wa5) expression vectors. FIG. 5B depicts levels of immunoprecipitated (IP) EGFR, ERBB2, and phosphorylated EGFR or ERBB2 in extracts from cells co-transfected with ERBB2 expression vector and wild type EGFR, $EGFR^{kd}$, or $EGFR^{Wa5}$ expression vectors as described for FIG. 5A. Only 0.3 and 0.5 µg of EGFR expression vectors are shown. After immunoprecipitation with anti-EGFR or anti-ERBB2 antibodies, the immune complexes were divided equally into three aliquots before electrophoresis and blotting to three different membranes for detection of EGFR, ERBB2, and pY. Triangles, dilution series of co-transfected constructs.

In FIG. 6A, EGFR monomers form ligand independent pre-dimers and, in one model, irreversible EGFR-Wa5 homodimers are preferentially formed. Upon ligand binding, dimers become stabilized and internalized, although they do not posses a fully activated kinase. When EGFR-Wa5 or Wa5-Wa5 homodimers form, they remain as inactive kinases. However, inter-dimer interactions might play major role in fully activating the kinases of wild type receptor. Only one out of 16 combinations in this model will have EGFR dimer-dimer interactions, thus resulting in a dramatic reduction in overall ligand-induced phosphorylation when an equal numbers of EGFR and Wa5 receptors exist. In FIG. 6B, unlike EGFR, which is predominately on the cell surface, ERBB2 is primarily in cytoplasmic vesicles. Similar to the homodimers, ligand-stabilized EGFR dimers get internalized and can then form hetero-tetrameric interactions with ERBB2. Since the kinase of ERBB2 has much greater activity than EGFR, complexes with Wa5 do not inhibit phosphorylation. Dark grey, black, and light grey lines indicate EGFR, Wa5, and ERBB2 receptors, respectively. Single lines, monomers; double lines, dimers; circles, ligand; black ovals, inactive tyrosine kinases; light grey explosions, active kinases; P, phosphorylation sites.

BRIEF DESCRIPTION OF THE SEQUENCE LISTING

Figure 1:
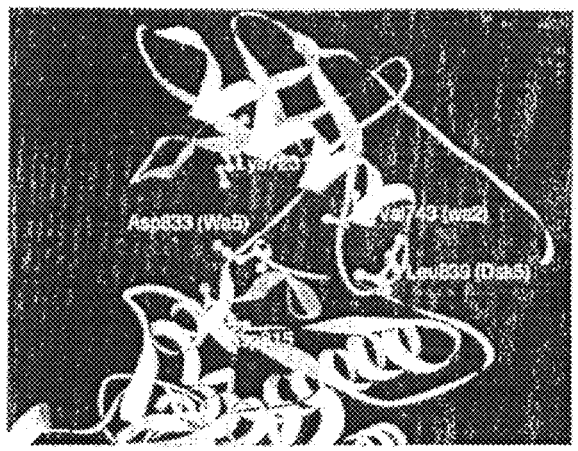
FIGS. 1A and 1B disclose the sequence and structure of the Wa5 mutation.

SEQ ID NOs: 1 and 2 present the nucleotide and amino acid sequences of human EGFR corresponding to GEN-BANK® Accession Numbers NM_005228 and NP_005219, respectively.

SEQ ID NOs: 3 and 4 present the nucleotide and amino acid sequences of mouse EGFR corresponding to GEN-BANK® Accession Numbers NM_207655 and NP_997538, respectively.

SEQ ID NOs: 5 and 6 present the nucleotide and amino acid sequences of the mouse $EGFR^{Wa5}$, respectively. SEQ ID NO: 5 differs from SEQ ID NOs: 3 by the substitution of a G for an A at nucleotide 2850, resulting in a substitution of Gly for Asp at amino acid 857. Note that because EGFR has a 24 amino acid signal sequence, Asp857 in SEQ ID NOs: 2, 4, or 6 is Asp833 as referred to herein.

SEQ ID NOs: 7-9 are the sequences of oligonucleotide primers that are used in polymerase chain reaction amplifications of the wild type and Wa5 alleles. SEQ ID NOs: 7 and 9 together can be used to amplify the wild type allele, and SEQ ID NOs: 8 and 9 can be used to amplify the Wa5 allele.

SEQ ID NOs: 10-21 are the nucleic acid and amino acid sequences of human and murine ERBB2, 3, and 4 as found in the GENBANK® database under the following Accession Nos.:

|  | Human | | Mouse | |
|---|---|---|---|---|
|  | Nucleic Acid | Amino Acid | Nucleic Acid | Amino Acid |
| ERBB2 | NM_004448; SEQ ID NO: 10 | NP_004439.2; SEQ ID NO: 11 | NM_001003817; SEQ ID NO: 12 | NP_001003817.1; SEQ ID NO: 13 |
| ERBB3 | NM_001982; SEQ ID NO: 14 | NP_001973.2; SEQ ID NO: 15 | AY686636.1; SEQ ID NO: 16 | AAT95433.1; SEQ ID NO: 17 |
| ERBB4 | NM_005235; SEQ ID NO: 18 | NP_005226.1; SEQ ID NO: 19 | XM_136682; SEQ ID NO: 20 | XP_136682.4; SEQ ID NO: 21 |

DETAILED DESCRIPTION

As disclosed herein, the $Egfr^{Wa5}$ mutation is a kinase dead antimorphic allele of Egfr that abolishes kinase activity of Egfr homodimers. However, Wa5 does not affect kinase activity in Egfr/ERBB2 heterodimers. Thus, there is a qualitative difference in the way that an Egfr molecule interacts with other Egfr molecules to form homodimers as compares with the interaction between Egfr and ERBB2 during the formation of heterodimers. This qualitative difference can be exploited to specifically inhibit the activity of heterodimers of EGFR with other members of the ERBB family.

I. Definitions

All technical and scientific terms used herein, unless otherwise defined below, are intended to have the same meaning as commonly understood by one of ordinary skill in the art, and references to techniques employed herein are intended to refer to the techniques as commonly understood in the art, including variations on those techniques or substitutions of equivalent techniques which would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including in the claims.

As used herein, unless specifically indicated otherwise, the word "or" is used in the "inclusive" sense of "and/or" and not the "exclusive" sense of "either/or".

As used herein, the term "ERBB family member" refers to a nucleic acid encoding a member of the ERBB family including, but not limited to ERBB1/HER1/EGFR, ERBB2/HER2/NEU, ERBB3/HER3, and ERBB4/HER4, or a polypeptide encoded by such a nucleic acid. These genes and gene products are found in a diversity of species. In some embodiments, the ERBB family members are mammalian ERBB family members. Representative mammals include human, mice, and rats. The nucleic acid and amino acid sequences for numerous ERBB family members are present in publicly available databases (e.g. GENBANK®, available from the website of the National Center for Biotechnology Information (NCBI)), and include the nucleic acid and amino acid sequences presented in SEQ ID NOs: 1-6 and 10-21. With regard to particular members of the ERBB family and as indicated above, each member of the family is known by at least two different names. For example, ERBB1, HER1, and EGFR all refer to the same gene and/or gene product, as do ERBB2, HER2, and NEU.

Additionally, consistent with usage in the art, identifications of genes or gene products that are presented in all capital letters refer to human genes and/or gene products or are referring to a family member without reference to the species from which it is derived. For genes and gene products from murine sources (e.g., mice), the first letter is capitalized and other letters are presented in lower case. Also typically, references to genes are presented in italics, and references to polypeptides are presented in normal type. Thus, EGFR refers to either a human EGFR gene or to an EGFR gene generally (i.e., without reference to a particular species). Similarly, EGFR refers to a human EGFR polypeptide, or to an EGFR polypeptide without reference to a particular species of origin. Egfr refers to a mouse Egfr gene, and Egfr refers to a mouse Egfr polypeptide. Furthermore, different alleles of the ERBB family can be represented in superscript form (e.g. $Egfr^{Wa5}$ or $EGFR^{kd}$) or, in the absence of specific reference to the ERBB family member when the specific ERBB family member is clear, in normal sized type (e.g., Wa5 or kd). The absence of a specific superscripted allele name indicates that the allele is a wild type allele or that the gene is being referred to generally without reference to a specific allele. The same italicization rules apply when a specific allele is identified.

As used herein, the terms "ligand" and "binding molecule", and grammatical variants thereof, refer to a molecule or other chemical entity having a capacity for binding to a target. A ligand can comprise a peptide, an oligomer, a small molecule (e.g., a chemical compound), an antibody or fragment thereof, and/or any other affinity agent. In some embodiments, a ligand is a natural ligand of an ERBB family member such as EGF, TGFα, betacellulin, heparin-binding-EGF, epiregulin, or any other natural ligand for an ERBB family member. In some embodiments, a ligand is an artificial ligand such as an antibody or a small molecule that binds to an EGFR heterodimer. In some embodiments, the phrase "binding molecules" refers to molecules (e.g. antibodies or small molecules) that modulate the activity of EGFR heterodimers. In some embodiments, a binding molecule prevents the formation of EGFR heterodimers. In some embodiments, a binding molecule prevents signal transduction via an EGFR heterodimer.

As used herein, the phrase "EGFR heterodimer" refers to a heterodimer between EGFR/ERBB1/HER1 and another member of the ERBB family. Unless otherwise indicated, the term "heterodimer" also refers to a heterodimer containing EGFR/ERBB1/HER1 and another ERBB family member. Exemplary heterodimers include heterodimers of EGFR and ERBB2, of EGFR and ERBB3, and of EGFR and ERBB4.

Additionally, the terms "heterodimer" and "homodimer" refer not only to interactions of two molecules (i.e. to form dimers), but also to higher order interactions of more than two molecules. Thus, unless otherwise indicated, the term "heterodimer" is intended to encompass interactions of, for example, three, four, five, six, seven, eight or more members of the ERBB family, wherein at least two of the interacting molecules are different family members. Similarly, the term "homodimer" is intended to encompass interactions of, for example, three, four, five, six, seven, eight or more members of the ERBB family, wherein all of the interacting molecules are the same.

As used herein, the term "modulate", and grammatical variants thereof, refers to an increase, decrease, or other alteration of any or all biological activities or properties of an ERBB family member. Similarly, the term "modulator" refers to a compound (e.g. a antibody, antibody derivative, or small molecule) that in some embodiments inhibits the formation of a heterodimer of EGFR with another ERBB family member, thereby modulating signal transduction through the heterodimer, or modulates any or all biological activities or properties of a heterodimer of EGFR with another family member by interacting (e.g. specifically binding to) the heterodimer.

The term "small molecule" as used herein refers to a compound, for example an organic compound, with a molecular weight in some embodiments of less than about 1,000 daltons, in some embodiments less than about 750 daltons, in some embodiments less than about 600 daltons, and in some embodiments less than about 500 daltons. A small molecule also has a computed log octanol-water partition coefficient that in some embodiments is in the range of about −4 to about +14, and in some embodiments is in the range of about −2 to about +7.5.

The term "binding" refers to an affinity between two molecules, for example, a ligand (e.g., a ligand of an ERBB family member) and a target (e.g., an ERBB family member). In some embodiments, the term "binding" refers to a specific binding of one molecule for another in a mixture of molecules. The binding of a ligand to a target molecule can be considered specific if the binding affinity is about $1 \times 10^4 \, M^{-1}$ to about $1 \times 10^6 \, M^{-1}$ or greater. For example, the binding of an antibody to an antigen can be thought of as having at least two components: an affinity, which refers to the strength at which the antibody binds an antigen, and a specificity, which refers to the level of cross-reactivity an antibody displays between closely related antigens.

The phrase "specifically (or selectively) binds", when referring to the binding capacity of a ligand, refers to a binding reaction which is determinative of the presence of the protein in a heterogeneous population of proteins and other biological materials. In some embodiments, the binding of a modulator is considered to be specific, that is the modulator binds to an EGFR heterodimer but does not appreciably bind to either EGFR homodimers or homodimers of other ERBB family members. As disclosed herein, the interaction of EGFR with other ERBB molecules is qualitatively different than interactions among EGFR molecules or among ERBB (non-EGFR) molecules.

The phases "substantially lack binding" or "substantially no binding", as used herein to describe binding of a ligand in a control tissue, refers to a level of binding that encompasses non-specific or background binding, but does not include specific binding.

The term "about", as used herein when referring to a measurable value such as an amount of weight, time, dose, etc., is meant to encompass variations of in some embodiments ±20%, in some embodiments ±10%, in some embodiments ±5%, in some embodiments ±1%, and in some embodiments ±0.1% from the specified amount, as such variations are appropriate to perform the disclosed methods.

II. Identification of Ligands that Bind To EGFR Heterodimers

In some embodiments, the presently disclosed subject matter provides methods for identifying ligands (e.g. antibodies or small molecules) that specifically bind to EGFR/ERBB heterodimers (e.g. heterodimers of EGFR and another ERBB family member) and modulate the activity of the EGFR/ERBB heterodimer. In some embodiments, the presently disclosed subject matter provides methods for identifying ligands (e.g. antibodies or small molecules) that prevent the heterodimerization of two different ERBB family members by binding to one or the other. In some embodiments, the method comprises (a) contacting a first structure comprising an EGFR/ERBB heterodimer with a first solution, the first solution comprising the plurality of compounds; (b) removing any compounds bound to the first structure to produce a second solution; (c) contacting a second structure comprising an EGFR homodimer with the second solution, wherein the first structure and the second structure are identical except that the second structure does not contain an ERBB family member other than EGFR; (d) recovering any unbound compounds to produce a third solution, whereby a compound that binds to a heterodimer of EGFR and another ERBB family member is identified.

In some embodiments, the method further comprises (e) contacting a third structure comprising an EGFR/ERBB heterodimer with the third solution; and (f) detecting binding of a compound to the EGFR/ERBB heterodimer on the third structure. In some embodiments, the method further comprises negatively selecting the plurality of compounds by contacting the plurality of compounds with a structure that is identical to the first and second structures except that it does not contain any ERBB family members. Exemplary structures are cells and cell components (e.g. membrane fractions), although other structures such as solid supports can also be employed with the methods disclosed herein. Thus, if the structures are cells, negative selection can be performed on a cell that does not express any ERBB family members. Additional negative selection steps can including contacting a cell that contains only homodimers of ERBB family members. The negative selections step(s) can be performed before or after contacting the structure comprising the EGFR heterodimer with the plurality of potential binding compounds. For example, 32D cells which are devoid of all EGFR and ERBB molecules and do not express any of their cognate ligands can be used to express EGFR and ERBB molecules, either individually or in combinations, to screen for interactions as described above. Exogenous ligands can be added to screen for receptor interactions that are specific for EGFR/ERBB heterodimers. In particular, betacellulin, heparin-binding-EGF, and epiregulin can be used since they are reported to be selective for EGFR/ERBB heterodimer interactions. Likewise, COS cells, which are also devoid of EGFR and ERBB receptors but which express endogenous ligands, can be used to distinguish unique EGFR/ERBB heterodimers.

As described hereinabove, the Egfr$^{Wa5}$ mutation is a kinase dead antimorphic allele of Egfr that abolishes kinase activity of Egfr homodimers but does not affect kinase activity in Egfr/ERBB2 heterodimers. Thus, there is a qualitative difference in the way that an Egfr molecule interacts with other Egfr molecules to form homodimers as compares with the interaction between Egfr and ERBB2 during the formation of heterodimers. This qualitative difference can be exploited to specifically inhibit the activity of heterodimers of EGFR with other members of the ERBB family.

As used herein, the terms "first structure", "second structure", and "third structure" refer to any structure that comprises one or more ERBB family member polypeptides and allows the one or more ERBB family member polypeptides to form homodimers and/or heterodimers between the one or more ERBB family member polypeptides in the absence of an EGFR heterodimer binding molecule as disclosed herein. Representative structures include cells and components of cells, including for example, membrane fractions from cells.

In some embodiments, the first, second, and third structures are cells that either normally express one or more ERBB family member polypeptides or have been engineered to express one or more ERBB family member polypeptides. Methods for producing expression vectors that encode members of the ERBB family and for transforming mammalian cells with these vectors to express the one or more ERBB family members in the transformed cells are known in the art.

In some embodiments, ligands that specifically bind to EGFR heterodimers are isolated from a library of potential ligands. As used herein, the term "library" means a collection of molecules. A library can contain a few or a large number of different molecules, varying from at least two molecules to several billion molecules or more. A molecule can comprise a naturally occurring molecule, or a synthetic molecule that is not found in nature. Optionally, a plurality of different libraries can be employed simultaneously for screening.

Representative libraries include but are not limited to a peptide library (U.S. Pat. Nos. 6,156,511, 6,107,059, 5,922,545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168,912 and 5,738,996), a library of antibodies or antibody fragments (for example, an scFv library or an Fab antibody library; U.S. Pat. Nos. 6,174,708, 6,057,098, 5,922,545, 5,840,479, 5,780,225, 5,702,892, and 5,667,988), a library of nucleic acid-protein fusions (U.S. Pat. No. 6,214,553), and a library of any other affinity agent that can potentially bind to an irradiated tumor (e.g., U.S. Pat. Nos. 5,948,635, 5,747,334, and 5,498,538). In some embodiments, a library is a phage-displayed antibody library. In some embodiments, a library is a phage-displayed scFv library. In some embodiments, a library is a phage-displayed Fab library. In some embodiments, a library is a soluble scFv antibody library.

The molecules of a library can be produced in vitro, or they can be synthesized in vivo, for example by expression of a molecule in vivo. Also, the molecules of a library can be displayed on any relevant support, for example, on bacterial pili (Lu et al., 1995) or on phage (Smith, 1985).

A library can comprise a random collection of molecules. Alternatively, a library can comprise a collection of molecules having a bias for a particular sequence, structure, conformation, or in the case of an antibody library, can be biased in favor of antibodies that bind to a particular antigen or antigens (for example, an EGFR heterodimer). See e.g., U.S. Pat. Nos. 5,264,563 and 5,824,483. Methods for preparing libraries containing diverse populations of various types of molecules are known in the art, for example as described in U.S. patents cited herein above. Numerous libraries are also commercially available.

II.A. Peptide Libraries

In some embodiments, a peptide library comprises peptides comprising three or more amino acids, in some embodiments at least five, six, seven, or eight amino acids, in some embodiments up to 50 amino acids or 100 amino acids, and in some embodiments up to about 200 to 300 amino acids.

The peptides can be linear, branched, or cyclic, and can include non-peptidyl moieties. The peptides can comprise naturally occurring amino acids, synthetic amino acids, genetically encoded amino acids, non-genetically encoded amino acids, and combinations thereof.

A biased peptide library can also be used, a biased library comprising peptides wherein one or more (but not all) residues of the peptides are constant. For example, an internal residue can be constant, so that the peptide sequence is represented as:

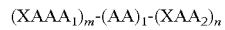

$(XAAA_1)_m\text{-}(AA)_1\text{-}(XAA_2)_n$ where $XAA_1$ and $XAA_2$ are any amino acid, wherein $XAA_1$ and $XAA_2$ are the same or different amino acids, m and n indicate a number XAA residues, wherein m and n are independently chosen from the range of 2 residues to 20 residues in some embodiments, and from the range of 4 residues to 9 residues in some embodiments, and AA is the same amino acid for all peptides in the library. In some embodiments, AA is located at or near the center of the peptide. More specifically, in some embodiments m and n are not different by more than 2 residues, and in some embodiments m and n are equal.

In some embodiments, a library is employed in which AA is tryptophan, proline, or tyrosine. In some embodiments, AA is phenylalanine, histidine, arginine, aspartate, leucine, or isoleucine. In some embodiments, AA is asparagine, serine, alanine, or methionine. In some embodiments, AA is cysteine or glycine.

A biased library used for screening also includes a library comprising molecules previously selected by other screening methods.

In some embodiments of the presently disclosed subject matter, the method for screening is performed using a phage peptide library. Phage display is a method to discover peptide ligands while minimizing and optimizing the structure and function of proteins. Phage are used as a scaffold to display recombinant libraries of peptides and provide a vehicle to recover and amplify the peptides that bind to antigens in vivo or in vitro.

The T7 phage has an icosahedral capsid made of 415 proteins encoded by gene 10 during its lytic phase. The T7 phage display system has the capacity to display peptides up to 15 amino acids in size at a high copy number (415 per phage). Unlike filamentous phage display systems, peptides displayed on the surface of T7 phage are not capable of peptide secretion. T7 phage also replicate more rapidly and are extremely robust when compared to other phage. The stability allows for bioscreening selection procedures that require persistent phage infectivity. Accordingly, the use of T7-based phage display is an aspect of some embodiments of the presently disclosed subject matter. Example 9 describes a representative method for preparation of a T7 phage peptide library that can be used to perform the screening methods disclosed herein.

A phage peptide library to be used in accordance with the screening methods of the presently disclosed subject matter can also be constructed in a filamentous phage, for example M13 or an M13-derived phage. In some embodiments, the encoded antibodies are displayed at the exterior surface of the phage, for example by fusion to the product of M13 gene III. Methods for preparing M13 libraries can be found in Sambrook & Russell, 2001, among other places.

II.B. Phage Antibody Libraries

In some embodiments, a ligand that binds to an EGFR heterodimer is an antibody, or a fragment thereof. To identify antibodies and fragments thereof that bind to EGFR heterodimers, libraries can be screened using the methods disclosed herein. Libraries that can be screened using the disclosed methods include, but are not limited to libraries of phage-displayed antibodies and antibody fragments, and libraries of soluble antibodies and antibody fragments.

"Fv" is the minimum antibody fragment that contains a complete antigen recognition and binding site. In a two-chain Fv species, this region consists of a dimer of one heavy and one light chain variable domain in tight, non-covalent association. In a single-chain Fv species (scFv), one heavy and one light chain variable domain can be covalently linked by a flexible peptide linker such that the light and heavy chains can associate in a "dimeric" structure analogous to that in a two-chain Fv species. It is in this configuration that the three complementarity-determining regions (CDRs) of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv, see Pluckthun, 1994.

The term "antibodies and fragments thereof", and grammatical variations thereof, refers to immunoglobulin molecules and immunologically active portions of immunoglobulin molecules; i.e., molecules that contain an antigen-binding site that specifically bind an antigen. As such, the term refers to immunoglobulin proteins, or functional portions thereof, including polyclonal antibodies, monoclonal antibodies, chimeric antibodies, hybrid antibodies, single chain antibodies (e.g., a single chain antibody represented in a phage library), mutagenized antibodies, humanized antibodies, and antibody fragments that comprise an antigen binding site (e.g., Fab and Fv antibody fragments). Thus, "antibodies and fragments thereof" include, but are not limited to monoclonal, chimeric, recombinant, synthetic, semi-synthetic, or chemically modified intact antibodies having for example Fv, Fab, scFv, or F(ab)$_2$ fragments.

The immunoglobulin molecules of the presently disclosed subject matter can be of any type (e.g., IgG, IgE, IgM, IgD, IgA and IgY), class (e.g., IgG1, IgG2, IgG3, IgG4, IgA1 and IgA2), or subclass of immunoglobulin molecule. In some embodiments, the antibodies are human antigen-binding antibody fragments and include, but are not limited to, Fab, Fab' and F(ab')$_2$, Fd, single-chain Fvs (scFv), single-chain antibodies, disulfide-linked Fvs (sdFv), and fragments comprising either a $V_L$ or $V_H$ domain. Antigen-binding antibody fragments, including single-chain antibodies, can comprise the variable region(s) alone or in combination with the entirety or a portion of the following: hinge region, CH1, CH2, and CH3 domains. Also included in the presently disclosed subject matter are antigen-binding fragments comprising any combination of variable region(s) with a hinge region, CH1, CH2, and CH3 domains.

The antibodies and fragments thereof of the presently disclosed subject matter can be from any animal origin including birds and mammals. For example, the antibodies can be human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described, for example in, U.S. Pat. No. 5,939,598.

In some embodiments of the presently disclosed subject matter, an antibody library (for example, a library of scFv antibodies) can be used to perform the disclosed screening methods. In these embodiments, a ligand that binds to an EGFR heterodimer is an antibody or a fragment thereof that binds an EGFR heterodimer. Antibodies that bind EGFR heterodimers can be identified by screening a phage antibody library. Similarly, antibodies that prevent the formation of EGFR heterodimers can be identified by screening a phage antibody library. Such a library can be constructed, for example, in M13 or an M13-derived phage. See e.g., U.S. Pat. Nos. 6,593,081; 6,225,447; 5,580,717; and 5,702,892, all incorporated by reference herein.

Phage-displayed recombinant antibodies are genetically cloned and expressed on the tip of the M13 bacteriophage (McCafferty et al., 1990). M13 phage infects E. coli that carry an F' episome (plasmid) and constantly produce and secrete intact M13 virus particles without lysing the host cell. The components of the M13 phage include phage DNA, coat proteins, gene III attachment proteins, and other proteins that are fused to the phage proteins. There are 3-5 copies of the gene III attachment proteins located on the exterior of the phage that are responsible for phage attachment to receptors on E. coli cells.

In some embodiments, M13 phage-displayed recombinant antibodies can be created by linking DNA from antibody-producing B lymphocytes to the phage gene III DNA using the pCANTAB vector (see Example 10). The proteins encoded by the antibody in gene III DNA are fused to one another to produce an antibody-gene III fusion protein. A bacteriophage carrying the gene fusion will simultaneously contain the antibody DNA and express an antibody molecule on the gene III protein.

A representative, non-limiting approach to obtain and characterize antigen-specific recombinant antibodies or antibody fragments (for example, scFv antibodies or human Fab antibodies) is as follows. Phage antibody selections can be performed using antigens (e.g. isolated EGFR heterodimers) immobilized on solid supports or biotinylated antigens and streptavidin magnetic beads. An aliquot of a phage antibody library can be applied to a structure comprising the target. Nonspecific phage antibodies are thereafter washed off of the structure comprising the target, and phage that encode bound antibodies can be eluted and used to infect E. coli. Infected E. coli can be plated and rescued with helper phage to produce an target-enriched phage antibody library. The target-enriched library (i.e., a library pre-selected for binding to a particular antigen of interest) can be used in a second round of selection for binding to the structure comprising the target. Subsequent rounds of selection on targets and helper phage rescue can be used until the desired target-specific antibodies are obtained. Colonies stemming for phage antibody selections can be picked from agar plates manually or by using a colony picker (for example, the QPix2 Colony Picker from Genetix USA Inc., Boston, Mass., United States of America). Picked colonies can then be transferred to appropriate vessels, for example microwell plates, and can be used to produce soluble recombinant antibodies. See e.g., Example 10.

Phage-displayed recombinant antibodies have several advantages over polyclonal antibodies or hybridoma-derived monoclonal antibodies. Phage-displayed antibodies can be generated within 8 days. Recombinant antibody clones can be easily selected by panning a population of phage-displayed antibodies against immobilized antigen (McCafferty et al., 1990). The antibody protein and antibody DNA are simultaneously contained in one phage particle (Better et al., 1988). Liters of phage-displayed recombinant antibodies can be produced inexpensively from bacterial culture supernatant and the phage antibodies can be used directly in immunoassays or other procedures without purification.

Phage display technology makes possible the direct isolation of monovalent scFv antibodies. The small size of scFv antibodies makes it the antibody format of choice, for example, for tumor penetration and rapid clearance from the blood (Adams et al., 1995; Adams, 1998; Yokota et al., 1992). The human phage antibody library can be used to develop antibodies suitable for clinical trials. Human scFv antibodies have entered clinical trials (Hoogenboom & Winter, 1992). The human phage antibody library can be used to develop antibodies suitable for clinical trials. Anti-melanoma antibodies have been developed using these phage libraries (Cai & Garen, 1995), as well as antibodies to antigens found in ovarian carcinoma (Figini et al., 1998).

Using a phage-displayed approach for the production of antibodies, scFv antibody clones that bind to EGFR heterodimers are identified as disclosed herein. Fv regions are sequenced and bivalent functional reagents are designed and tested, for example using an assay as disclosed herein. Thus, an exemplary, but non-limiting source for an antibody, or derivative or fragment thereof, is a recombinant phage-displayed antibody library.

The recombinant phage can comprise antibody-encoding nucleic acids isolated from any suitable vertebrate species, including in alternative embodiments mammalian species such as human, mouse, and rat. Thus, in some embodiments the recombinant phage encode an antibody wherein both the variable and constant regions are encoded by nucleic acids isolated from the same species (for example, human, mouse, or rat). In some embodiments, the recombinant phage encode chimeric antibodies, wherein the phrase "chimeric antibodies" (and grammatical variations thereof) refers to antibodies having variable and constant domain regions that are derived from different species. For example, in some embodiments the chimeric antibodies are antibodies having murine variable domains and human constant domains.

The scFv antibodies of the presently disclosed subject matter also include humanized scFv antibodies. Humanized forms of non-human (for example, murine) scFv antibodies are chimeric scFv antibodies that contain minimal sequence derived from non-human immunoglobulins. Humanized scFv antibodies include human scFvs in which residues from a complementarity-determining region (CDR) are encoded by a nucleic acid encoding a CDR of a non-human species such as mouse, having the desired specificity, affinity, and capacity. In some instances, Fv framework residues of the human immunoglobulin are replaced by corresponding non-human residues. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; Presta, 1992). Thus, as used herein, the term "humanized" encompasses chimeric antibodies comprising a human constant region, including those antibodies wherein all of the residues are encoded by a human nucleic acid (see e.g., Shalaby et al., 1992; Mocikat et al., 1994).

II.C. Antibody Ligands

When phage-displayed antibodies bind to an antigen, they can be affinity-purified using the antigen. These affinity-purified phage can then be used to infect and introduce the antibody gene back into E. coli. The E. coli can then be grown and induced to express a soluble, non-phage-displayed, antigen-specific recombinant antibody. Phage display technology is especially useful for producing antibodies to antigens that are either poorly immunogenic, readily degraded, only transiently produced, and/or for which monoclonal and/or polyclonal antibodies are difficult to obtain.

Epitopes formed by the heterodimerization of ERBB family members are a high priority target because they might not be accessible to antibodies or other binding molecules because the heterodimerization of two or more different ERBB family members might be transient, and/or the heterodimer itself might be quickly endocytosed. Phage scFv antibodies, for example, can be developed to these proteins by use of phage-displayed antibody libraries. Negative selection of phage can be first performed on a control tissue, for example a tissue that expresses no ERBB family members or only expresses one family member (thus eliminating the possibility that heterodimers can form). This can eliminate antibodies that nonspecifically bind to, for example, antigens unrelated to EGFR heterodimers (e.g., other cellular components) or that bind to ERBB family homodimers. Unbound phage can then be recovered and incubated with purified EGFR heterodimers, for example, EGFR/ERBB2 heterodimers. High affinity phage can then be recovered, for example by use of washing at pH 1.

The term "isolated", as used in the context of a nucleic acid, peptide, or polypeptide, indicates that the nucleic acid or polypeptide exists apart from its native environment and is not a product of nature. An isolated nucleic acid or polypeptide can exist in a purified form or can exist in a non-native environment such as a transgenic host cell. In some embodiments of the presently disclosed subject matter, "isolated" refers to the purification of an scFv antibody from a target tissue to which it has bound.

Nucleic Acids. The terms "nucleic acid molecule" or "nucleic acid" each refer to deoxyribonucleotides or ribonucleotides and polymers thereof in single-stranded or double-stranded. Unless specifically limited, the term encompasses nucleic acids containing known analogues of natural nucleotides that have similar properties as the reference natural nucleic acid. The terms "nucleic acid molecule" or "nucleic acid" can also be used in place of "gene", "cDNA", or "mRNA". Nucleic acids can be synthesized, or can be derived from any biological source, including any organism.

The term "substantially identical", as used herein to describe a degree of similarity between nucleotide sequences, refers to two or more sequences that have in some embodiments at least about least 60%, in some embodiments at least about 70%, in some embodiments at least about 80%, in some embodiments about 90% to about 99%, in some embodiments about 95% to about 99%, and in some embodiments about 99% nucleotide identity, as measured using one of the following sequence comparison algorithms (described herein below) or by visual inspection. The substantial identity exists in some embodiments in nucleotide sequences of at least about 100 residues, in some embodiments in nucleotide sequences of at least about 150 residues, and in some embodiments in nucleotide sequences comprising a full length coding sequence.

Thus, substantially identical sequences can comprise mutagenized sequences, including sequences comprising silent mutations, or variably synthesized sequences. A mutation or variant sequence can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook & Russell, 2001 for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1M $Na^+$ ion, typically about 0.01 to 1M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the presently disclosed subject matter. In some embodiments, a probe nucleotide sequence hybridizes to a target nucleotide sequence in 7% sodium dodecyl sulfate (SDS), 0.5M $NaPO_4$, 1 mM ethylenediamine tetraacetic acid (EDTA) at 50° C. followed by washing in 2×SSC, 0.1% SDS at 50° C. In some embodiments, a probe and target sequence hybridize in 7% sodium dodecyl sulfate (SDS), 0.5M $NaPO_4$, 1 mM EDTA at 50° C. followed by washing in 1×SSC, 0.1% SDS at 50° C. In some embodiments, a probe and target sequence hybridize in 7% sodium dodecyl sulfate (SDS), 0.5M $NaPO_4$, 1 mM EDTA at 50° C. followed by washing in 0.5×SSC, 0.1% SDS at 50° C. In some embodiments, a probe and target sequence hybridize in 7% sodium dodecyl sulfate (SDS), 0.5M $NaPO_4$, 1 mM EDTA at 50° C. followed by washing in 0.1×SSC, 0.1% SDS at 50° C. In some embodiments, a probe and target sequence hybridize in 7% sodium dodecyl sulfate (SDS), 0.5M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Batzer et al., 1991; Ohtsuka et al., 1985; Rossolini et al., 1994.

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising in some embodiments about 8 or more deoxyribonucleotides or ribonucleotides, in some embodiments about 10-20 nucleotides, and in some embodiments about 20-30 nucleotides of a selected nucleic acid molecule. The primers of the presently disclosed subject matter encompass oligonucleotides of sufficient length and appropriate sequence so as to provide initiation of polymerization on a nucleic acid molecule of the presently disclosed subject matter.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook & Russell, 2001; Silhavy et al., 1984; Glover & Hames, 1995; Ausubel, 1995.

Polypeptides. As used herein, the phrase "substantially identical" refers to a nucleic acid sequence having in some embodiments at least about 45%, in some embodiments at least about 50%, in some embodiments at least about 60%, in some embodiments at least about 70%, in some embodiments at least about 80%, in some embodiments at least about 90%, in some embodiments at least about 95%, and in some embodiments at least about 99% sequence identity, when compared over the full length of the open reading frame of nucleic acid encoding a single chain antibody that binds to an EGFR heterodimer or that binds to an ERBB family member polypeptide to prevent its forming a heterodimer with another ERBB family member. Methods for determining percent identity are defined herein below.

Substantially identical polypeptides also encompass two or more polypeptides sharing a conserved three-dimensional structure. Computational methods can be used to compare structural representations, and structural models can be generated and easily tuned to identify similarities around important active sites or ligand binding sites. See Saqi et al., 1999; Barton, 1998; Henikoff et al., 2000; Huang et al., 2000.

Substantially identical proteins also include proteins comprising an amino acid sequence comprising amino acids that are functionally equivalent to amino acids of a single chain antibody that binds to an EGFR heterodimer or that binds to an ERBB family member polypeptide to prevent its forming a heterodimer with another ERBB family member. The term "functionally equivalent" in the context of amino acid sequences is known in the art and is based on the relative similarity of the amino acid side-chain substituents. See Henikoff & Henikoff, 2000. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine, and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982). It is known that certain amino acids can be substituted for other amino acids having a similar hydropathic index or score and still retain a similar biological activity. In some embodiments, amino acids for which the hydropathic indices are within ±2 of the original value are substituted for each other. In some embodiments, amino acids for which the hydropathic indices are within ±1 of the original value are substituted for each other. And in some embodiments, amino acids for which the hydropathic indices are within ±0.5 of the original value are substituted for each other in making changes based upon similar hydropathicity values.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, for example, with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In some embodiments, amino acids for which the hydrophilic indices are within ±2 of the original value are substituted for each other. In some embodiments, amino acids for which the hydrophilic indices are within ±1 of the original value are substituted for each other. And in some embodiments, amino acids for which the hydrophilic indices are within ±0.5 of the original value are substituted for each other in making changes based upon similar hydropathicity values.

The term "substantially identical" also encompasses polypeptides that are biologically functional equivalents. The term "functional", as used herein to describe polypeptides comprising antibody ligands, refers two or more antibodies that are immunoreactive with the same molecules. In some embodiments, the two or more antibodies specifically bind a same target molecule and substantially lack binding to a control antigen.

Techniques for detecting antibody-target molecule complexes are known in the art and include but are not limited to centrifugation, affinity chromatography, and other immunochemical methods. See also Manson, 1992; Law, 1996.

The presently disclosed subject matter also provides functional fragments of an antibody polypeptide. Such functional portion need not comprise all or substantially all of the polypeptide, but should comprise that region of the polypeptide that binds to the heterodimer.

Isolated polypeptides and recombinantly produced polypeptides can be purified and characterized using a variety of standard techniques that are known to the skilled artisan. See e.g., Schröder & Lübke, 1965; Schneider & Eberle, 1993; Bodanszky, 1993; Ausubel, 1995.

Nucleotide and Amino Acid Sequence Comparisons. The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain biological activity of a gene, gene product, or sequence of interest.

For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, for example, by the local homology algorithm disclosed in Smith & Waterman, 1981, by the homology alignment algorithm disclosed in Needleman & Wunsch, 1970, by the search for similarity method disclosed in Pearson & Lipman, 1988, by computerized implementations of these algorithms (GAP, BESTFIT, FASTA, and TFASTA in the GCG® WISCONSIN PACKAGE™, available from Accelrys Inc., San Diego, Calif., United States of America), or by visual inspection. See generally, Ausubel, 1995.

A representative algorithm for determining percent sequence identity and sequence similarity is the BLAST algorithm, which is described in Altschul et al., 1990. Software for performing BLAST analyses is publicly available through the website of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W)=11, an expectation (E)=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff, 1992.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1 in some embodiments, less than about 0.01 in some embodiments, and less than about 0.001 in some embodiments.

II.D. Peptide Ligands

A peptide of the presently disclosed subject matter can be subject to various changes, substitutions, insertions, and deletions where such changes provide for certain advantages in its use. Thus, the term "peptide" encompasses any of a variety of forms of peptide derivatives, which include amides, conjugates with proteins, cyclized peptides, polymerized peptides, conservatively substituted variants, analogs, fragments, peptoids, chemically modified peptides, and peptide mimetics. The term "peptide ligand" refers to a peptide as defined hereinabove that binds to an EGFR heterodimer or prevents the dimerization of EGFR and another ERBB family member. The modifications disclosed herein can also be applied as desired and as appropriate to antibodies, including scFv antibodies.

Peptides of the presently disclosed subject matter can comprise naturally occurring amino acids, synthetic amino acids, genetically encoded amino acids, non-genetically encoded amino acids, and combinations thereof. Peptides can include both L-form and D-form amino acids.

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Representative derivatized amino acids include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups can be derivatized to form salts, methyl and ethyl esters or other types of esters or hydrazides. Free hydroxyl groups can be derivatized to form O-acyl or O-alkyl derivatives. The imidazole nitrogen of histidine can be derivatized to form N-im-benzylhistidine.

The term "conservatively substituted variant" refers to a peptide comprising an amino acid residue sequence substantially identical to a sequence of a reference ligand of an EGFR heterodimer in which one or more residues have been conservatively substituted with a functionally similar residue and which displays the EGFR heterodimer binding activity or the ability to prevent formation of an EGFR heterodimer as described herein. The phrase "conservatively substituted variant" also includes peptides wherein a residue is replaced with a chemically derivatized residue, provided that the resulting peptide displays activities disclosed herein.

Examples of conservative substitutions include the substitution of one (non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another.

Peptides of the presently disclosed subject matter also include peptides comprising one or more additions and/or deletions or residues relative to the sequence of a peptide whose sequence is disclosed herein, so long as the requisite activities of the peptide are maintained. The term "fragment" refers to a peptide comprising an amino acid residue sequence shorter than that of a peptide disclosed herein.

Additional residues can also be added at either terminus of a peptide for the purpose of providing a "linker" by which the peptides of the presently disclosed subject matter can be conveniently affixed to a label or solid matrix, or carrier. Amino acid residue linkers are usually at least one residue and can be 40 or more residues, more often 1 to 10 residues, but do alone not constitute receptor tyrosine kinase ligands. Typical amino acid residues used for linking are tyrosine, cysteine, lysine, glutamic and aspartic acid, or the like. In addition, a peptide can be modified by terminal-$NH_2$ acylation (e.g., acetylation, or thioglycolic acid amidation) or by terminal-carboxylamidation (e.g., with ammonia, methylamine, and the like terminal modifications). Terminal modifications are useful, as is well known, to reduce susceptibility by proteinase digestion, and therefore serve to prolong half-life of the peptides in solutions, particularly biological fluids where proteases can be present.

Peptide cyclization is also a useful terminal modification because of the stable structures formed by cyclization and in view of the biological activities observed for such cyclic peptides as described herein. An exemplary method for cyclizing peptides is described by Schneider & Eberle, 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxyl termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

The term "peptoid" as used herein refers to a peptide wherein one or more of the peptide bonds are replaced by pseudopeptide bonds including but not limited to a carba bond ($CH_2$—$CH_2$), a depsi bond (CO—O), a hydroxyethylene bond (CHOH—$CH_2$), a ketomethylene bond (CO—$CH_2$), a methylene-oxy bond ($CH_2$—O), a reduced bond ($CH_2$—NH), a thiomethylene bond ($CH_2$—S), a thiopeptide bond (CS—NH), and an N-modified bond (—NRCO—). See e.g. Corringer et al., 1993; Garbay-Jaureguiberry et al., 1992; Tung et al., 1992; Urge et al., 1992; Pavone et al., 1993.

Peptides of the presently disclosed subject matter, including peptoids, can be synthesized by any of the techniques that are known to those skilled in the art of peptide synthesis. Synthetic chemistry techniques, such as a solid-phase Merrifield-type synthesis, can be used for reasons of purity, antigenic specificity, freedom from undesired side products, ease of production, and the like. A summary of representative techniques can be found in Stewart & Young, 1969; Merrifield, 1969; Fields & Noble, 1990; and Bodanszky, 1993. Solid phase synthesis techniques can be found in Andersson et al., 2000, references cited therein, and in U.S. Pat. Nos. 6,015,561; 6,015,881; 6,031,071; and 4,244,946. Peptide synthesis in solution is described by Schröder & Lübke, 1965. Appropriate protective groups usable in such synthesis are described in the above texts and in McOmie, 1973. Peptides that include naturally occurring amino acids can also be produced using recombinant DNA technology. In addition, peptides comprising a specified amino acid sequence can be purchased from commercial sources (e.g., Biopeptide Co., LLC of San Diego, Calif., United States of America and PeptidoGenics of Livermore, Calif., United States of America).

The term "peptide mimetic" as used herein refers to a ligand that mimics the biological activity of a reference peptide, by substantially duplicating the activities of the reference peptide, but it is not a peptide or peptoid. In some embodiments, a peptide mimetic has a molecular weight of less than about 700 daltons.

A peptide mimetic can be designed by: (a) identifying the pharmacophoric groups responsible for the activities of a peptide; (b) determining the spatial arrangements of the pharmacophoric groups in the active conformation of the peptide; and (c) selecting a pharmaceutically acceptable template upon which to mount the pharmacophoric groups in a manner that allows them to retain their spatial arrangement in the active conformation of the peptide. For identification of pharmacophoric groups responsible for an activity, mutant variants of the peptide can be prepared and assayed for the activity. Alternatively or in addition, the three-dimensional structure of a complex of the peptide and its target molecule can be examined for evidence of interactions, for example the fit of a peptide side chain into a cleft of the target molecule, potential sites for hydrogen bonding, etc. The spatial arrangements of the pharmacophoric groups can be determined by NMR spectroscopy or X-ray diffraction studies. An initial three-dimensional model can be refined by energy minimization and molecular dynamics simulation. A template for modeling can be selected by reference to a template database and will typically allow the mounting of 2-8 pharmacophores. A peptide mimetic is identified wherein addition of the pharmacophoric groups to the template maintains their spatial arrangement as in the peptide.

A peptide mimetic can also be identified by assigning a hashed bitmap structural fingerprint to the peptide based on its chemical structure, and determining the similarity of that fingerprint to that of each compound in a broad chemical database. The fingerprints can be determined using fingerprinting software commercially distributed for that purpose by Daylight Chemical Information Systems, Inc. (Mission Viejo, Calif., United States of America) according to the vendor's instructions. Representative databases include but are not limited to SPREI'95 (InfoChem GmbH of München, Germany), Index Chemicus (ISI of Philadelphia, Pa., United States of America), World Drug Index (Derwent of London, United Kingdom), TSCA93 (United States Environmental Protection Agency), MedChem (Biobyte of Claremont, Calif., United States of America), Maybridge Organic Chemical Catalog (Maybridge of Cornwall, England), Available Chemicals Directory (MDL Information Systems of San Leandro, Calif., United States of America), NCI96 (United States National Cancer Institute), Asinex Catalog of Organic Compounds (Asinex Ltd. of Moscow, Russia), and NP (InterBioScreen Ltd. of Moscow, Russia). A peptide mimetic of a reference peptide is selected as comprising a fingerprint with a similarity (Tanamoto coefficient) of at least 0.85 relative to the fingerprint of the reference peptide. Such peptide mimetics can be tested for bonding to an irradiated tumor using the methods disclosed herein. Additional techniques for the design and preparation of peptide mimetics can be found in U.S. Pat. Nos. 5,811,392; 5,811,512; 5,578,629; 5,817,879; 5,817,757; and 5,811,515.

Any peptide or peptide mimetic of the presently disclosed subject matter can be used in the form of a pharmaceutically acceptable salt. Suitable acids which are capable of the peptides with the peptides of the presently disclosed subject matter include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the presently disclosed subject matter include inorganic bases such as sodium hydroxide, ammonium hydroxide, potassium hydroxide and the like; and organic bases such as mono-di- and tri-alkyl and aryl amines (e.g. triethylamine, diisopropyl amine, methyl amine, dimethyl amine and the like), and optionally substituted ethanolamines (e.g. ethanolamine, diethanolamine and the like).

III. Applications

The presently disclosed subject matter also provides a method for suppressing the growth of a tumor associated with EGFR heterodimer activity in a subject, the method comprising administering to the subject bearing the tumor associated with EGFR heterodimer activity an effective amount of a EGFR heterodimer binding compound as disclosed herein, whereby growth of the tumor is suppressed In some embodiments, the method comprises contacting a tumor cell in a tumor with an EGFR heterodimer binding compound (for example, an antibody, peptide, or small molecule that specifically binds to an EGFR/ERBB heterodimer) under conditions sufficient to allow the EGFR heterodimer binding compound to inhibit the activity of the EGFR heterodimer. In some embodiments, the EGFR heterodimer binding compound is administered directly to a subject having a tumor. In some embodiments, a vector (for example, an expression vector, an adenoviral vector, or a retroviral vector) encoding an EGFR heterodimer binding compound is administered to the subject. For example, EGFR heterodimer binding compounds can be useful in the treatment of both primary and metastatic solid tumors and carcinomas of the breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries, choriocarcinoma and gestational trophoblastic disease; male genital tract including prostate, seminal vesicles, testes and germ cell tumors; endocrine glands including thyroid, adrenal, and pituitary; skin including hemangiomas, melanomas, sarcomas arising from bone or soft tissues and Kaposi's sarcoma; tumors of the brain, nerves, eyes, and meninges including astrocytomas, gliomas, glioblastomas, retinoblastomas, neuromas, neuroblastomas, Schwannomas and meningiomas; solid tumors arising from hematopoietic malignancies such as leukemias and including chloromas, plasmacytomas, plaques and tumors of mycosis fungoides and cutaneous T-cell lymphoma/leukemia; lymphomas including both Hodgkin's and non-Hodgkin's lymphomas.

III.A. Subjects

The subject treated in the presently disclosed subject matter in its many embodiments is desirably a human subject, although it is to be understood that the principles of the presently disclosed subject matter indicate that the presently disclosed subject matter is effective with respect to invertebrate and to all vertebrate species, including mammals, which are intended to be included in the term "subject". Moreover, a mammal is understood to include any mammalian species in which treatment or prevention of cancer is desirable, particularly agricultural and domestic mammalian species.

The methods of the presently disclosed subject matter are particularly useful in the treatment of warm-blooded vertebrates. Thus, the presently disclosed subject matter concerns mammals and birds.

More particularly provided is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economic importance to humans. Thus, contemplated is the treatment of livestock, including, but not limited to, domesticated swine (pigs and hogs), ruminants, horses, poultry, and the like.

III.B. Formulation

The EGFR heterodimer binding compounds of the presently disclosed subject matter, or vectors encoding the same, comprise in some embodiments a composition that includes a pharmaceutically acceptable carrier.

For example, suitable formulations can include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS, in some embodiments in the range of 0.1 to 10 mg/ml, in some embodiments about 2.0 mg/ml; and/or mannitol or another sugar, for example in the range of 10 to 100 mg/ml, in some embodiments about 30 mg/ml; and/or phosphate-buffered saline (PBS).

It should be understood that in addition to the ingredients particularly mentioned above the formulations of this presently disclosed subject matter can include other agents conventional in the art having regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, the cytokines IFN-α, IFN-γ, IL2, IL4, IL6, TNF, or other cytokine affecting immune cells. In accordance with this aspect of the presently disclosed subject matter, the disclosed EGFR heterodimer binding compounds or vectors encoding the same can be administered in combination therapy with one or more of these cytokines.

III.C. Administration

Administration of the compositions of the presently disclosed subject matter can be by any method known to one of ordinary skill in the art, including, but not limited to intravenous administration, intrasynovial administration, transdermal administration, intramuscular administration, subcutaneous administration, topical administration, rectal administration, intravaginal administration, intratumoral administration, oral administration, buccal administration, nasal administration, parenteral administration, inhalation, and insufflation. In some embodiments, suitable methods for administration of a nucleic acid molecule of the presently disclosed subject matter (for example, using an expression vector) include but are not limited to intravenous or intratumoral injection. Alternatively, a nucleic acid molecule can be deposited at a site in need of treatment in any other manner, for example by spraying a composition comprising a nucleic acid molecule within the pulmonary pathways. The particular mode of administering a composition of the presently disclosed subject matter depends on various factors, including the distribution and abundance of cells to be treated, the vector employed, additional tissue- or cell-targeting features of the vector, and mechanisms for metabolism or removal of the vector from its site of administration. For example, relatively superficial tumors can be injected intratumorally. By contrast, internal tumors can be treated by intravenous injection.

In some embodiments, the method of administration encompasses features for regionalized delivery or accumulation at the site in need of treatment. In some embodiments, an EGFR heterodimer binding compound or expression vector encoding the same is delivered intratumorally. In some embodiments, selective delivery of an EGFR heterodimer binding compound or vector encoding the same to a tumor is accomplished by intravenous injection of the construct For delivery of an EGFR heterodimer binding compound or vector encoding the same to pulmonary pathways, an EGFR heterodimer binding compound or vector encoding the same of the presently disclosed subject matter can be formulated as an aerosol or coarse spray. Methods for preparation and administration of aerosol or spray formulations can be found, for example, in Cipolla et al., 2000, and in U.S. Pat. Nos. 5,858,784; 6,013,638; 6,022,737; and 6,136,295.

III.D. Dose

An effective dose of a composition of the presently disclosed subject matter is administered to a subject in need thereof. A "therapeutically effective amount" is an amount of the composition sufficient to produce a measurable response (e.g., a decrease in the growth rate of a tumor). In some embodiments, an activity that inhibits tumor growth is measured. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved.

The potency of a composition can vary, and therefore a "therapeutically effective" amount can vary. However, using the assay methods described herein below, one skilled in the art can readily assess the potency and efficacy of a candidate modulator of this presently disclosed subject matter and adjust the therapeutic regimen accordingly.

After review of the disclosure of the presently disclosed subject matter presented herein, one of ordinary skill in the art can tailor the dosages to an individual patient, taking into account the particular formulation, method of administration to be used with the composition, and tumor size. Further calculations of dose can consider patient height and weight, severity and stage of symptoms, and the presence of additional deleterious physical conditions. Such adjustments or variations, as well as evaluation of when and how to make such adjustments or variations, are well known to those of ordinary skill in the art of medicine.

For example, for local administration of viral vectors, previous clinical studies have demonstrated that up to $10^{13}$ plaque-forming units (pfu) of virus can be injected with minimal toxicity. In human patients, $1 \times 10^9$-$1 \times 10^{13}$ pfu are routinely used (see Habib et al., 1999). To determine an appropriate dose within this range, preliminary treatments can begin with $1 \times 10^9$ pfu, and the dose level can be escalated in the absence of dose-limiting toxicity. Toxicity can be assessed using criteria set forth by the National Cancer Institute and is reasonably defined as any grade 4 toxicity or any grade 3 toxicity persisting more than 1 week. Dose is also modified to maximize anti-tumor or anti-angiogenic activity. Representative criteria and methods for assessing anti-tumor and/or anti-angiogenic activity are described herein below. With replicative virus vectors, a dosage of about $1 \times 10^7$ to $1 \times 10^8$ pfu can be used in some instances.

An expression construct as disclosed herein can be packaged into a vector (for example, an viral vector including, but not limited to an adenovirus vector, an adeno-associated virus vector, or a retroviral vector) and the prepared virus titer reaches at least $1 \times 10^6$-$1 \times 10^7$ pfu/ml. In some embodiments, the viral vector is administered in the amount of 1.0 pfu/target cell. Thus, administration of a minimal level of viral vector to thereby provide a therapeutic level of an EGFR heterodimer binding compound encoded by a viral vector comprises an aspect of the presently disclosed subject matter.

EXAMPLES

The following Examples have been included to illustrate modes of the presently disclosed subject matter. Certain aspects of the following Examples are described in terms of techniques and procedures found or contemplated by the present co-inventors to work well in the practice of the presently disclosed subject matter. These Examples illustrate standard laboratory practices of the co-inventors. In light of the present disclosure and the general level of skill in the art, those of skill will appreciate that the following Examples are intended to be exemplary only and that numerous changes, modifications, and alterations can be employed without departing from the scope of the presently disclosed subject matter.

Example 1

Egfr$^{Wa5}$ Mutation Identification

All exons (Reiter et al., 2001), along with immediate flanking regions, of Egfr were amplified by polymerase chain reaction (PCR) from Egfr$^{wa5}$/+, BALB/c, C3H, and C57BL/6 genomic DNA using intronic primers that were also used for subsequent sequence analysis. PCR products were purified using the multiscreen PCR 96-well filtration system (Millipore Corp., Billerica, Mass., United States of America) on a BIOMEK® 2000 robotic platform (Beckman Coulter, Inc., Fullerton, Calif., United States of America) and sequenced directly using BIG DYE™ terminator cycle sequencing (Applied Biosystems, Inc., Foster City, Calif., United States of America). Sequences were analyzed using the SEQUENCER™ program (Gene Codes Corp., Ann Arbor, Mich., United States of America) to identify the causative mutation in Egfr$^{Wa5}$.

Example 2

Mouse Strains, Crosses, and Genotyping

The Egfr$^{Wa5}$ mutation was maintained by intercrossing Egfr$^{WA5}$/+ mice on a mixed genetic background containing contributions from BALB/c, C3H, and C57BL/6J. The Egfr$^{wa2}$/+ and Egfr$^{tm1Mag}$/+ (Threadgill et al., 1995) mutations were maintained on C57BL/6J congenic or 129S6/SvEvTAC isogenic backgrounds, respectively. Tgfa$^{tm1Dcl}$ null mice were maintained on a mixed genetic background of 129S6/SvEvTAC and C57BL/6J (Luetteke et al., 1993). The Apc$^{min}$ mutation (Moser et al., 1993) was maintained as congenic on a C57BL/6J background.

Complementation studies were performed by crossing Egfr$^{tm1Mag}$/+ females with Egfr$^{Wa5}$/+ males. Egfr$^{Wa5}$/+ female mice were bred to Apc$^{Min}$/+ male mice, producing Apc$^{Min}$/+ mice on wild type and Egfr$^{Wa5}$/+ backgrounds. To generate Tgfa$^{tm1Dcl/tm1Dcl}$, Egfr$^{Wa5}$/+ double-mutant mice, Tgfa$^{tm1Dcl/tm1Dcl}$ females were mated to Tgfa$^{tm1/Dcl}$/+, Egfr$^{Wa5}$/+ males. In order to generate compound heterozygous animals, Egfr$^{wa2}$/+ females were crossed to Egfr$^{Wa5}$/+ males. The morning a vaginal plug was detected was defined as 0.5 day of embryonic development (0.5 dpc). Mice were fed Purina Mills Lab Diet 5058 (Purina Mills, LLC, St. Louis, Mo., United States of America) under specific pathogen-free conditions in an American Association for the Accreditation of Lab Animal Care approved facility. Mice were euthanized by $CO_2$ asphyxiation.

Embryonic yolk sacs from embryos or tail clips from neonates were used to extract DNA for genotype determination by PCR. The genotype for the Egfr$^{Wa5}$ allele was determined by PCR using three primers: mEgfr-Ex21-S5,5'-gcatgtcaagatcacaga-3' (SEQ ID NO: 7); mEgfr-Ex21-S6,5'-gcatgtcaagatcacagg-3' (SEQ ID NO: 8); and mEgfr-In21-As1, 5'-tagagaatgaccctgacgag-3' (SEQ ID NO: 9). The mEgfr-Ex21-S5 and mEgfr-In21-As1 primers amplify a 228-base pair (bp) product specific for the wild type Egfr allele and primers mEgfr-Ex21-S6 and mEgfr-In21-As1 amplify a 228-bp product specific for the Egfr$^{Wa5}$ allele. Genotypes for the Egfr$^{tm1Mag}$, Egfr$^{wa2}$, Apc$^{Min}$, Mom1, and Tgfa$^{tm1Dcl}$ alleles were determined by PCR as previously described (Luetteke et al., 1993; Roberts et al., 2001).

Example 3

In Vivo Phosphorylation Assays

Neonatal pups were injected subcutaneously with 10 µl/g body weight of phosphate-buffered saline (PBS) or 0.5, 1.0, or 10 µg/g body weight of EGF (R&D Systems Inc., Minneapolis, Minn., United States of America) in PBS. After 10 minutes, liver and skin were harvested, frozen in liquid nitrogen, and stored at −80° C. The frozen tissues were homogenized in 5-10 volumes (5-10 ml/g tissue) of homogenization buffer consisting of 20 mM HEPES, pH 7.4, 150 mM NaCl, 10% glycerol, 1% Triton X-100, 1 mM PMSF, 10 µg/ml of leupeptin, 10 µg/ml of aprotinin, 1 mM sodium vanadate, and 10 mM β-glycerophosphate at 4° C. The tissue lysates were cleared by centrifugation for 10 minutes at 4° C. and protein concentrations were determined by the Bradford assay (Bio-Rad Laboratories, Hercules, Calif., United States of America). An equal amount of protein lysate (15 µg) was separated by denaturing 7.5% sodium dodecylsulfate polyacrylamide gel electrophoresis (SDS-PAGE) and transferred to PVDF membranes (Bio-Rad Laboratories). Protein blots were incubated with recombinant antiphosphotyrosine antibody conjugated with horseradish peroxidase (BD Biosciences Pharmingen, San Diego, Calif., United States of America) or polyclonal rabbit anti-EGFR antibody (Lab Vision/NeoMarkers, Montréal, Québec, Canada) and detected with an enhanced chemiluminesence system (Amersham Biosciences, Piscataway, N.J., United States of America).

Example 4

Cell Culture and Transfection

Chinese hamster ovary (CHO) cells were grown in Dulbecco's modified Eagle's 1 medium (DMEM) supplemented with 10% fetal bovine serum (FBS), nonessential amino acids, and penicillin/streptomycin. CHO cells in 60-mm dishes at 50%-70% confluency were transfected with human EGFR expression vectors in pcDNA3.1 (Invitrogen Corporation, Carlsbad, Calif., United States of America) using FuGENE 6 transfection reagent (Roche Applied Science, Palo Alto, Calif., United States of America) and cell extracts were prepared at 24 hour after transfection as described previously (Fitch et al., 2003). The Asp855Gly (Wa5) change was introduced into a human EGFR expression vector by site-directed mutagenesis using GENEEDITOR™ (Promega Corp., Madison, Wis., United States of America) and the entire coding regions were verified by sequence analysis. An equal amount of protein (12 µg) was separated by denaturing 6% SDS-PAGE and analyzed by western blot analysis as described above.

Example 5

Chemical Cross-Linking

Chemical cross-linking of EGFR was carried out as described previously (Qian et al., 1994). Briefly, CHO cells transfected with EGFR expression vectors in 6-well plates for 24 hours were washed twice with cold PBS. One milliliter of PBS containing 2 mM bis(sulfosuccinimidyl) suberate ($BS_3$; Pierce Biotechnology, Inc., Rockford, Ill., United States of America) was added and incubated at room temperature for 30 minutes with rocking of the plates. The reaction was stopped by washing twice with cold 20 mM Tris-HCl, pH 7.4/150 mM NaCl and cell lysates were prepared as described above. Protein concentration was measured using the Bradford assay (Bio-Rad Laboratories, Hercules, Calif., United States of America). An equal amount (12 µg) of protein was separated by 6% SDS-PAGE, transferred to PVDF membranes and subjected to western blot analysis as described above.

Example 6

FLAG-Tag and Immunoprecipitation-Western Blot

A Xba I to Dra III fragment of the human EGFR expression vector was replaced with a Sac I to Dra III fragment of pBK-Flag-EGFR (Kim et al., 2003) containing the FLAG epitope immediately after the signal sequence to generate N-terminal FLAG-tagged wild-type (fWt), kd (fkd) and Wa5 (fWa5) EGFR expression vectors. Wild-type EGFR expression vectors were co-transfected with an equal quantity (0.2 µg) of EGFR$^f$, EGFR$^{fkd}$, or EGFR$^{fWa5}$ expression vector and cell extracts were prepared 24 hours after transfection as described above. Cell lysates (200 µg) were immunoprecipitated with 5 µg of monoclonal anti-FLAG M2 antibody (Sigma-Aldrich Co., St. Louis, Mo., United States of America) overnight at 4° C. and then for 2 hours after addition of 30 µl of Protein G-agarose (Pierce Biotechnology, Inc.). Immunoprecipitated complexes were washed three times with TBS buffer (50 mM Tris-HCl, pH 7.4/150 mM NaCl) and the bound proteins were eluted by boiling for 5 minutes in 2×SDS sample buffer (125 mM Tris-HCl, pH 6.8/4% SDS/ 20% glycerol/0.05% bromophenol blue). For the immunoprecipitation of EGFR or ERBB2, cell lysates (100 µg) were incubated overnight with 5 µg of monoclonal anti-EGFR antibody (clone 528) or 3 µg of polyclonal anti-ERBB2 antibody (Santa Cruz Biotechnology, Inc., Santa Cruz, Calif., United States of America) at 4° C. After 2 hours of incubation with 30 µl of Protein G-agarose, immunoprecipitated complexes were washed four times with HNTG buffer (20 mM HEPES, pH 7.5/150 mM NaCl/0.1% Triton X-100/10% glycerol) and the bound proteins were eluted as described above. One-sixth of the immunoprecipitate volumes were separated by 6% SDS-PAGE, transferred to PVDF membranes and subjected to western blot analysis. For the detection of the FLAG epitope, the same antibody was used for western blot analysis as for immunoprecipitation.

Example 7

Intestinal Macroadenoma Analysis

The small intestines from pylorus to cecum and the colons were dissected from 3-month-old mice, flushed gently with PBS to remove fecal material, cut longitudinally, and splayed flat on Whatman 3MM paper (Whatman Inc., Florham Park, N.J., United States of America). The gastrointestinal tracts were fixed overnight at 4° C. in 10% neutral buffered formalin (Sigma-Aldrich Co., St. Louis, Mo., United States of America) before storing in 70% ethanol. The number and diameter of macroadenoma polyps were characterized as previously described (Roberts et al., 2001). The Mann-Whitney paired rank sum test was used to analyze the association between genotype and polyp number and size. Statistical analysis was performed using StatView (SAS Institute Inc., Cary, N.C., United States of America).

Discussion of Examples 1-7

Wa5 has a point mutation in a highly conserved residue within Egfr and causes embryonic and perinatal lethality. Previous analysis of ENU-induced mutations causing dominant visible phenotypes detected Wa5 as a mutation that causes open eyes at birth, curly whiskers, and a wavy coat similar to the recessive $Tgfa^{wa1}$ and $Egfr^{wa2}$ mutations (Thaung et al., 2002). Since genetic mapping localized the mutation to proximal Chromosome 11 near the Egfr locus, a complementation cross was performed with an $Egfr^{tm1Mag}$ null allele (see Table 1). The Wa5 allele failed to complement $Egfr^{tm1Mag}$, supporting the fact that Wa5 is a new allele of Egfr ($Egfr^{Wa5}$). The entire coding region from EgfrWa5 transcripts was sequenced, and a single-point mutation was identified that creates a missense mutation (GAT to GGT) in exon 21; this change results in a D833G amino acid change within the tyrosine kinase domain (see FIG. 1A), altering a DFG motif that is ubiquitously conserved in all functional protein kinases (Hanks et al., 1988). The Lys723 residue binds Mn•ATP that is aligned within the active site by Asp833 for catalysis at Asp815 (Coker et al., 1994). The previously characterized $Egfr^{wa2}$ (Helmrath et al., 1997; Egger et al., 2000; Wang et al., 2003) and $Egfr^{Dsk5}$ (Fitch et al., 2003) mutations, which result in changes at Val743 and Leu839 probably alter the structure of the active site since they are in an alpha-helix (ac) and the activation loop, respectively, rather than the catalytic loop (see FIG. 1B).

TABLE 1

Wa5 and $Egfr^{tm1Mag}$ Complementation Cross - Results from 3 Litters Genotypes

| +/+ | Wa5/+ | Egfrtm1 Mag/+ | Egfrtm1Mag/Wa5 |
|-----|-------|---------------|----------------|
| 7   | 14    | 6             | 0              |

Tyrosine kinases lacking the conserved DFG motif are Kinase dead (Kroiher et al., 2001) and hypothesized to negatively regulate active kinases when oligomerized. In this manner, $Egfr^{Wa5}$ appears to be acting as an antimorphic allele, distinctly different than the previously characterized dominant hypermorphic mutation $Egfr^{Dsk5}$ (Fitch et al., 2003).

Since $Egfr^{Wa5}$ failed to complement the $Egfr^{tm1Mag}$ null allele, the survival of $Egfr^{Wa5}$ homozygous embryos generated from $Egfr^{Wa5}/+$ intercrosses was analyzed. Morphologically normal $Egfr^{Wa5/Wa5}$ embryos were observed at 10.5 dpc in expected Mendelian ratios (see Table 2). Lethality of the majority of $Egfr^{Wa5/Wa5}$ embryos (71%) occurs between 10.5 and 12.5 dpc; a similar age of embryonic lethality was found to be caused by homozygosity for the $Egfr^{tm1Mag}$ null allele (Threadgill et al., 1995). Morphologically abnormal and severely degenerated embryos at 10.5-14.5 dpc were either $Egfr^{Wa5}/+$ (25%) or $Egfr^{Wa5/Wa5}$ (75%). Although a few $Egfr^{Wa5/Wa5}$ embryos developed to later stages of gestation, no $Egfr^{Wa5/Wa5}$ embryos survived postnatally; despite being grossly normal in size, three newborn $Egfr^{Wa5/Wa5}$ pups were found dead shortly after birth. This result is consistent with that observed for the $Egfr^{tm1Mag}$ null allele where embryos homozygous for $Egfr^{tm1Mag}$ display variable embryonic and early postnatal lethality that is dependent upon genetic background (Strunk et al., 2004).

TABLE 2

Viability of $Egfr^{Wa5}$ Homozygotes from $Egfr^{Wa5}/+$ Intercrosses

| Stage[a] | Genotypes[b] | | | Litters |
|----------|-----|---------------|------------------|---------|
|          | +/+ | $Egfr^{Wa5}/+$ | $Egfr^{Wa5/Wa5}$ |         |
| 10.5 dpc | 12 (0) | 26 (2) | 14 (4) | 8  |
| 12.5 dpc | 22 (0) | 40 (0) | 6 (3)  | 10 |
| 14.5 dpc | 13 (0) | 30 (1) | 6 (2)  | 8  |
| P0       | 20     | 40     | 3      | 11 |
| P21      | 20     | 39     | 0      | 11 |

[a]dpc, embryonic day and P, postnatal day.
[b]Number of normal (abnormal) embryos or live pups.

$Egfr^{Wa5}$ allele enhances the recessive $Egfr^{wa2}$ hypomorphic and $Tgfa^{TM1Dcl}$ null phenotypes. On a mixed genetic background, $Egfr^{wa2}$ homozygous pups surviving to adulthood are fertile, and show defects only in hair follicle morphogenesis (Luetteke et al., 1994). Therefore, to determine the effects of further reduction in EGFR activity, $Egfr^{wa2}/+$ females were crossed with $Egfr^{Wa5}/+$ males to generate $Egfr^{wa2/Wa5}$ compound heterozygotes (see Table 3). When compared to wild type littermates, only half of the predicted $Egfr^{wa2/Wa5}$ compound pups were born, although those surviving were normal in size at birth. Nine of 16 $Egfr^{wa2/Wa5}$ pups died during the first two days after birth, while three $Egfr^{wa2/Wa5}$ pups became progressively more runted, dying between two and three weeks of age. Four of 16 $Egfr^{wa2/Wa5}$ compound mutants, including three males and one female, survived as long as three months after birth. These $Egfr^{wa2/Wa5}$ compound mutants showed severe growth retardation with a body weight ranging from 30% to 50% of the control littermates. Although hair development of $Egfr^{wa2/Wa5}$ pups was initially similar to that of $Egfr^{wa2/Wa2}$ pups, $Egfr^{wa2/Wa5}$ compound mutant mice underwent a complete hair loss around 8 weeks of age; new hair growth resumed at 2 months of age. Craniofacial malformations, including an underdeveloped lower jaw and narrow, elongated, and asymmetric snouts, were also observed in $Egfr^{wa2/Wa5}$ compound-mutant mice, similar to the phenotype described previously in Egfr nullizygous mice (Miettinen et al., 1999). The only female $Egfr^{wa2/Wa5}$ mutant that survived postweaning showed a delay in vaginal opening until 11 weeks of age, an increase in severity of a phenotype reported for Egfr$^{wa2/wa2}$ mice that show delayed vaginal opening at 7.5 weeks (Apostolakis et al., 2000). Neither gender produced offspring by 3 months of age, suggesting they might also have fertility defects.

Similar to the Egfr$^{wa2}$ mutation, transforming growth factor α(TGFA) deficiency gives rise to coat and eye abnormalities (Luetteke et al., 1993; Mann et al., 1993). Since TGFA is one of the major ligands for EGFR, the phenotypic severity of Tgfa$^{tm1Dcl/tm1Dcl}$, Egfr$^{Wa5}$/+ double mutants produced by crossing Tgfa$^{tm1Dcl}$ nullizygous females to Egfr$^{Wa5}$/+, Tgfa$^{tm1Dcl}$/+ males. Double-mutant Tgfa$^{tm1Dcl/tm1Dcl}$, Egfr$^{Wa5}$/+ pups were born at expected ratios and were normal in size at birth. However, these mice had reduced postnatal growth rates resulting in a noticeable decrease in body size by 1 week of age relative to their littermates. Similar to Egfr$^{wa2/Wa5}$ compound mutants, Tgfa$^{tm1Dcl/tm1Dcl}$, Egfr$^{Wa5}$/+ double mutants showed an approximate 25% reduction in body weight by 6 weeks of age when compared with Tgfa$^{tm1Dcl}$ homozygous or Egfr$^{Wa5}$ heterozygous littermates. Additionally, two Tgfa$^{tm1Dcl/tm1Dcl}$, Egfr$^{Wa5}$/+ double mutants showed smaller lower jaws. Interestingly, unlike body weight, the coat phenotype of the double-mutant pups was not exacerbated and remained indistinguishable from Egfr$^{Wa5}$/+ or Tgfa$^{tm1Dcl/tm1Dcl}$ single-mutant mice.

EgfrWa5 allele reduces the multiplicity but not growth of Apc$^{Min}$-meditated intestinal tumors. It has been previously showed that Apc$^{Min}$-mediated intestinal tumor multiplicity is dramatically reduced in Egfr$^{wa2/wa2}$ mice (Roberts et al., 2001). Therefore, to functionally verify the reduced activity of Egfr$^{Wa5}$, Apc$^{Min}$/+ mice were crossed with Egfr$^{Wa5}$/++ mice to generate Apc$^{Min}$/+ Egfr$^{Wa5}$/+ double heterozygotes. Three month-old Apc$^{Min}$+ Egfr$^{Wa5}$/+ mice had a 46% reduction in the average number of macroscopic intestinal polyps (>0.3 mm) compared with Apc$^{Min}$+ littermates wild type for Egfr (Egfr$^{Wa5}$/+; 7.4±1.7; Egfr+/+; 13.7±2.6; p=0.03; see FIG. 2A). Since the cross was segregating alleles at the major Apc$^{Min}$ modifier locus Mom1, each mouse was genotyped for resistance (r) or susceptibility (s) at the Mom1 locus. On a Mom1$^{r/s}$ heterozygous background, Apc$^{Min}$/+ Egfr$^{Wa5}$/+ mice showed 53% fewer intestinal polyps than Apc$^{Min}$/+ mice, whereas on a Mom1$^{r/s}$ background, Apc$^{Min}$/+ Egfr$^{Wa5}$/+ mice showed a 32% reduction in tumor number when compared with Apc$^{Min}$/+. Apc$^{Min}$/+ mice on a Mom1$^{r/s}$ background showed a 42% reduction in polyp multiplicity, independent of Egfr$^{Wa5}$ status, compared with a Mom1$^{s/s}$ background (p=0.03), consistent with a previous report (Gould et al., 1996). No gender-dependent differences in polyp multiplicity were observed.

Figure 2:
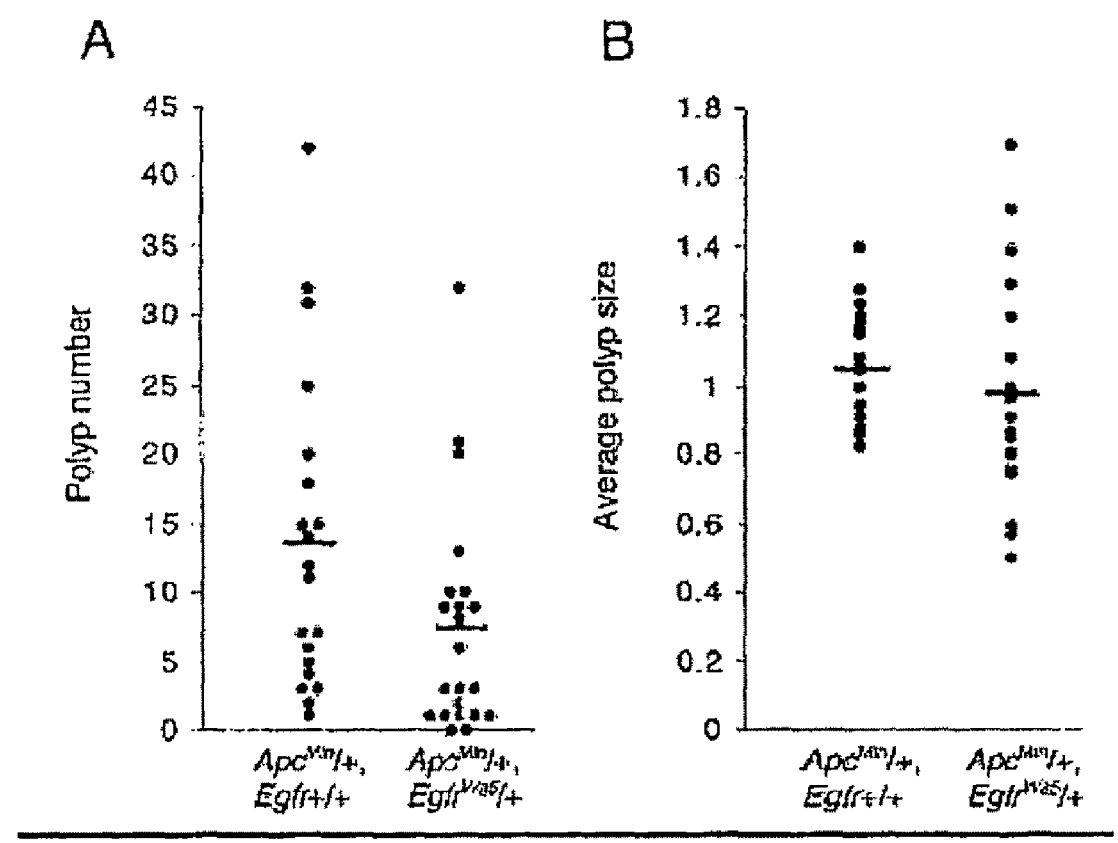
FIGS. 2A and 2B depict the effect of $Egfr^{Wa5}$ on $Apc^{Min}$-mediated intestinal tumorigenesis.

As disclosed previously for Egfr$^{wa2}$, mice carrying one Egfr$^{Wa5}$ allele caused no reduction in tumor size; the average polyp diameter in Apc$^{Min}$/+, Egfr$^{Wa5}$/+ mice was 0.97±0.07 mm compared with 1.05±0.04 mm in Apc$^{Min}$/+ mice (p=0.17; see FIG. 2B). Apc$^{Min}$/+ mice on a Mom1$^{r/s}$ background showed a 16% reduction in polyp size, independent of Egfr$^{Wa5}$ status, compared
with a Mom1$^{s/s}$ background (p=0.0003) as previously reported (Gould et al., 1996). There were no significant differences in polyp size related to gender.

Figure 3:
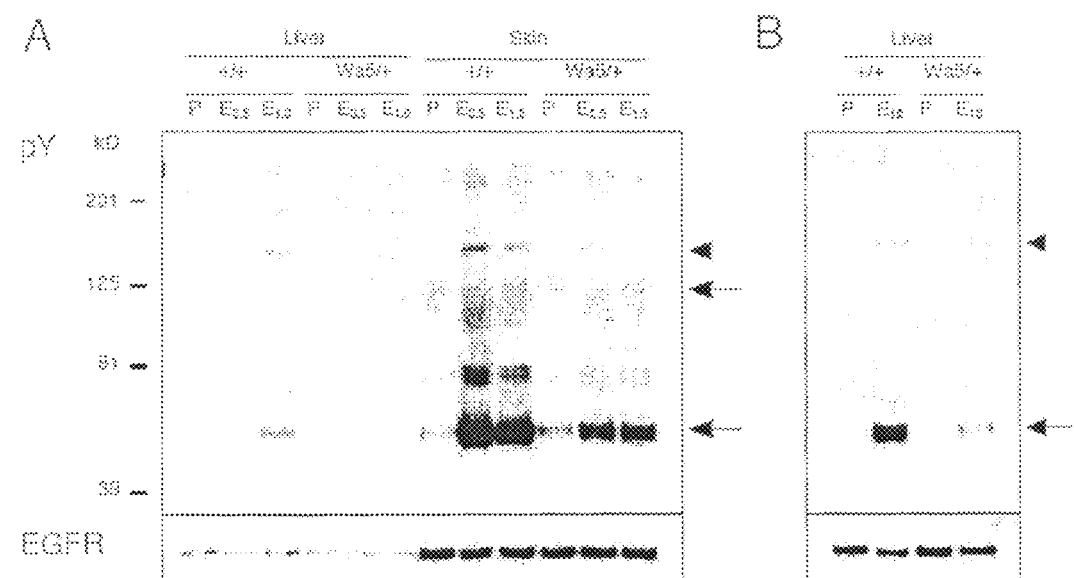
FIGS. 3A and 3B depict EGF-induced tyrosine phosphorylation in vivo.

In vivo tyrosine kinase activity is attenuated in Egfr$^{Wa5}$ heterozygous mutants. Exposure of exogenous EGF rapidly induces tyrosine phosphorylation of EGFR, along with 55- and 120-kD proteins, in multiple tissues of newborn mice (Donaldson & Cohen, 1992; Luetteke et al., 1994). Although high doses of EGF induce equivalent EGFR phosphorylation in Egfr$^{wa2/wa2}$ and Egfr wild type neonates, low doses of exogenous EGF result in diminished EGFR phosphorylation in Egfr$^{wa2/wa2}$ mice, particularly in skin (Luetteke et al., 1994). In order to characterize the in vivo phosphorylation levels of the Egfr$^{Wa5}$ mutant receptor, wild type and Egfr$^{Wa5}$/+ littermates were injected subcutaneously with either PBS or EGF at 2 or 7 days of age. Similar to EGFR activity in Egfr$^{wa2/wa2}$ mice, phosphorylation levels of EGFR and other proteins in Egfr$^{Wa5}$/+ mice were greatly attenuated at lower doses of EGF (0.5 or 1.0 µg/g body weight) in liver and skin (see FIG. 3A). However, at pharmacological doses of EGF (10 µg/g body weight), tyrosine phosphorylation of EGFR and the 55-kD protein was also greatly attenuated in Egfr$^{Wa5}$/+ mice (see FIG. 3B), in contrast to the normal level of tyrosine phosphorylation previously observed in Egfr$^{wa2/wa2}$ mice (Luetteke et al., 1994). Total levels of EGFR were identical between wild type and Egfr$^{Wa5}$/+ mice, indicating that attenuation of tyrosine phosphorylation in Egfr$^{Wa5}$/+ is not due to differential receptor expression but to an inhibitory affect of the Wa5 receptor on wild type EGFR.

Egfr$^{wa5}$ codes for a kinase-dead, dominant negative receptor. All in vivo analyses suggested that the Egfr$^{wa5}$ allele reduces total EGFR activity, even when heterozygous with an Egfr wild type allele. In stark contrast, the Egfr$^{tm1Mag}$ null and Egfr$^{wa2}$ hypomorphic alleles have no detectable heterozygous phenotype. Thus, Egfr$^{Wa5}$ satisfies the genetic definition of an antimorphic allele and would be one of the few documented mammalian antimorphic alleles; the other validated examples are the T$^c$, Clock$^{m1Jt}$, Crebbp$^{Gt(U-san)112Imeg}$, and Fbn1$^{Tsk}$ alleles (MacMurray & Shin, 1988; King et al., 1997; Oike et al., 1999; Gayraud et al., 2000). Therefore, to assess the mechanism by which Egfr$^{Wa5}$ inhibits wild type EGFR signaling, wild type human EGFR, EGFR$^{kd}$, and EGFR$^{Wa5}$ expression vectors were transiently transfected into CHO cells for in vitro analysis. The EGFR$^{kd}$ mutation was used as a control for an inactive kinase as this mutant cannot utilize ATP and thus is kinase dead (Honegger et al., 1987). Since CHO cells lack endogenous detectable EGFR, total EGFR levels proportionately increased in wild type, kd, and Wa5 EGFR-expressing cells with increasing quantities of their respective expression vector (FIG. 4A), indicating that the mutations in EGFR$^{kd}$ and EGFR$^{Wa5}$ do not impair EGFR translation. Because CHO cells express endogenous EGFR ligands, the phosphorylation of wild type EGFR increased proportionately depending on the quantity of transfected expression vector in the absence of additional exogenous EGF treatment. In contrast, the kd and Wa5 mutants had no detectable phosphorylation, suggesting that they are inactive kinases.

Figure 4:
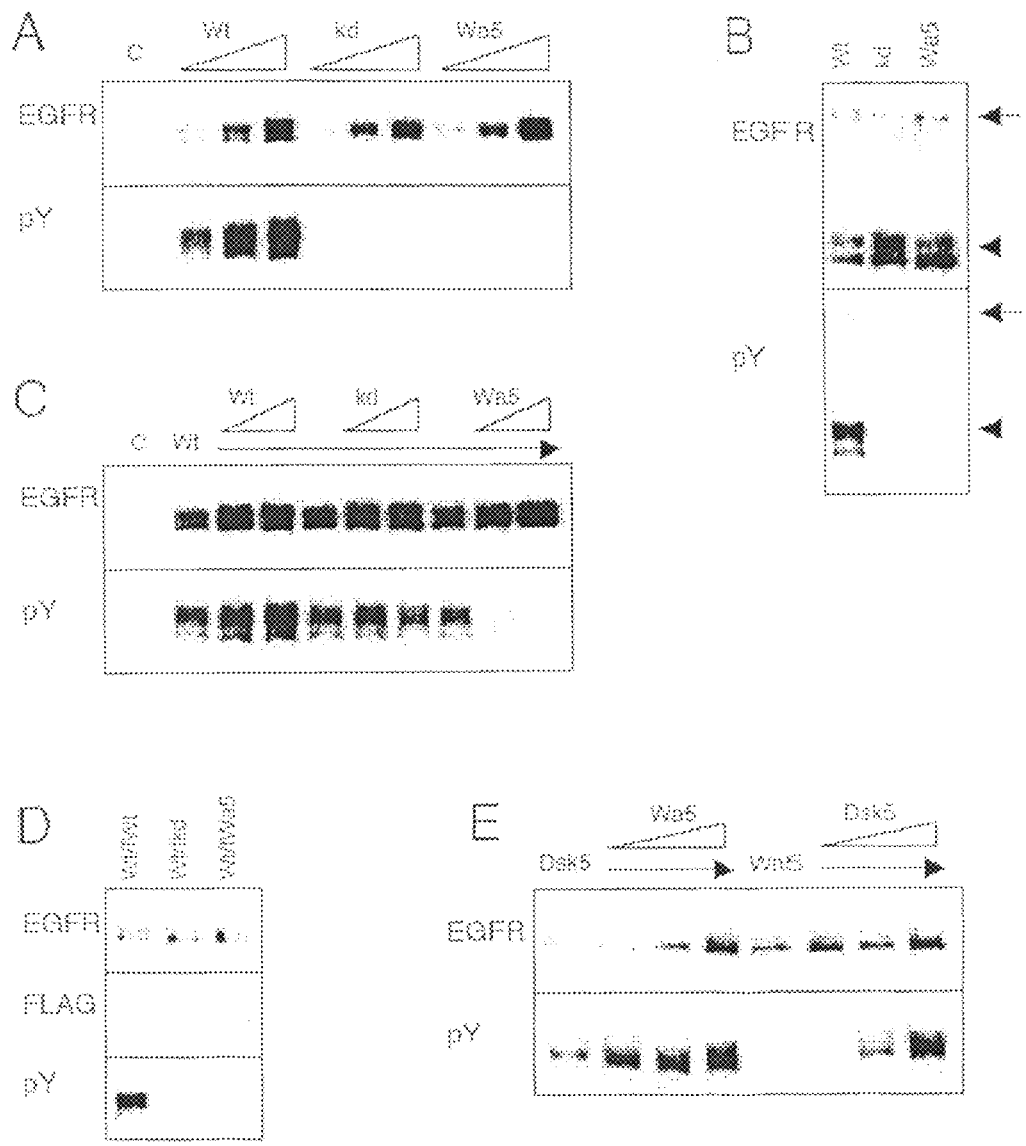
FIGS. 4A-4E depict western blot analysis of extracts from CHO cells transiently transfected with wild type and mutant EGFR expression vectors.

Since receptor dimerization is essential for activation of EGFR kinase activity under normal conditions, cross-linking assays using wild type, kd and Wa5 EGFR expressing cells were performed to determine whether Wa5 has an inactive kinase due to an inability to form ligand-dependent dimers. CHO cells were transiently transfected with 0.5 µg of each expression vector and treated 24 hours later with the cross-linking agent BS3. EGFR and the two mutants forms, kd and Wa5, underwent equivalent levels of homodimerization indicating that neither mutation affected dimerization (FIG. 4B). Dimers with the two mutants showed absence of tyrosine phosphorylation, suggesting that Wa5 might function as a dominant negative receptor.

The effect of co-expressing mutant receptors with wild type EGFR to determine the mechanism underlying the Egfr$^{Wa5}$ antimorphic allele was then analyzed. Wild type EGFR expression vector (0.2 µg) was co-transfected individually or with half (0.1 µg) or equal (0.2 µg) molar ratios of wild type EGFR, EGFR$^{kd}$, or EGFR$^{Wa5}$ expression vectors. The total amount of expression vector used was in the linear range of total EGFR expression (FIG. 4A). Total EGFR levels increased proportionately with increasing quantities of co-transfected vector for each of the three expression vectors (FIG. 4C). Similarly, EGFR phosphorylation levels increased proportionately with the quantity of wild type EGFR expression vector when transfected alone. However, phosphorylation of total EGFR remained constant in cells co-transfected with the EGFR$^{kd}$ expression vector despite increasing levels of total EGFR, suggesting that the kd mutant, although kinase dead, does not inhibit the activity of wild type EGFR when co-transfected with an equal molar ratio. Interestingly, phosphorylation of total EGFR decreased in proportion to the level of Egfr$^{Wa5}$ expression vector. Less than 10% of wild type EGFR phosphorylation levels was detected in the cells co-transfected with equal molar ratios of the EGFR$^{Wa5}$ and wild type EGFR expression vectors compared with wild type EGFR alone. This result establishes that the Wa5 receptor can potently inhibit activation of wild type EGFR. Furthermore, this result suggests that EGFR inhibition by the Wa5 mutant is due to a novel mechanism since the kd mutant, which also lacks a functional kinase, did not inhibit EGFR activation; and since classical cytoplasmic-tail truncated dominant negative receptors require over-expression to inhibit EGFR signaling (Xie et al., 1997).

To directly compare the phosphorylation status of EGFR-EGFR, EGFR-kd and EGFR-Wa5 complexes, the FLAG (f) epitope was employed to tag the N-termini of the mature receptors, after the signal peptide. CHO cells were transiently co-transfected with wild type EGFR expression vector and an equal quantity of wild type EGFR$^f$, EGFR$^{fkd}$, or EGFR$^{fWa5}$ FLAG-tagged expression vectors. This permitted an analysis of the phosphorylation status of fEGFR, fkd, and fWa5 after immunoprecipitation of cell extracts using an anti-FLAG antibody (FIG. 4D). The three transfections had similar levels of EGFR and FLAG reactivity after immunoprecipitation with an anti-FLAG antibody indicating they had similar expression of FLAG-tagged protein in each transfection. However, the phosphorylation of fkd was dramatically reduced in cells co-transfected with EGFR and EGFR$^{fkd}$ expression vectors suggesting that two active kinases are required for optimal EGFR activation and that kd is phosphorylated, albeit at reduced levels, by EGFR. Nonetheless, dimerization of fkd and EGFR still resulted in phosphorylation indicating that EGFR-fkd homodimers have kinase activity. Conversely, phosphorylation was not detected in EGFR-fWa5 complexes indicating that Wa5 cannot be phosphorylated by EGFR and that EGFR-Wa5 homodimers lack kinase activity. EGFR expression vectors with C-terminal FLAG tags exhibit similar results to the N-terminal tagged proteins showing that the location of the FLAG tag does not adversely affect activation of EGFR.

The results using co-transfections with wild type EGFR suggested that Wa5 inhibits EGFR activation by inducing or preventing a conformational change that inactivates the EGFR kinase domain or by preventing the receptor from becoming a substrate in a transphosphorylation reaction. To distinguish between these two potential mechanisms, the hyper-activatable Dsk5 was employed, produced by the EGFR$^{Dsk5}$ hypermorph allele (Fitch et al., 2003). Co-transfection of EGFR$^{Dsk5}$ and EGFR$^{Wa5}$ expression vectors revealed that Wa5 does not inhibit Dsk5 kinase activity (FIG. 4E): Wa5 can be a substrate for Dsk5. EGFR phosphorylation increased proportionally to the quantity of EGFR$^{Wa5}$ expression vector co-transfected with EGFR$^{Dsk5}$ suggesting that Wa5 was phosphorylated by hyper-activatable Dsk5. This result provides evidence that Wa5 inhibits wild type EGFR by disrupting kinase activation within oligomeric complexes rather than by inducing a conformational change leading to defective substrate utilization.

Example 8

EGFR$^{Wa5}$ does not Inhibit EGFR/ERBB2 Heterodimeric Complexes

Figure 5:
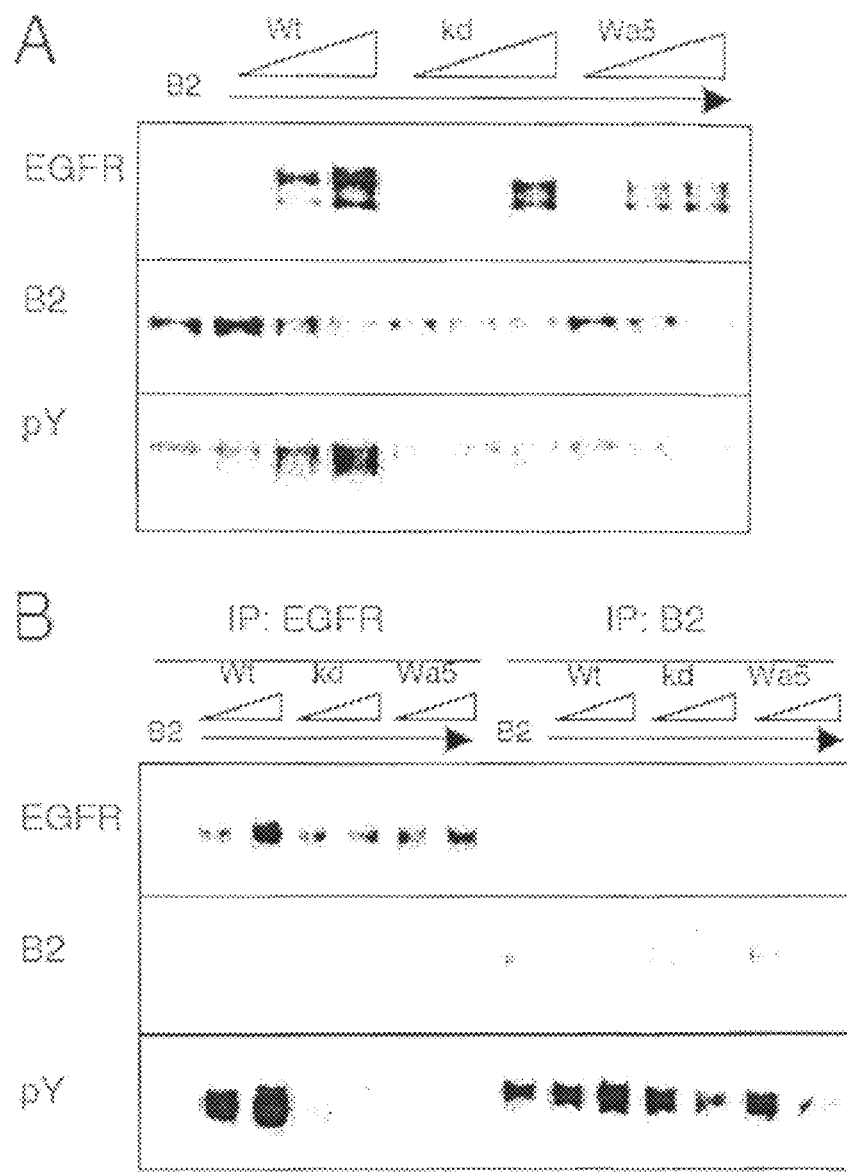
FIGS. 5A and 5B depict western blot analysis of extracts from CHO cells transiently transfected with ERBB2 and mutant EGFR expression vectors.

Similar to Dsk5, the kinase of the EGFR-related protein, ERBB2, has much greater activity with constitutive activation when over-expressed. Since ERBB2 is the preferential heterodimerization partner for EGFR and other ERBB receptors (Graus-Porta et al., 1997), whether Wa5 also inhibits heterodimeric complexes with ERBB2 was investigated. ERBB2 expression vector (0.1 mg) was co-transfected individually or with 0.1 µg, 0.3 µg or 0.5 µg of EGFR, EGFR$^{kd}$ or EGFR$^{Wa5}$ expression vectors. Total EGFR levels were proportionally increased with increasing quantities of co-transfected vector for all three EGFR expression vectors (FIG. 5A). However, ERBB2 levels decreased proportionally with increasing quantities of co-transfected EGFR expression vector. Co-transfection of ERBB2$^{K732M}$, coding for a kinase dead mutant of ERBB2, and EGFR$^{kd}$ expression vectors exhibited similar results showing that the reduction in ERBB2 levels was independent of the phosphorylation status of either EGFR or ERBB2, and most likely is a result of transcriptional interference or altered intracellular trafficking as previously reported (Worthylake & Wiley, 1997).

Phosphorylation of both EGFR and ERBB2 increased in cells co-transfected with wild type EGFR and ERBB2 expression vectors in proportion to the level of total EGFR (FIG. 5A). However, with EGFR$^{kd}$ and EGFR$^{Wa5}$ co-transfections, the level of ERBB2 phosphorylation was dependent on the level of ERBB2 and was not reduced by increasing levels of kd or Wa5. Interestingly, co-transfection of ERBB2 and either EGFR$^{kd}$ or EGFR$^{Wa5}$ expression vectors resulted in phosphorylation of kd and Wa5, respectively (FIG. 5A), although kd and Wa5 alone did not exhibit phosphorylation (FIG. 4A). The respective receptors were also immunoprecipitated for western blot analysis to confirm this result since separation of EGFR and ERBB2 by SDS-PAGE is often ambiguous in cells overexpressing both receptors. Equal quantities of ERBB2 expression vector (0.1 µg) was co-transfected with 0.3 µg or 0.5 µg of wild type EGFR, EGFR$^{kd}$, or EGFR$^{Wa5}$ expression vectors followed by immunoprecipitation of the cell extracts with either anti-EGFR or anti-ERBB2 antibodies (FIG. 5B). The immunoprecipitation-western blot analysis produced a similar result as shown in FIG. 5A (draft); Wa5 phosphorylation levels were slightly reduced compared to that of kd when controlled for EGFR levels. However, both EGFR mutants exhibited phosphorylation indicating that ERBB2 phosphorylates these EGFR mutants and that ERBB2 kinase activity is not inhibited by either kd or Wa5.

Discussion of Example 8

Since the in vivo and in vitro data strongly suggests that a simple dimer model cannot explain the potent antimorphic activity of Egfr$^{Wa5}$, it is suggested that an alternative tetrameric or oligomeric model is more consistent with the activity of Wa5. Structural analysis of protein kinases in "on" and "off" states has revealed that conformational plasticity is central to the mechanism of kinase activity regulation. Auto-phosphorylation within the activation loop of the kinase domain causes conformational changes, removing substrate binding inhibition and properly positioning the catalytic groups (Huse & Kuriyan, 2002). However, the tyrosine kinase domain of EGFR is highly unusual in that phosphorylation of the activation loop does not occur to promote its activity (Gotoh et al., 1992). The crystal structure of the unphosphorylated EGFR kinase domain suggests that the EGFR activation loop adopts a conformation observed only in other kinases that are phosphorylated and activated (Stamos et al., 2002).

Although it is well established that ligand-induced dimerization increases the tyrosine kinase activity of EGFR, the mechanism by which EGFR kinase is activated is not clearly understood (Schlessinger, 2000). It is thought that ligand-stabilized extracellular dimerization induces cytoplasmic dimerization in which the activation loops are stabilized in a conformation favorable for catalysis. The results disclosed herein suggest that EGFR-Wa5 dimers do not support a conformation necessary for catalysis and thus Wa5 acts as dominant negative like EGFR truncation mutants lacking most of the cytoplasmic domain (Kashles et al., 1991). A simple dimmer model would suggest that $EGFR^{Wa5/}$+ cells should have at least 25% of wild type activity, much greater than what was actually observed. Rather, similar to the dominant-negative effect of the $KIT^{E839K}$ mutant on wild type KIT phosphorylation (Longley et al., 1999), a more drastic reduction of phosphorylation in CHO cells suggests that EGFR-Wa5 dimers may interfere with kinase activity of wild type dimers through tetramer or high-order inter-molecular process between ligand-stabilized dimers (Sherrill, 1997; see FIG. 6A).

Consequently, a model that is more consistent with the present analysis of Wa5 consists of membrane-bound pre-dimers, stabilized by ligand binding, that are not yet fully activated. Rather than the 25% of normal kinase activity level predicted in $EGFR^{Wa5}/+$ cells based upon a dimer model, substantially less wa observed, lower than 10% activity, suggesting that the signal has been further diluted. More consistent with this observation is tetrameric or high-order complexes underlying the activated receptors (Honegger et al., 1989; Murali et al., 1996; Huang et al., 1998). Using a tetramer model, only one-sixteenth of the complexes would be fully active; all others would contain at least one Wa5 receptor, thus disrupting full activation of the receptor complexes. Therefore, the currently proposed model suggests that dimers become stabilized upon ligand binding, but must aggregate to become fully activated. Upon activation, they could then efficiently propagate a signaling cascade.

Consistent with this model would be a quarternary complex that is required to activate members within the respective dimers of the tetrameric complex and that these complexes are essentially kinase dead when containing a Wa5 receptor and incapable of further aggregation to activate EGFR-Wa5 dimers. For example, upon stabilization of dimers by ligand binding, the dimers might be internalized and it is within cytoplasmic vesicles that these higher order complexes might form (Wang et al., 2002; Wiley, 2003). Removal from the cell surface provides one potential mechanism by which Wa5 can permanently inhibit complexes containing wild type receptors and preventing disassociation and reassociation of wild type EGFR dimers. Although it cannot be formally ruled out that Wa5 forms stable, inactive dimers with EGFR (FIG. 6A), this instantly disclosed data suggests otherwise. A greater level of interaction between EGFR and Wa5 in the FLAG-tagged experiments would have been expected to have been observed if this were the case.

Figure 6:
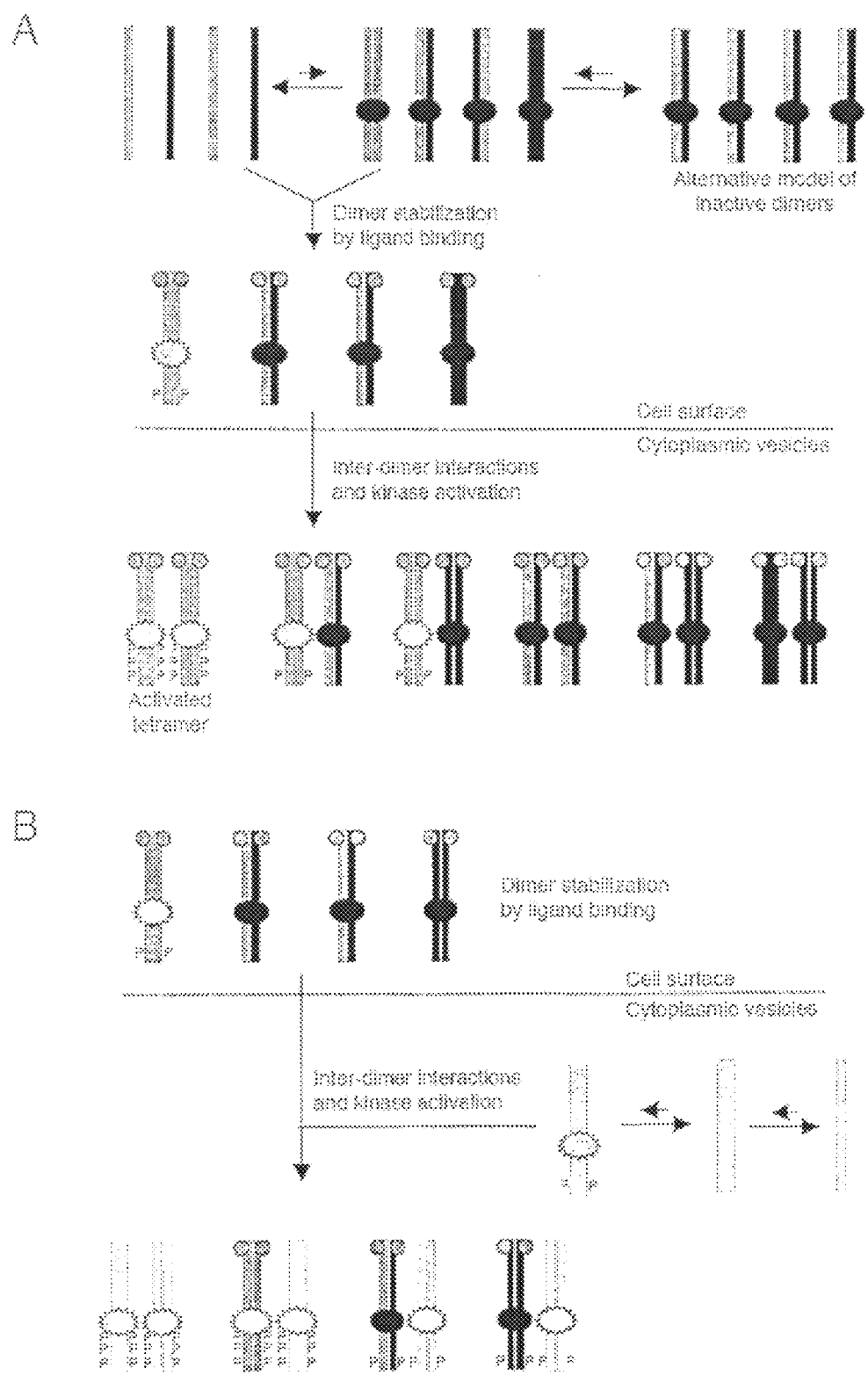
FIGS. 6A and 6B depict a model for Wa5 antimorphic action.

The model proposed herein for homodimeric interactions is also consistent with heterodimeric interactions (FIG. 6B). Previous studies have suggested that ERBB2 remains in cytoplasmic vesicles in non-transformed cells while EGFR is predominately on the cell surface (Worthylake & Wiley, 1997), consistent with the lack a known ligand for ERBB2. Upon EGFR activation, ERBB2 becomes trans-phosphorylated, most likely by internalized vesicles containing ligand-stabilized EGFR dimers. This model also suggests that EGFR and ERBB2 do not form stabilized dimers but rather are part of tetrameric or higher-order complexes. Furthermore, this model is consistent with lateral signal propagation between activated receptors (Graus-Porta et al., 1997). Lastly, phosphorylation of Wa5 by ERBB2 suggests that Wa5 does not inhibit these higher-order heteromeric complexes when highly active kinases are present. Thus, this is also consistent with the inability of Wa5 to inhibit Dsk5 mutant receptors that act very similar to ERBB2.

Example 9

Preparation of a Recombinant Peptide Library in Phage

A population of DNA fragments encoding recombinant peptide sequences is cloned into the T7 SELECT™ vector (Novagen, Madison, Wis., United States of America). Cloning at the Eco RI restriction enzyme recognition site places the recombinant peptide in-frame with the 10B protein such that the peptide is displayed on the capsid protein. The resulting reading frame requires an AAT initial codon followed by a TCX codon.

The molar ratio between insert and vector is 1:1. Size-fractionated cDNA inserts are prepared by gel filtration on sepharose 4B and ranged from 27 base pairs to 33 base pairs. cDNAs are ligated by use of the DNA ligation kit (Novagen, Madison, Wis., United States of America). Recombinant T7 DNA is packaged according to the manufacturer's instructions and amplified prior to bioscreening in animal tumor models. The diversity of the library can be at least $10^6$.

Example 10

Production of a Phage-Displayed scFv Antibody Library

A phage-displayed antibody library is constructed based upon previously published methodologies (see Pope et al., 1996). Briefly, spleens from outbred newborn and three-to-four week old mice and rats are used as a source of antibody-encoding genetic material to produce a library of about $2\times10^9$ members. The antibody-encoding genetic material is cloned into the pCANTAB phagemid vector.

The pCANTAB vector contains an amber stop codon that is located downstream of the scFv coding sequences and upstream of the M13 gene III coding sequences. *E. coli* TG1 cells (a supE strain of *E. coli*) contain a suppressor tRNA that inserts a glutamic acid residue in response to an UAG (amber) stop codon. The amber stop codon is about 14% efficient. Therefore, the scFv antibody amino acid sequences will be fused to M13 phage gene III amino acid sequences about 14% of the time, and will be produced as a soluble, non-fusion protein about 86% of the time when the library is grown in TG1 cells. In contrast, *E. coli* strain HB2151 does not contain the amber stop codon, and thus only soluble non-fused scFv will be produced when the library is grown in HB2151.

REFERENCES

The references listed below as well as all references cited in the specification are incorporated herein by reference to the extent that they supplement, explain, provide a background for or teach methodology, techniques and/or compositions employed herein.

Adams G P (1998) Improving the tumor specificity and retention of antibody-based molecules. In Vivo 12:11-21.

Adams G P, McCartney J E, Wolf E J, Eisenberg J, Tai M S, Huston J S, Stafford W F 3rd, Bookman M A, Houston L L & Weiner L M (1995) Optimization of in vivo tumor targeting in SCID mice with divalent forms of 741F8 anti-c-ERBB2 single-chain Fv: effects of dose escalation and repeated i.v. administration. *Cancer Immunol Immunother* 40:299-306.

Altschul S F, Gish W, Miller W, Myers E W & Lipman D J (1990) Basic Local Alignment Search Tool. *J Mol Biol* 215:403-410.

Andersson L, Blomberg L, Flegel M, Lepsa L, Nilsson B & Verlander M (2000) Large-scale synthesis of peptides. *Biopolymers* 55:227-250.

Apostolakis E M, Garai J, Lohmann J E, Clark J H & O'Malley B W (2000) Epidermal growth factor activates reproductive behavior independent of ovarian steroids in female rodents. *Mol Endocrinol* 14:1086-1098.

Ausubel F, ed (1995) *Short Protocols in Molecular Biology*, 3rd ed. Wiley, New York, United States of America.

Barton G J (1998) Protein Sequence Alignment Techniques. *Acta Crystallogr D Biol Crystallogr* 54:1139-1146.

Batzer M A, Carlton J E & Deininger P L (1991) Enhanced evolutionary PCR using oligonucleotides with inosine at the 3'-terminus. *Nucleic Acids Res* 19:5081.

Better M, Chang C P, Robinson R R & Horwitz A H (1988) *Escherichia coli* secretion of an active chimeric antibody fragment. *Science* 240:1041-3.

Bodanszky M (1993) *Principles of Peptide Synthesis*, 2nd rev. ed. Springer-Verlag, New York, N.Y., United States of America.

Cai X & Garen A (1995) Anti-melanoma antibodies from melanoma patients immunized with genetically modified autologous tumor cells: selection of specific antibodies from single-chain Fv fusion phage libraries. *Proc Natl Acad Sci USA* 92:6537-41.

Carpenter G & Wahl M I (1990) The epidermal growth factor family. In *Handbook of Experimental Pharmacology, Peptide Growth Factors and Their Receptors I* (ed. Sporn M B & Roberts A B), pp. 69-171. Springer-Verlag, New York, N.Y., United States of America.

Cipolla D C, Gonda I, Shak S, Kovesdi I, Crystal R & Sweeney T D (2000) Coarse Spray Delivery to a Localized Region of the Pulmonary Airways for Gene Therapy. *Hum Gene Ther* 11:361-371.

Coker K J, Staros J V & Guyer C A (1994) A kinase-negative epidermal growth factor receptor that retains the capacity to stimulate DNA synthesis. *Proc Natl Acad Aci USA* 91:6967-6971.

Corringer P J, Weng J H, Ducos B, Durieux C, Boudeau P, Bohme A & Roques B P (1993) CCK-B agonist or antagonist activities of structurally hindered and peptidase-resistant Boc-CCK4 derivatives. *J Med Chem* 36:166-172.

Coussens L, Yang-Feng T L, Liao Y-C, Chen E, Gray A, et al., (1985) Tyrosine kinase receptor with extensive homology to EGF receptor shares chromosomal location with neu oncogene. *Science* 230:1132-1139.

Donaldson, R W & Cohen S (1992) Epidermal growth factor stimulates tyrosine phosphorylation in the neonatal mouse: association of a M(r) 55,000 substrate with the receptor. *Proc Natl Acad Sci USA* 89:8477-81.

Egger B, Buchler M W, Lakshmanan J, Moore P & Eysselein V E (2000) Mice harboring a defective epidermal growth factor receptor (waved-2) have an increased susceptibility to acute dextran sulfate-induced colitis. *Scand J Gastroenterol* 35:1181-7.

Fields G B & Noble R L (1990) Solid phase peptide synthesis utilizing 9-fluorenylmethoxycarbonyl amino acids. *Int J Pept Protein Res* 35:161-214.

Figini M, Obici L, Mezzanzanica D, Griffiths A, Colnaghi M I, Winter G & Canevari S (1998) Panning phage antibody libraries on cells: isolation of human Fab fragments against ovarian carcinoma using guided selection. *Cancer Res* 58:991-6.

Fitch, K R, McGowan K A, van Raamsdonk C D, Fuchs H, Lee D, Puech A, Herault Y, Threadgill D W, Hrabe de Angelis M & Barsh G S (2003) Genetics of dark skin in mice. *Genes Dev* 17:214-28.

Garbay-Jaureguiberry C, Ficheux D & Roques B P (1992) Solid phase synthesis of peptides containing the non-hydrolysable analog of (O)phosphotyrosine, p(CH2PO3H2) Phe. Application to the synthesis of 344-357 sequences of the beta 2 adrenergic receptor. *Int J Pept Protein Res* 39:523-527.

Gayraud B, Keene D R, Sakai L Y & Ramirez F (2000) New insights into the assembly of extracellular microfibrils from the analysis of the fibrillin 1 mutation in the Tight skin mouse. *J Cell Biol* 150:667-680.

Glover D M & Hames B D (1995) DNA Cloning: A Practical Approach, 2nd ed. IRL Press at Oxford University Press, Oxford, England.

Gotoh, N, Tojo A, Hino M, Yazaki Y & Shibuya M (1992) A highly conserved tyrosine residue at codon 845 within the kinase domain is not required for the transforming activity of human epidermal growth factor receptor. *Biochem Biophys Res Commun* 186:768-74.

Gould, K A, Dietrich W F, Borenstein N, Lander E S & Dove W F (1996) Mom1 is a semi-dominant modifier of intestinal adenoma size and multiplicity in Min/+ mice. *Genetics* 144:1769-1776.

Graus-Porta, D, Beerli R R, Daly J M & Hynes N E (1997) ERBB2, the preferred heterodimerization partner of all ErbB receptors, is a mediator of lateral signaling. *EMBO J.* 16:1647-1655.

Gullick W J (1998) Type I growth factor receptors: current status and future work. *Biochem Soc Symp* 63:193-198.

Habib N A, Hodgson H J, Lemoine N & Pignatelli M (1999) A Phase I/Ii Study of Hepatic Artery Infusion with wtp53-CMV-Ad in Metastatic Malignant Liver Tumours. *Hum Gene Ther* 10:2019-2034.

Hanks S K, Quinn A M & Hunter T (1988) The protein kinase family: conserved features and deduced phylogeny of the catalytic domains. *Science* 241:42-52.

Helmrath M A, Erwin C R & Warner M D (1997) A defective EGF-receptor in waved-2 mice attenuates intestinal adaptation. *J Surg Res* 69:76-80.

Henikoff J G, Pietrokovski S, McCallum C M & Henikoff S (2000) Blocks-Based Methods for Detecting Protein Homology. *Electrophoresis* 21:1700-1706.

Henikoff S & Henikoff J G (2000) Amino Acid Substitution Matrices. *Adv Protein Chem* 54:73-97.

Henikoff S & Henikoff J G (1992) Amino Acid Substitution Matrices from Protein Blocks. *Proc Natl Acad Sci USA* 89:10915-10919.

Hoogenboom H R & Winter G (1992) By-passing immunisation. Human antibodies from synthetic repertoires of germline VH gene segments rearranged in vitro. *J Mol Biol* 227:381-8.

Honegger A M, Dull T J, Felder S, Van Obberghen E, Bellot F, Szapary D, Schmidt A, Ullrich A & Schlessinger J (1987) Point mutation at the ATP binding site of EGF receptor abolishes protein-tyrosine kinase activity and alters cellular routing. *Cell* 51: 199-209.

Honegger A M, Kris R M, Ullrich A & Schiessinger J (1989) Evidence that autophosphorylation of solubilized receptors for epidermal growth factor is mediated by intermolecular cross-phosphorylation. *Proc Natl Acad Aci USA* 86:925-929.

Huang C C, Novak W R, Babbitt P C, Jewett A I, Ferrin T E & Klein T E (2000) Integrated Tools for Structural and Sequence Alignment and Analysis. *Pac Symp Biocomput:* 230-241.

Huang G C, Ouyang X & Epstein R J (1998) Proxy activation of protein ERBB2 by heterologous ligands imllies a heterotetrameric mode of receptor tyrosine kinase interaction. *Biochem J* 331:113-119.

Huse M & Kuriyan J (2002) The conformational plasticity of protein kinases. *Cell* 109:275-282.

Jones P T, Dear P H, Foote J, Neuberger M S & Winter G (1986) Replacing the complementarity-determining regions in a human antibody with those from a mouse. *Nature* 321:522-525.

Karlin S & Altschul S F (1993) Applications and Statistics for Multiple High-Scoring Segments in Molecular Sequences. *Proc Natl Acad Sci USA* 90:5873-5877.

Kashles O, Yarden J, Fischer R, Ullrich A & Schlessinger J (1991) A dominant negative mutation suppresses the function of normal epidermal growth factor receptors by heterodimerization. *Mol Cell Biol* 11:1454-1463.

Kim J, Ahn S, Guo R & Daaka Y (2003) Regulation of epidermal growth factor receptor internalization by G protein-coupled receptors. *Biochem* 42:2887-94.

King D P, Vitaterna M H, Chang A M, Dove W F, Pinto L H, Turek F W & Takahashi J S (1997) The mouse Clock mutation behaves as an antimorph and maps within the W19H deletion, distal of Kit. *Genetics* 146:1049-1060.

Kraus M H, Issing W, Miki T, Popescu N C & Aaronson S A (1989) Isolation and characterization of ERBB3, a third member of the ERBB/epidermal growth factor receptor family: evidence for overexpression in a subset of human mammary tumors. *Proc Natl Acad Sci USA* 86:9193-9197.

Kroiher, M, Miller M A & Steele R E (2001) Deceiving appearances: signaling by "dead" and "fractured" receptor protein-tyrosine kinases. *Bioessays* 23:69-76.

Kyte J & Doolittle R F (1982) A simple method for displaying the hydropathic character of a protein. *J Mol Biol* 157:105-132.

Law B (1996) *Immunoassay: A Practical Guide*. Taylor & Francis, London, England.

Lee D, Cross S H, Strunk K E, Morgan J E, Bailey C L, Jackson I J & Threadgill D W (2004) Wa5 is a novel ENU-induced antimorphic allele of the epidermal growth factor receptor. *Mamm Genome* 15:525-36.

Longley B J, Jr, Metcalfe D D, Tharp M, Wang X, Tyrrell L, Lu S Z, Heitjan D & Ma Y (1999) Activating and dominant inactivating c-KIT catalytic domain mutations in distinct clinical forms of human mastocytosis. *Proc Natl Acad Sci USA* 96:1609-14.

Lu Z, Murray K S, Van Cleave V, LaVallie E R, Stahl M L & McCoy J M (1995) Expression of thioredoxin random peptide libraries on the *Escherichia coli* cell surface as functional fusions to flagellin: a system designed for exploring protein-protein interactions. *Biotechnology (NY)* 13:366-372.

Luetteke N C, Phillips H K, Qiu T H, Copeland N G, Earp H S, Jenkins N A & Lee D C (1994) The mouse waved-2 phenotype results from a point mutation in the EGF receptor tyrosine kinase. *Genes Dev* 8:399-413.

Luetteke N C, Qiu T H, Peiffer R L, Oliver P, Smithies O & Lee D C (1993) TGF alpha deficiency results in hair follicle and eye abnormalities in targeted and waved-1 mice. *Cell* 73:263-278.

MacMurray A & Shin H S (1988) The antimorphic nature of the Tc allele at the mouse T locus. *Genetics* 120:545-550.

Mann G B, Fowler K J, Gabriel A, Nice E C, Williams R L & Dunn A R (1993) Mice with a null mutation of the TGF alpha gene have abnormal skin architecture, wavy hair, and curly whiskers and often develop corneal inflammation. *Cell* 73:249-61.

Manson M M (1992) *Immunochemical Protocols*. Humana Press, Totowa, N.J., United States of America.

McCafferty J, Griffiths A D, Winter G & Chiswell D J (1990) Phage antibodies: filamentous phage displaying antibody variable domains. *Nature* 348:552-4.

McOmie J F W. (1973) Protective Groups in Organic Chemistry, Plenum Press, London, England.

Merrifield R B (1969) Solid-phase peptide synthesis. *Adv Enzymol Relat Areas Mol Biol* 32:221-296.

Miettinen P J, Chin J R, Shum L, Slavkin H C, Shuler C F, Derynck R & Werb Z (1999) Epidermal growth factor receptor function is necessary for normal craniofacial development and palate closure. *Nature Genetics* 22:69-73.

Mocikat R, Kutemeier G, Hoffmann-Fezer G & Thierfelder S (1994) A mouse model for the preclinical evaluation of immunosuppressive effector functions of human isotypes. The human IgG1 isotype is superior to IgG3. *Transplantation* 57:405-11.

Moscatello D K, Holgado-Madruga M, Godwin A K, Ramirez G, Gunn G, Zoltick P W, Biegel J A, Hayes R L & Wong A J (1995). Frequent expression of a mutant epidermal growth factor receptor in multiple human tumors. *Cancer Res* 55:5536-9.

Moser A R, Mattes E M, Dove W F, Lindstrom M J, Haag J D & Gould M N. (1993) ApcMin, a mutation in the murine Apc gene, predisposes to mammary carcinomas and focal alveolar hyperplasias. *Proc Natl Acad Sci USA* 90:8977-81.

Murali R, Brennan P J, Kieber-Emmons T & Greene M I (1996) Structural analysis of p185c-neu and epidermal growth factor receptor tyrosine kinases: oligomerization of kinase domains. *Proc Natl Acad Sci USA* 93:6252-7.

Needleman S B & Wunsch C D (1970) A General Method Applicable to the Search for Similarities in the Amino Acid Sequence of Two Proteins. *J Mol Biol* 48:443-453.

Ohtsuka E, Matsuki S, Ikehara M, Takahashi Y & Matsubara K (1985) An alternative approach to deoxyoligonucleotides as hybridization probes by insertion of deoxyinosine at ambiguous codon positions. *J Biol Chem* 260:2605-2608.

Oike Y, Hata A, Mamiya T, Kaname T, Noda Y, Suzuki M, Yasue H, Nabeshima T, Araki K & Yamamura K (1999) Truncated CBP protein leads to classical Rubinstein-Taybi syndrome phenotypes in mice: implications for a dominant-negative mechanism. *Hum Mol Genet* 8:387-396.

Pavone V, Di Blasio B, Lombardi A, Maglio O, Isernia C, Pedone C, Benedetti E, Altmann E & Mutter M (1993) Non coded C alpha, alpha-disubstituted amino acids. X-ray diffraction analysis of a dipeptide containing (S)-alpha-methylserine. *Int J Pept Protein Res* 41:15-20.

Pearson W R & Lipman D J (1988) Improved Tools for Biological Sequence Comparison. *Proc Natl Acad Sci USA* 85:2444-2448.

Plowman G D, Culouscou J-M, Whitney G S, Green J M, Carlton G W, Foy L, Neubauer M G & Shoyab M (1993) Ligand-specific activation of HER4/p180erbB4, a fourth member of the epidermal growth factor receptor family. *Proc Natl Acad Sci USA* 90:1746-1750.

Plowman G D, Whitney G S, Neubauer M G, Green J M, McDonald V L, Todaro G J & Shoyab M (1990) Molecular cloning and expression of an additional epidermal growth factor receptor-related gene. *Proc Natl Acad Sci USA* 87: 4905-4909.

Pluckthun A (1994) in *The Pharmacology of Monoclonal Antibodies*, vol. 113, pp. 269-315, Rosenburg & Moore (eds.), Springer-Verlag, New York, N.Y., United States of America.

Pope A, Pritchard K, Williams A, Roberts A, Hackett J R, Mandecki W & Johnson K S (1996) In vitro selection of a high affinity antibody to oestradiol using a phage display human antibody library. *Immunotechnology* 2:209-217.

Presta L G (1992) Antibody engineering. *Curr Op Struct Biol* 2:593-596.

Qian X, LeVea C M, Freeman J K, Dougall W C, & Greene M I (1994) Heterodimerization of epidermal growth factor receptor and wild-type or kinase deficient Neu: a mechanism of interreceptor kinase activation and transphosphorylation. *Proc Natl Acad Sci USA* 91:1500-1504.

Rasheed B K, Wiltshire R N, Bigner S H & Bigner D D (1999) Molecular pathogenesis of malignant gliomas. *Curr Opin Oncol* 11:162-7.

Reiter J L, Threadgill D W, Eley G D, Strunk K E, Danielsen A J, Schehl-Sinclair C, Pearsall R S, Green P J, Yee D, Lampland A L, Balasubrarmaniam, Crossley T O, Magnuson T R, James C D & Maihle N J (2001) Comparative genomic sequence analysis and isolation of human and mouse alternative EGFR transcripts encoding truncated receptor isoforms. *Genomics* 71:1-20.

Riechmann L, Clark M, Waldmann H & Winter G (1988) Reshaping human antibodies for therapy. *Nature* 332:323-329.

Roberts, R B, Min L, Washington M K, Olsen S J, Settle S H, Coffey R J & Threadgill D W (2001) Importance of epidermal growth factor receptor signaling in establishment of adenomas and maintenance of carcinomas during intestinal tumorigenesis. *Proc Natl Acad Sci USA* 99:1521-1526.

Rossolini G M, Cresti S, Ingianni A, Cattani P, Riccio M L & Satta G (1994) Use of deoxyinosine-containing primers vs degenerate primers for polymerase chain reaction based on ambiguous sequence information. *Mol Cell Probes* 8:91-98.

Sambrook J & Russell D (2001), *Molecular Cloning: A Laboratory Manual*, 3rd ed. Cold Spring Harbor Laboratory Press, Cold Spring Harbor, N.Y., United States of America.

Saqi M A, Wild D L & Hartshorn M J (1999) Protein Analyst—a Distributed Object Environment for Protein Sequence and Structure Analysis. *Bioinformatics* 15:521-522.

Schlessinger J (2000) Cell signaling by receptor tyrosine kinases. *Cell* 103:211-25.

Schneider C H & Eberle A N (1993) *Peptides, 1992: Proceedings of the Twenty-Second European Pentide Symposium*, Sep. 13-19, 1992, Interlaken, Switzerland. Escom, Leiden, The Netherlands.

Schröder E & Lübke K (1965) *The Peptides*. Academic Press, New York, N.Y., United States of America.

Shalaby M R, Shepard H M, Presta L, Rodrigues M L, Beverley P C, Feldmann M & Carter P (1992) Development of humanized bispecific antibodies reactive with cytotoxic lymphocytes and tumor cells overexpressing the HER2 protooncogene. *J Exp Med* 175:217-25.

Sherrill J M (1997) Self-phosphorylation of epidermal growth factor receptor is an intermolecular reaction. *Biochem* 36:12890-6.

Silhavy T J, Berman M L, Enquist L W & Cold Spring Harbor Laboratory. (1984) *Experiments with Gene Fusions*. Cold Spring Harbor Laboratory, Cold Spring Harbor, N.Y., United States of America.

Smith G P (1985) Filamentous fusion phage: novel expression vectors that display cloned antigens on the virion surface. *Science* 228:1315-1317.

Smith T F & Waterman M (1981) Comparison of Biosequences. *Adv Appl Math* 2:482-489.

Stamos J Sliwkowski M X & Eigenbrot C (2002) Structure of the epidermal growth factor receptor kinase domain alone and in complex with a 4-anilinoquinazoline inhibitor. *J Biol Chem* 277:46265-46272.

Stewart J M & Young J D (1969) *Solid Phase Peptide Synthesis*, Freeman, San Francisco, Calif., United States of America.

Strunk K E, Amann V & Threadgill D W (2004) Phenotypic variation resulting from a deficiency of epidermal growth factor receptor in mice is caused by extensive genetic heterogeneity that can be genetically and molecularly partitioned. *Genetics* 167:1821-32.

Thaung C, West K, Clark B J, McKie L, Morgan J E, Arnold K, Nolan P M, Peters J, Hunter A J, Brown S D, Jackson I J & Cross S H (2002) Novel ENU-induced eye mutations in the mouse: models for human eye disease. *Hum Mol Genet.* 11:755-67.

Threadgill D W, Dlugosz A A, Hansen L A, Tennenbaum T, Lichti U, Yee D, LaMantia C, Mourton T, Herrup K, Harris R C, Barnard J A, Yuspa S H, Coffey R J & Magnuson T (1995) Targeted disruption of mouse EGF receptor: effect of genetic background on mutant phenotype. *Science* 269: 230-234.

Tijssen P (1993) Laboratory Techniques in Biochemistry and Molecular Biology-Hybridization with Nucleic Acid Probes. Elsevier, New York, N.Y., United States of America.

Tung C H, Zhu T, Lackland H & Stein S (1992) An acridine amino acid derivative for use in Fmoc peptide synthesis. *Pept Res* 5:115-118.

Urge L, Otvos L, Jr., Lang E, Wroblewski K, Laczko I & Hollosi M (1992) Fmoc-protected, glycosylated asparagines potentially useful as reagents in the solid-phase synthesis of N-glycopeptides. *Carbohydr Res* 235:83-93.

U.S. Pat. No. 4,244,946
U.S. Pat. No. 4,554,101
U.S. Pat. No. 5,223,409
U.S. Pat. No. 5,264,563
U.S. Pat. No. 5,498,538
U.S. Pat. No. 5,578,629
U.S. Pat. No. 5,580,717
U.S. Pat. No. 5,650,489
U.S. Pat. No. 5,667,988
U.S. Pat. No. 5,702,892
U.S. Pat. No. 5,738,996
U.S. Pat. No. 5,747,334
U.S. Pat. No. 5,756,291
U.S. Pat. No. 5,780,225
U.S. Pat. No. 5,811,392
U.S. Pat. No. 5,811,512
U.S. Pat. No. 5,811,515
U.S. Pat. No. 5,817,757
U.S. Pat. No. 5,817,879

U.S. Pat. No. 5,824,483
U.S. Pat. No. 5,840,479
U.S. Pat. No. 5,858,670
U.S. Pat. No. 5,858,784
U.S. Pat. No. 5,922,545
U.S. Pat. No. 5,939,598
U.S. Pat. No. 5,948,635
U.S. Pat. No. 6,013,638
U.S. Pat. No. 6,015,561
U.S. Pat. No. 6,015,881
U.S. Pat. No. 6,022,737
U.S. Pat. No. 6,031,071
U.S. Pat. No. 6,057,098
U.S. Pat. No. 6,107,059
U.S. Pat. No. 6,136,295
U.S. Pat. No. 6,156,511
U.S. Pat. No. 6,168,912
U.S. Pat. No. 6,174,708
U.S. Pat. No. 6,180,348
U.S. Pat. No. 6,214,553
U.S. Pat. No. 6,225,447
U.S. Pat. No. 6,593,081
Wang Z Q, Chen J K, Wang S W, Moeckel G & Harris R C (2003) Importance of functional EGF receptors in recovery from acute nephrotoxic injury. *J Am Soc Nephrol* 14:3147-3154.

Wang Y, Pennock S, Chen X & Wang Z (2002) Endosomal signaling of epidermal growth factor receptor stimulates signal transduction pathways leading to cell survival. *Mol Cell Biol* 22:7279-7290.

Wiley H S (2003) Trafficking of the ErbB receptors and its influence on signaling. *Exp Cell Res* 284:78-88.

Wong A J, Ruppert J M, Bigner S H, Grzeschik C H, Humphrey P A, Bigner D S & Vogelstein B (1992) Structural alterations of the epidermal growth factor receptor gene in human gliomas. *Proc Natl Acad Sci USA* 89:2965-9.

Worthylake R & Wiley H S (1997) Structural aspects of the epidermal growth factor receptor required for transmodulation of ERBB2/neu. *J Biol Chem* 272:8594-601.

Xie W, Paterson A J, Chin E, Nabell L M & Kudlow J E (1997) Targeted expression of a dominant negative epidermal growth factor receptor in the mammary gland of transgenic mice inhibits pubertal mammary duct development. *Mol Endocrinol* 11:1766-81.

Yokota T, Milenic D, Whitlow M & Schlom J (1992) Rapid Tumor Penetration of a Single-Chain Fv and Comparison with Other Immunoglobulin Forms. *Cancer Res* 52:3402-3408.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method for screening a plurality of compounds for an ability to bind to a heterodimer of EGFR and another ERBB family member, the method comprising:
   (a) contacting a first structure comprising an EGFR/ERBB heterodimer with a first solution, the first solution comprising the plurality of compounds, wherein the EGFR/ERBB heterodimer comprises an ERBB family member comprising the amino acid sequence set forth in SEQ ID NO: 6;
   (b) removing any compounds bound to the first structure to produce a second solution;
   (c) contacting a second structure comprising an EGFR homodimer with the second solution, wherein the first structure and the second structure are identical except that the second structure does not contain an ERBB family member other than EGFR; and
   (d) recovering any unbound compounds to produce a third solution,
   whereby a compound that binds to a heterodimer of EGFR and another ERBB family member is identified.

2. The method of claim 1, wherein the plurality of compounds comprises a plurality of antibodies.

3. The method of claim 2, wherein the plurality of compounds comprises phage-displayed antibodies.

4. The method of claim 3, wherein the plurality of compounds comprises a phage-displayed antibody library.

5. The method of claim 4, wherein the phage-displayed antibody library comprises a phage-displayed single chain variable fragment (scFv) library or a phage-displayed Fab library.

6. The method of claim 3, wherein the phage-displayed antibodies are humanized.

7. The method of claim 1, wherein the first structure comprises a cell that expresses EGRF and the ERBB family member comprising the amino acid sequence set forth in SEQ ID NO: 6, or an isolated membrane fraction of said cell.

8. The method of claim 7, wherein the cell is a recombinant cell that does not normally express any ERBB family member or ErbB ligand, but has been engineered to express a human EGFR and at least one other human ERBB family member.

9. The method of claim 1, wherein the second structure comprises a cell that expresses EGRF but no other ERBB family member, or an isolated membrane fraction of said cell.

10. The method of claim 9, wherein the cell is a recombinant cell that does not normally express any ERBB family member or ErbB ligand, but has been engineered to express a human EGFR.

11. The method of claim 1, further comprising:
   (a) contacting a third structure comprising an EGFR/ERBB heterodimer with the third solution, wherein the EGFR/ERBB heterodimer comprises an ERBB family member comprising the amino acid sequence set forth in SEQ ID NO: 6; and
   (b) detecting binding of a compound to the EGFR/ERBB heterodimer on the third structure.

12. The method of claim 1, further comprising negatively selecting the plurality of compounds by contacting the plurality of compounds with a structure that is identical to the first and second structures except that it does not contain any ERBB family members.

* * * * *